United States Patent
Belema et al.

(10) Patent No.: US 11,505,543 B2
(45) Date of Patent: Nov. 22, 2022

(54) 4-OXO-3,4-DIHYDROQUINAZOLINE COMPOUNDS AS INHIBITORS OF HUMAN IMMUNODEFICIENCY VIRUS REPLICATION

(71) Applicant: VIIV HEALTHCARE UK (NO.5) LIMITED, Middlesex (GB)

(72) Inventors: Makonen Belema, Wallingford, CT (US); John A. Bender, Wallingford, CT (US); David B. Frennesson, Wallingford, CT (US); Eric P. Gillis, Branford, CT (US); Christiana Iwuagwu, Branford, CT (US); John F. Kadow, Branford, CT (US); B. Narasimhulu Naidu, Branford, CT (US); Kyle E. Parcella, Branford, CT (US); Kevin M. Peese, Branford, CT (US); Ramkumar Rajamani, Wallingford, CT (US); Mark G. Saulnier, Wallingford, CT (US); Alan Xiangdong Wang, Wallingford, CT (US); Manoj Patel, Branford, CT (US); Michael S. Bowsher, Branford, CT (US)

(73) Assignee: VIIV HEALTHCARE UK (NO.5) LIMITED, Middlesex (GB)

(*) Notice: Subject to any disclaimer, the term of this patent is extended or adjusted under 35 U.S.C. 154(b) by 15 days.

(21) Appl. No.: 17/042,413

(22) PCT Filed: Apr. 11, 2019

(86) PCT No.: PCT/IB2019/052990
§ 371 (c)(1),
(2) Date: Sep. 28, 2020

(87) PCT Pub. No.: WO2019/198024
PCT Pub. Date: Oct. 17, 2019

(65) Prior Publication Data
US 2021/0024503 A1    Jan. 28, 2021

Related U.S. Application Data

(60) Provisional application No. 62/750,336, filed on Oct. 25, 2018, provisional application No. 62/732,741, filed on Sep. 18, 2018, provisional application No. 62/689,995, filed on Jun. 26, 2018, provisional application No. 62/655,881, filed on Apr. 11, 2018.

(51) Int. Cl.
| | | |
|---|---|---|
| C07D 401/14 | (2006.01) |
| C07D 403/14 | (2006.01) |
| C07D 405/14 | (2006.01) |
| A61K 31/517 | (2006.01) |
| A61P 31/18 | (2006.01) |
| C07D 403/12 | (2006.01) |
| C07D 413/14 | (2006.01) |
| C07D 491/052 | (2006.01) |

(52) U.S. Cl.
CPC ............ *C07D 403/14* (2013.01); *A61P 31/18* (2018.01); *C07D 401/14* (2013.01); *C07D 403/12* (2013.01); *C07D 405/14* (2013.01); *C07D 413/14* (2013.01); *C07D 491/052* (2013.01)

(58) Field of Classification Search
CPC .. C07D 401/14; C07D 403/14; C07D 405/14; A61K 31/517; A61P 31/18
See application file for complete search history.

(56) References Cited

U.S. PATENT DOCUMENTS

2020/0360384 A1* 11/2020 Gillis .................. A61K 31/517

FOREIGN PATENT DOCUMENTS

| WO | WO 2013/006738 A1 | 1/2013 |
| WO | WO 2014/110297 A1 | 7/2014 |
| WO | WO 2014/110298 A1 | 7/2014 |
| WO | WO 2014/134566 A2 | 9/2014 |
| WO | WO 2016/033243 A1 | 3/2016 |
| WO | WO 2018/203235 A1 | 11/2018 |
| WO | 2020/084480 A1 | 4/2020 |
| WO | 2020/084492 A1 | 4/2020 |

* cited by examiner

*Primary Examiner* — Bruck Kifle
(74) *Attorney, Agent, or Firm* — Nora L. Stein

(57) ABSTRACT

Compounds of Formula I, including pharmaceutically acceptable salts thereof, and compositions and methods for treating human immunodeficiency virus (HIV) infection are set forth:

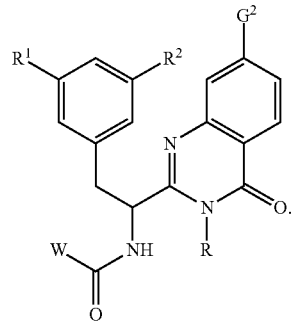

Formula I

4 Claims, No Drawings

4-OXO-3,4-DIHYDROQUINAZOLINE COMPOUNDS AS INHIBITORS OF HUMAN IMMUNODEFICIENCY VIRUS REPLICATION

This application is a § 371 of International Application No. PCT/IB2019/052990, filed 11 Apr. 2019, which claims the benefit of U.S. Provisional Application Nos. 62/750,336, filed 25 Oct. 2018; 62/732,741, filed 18 Sep. 2018; 62/689,995, filed 26 Jun. 2018; and 62/655,881, filed 11 Apr. 2018.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Acquired immunodeficiency syndrome (AIDS) is the result of infection by HIV. HIV continues to be a major global public health issue. Current therapy for HIV-infected individuals typically consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase strand transfer inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity (cobicistat) has recently been approved for use in combinations with antiretroviral agents (ARVs) that require boosting.

Despite the armamentarium of agents and drug combinations, there remains a medical need for new anti-retroviral agents, due in part to the need for chronic dosing to combat infection. Significant problems related to long-term toxicities are documented, creating a need to address and prevent these co-morbidities (e.g. CNS, CV/metabolic, renal disease). Also, increasing failure rates on current therapies continue to be a problem, due either to the presence or emergence of resistant strains or to non-compliance attributed to drug holidays or adverse side effects. For example, despite therapy, it has been estimated that 63% of subjects receiving combination therapy remained viremic, as they had viral loads >500 copies/mL (Oette, M, Kaiser, R, Daumer, M, et al. Primary HIV Drug Resistance and Efficacy of First-Line Antiretroviral Therapy Guided by Resistance Testing. J Acq Imm Def Synd 2006; 41(5):573-581). Among these patients, 76% had viruses that were resistant to one or more classes of antiretroviral agents. As a result, new drugs are needed that are easier to take, have high genetic barriers to the development of resistance and have improved safety over current agents. In this panoply of choices, novel MOAs that can be used as part of the preferred HAART regimen can still have a major role to play since they should be effective against viruses resistant to current agents.

Certain potentially therapeutic compounds have now been described in the art and set forth in Blair, Wade S. et. al. Antimicrobial Agents and Chemotherapy (2009), 53(12), 5080-5087, Blair, Wade S. et al. PLoS Pathogens (2010), 6(12), e1001220, Thenin-Houssier, Suzie; Valente, Susana T. Current HIV Research, 2016, 14, 270-282, and PCT Patent applications with the following numbers: WO 2012065062, WO 2013006738, WO 2013006792, WO 2014110296, WO 2014110297, WO 2014110298, WO 2014134566, WO 2015130964, and WO 2016033243.

SUMMARY OF THE INVENTION

Briefly, in one aspect, the present invention discloses a compound of Formula I,

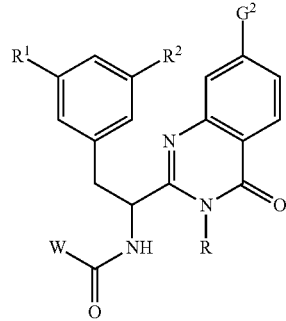

Formula I or a pharmaceutically acceptable salt thereof, wherein:
each $R^1$ and $R^2$ is independently H, F, or Cl;
$G^2$ is selected from:

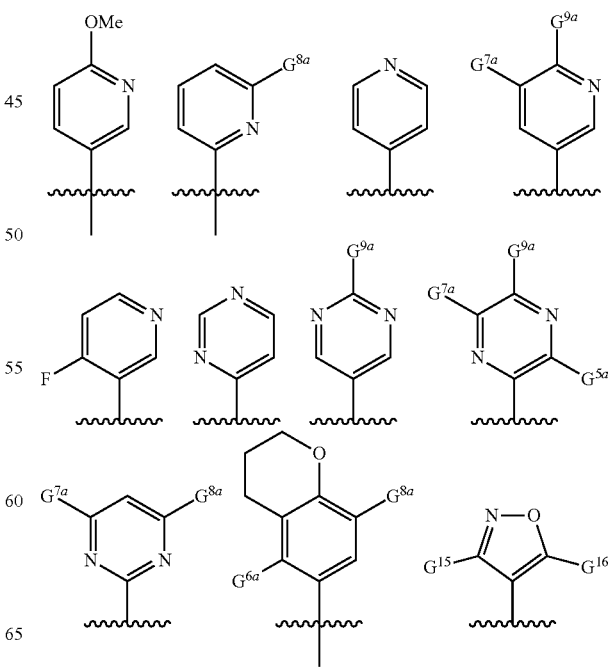

-continued

G⁵ is hydrogen, methyl, fluoro, chloro, phenyl, $OC_1$-$C_3$alkyl, cyano, —$CH_2OH$, OPh, or —$SO_2(C_1$-$C_3$alkyl);
G⁵ᵃ is hydrogen or methyl;
G⁶ is hydrogen, methyl, fluoro, chloro, phenyl, $OC_1$-$C_3$alkyl, or OPh;
G⁶ᵇ is hydrogen or methyl;
G⁷ is hydrogen, methyl, fluoro, chloro, phenyl, $OC_1$-$C_3$alkyl, OPh, COOH, or CON(G¹⁰)(G¹¹);
G⁷ᵃ is hydrogen, methyl, or fluoro;
G⁸ is hydrogen, $C_1$-$C_4$alkyl, fluoro, chloro, phenyl, $OC_1$-$C_3$alkyl, OPh, COOH, cyano, —$CH_2OH$, —$SO_2(C_1$-$C_3$ alkyl) or CON(G¹⁰)(G¹¹);
G⁸ᵃ is hydrogen, methyl or $OC_1$-$C_3$alkyl;
G⁸ᵇ is hydrogen or fluoro;
G⁹ is hydrogen, $C_1$-$C_4$ alkyl, fluoro, chloro, phenyl, $OC_1$-$C_3$alkyl, OPh, COOH, CON(G¹⁰)(G¹¹), $C(CH_3)_2CH_2OH$, or —$SO_2$-morpholine wherein methyl is optionally substituted with 1-3 fluorines;
G⁹ᵃ is hydrogen, $C_1$-$C_4$alkyl, or fluoro;
G¹⁰ is hydrogen or methyl;
G¹¹ is hydrogen or methyl;
or G¹⁰ and G¹¹ are joined together to form a piperidine
G¹² is hydrogen or $C_1$-$C_3$alkyl;
G¹³ is hydrogen or $C_1$-$C_3$alkyl;
G¹⁴ is hydrogen or $C_1$-$C_3$alkyl;
G¹⁵ is hydrogen or $C_1$-$C_3$alkyl;
G¹⁶ is hydrogen or $C_1$-$C_3$alkyl;
R is -continued R³ is hydrogen, Cl, or F;
R⁴ is hydrogen, $C_1$-$C_3$alkyl, or $C_3$-$C_6$cycloalkyl—wherein $C_1$-$C_3$alkyl or $C_3$-$C_6$cycloalkyl is optionally substituted with 1-3 fluorines;
R⁵ is $C_1$-$C_6$alkyl, $C_3$-$C_6$cycloalkyl, or NG¹², G¹³;
R⁶ and R⁷ are each independently hydrogen, chlorine, or fluorine;
R¹⁰ is hydrogen, chlorine, fluorine, —$C_1$-$C_3$alkyl, —$SO_2C_1$-$C_3$alkyl, —$SO_2C_3$-$C_6$cycloalkyl, —$SO_2NR^aR^b$, wherein —$C_1$-$C_3$alkyl is optionally substituted with 1-3 fluorines or R¹⁰ is selected from the following:

R¹¹ is hydrogen, chlorine, or fluorine;
R¹² is hydrogen, chlorine, fluorine, —$C_1$-$C_3$alkyl, or —$C_3$-$C_6$cycloalkyl, wherein —$C_1$-$C_3$alkyl is optionally substituted with 1-3 fluorines;
R^a and R^b are independently H, —$C_1$-$C_3$alkyl, or together with the N to which they are attached form a morpholine, azetidine, pyrrolidine, piperidine, piperazine, N-Me piperazine, or is selected from the following:

-continued

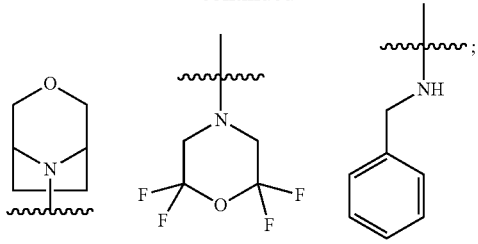

W is selected from:

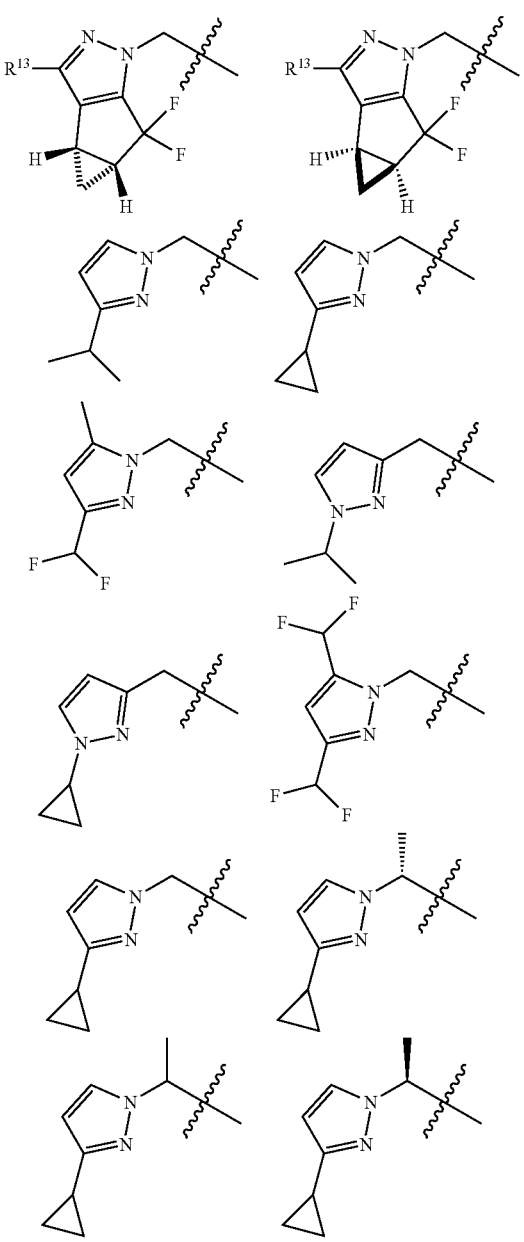

wherein $R^{13}$ is methyl optionally substituted with 1 to 3 fluorines.

In another aspect, the present invention discloses a composition comprising a compound of Formula I or a pharmaceutically acceptable salt thereof.

In another aspect, the present invention discloses a method of treating HIV infection comprising administering a composition comprising a compound of Formula I or a pharmaceutically acceptable salt thereof to a patient.

In another aspect, the present invention discloses a compound of Formula (I) or pharmaceutically acceptable salt thereof for use in therapy.

In another aspect, the present invention discloses a compound of Formula (I) or pharmaceutically acceptable salt thereof for use in treating HIV infection.

In another aspect, the present invention discloses the use of a compound of Formula (I) or pharmaceutically acceptable salt thereof in the manufacture of a medicament for the treatment of HIV infection.

DETAILED DESCRIPTION OF THE INVENTION

Preferably at least one of $R^1$ and $R^2$ is F or Cl. More preferably $R^1$ and $R^2$ are F.

Preferably W is one of the following:

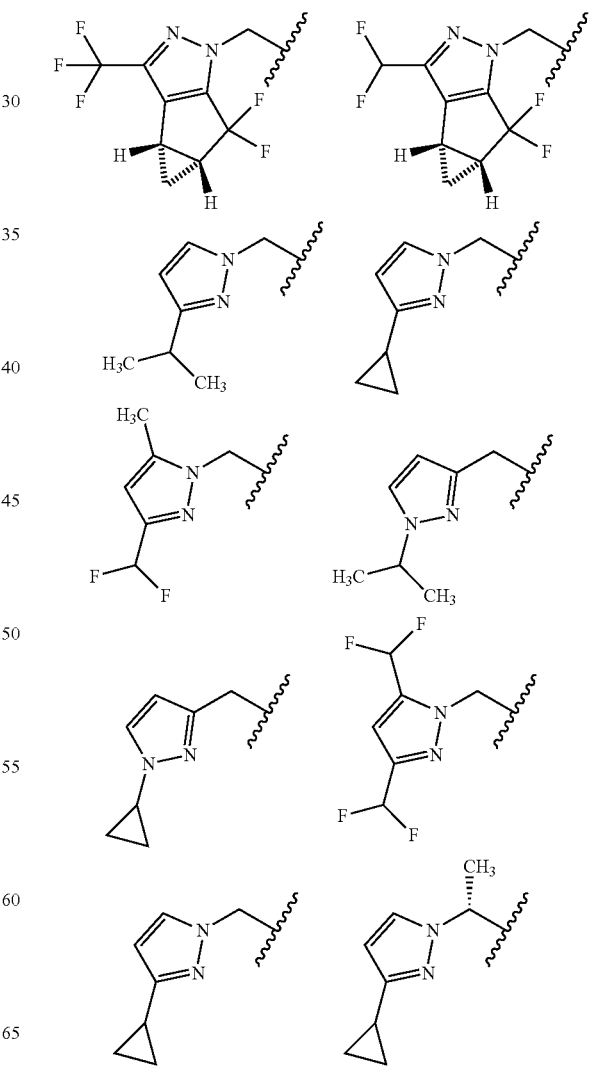

-continued
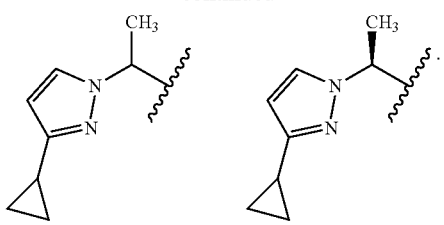
More preferably W is
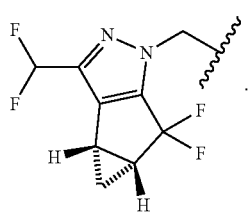
Preferably R is
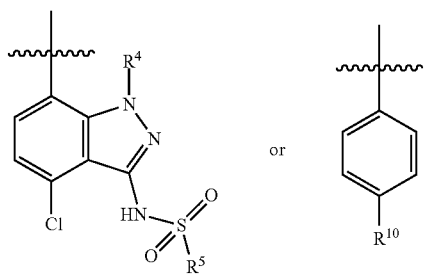
wherein $R^4$ is methyl, 2,2-difluoroethyl, 2,2,2-trifluoroethyl, or cyclopropyl; $R^5$ is methyl or cyclopropyl; $R^6$ is H, $R^7$ is H, and $R^{10}$ is —$SO_2$ morpholine.
Preferably $G^2$ is one of the following:
-continued
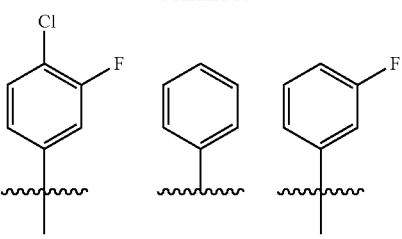
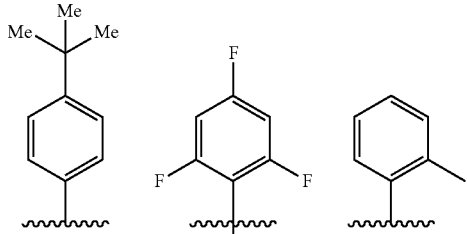
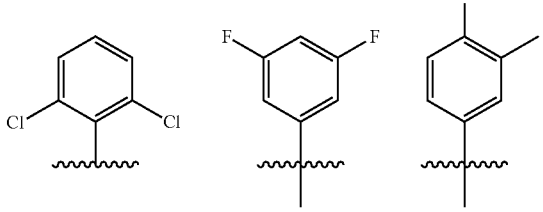
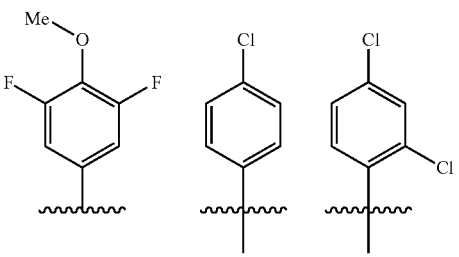
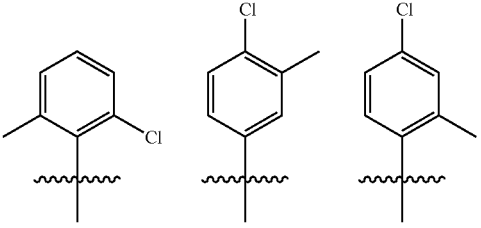
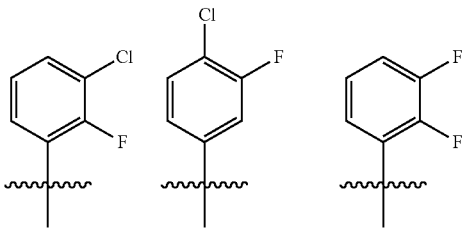
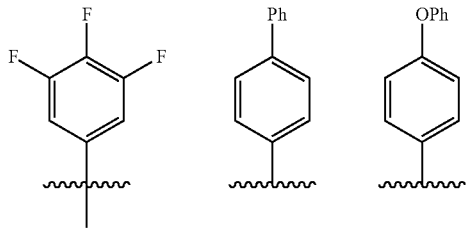

-continued
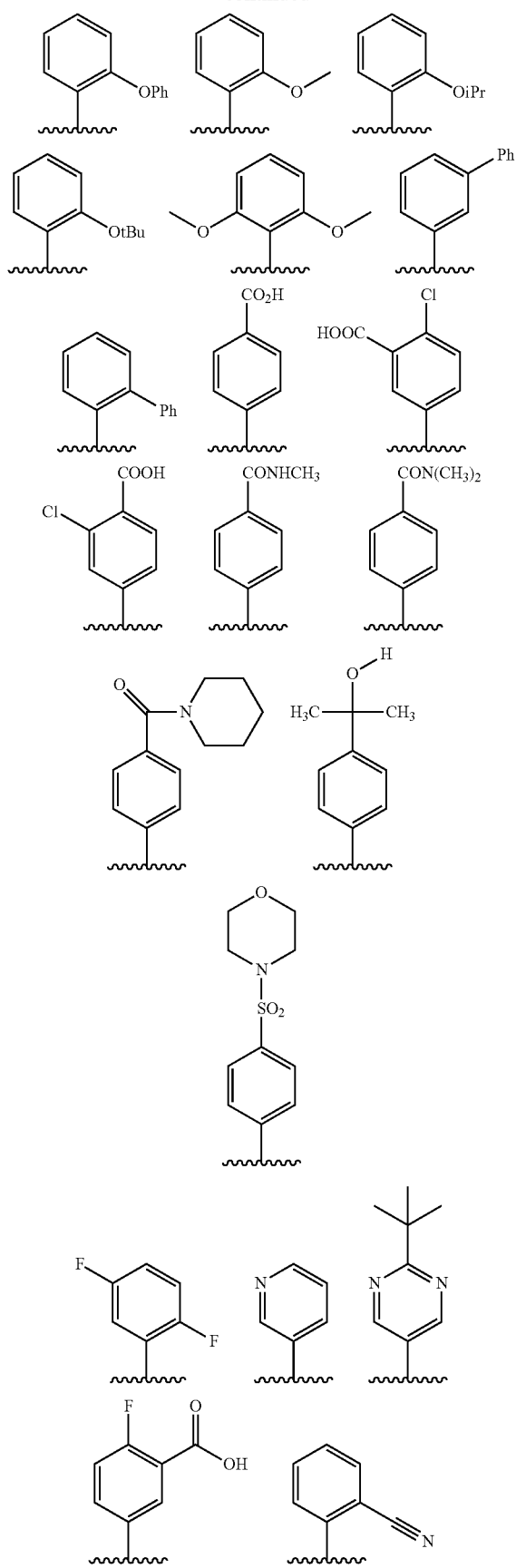
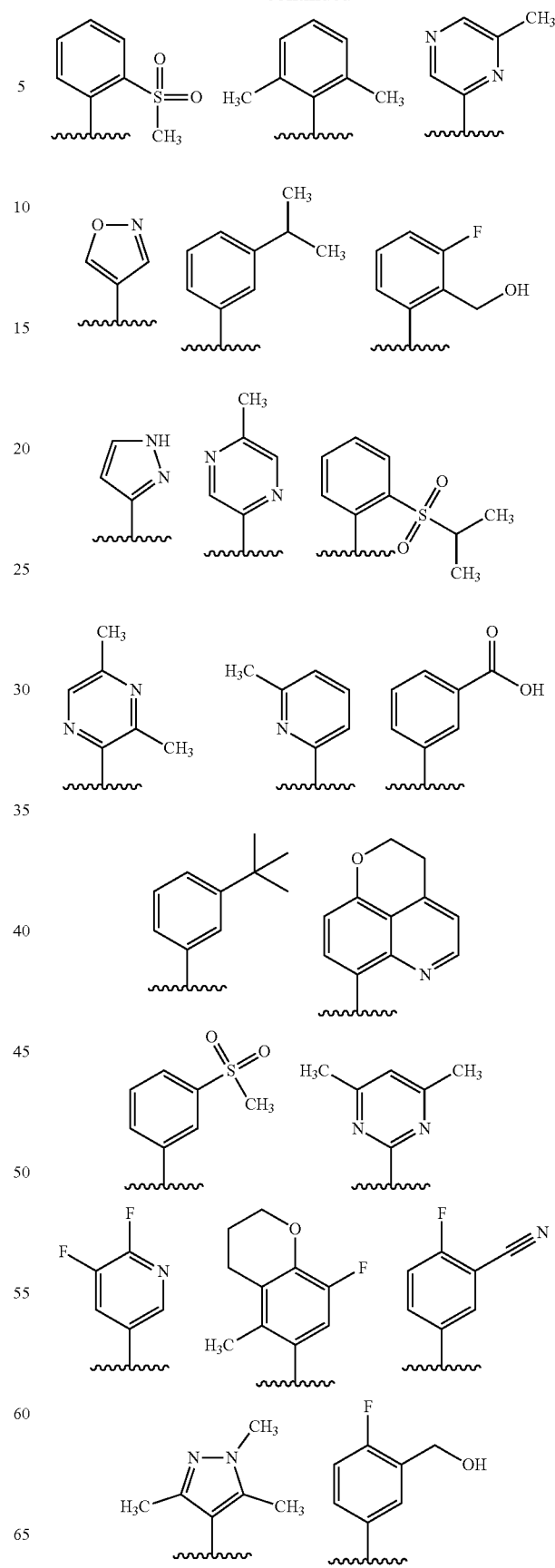

-continued
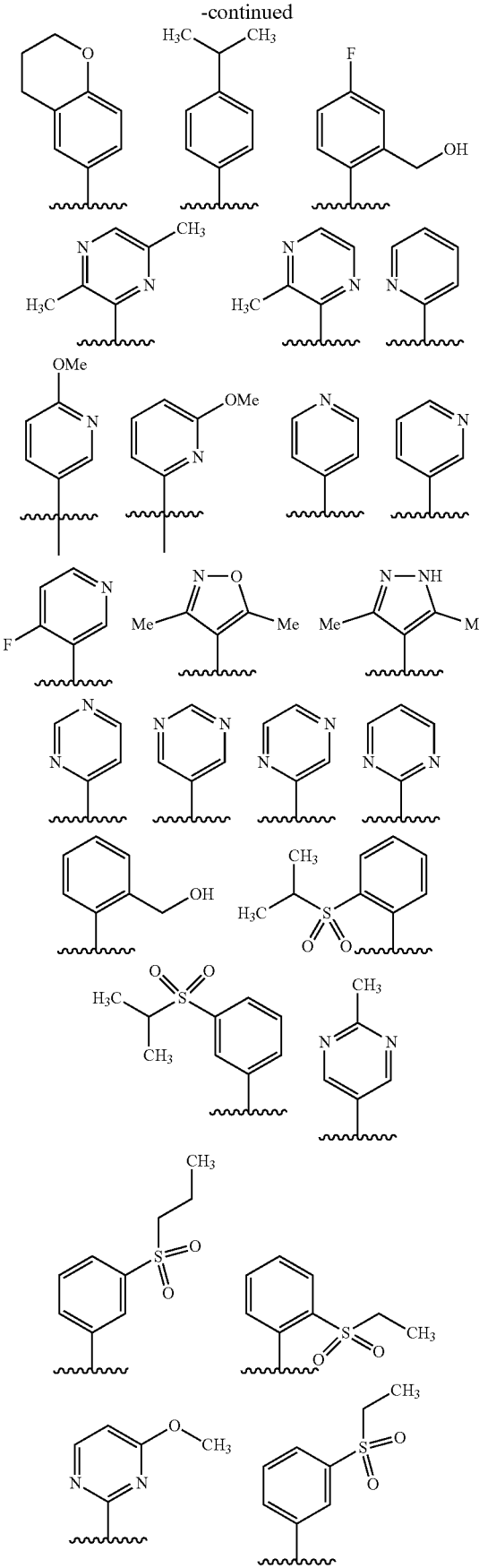
-continued
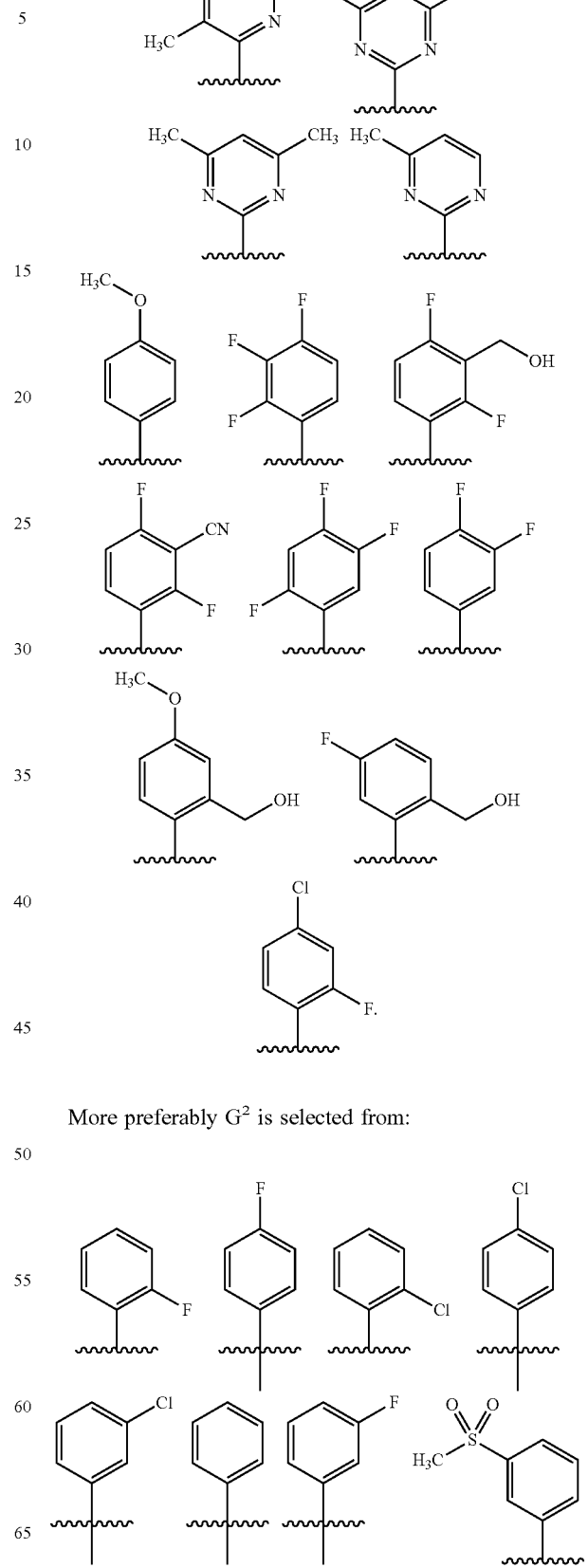
More preferably $G^2$ is selected from:

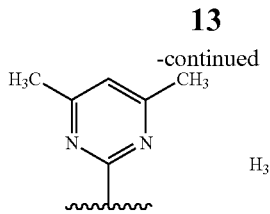

Preferably, the compounds and salts of this invention are those in which the stereochemistry of the carbon to which W—C(O)NH— is bonded is as depicted below.

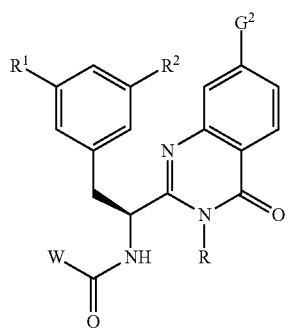

A preferred subset of the compounds and salts of this invention are compounds of Formula III, or a pharmaceutically acceptable salt thereof:

Formula III

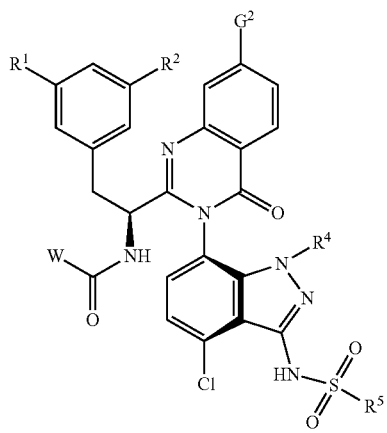

wherein:
each $R^1$ and $R^2$ is independently H, F, or Cl;
$G^2$ is selected from:

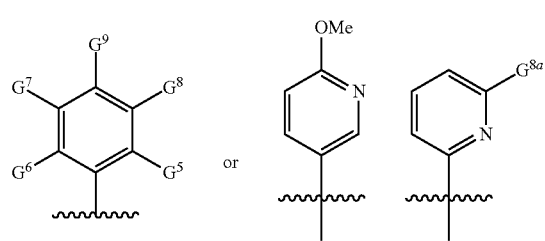

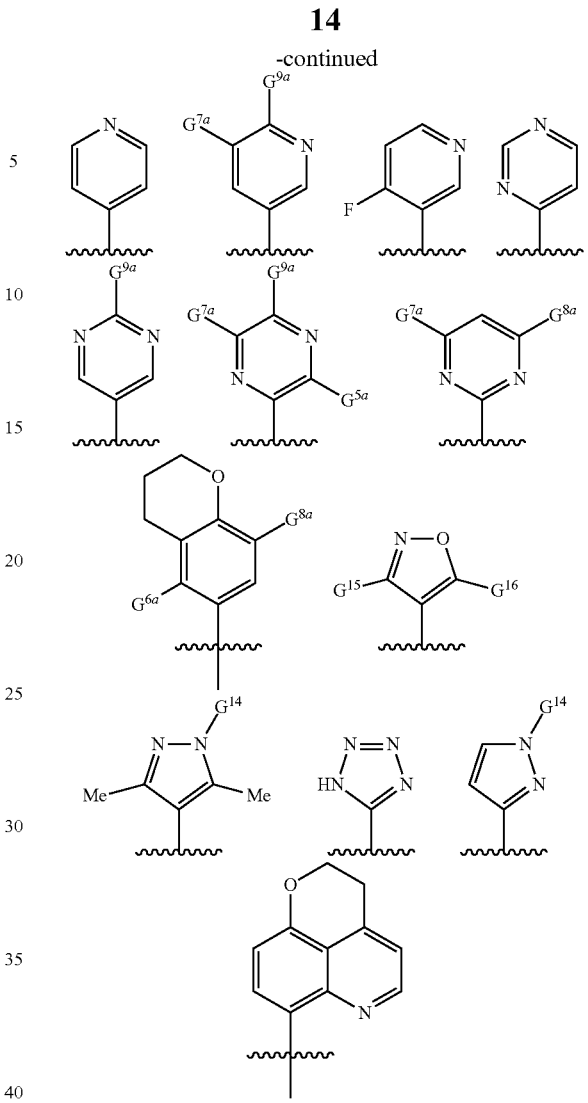

$G^5$ is hydrogen, methyl, fluoro, chloro, phenyl, $OC_1$-$C_3$alkyl, cyano, —$CH_2OH$, OPh, or —$SO_2(C_1$-$C_3$alkyl);
$G^{5a}$ is hydrogen or methyl;
$G^6$ is hydrogen, methyl, fluoro, chloro, phenyl, $OC_1$-$C_3$alkyl, or OPh;
$G^{6b}$ is hydrogen or methyl;
$G^7$ is hydrogen, methyl, fluoro, chloro, phenyl, $OC_1$-$C_3$alkyl, OPh, COOH, or $CON(G^{10})(G^{11})$;
$G^{7a}$ is hydrogen, methyl, or fluoro;
$G^8$ is hydrogen, $C_1$-$C_4$ alkyl, fluoro, chloro, phenyl, O $C_1$-$C_3$alkyl, OPh, COOH, cyano, —$CH_2OH$, —$SO_2(C_1$-$C_3$alkyl) or $CON(G^{10})(G^{11})$;
$G^{8a}$ is hydrogen, methyl or $OC_1$-$C_3$alkyl;
$G^{8b}$ is hydrogen or fluoro;
$G^9$ is hydrogen, $C_1$-$C_4$ alkyl, fluoro, chloro, phenyl, $OC_1$-$C_3$alkyl, OPh, COOH, $CON(G^{10})(G^{11})$, $C(CH_3)_2CH_2OH$, or —$SO_2$-morpholine wherein methyl is optionally substituted with 1-3 fluorines;
$G^{9a}$ is hydrogen, $C_1$-$C_4$alkyl, or fluoro;
$G^{10}$ is hydrogen or methyl;
$G^{11}$ is hydrogen or methyl;
or $G^{10}$ and $G^{11}$ are joined together form a piperidine
$G^{12}$ is hydrogen or $C_1$-$C_3$alkyl;
$G^{13}$ is hydrogen or $C_1$-$C_3$alkyl;
$G^{14}$ is hydrogen or $C_1$-$C_3$alkyl;

$G^{15}$ is hydrogen or $C_1$-$C_3$alkyl;
$G^{16}$ is hydrogen or $C_1$-$C_3$alkyl;
$R^4$ is methyl, 2,2-difluoroethyl, or 2,2,2-trifluoroethyl; $R^5$ is methyl or cyclopropyl;
and W is one of the following:
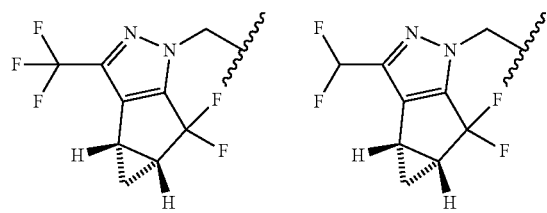
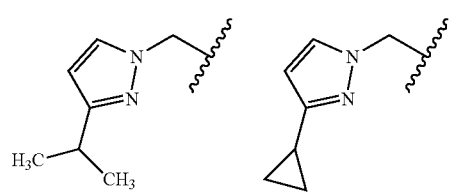
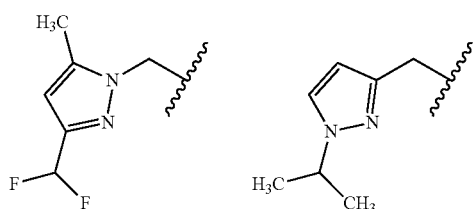
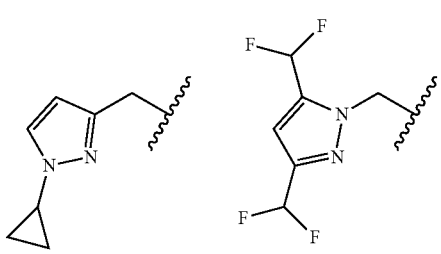
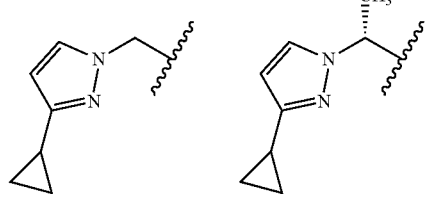
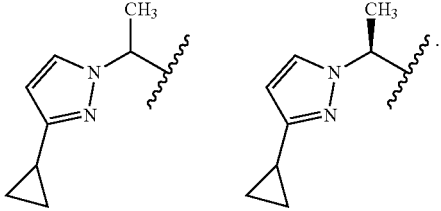
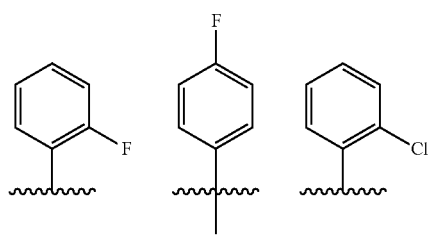
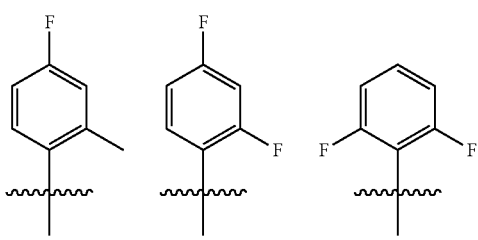
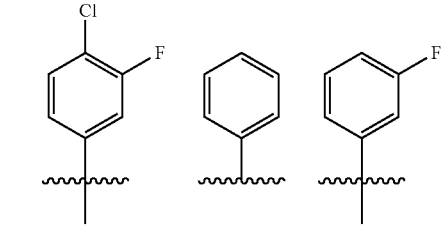
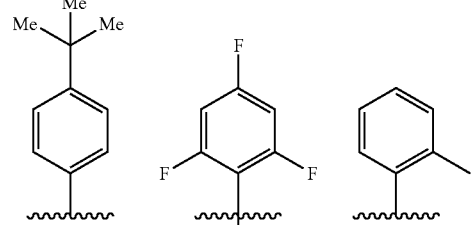
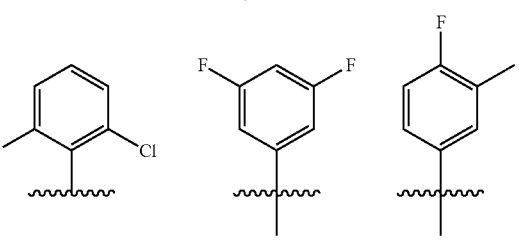
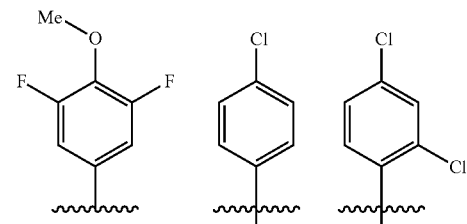
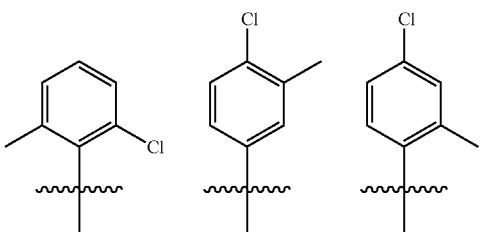
Preferably, for compounds and salts of Formula II, $G^2$ is one of the following:

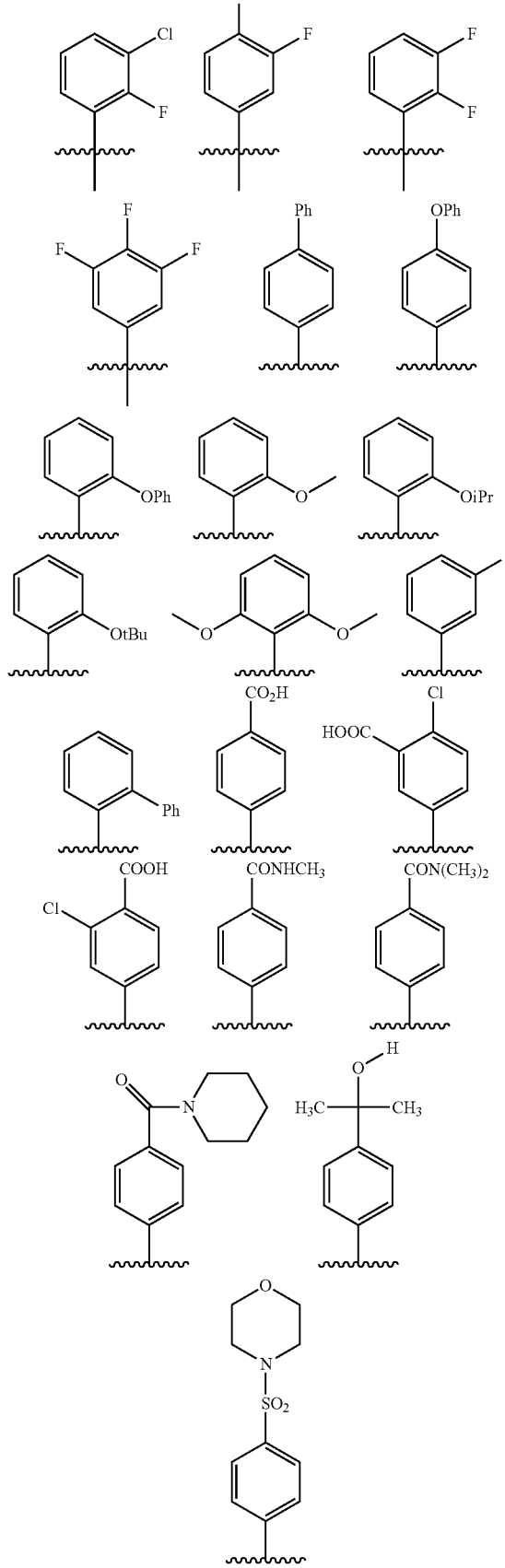
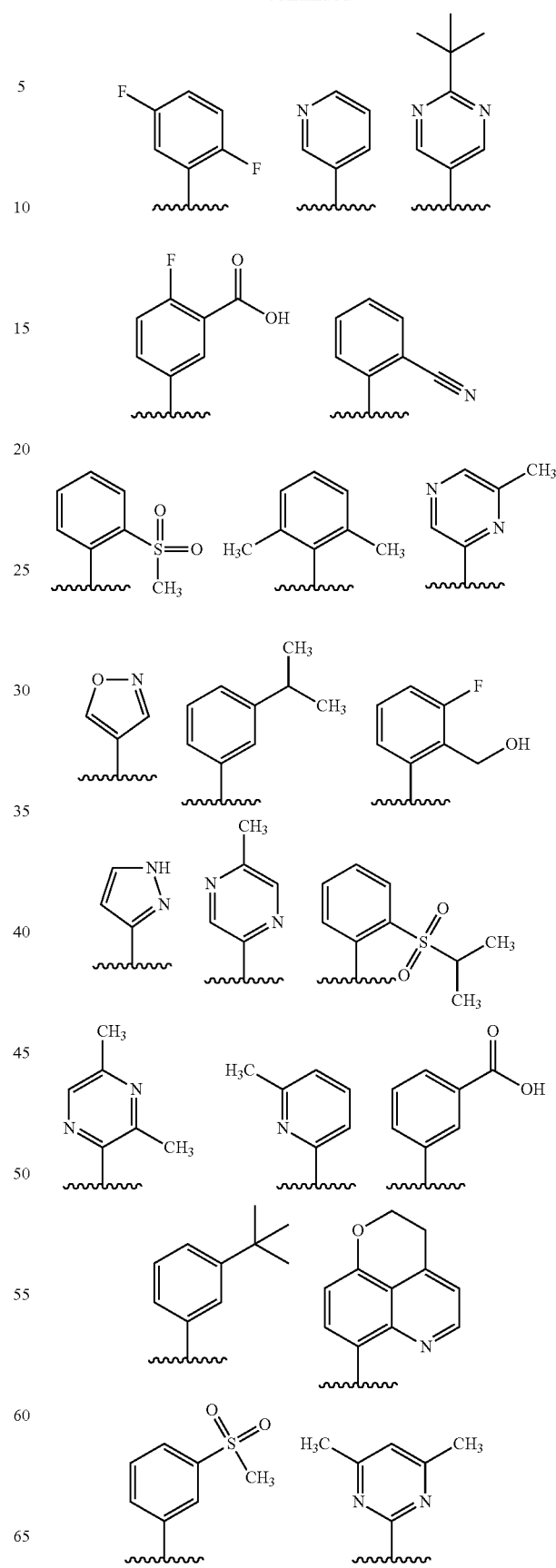

-continued
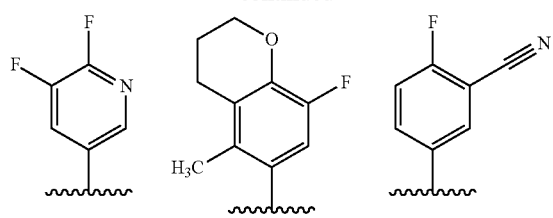
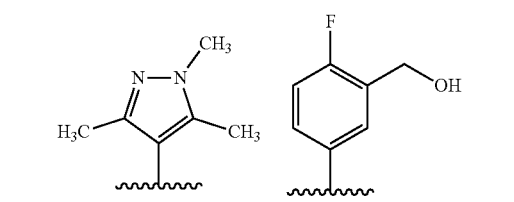
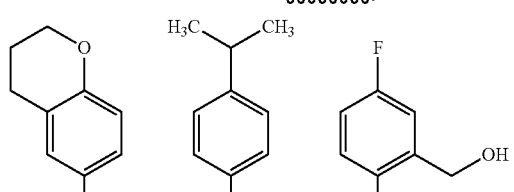
-continued
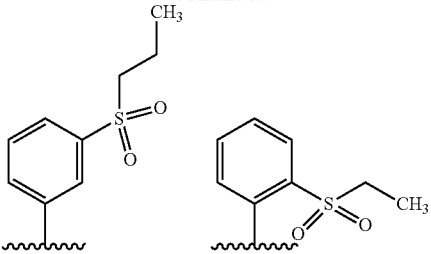
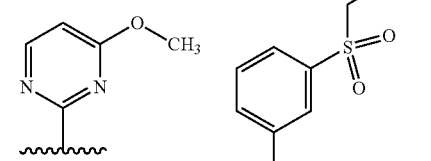
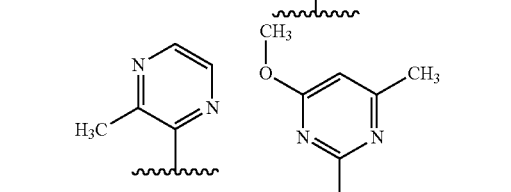
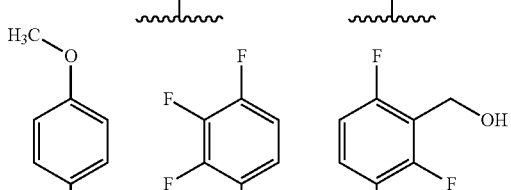
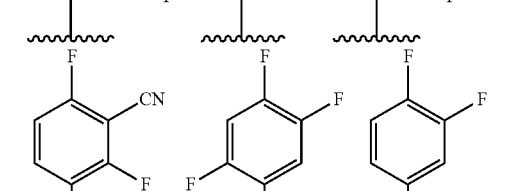
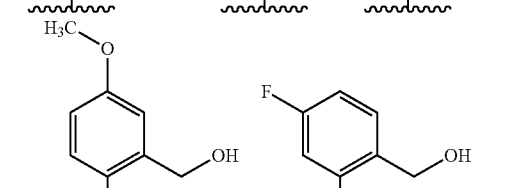
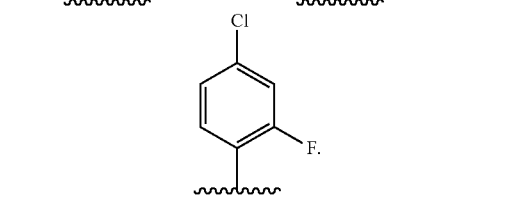
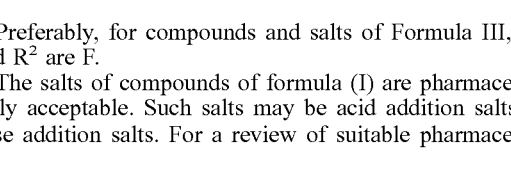
Preferably, for compounds and salts of Formula III, $R^1$ and $R^2$ are F.
The salts of compounds of formula (I) are pharmaceutically acceptable. Such salts may be acid addition salts or base addition salts. For a review of suitable pharmaceutically acceptable salts see Berge et al, J. Pharm, Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of compounds of formula (I) and their pharmaceutically acceptable salts and are included within the scope of the invention. All possible stoichiometric and non-stoichiometric forms of the salts of compounds of formula (I) are included within the scope of the invention. Acid and base addition salts may be prepared by the skilled chemist, by treating a compound of formula (I) with the appropriate acid or base in a suitable solvent, followed by crystallisation and filtration.

Some of the compounds of the invention exist in stereoisomeric forms. The invention includes all stereoisomeric forms of the compounds including enantiomers and diastereromers including atropisomers. The term homochiral is used as a descriptor, per accepted convention, to describe a structure which is a single stereoisomer. Absolute stereochemistry was not assigned in all cases. Thus the compound is drawn at the chiral center as unspecified but labelled as homochiral and in the procedures it is identified by its properties such as for example first eluting off a normal or chiral column per the conventions of chemists. It should be noted that the provided experimental procedures teach how to make the exact compound even if not drawn with absolute configuration. Methods of making and separating stereoisomers are known in the art. The invention includes all tautomeric forms of the compounds. The invention includes atropisomers and rotational isomers.

For the compounds of Formula I, the scope of any instance of a variable substituent can be used independently with the scope of any other instance of a variable substituent. As such, the invention includes combinations of the different aspects. In some examples, the stereochemistry of all the centers were not unambiguously assigned so they can be referred to as diastereomer 1 and diastereomer 2 or enantiomer 1 or enantiomer 2 etc. and these are understood by chemists skilled in the art. In other cases, atropisomers can be observed and these are understood to convert at slow or fast rates or even not at all depending on the conditions for handling the compound. These are referred to as mixtures of atropisomers where they interconvert at ambient temperatures or as atropisomer 1 and atropisomer 2 where they were isolated. Since the compounds are identified by their properties rather than exact structural assignment from a crystal structure, it is understood in the art that where not specified, atropisomers are covered and inferred to be covered by the chemical structure.

In the method of this invention, preferred routes of administration are oral and by injection to deliver subcutaneously.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including multiple compounds; or (2) separate pharmaceutical compositions each including one of the compounds. Alternatively, the combination may be administered separately in a sequential manner wherein one treatment agent is administered first and the other second or vice versa, and the different agents could be administered on different schedules if appropriate. Such sequential administration may be close in time or remote in time. The amounts of the compound(s) of Formulas I, II, or III or salts thereof and the other pharmaceutically active agent(s) and the relative timings of administration will be selected in order to achieve the desired combined therapeutic effect.

As such, the compounds of the present invention may be used in combination with one or more additional agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 (Fostemsavir) and BMS-626529 (Temsavir), 5-Helix and similar agents;

Integrase inhibitors such as raltegravir, elvitegravir, (dolutegravir), (cabotegravir), and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s). The method of administering a compound of this invention in a combination of single agents or as a coformulation. The possibilities for formulation of components alone or as a coformulation may be tablets or capsules for oral dosing or as suspensions or other forms for use as long acting drugs after sc it IM injection.

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenyl-methyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 (cobicistat) is a compound for use as a pharmacological enhancer.

In one embodiment of the present invention, a compound of Formula I is used in combination with ritonavir. In one embodiment, the combination is an oral fixed dose combination. In another embodiment, the compound of Formula I is formulated as a long acting parenteral injection and ritonavir is formulated as an oral composition. In one embodiment, is a kit containing the compound of Formula I formulated as a long acting parenteral injection and ritonavir formulated as an oral composition. In another embodiment, the compound of Formula I is formulated as a long acting parenteral injection and ritonavir is formulated as an injectable composition. In one embodiment, is a kit containing the compound of Formula I formulated as a long acting parenteral injection and ritonavir formulated as an injectable composition.

In another embodiment of the present invention, a compound of Formula I is used in combination with GS-9350. In one embodiment, the combination is an oral fixed dose combination. In another embodiment, the compound of Formula I is formulated as a long acting parenteral injection and GS-9350 is formulated as an oral composition. In one embodiment, is a kit containing the compound of Formula I formulated as a long acting parenteral injection and GS-9350 formulated as an oral composition. In another embodiment, the compound of Formula I is formulated as a long acting parenteral injection and GS-9350 is formulated as an injectable composition. In one embodiment, is a kit containing the compound of Formula I formulated as a long acting parenteral injection and GS-9350 formulated as an injectable composition.

EXAMPLES

The compounds of the invention according to the various embodiments can be made by various methods available in the art, including those of the following schemes and in the schemes and information in the specific examples which follow. Chemists skilled in the art will recognize that the chemistry in the specific examples provide methods which may be analogously applied to synthesize many of the other compounds of the invention. The structure numbering and variable numbering shown in the synthetic schemes may be distinct from, and should not be confused with, the structure or variable numbering in the claims or the rest of the specification. The variables in the schemes are meant only to illustrate how to make some of the compounds of the invention. Scheme 1 and 2 show examples of general methods which could be used for preparing the compounds of the invention. Unless specified, starting materials are either available commercially or their preparations are in the published art or they can be prepared using methods in the art that have been used for closely related compounds. As shown in Scheme 1 below the input for step a are three components, an amino acid, an anilino acid, and an aniline or heteroaryl aniline. As shown, W may be already present in the amino acid input for step A or as shown in the alternative input, the amine may be masked with a protecting group such as for example Boc. Likewise, the substituents J found in the anilino acid input starting materials for the synthesis may be either the final substituent -$G^2$ found in final compounds in the invention or alternatively, J may instead be a halogen or triflate or the like to use as a handle for installing the final $G^2$ as shown in Scheme 2. Example conditions are shown. The actual examples describe more detailed conditions for step a. As shown, if a protecting group is utilized on the amino acid, it may be removed as described in step b and coupled with an acid as shown in step C to give the final compounds of the invention. Scheme 2 shows one general method for preparing final compounds of the invention via a suitable $G^2$ boronate using a Suzuki coupling. Alternative couplings or reagents to effect the transformation would be familiar to a typical chemist. It should be recognized that the order of reactions could be changed if desired such as step d done before carrying out step b and step c.

Scheme 1

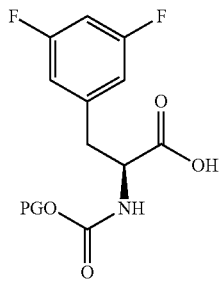

PG = Protecting group which
is an amine protecting group
such as
tBuOC(O)——

J may either = ——$G^2$
as defined by description of invention or

J = ——Br, ——Cl, ——OTf,
or the which may be used to install
$G^2$ via Suzuki or Stille coupling or related methodology or

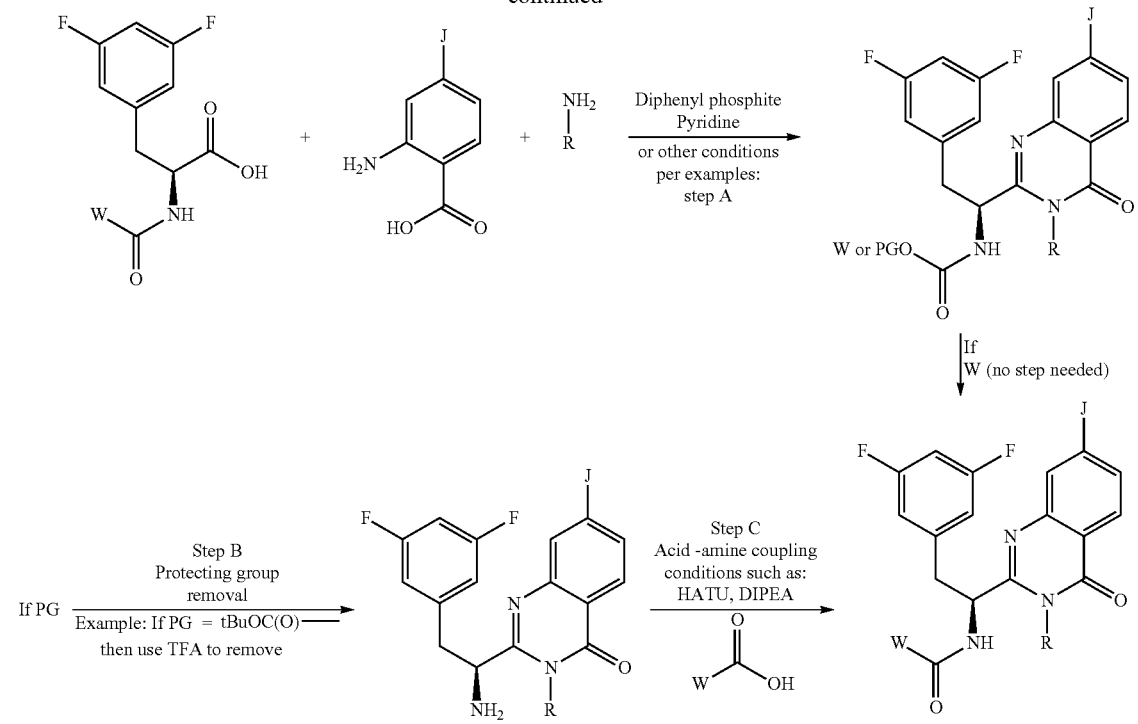

Scheme 2

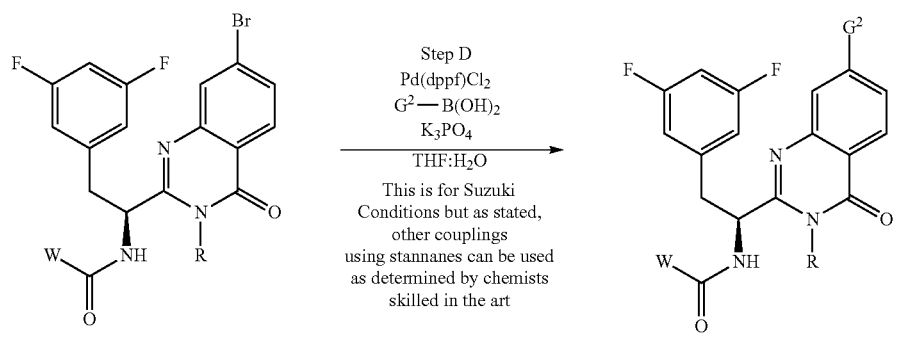

If J = C-Br for example
then these are intermediates used to
make compounds of the invention Compounds of the Invention Abbreviations used in the schemes generally follow conventions used in the art. Some specific chemical abbreviations used in the examples are defined as follows: "DMF" for N,N-dimethylformamide; "MeOH" for methanol; "Ar" for aryl; "TFA" for trifluoroacetic acid; "BOC" for t-butoxycarbonate, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HATU" for (1-[Bis(dimethylamino)methylene]-1H-1,2,3-triazolo[4,5-b]pyridinium 3-oxid hexafluorophosphate) "DIEA" for diisopropylethylamine.

Certain other abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t"

for triplet, "q" for quartet, "m" for multiplet, "br" for broad, "Hz" for hertz, and "α", "β", "R", "S", "E", and "Z" are stereochemical designations familiar to one skilled in the art.

The following examples are provided by way of illustration only and should not be construed as limiting the scope of the invention. Table 1 presents additional compounds of the invention prepared using similar methods. Absolute stereochemistry was not determined in all instances. In the examples where absolute stereochemistry has not been assigned, isomers or slowly interconverting atropisomers that were separated by chiral or other chromatography are labelled as "First", "Second", etc. as per their order of elution from the column.

N-(1-(3-(4-chloro-3-(N-(4-methoxybenzyl)methyl-sulfonamido)-1-methyl-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

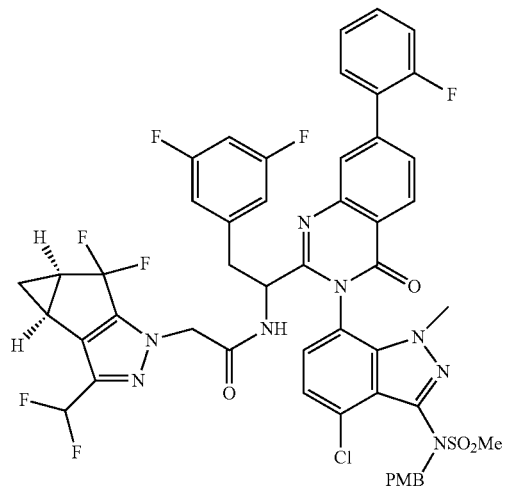

To a dry reaction vial under nitrogen was added (S)-2-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-3-(3,5-difluorophenyl)propanoic acid (30 mg, 0.067 mmol), 3-amino-2'-fluorobiphenyl-4-carboxylic acid (15.51 mg, 0.067 mmol) and anhydrous Pyridine (700 µL). The reaction was flushed with argon, treated with diphenyl phosphite (45.5 µL, 0.235 mmol), capped heated at 75° C. for 2 h. The reaction was then treated with N-(7-amino-4-chloro-1-methyl-1H-indazol-3-yl)-N-(4-methoxybenzyl)methanesulfonamide (35 mg, 0.089 mmol) and heated at 75° C. for 18 h to afford the title compound that was used "as is" without purification in subsequent steps. LC/MS m/z=1019.5 (M+H)+: Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.73 min.

N-((S)-1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 2) and Example 1

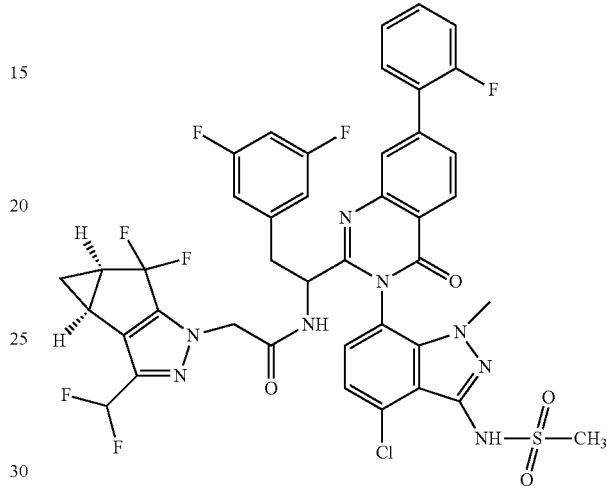

Mix of two stereoisomers

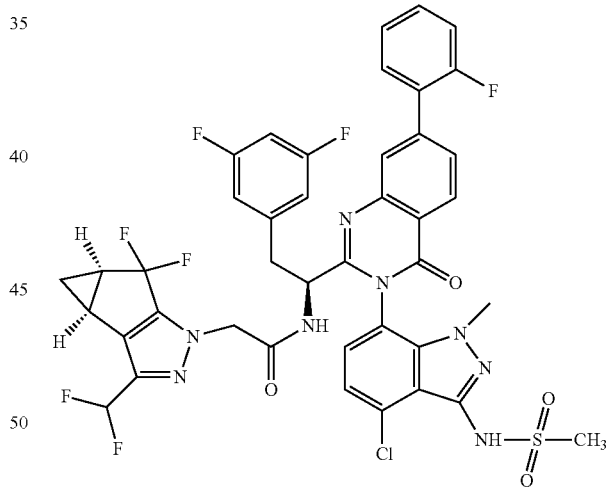

A mixture of indicated isomer and a stereoisomer

To a solution of N-(1-(3-(4-chloro-3-(N-(4-methoxybenzyl)methylsulfonamido)-1-methyl-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (68 mg, 0.067 mmol) in anhydrous dichloromethane (1.0 mL) was added TFA (2 mL, 26.0 mmol). The reaction was capped, swirled gently for 5 min, then treated with neat triflic acid (25 µL, 0.282 mmol) and allowed to stand at room temp for 30 min. The reaction was treated with additional triflic acid (25 µL, 0.282 mmol) and allowed to stand at room temp for 1 h. The solvent was removed under a gentle stream of nitrogen, and the residue was redissolved dichloromethane (1 mL) and treated with a solution of 10% N-methylmorpholine in dichloromethane (3 mL). The solvent was evaporated under a gentle stream of nitrogen and the crude material was purified via preparative LC/MS to afford two fractions, each as a mixture of two stereoisomers.

Example 1

First eluting peak, 4.4 mg. LC/MS m/z=899.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.3 min.

Example 2

Second eluting peak, 11.2 mg. LC/MS m/z=899.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.35 min. $^1$H NMR (500 MHz, DMSO-d$_6$, water suppression) δ9.24-9.15 (m, 1H), 8.32 (d, J=8.2 Hz, 1H), 7.99 (s, 1H), 7.86 (br d, J=7.9 Hz, 1H), 7.78-7.69 (m, 2H), 7.62-7.53 (m, 1H), 7.49-7.40 (m, 3H), 7.10-6.76 (m, 2H), 6.67 (br d, J=6.4 Hz, 2H), 4.70-4.47 (m, 3H), 3.60-2.37 (m), 1.35 (br d, J=6.1 Hz, 1H), 1.24 (s, 1H), 0.86 (br d, J=7.0 Hz, 1H)

N-(7-amino-1-methyl-1H-indazol-3-yl)-N-(4-methoxybenzyl)methanesulfonamide

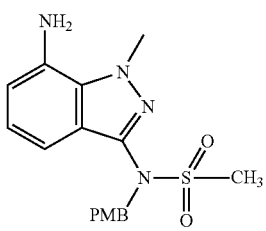

To a suspension of N-(7-amino-4-chloro-1-methyl-1H-indazol-3-yl)-N-(4-methoxybenzyl)methanesulfonamide (100 mg, 0.253 mmol) in MeOH (20 mL) was added palladium hydroxide on carbon (22 mg, 0.157 mmol). The reaction was flushed with nitrogen, capped and then purged with nitrogen for 10 min. The reaction was stirred at room temp under a balloon of H2 for 18 h. The catalyst was filtered off thru a small pad of celite, washed well with MeOH and evaporated to dryness to give the title compound, 91 mg, that was used "as is" without further purification in subsequent step(s). LC/MS m/z=743.4 (2M+Na): Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.31 min.

tert-butyl (S)-(1-(3-(4-chloro-3-(N-(4-methoxybenzyl)methylsulfonamido)-1-methyl-1H-indazol-7-yl)-7-(2-fluorophenyl)-4-oxo-3,4-dihydroquinazolin-2-yl)-2-(3,5-difluorophenyl)ethyl)carbamate

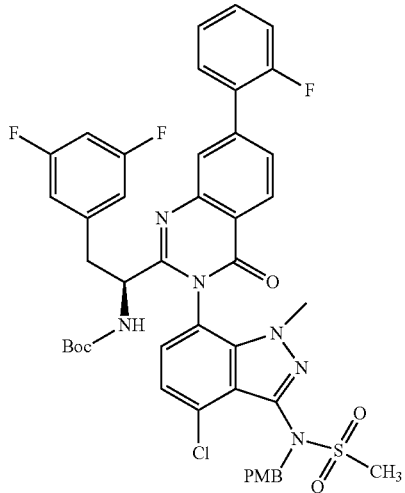

To a dry reaction vial under nitrogen was added (S)-2-((tert-butoxycarbonyl)amino)-3-(3,5-difluorophenyl)propanoic acid (114 mg, 0.380 mmol), 3-amino-2'-fluorobiphenyl-4-carboxylic acid (88 mg, 0.380 mmol), N-(7-amino-4-chloro-1-methyl-1H-indazol-3-yl)-N-(4-methoxybenzyl)methanesulfonamide (150 mg, 0.380 mmol), diphenyl phosphite (300 µL, 1.550 mmol) and anhydrous Pyridine (1.5 mL). The reaction was flushed well with nitrogen and heated at 75-80° C. for 20 h. The solvent was removed under a gentle stream of nitrogen and the crude material was purified via silica gel chromatography (24 g SiO$_2$ column, 0-100% ethyl acetate:dichloromethane) to afford the title compound, 309.6 mg. LC/MS m/z=817.3 (M-55); Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.96 min.

(S)-N-(7-(2-(1-amino-2-(3,5-difluorophenyl)ethyl)-7-(2-fluorophenyl)-4-oxoquinazolin-3(4H)-yl)-4-chloro-1-methyl-1H-indazol-3-yl)methanesulfonamide

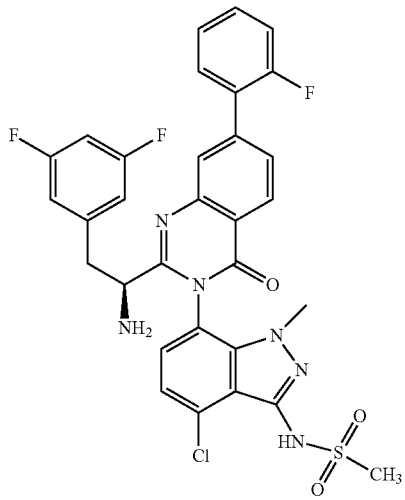 [SMILES: Cn1nc(NS(C)(=O)=O)c2c(Cl)ccc(-n3c([C@@H](N)Cc4cc(F)cc(F)c4)nc4cc(-c5ccccc5F)ccc4c3=O)c21]

To a solution of tert-butyl (S)-(1-(3-(4-chloro-3-(N-(4-methoxybenzyl)methylsulfonamido)-1-methyl-1H-indazol-7-yl)-7-(2-fluorophenyl)-4-oxo-3,4-dihydroquinazolin-2-yl)-2-(3,5-difluorophenyl)ethyl)carbamate (309.6 mg, 0.354 mmol) in anhydrous dichloromethane (5 mL) was added TFA (15 mL, 195 mmol). The reaction was allowed to stand at room temp for 10 min, treated with triflic acid (160 µL, 1.802 mmol), allowed to stand at room temp for 30 min and the volatiles were removed under a gentle stream of nitrogen. The residue was suspended in dichloromethane (10 mL), quenched with saturated aqueous K2CO3 (20 mL), diluted with ethyl acetate (210 mL) and the organic layer was washed with aqueous saturated NaHCO3 (1×15 mL). The water layer was back extracted with ethyl acetate (1×35 mL), the organic layers were combined, washed with brine (1×20 mL), dried over Na2SO4, filtered and evaporated to dryness to afford the title compound, 309.6 mg. LC/MS m/z=653.2 (M+H)$^+$; Column: Waters Aquity UPLC BEH C18, 2.1 mm×50 mm, 1.7 µm particles; Mobile Phase A: 100% water with 0.05% TFA; Mobile Phase B: 100% acetonitrile with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.64 min.

(S)-N-(1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)acetamide (Example 4 and Example 3)

Example 3

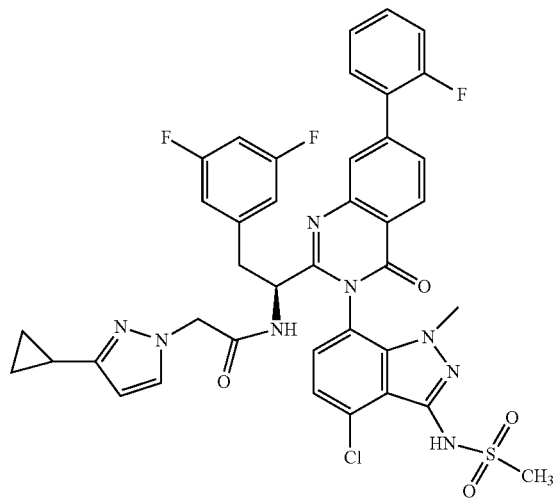

Mix of enantiomers of unknown proportion

Example 4

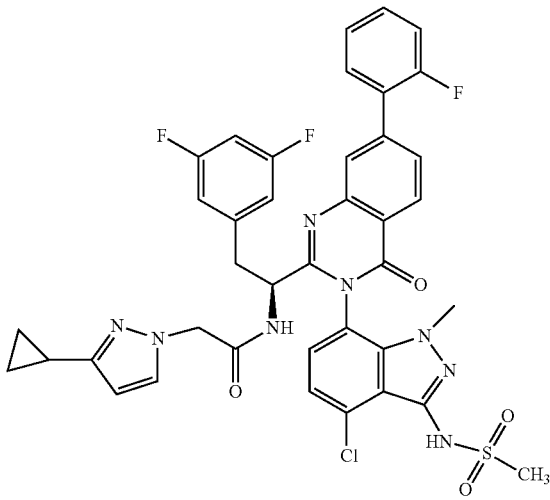

Mix of enantiomers of unknown proportion

To a solution of (S)-N-(7-(2-(1-amino-2-(3,5-difluorophenyl)ethyl)-7-(2-fluorophenyl)-4-oxoquinazolin-3(4H)-yl)-4-chloro-1-methyl-1H-indazol-3-yl)methanesulfonamide (50 mg, 0.077 mmol) in anhydrous DMF (800 µL) was added (3-cyclopropyl-1h-pyrazol-1-yl)acetic acid (13 mg, 0.078 mmol), and 1-hydroxy-7-azabenzotriazole (4 mg, 0.029 mmol). The reaction was flushed with nitrogen, treated with N-methylmorpholine (85 µL, 0.773 mmol), EDC (25 mg, 0.130 mmol) and allowed to stand at room temp for 3 h. The reaction was treated with 7MNH3/MeOH (100 µlit) and the crude reaction was purified via preparative LC/MS to afford two fractions, each as a mixture of stereoisomers but where one stereoisomer dominates.

Example 3

First eluting peak, 7.0 mg. LC/MS m/z=801.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.22 min.

Example 4

Second eluting peak, 26.3 mg. LC/MS m/z=801.1 (M+H)$^+$. Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.32 min. $^1$H NMR (500 MHz, DMSO-d$_6$, water suppression) δ8.86 (br d, J=8.2 Hz, 1H), 8.32 (br d, J=8.2 Hz, 1H), 7.99 (s, 1H), 7.85 (br d, J=8.2 Hz, 1H), 7.77-7.67 (m, 2H), 7.57 (br d, J=6.1 Hz, 1H), 7.48-7.39 (m, 3H), 7.26 (s, 1H), 7.01 (br t, J=9.3 Hz, 1H), 6.70 (br d, J=7.3 Hz, 2H), 5.84 (s, 1H), 4.61 (br t, J=9.3 Hz, 1H), 4.42-4.35 (m, 1H), 4.32-4.22 (m, 1H), 3.59 (s), 3.46-

2.95 (m), 2.23 (br d, J=5.2 Hz, 1H), 1.73 (br d, J=7.9 Hz, 1H), 0.73 (br d, J=7.9 Hz, 2H), 0.51 (br s, 2H)

N-((S)-1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 6) and Example 5

Example 5

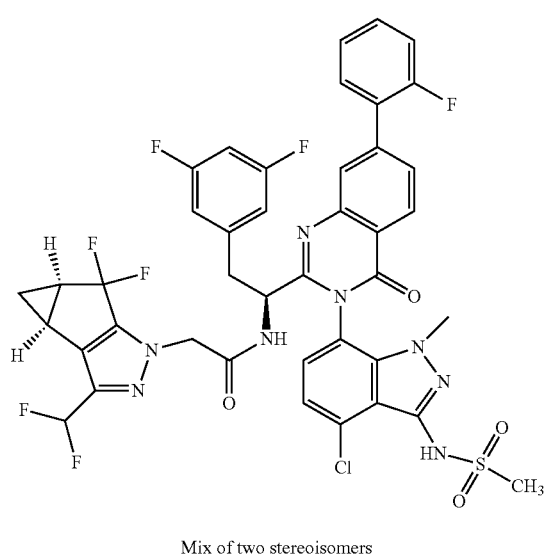

Mix of two stereoisomers

Exmaple 6

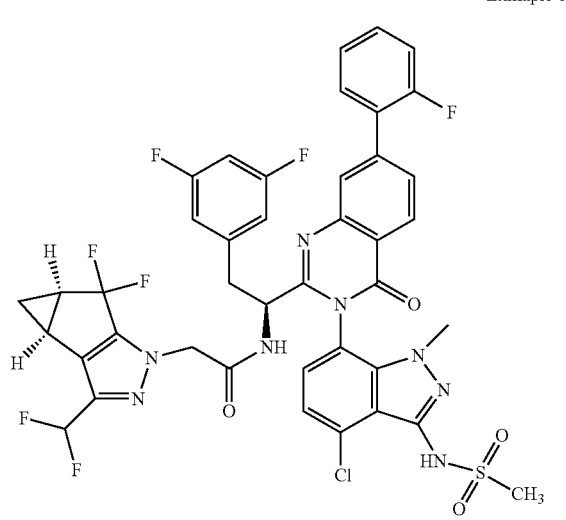

A mixture of indicated isomer and a stereoisomer

To a dry reaction vial under nitrogen was added (S)-N-(7-(2-(1-amino-2-(3,5-difluorophenyl)ethyl)-7-(2-fluorophenyl)-4-oxoquinazolin-3(4H)-yl)-4-chloro-1-methyl-1H-indazol-3-yl)methanesulfonamide (168 mg, 0.257 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (68.0 mg, 0.257 mmol), 1-hydroxy-7-azabenzotriazole (10 mg, 0.073 mmol) and anhydrous DMF (2 mL).

The reaction was flushed with nitrogen, treated with N-methylmorpholine (225 μL, 2.046 mmol), EDC (84 mg, 0.438 mmol), and stirred at room temp for 18 h. The reaction was treated 7M NH3/MeOH (100 μL) and the crude reaction was purified via preparative LC/MS to afford two elutes.

Example 5

First eluting peak, 14.7 mg. LC/MS m/z=899.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.45 min.

Example 6

Second eluting peak, 43.5 mg. LC/MS m/z=899.1 (M+H)$^+$. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Retention Time: 2.49 min. Analytical SCF chromatography (Chiralpak IC column, 25% 2-propanol, 0.1% DEA in CO2, 150 bar, 220/254 nm) of this elute indicates >95% chiral purity.

2-(1-cyclopropyl-3,5-dimethyl-1H-pyrazol-4-yl)acetic acid

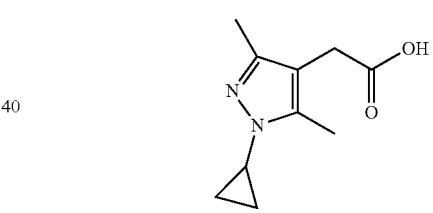

To a dry pressure vial under nitrogen was added (3,5-dimethyl-1H-pyarzol-4-yl)acetic acid tert butyl ester (250 mg, 1.189 mmol) and anhydrous DMSO (2 mL). The reaction was flushed with argon and then treated with potassium tert-butoxide, 1.0M in THF (1.2 mL, 1.200 mmol). The reaction was stirred at RT under argon flow for 4 min, then the reaction was treated with cyclopropyl bromide (300 μL, 3.74 mmol) and immediately capped. The vial was heated in a 150° C. oil bath. After cooling, the crude material was purified by preparative HPLC: Varian LC conditions (10-100% B over 15 minutes, 20 total run time; B solvent 95% acetonitrile/10 mM ammonium acetate water, Waters X-Bridge Prep OBD C18 30×100 mm, 5 micron, UV @220 nm, 4×0.5 mL injections in DMSO; Rt 9.9 min) to give 24 mg of an off-white residue after concentration under vacuum. TFA (4 mL) was added to the residue and stirred at RT for 30 min. After concentration under a stream of nitrogen 18 mg of 2-(1-cyclopropyl-3,5-dimethyl-1H-pyrazol-4-yl)acetic acid was obtained as a residue and used as is for next reaction. LC/MS m/z=195.0 (M+1)$^+$. Column: Waters Aquity UPLC BEH C18, 2.1 mm×50 mm, 1.7 μm particles; Mobile Phase A: 100% water with 0.05% TFA;

Mobile Phase B: 100% acetonitrile:water with 0.05% TFA; Temperature: 40° C.; Gradient: 2% B to 98% B over 1.5 min, then a 1.5 min hold at 100% B; Flow: 0.8 mL/min; Detection: UV (220 nm); Retention Time: 1.13 min.

N-(7-bromo-4-chloro-1-methyl-1H-indazol-3-yl)methanesulfonamide

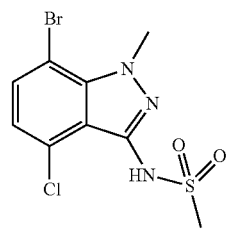 [SMILES: Cn1nc(NS(C)(=O)=O)c2c(Cl)ccc(Br)c21]

To a solution of 7-bromo-4-chloro-1-methyl-1H-indazol-3-amine (1.40 g, 5.37 mmol) in DCM (30 mL) was added Hunig's Base (3.75 mL, 21.5 mmol) and then the reaction was cooled in an ice bath and methanesulfonyl chloride (1.26 mL, 16.1 mmol) was added. The reaction mixture was stirred at this temperature for 1 h (precipitate formed). Mixture was then diluted with dichloromethane (100 mL) and washed with water, 1 M HCl and brine, dried ($Na_2SO_4$), filtered and concentrated in vacuo. The residue was taken up in EtOH (30 ml) and 10 ml of 20% aq. NaOH. The resulted mixture heated with a heat gun until it became a homogeneous solution and stirred at rt for 30 min. The mixture was diluted with water (80 mL) and acidified with 1 N HCl (60 mL). The precipitate was filtered, washed with water, and dried in vacuo to afford the title product (1.5 g) as an off-white solid. $^1$H NMR (500 MHz, $CDCl_3$) δ7.48 (d, J=7.9 Hz, 1H), 7.24 (br s, 1H), 6.95 (d, J=7.9 Hz, 1H), 4.38 (s, 3H), 3.42 (s, 3H). LC/MS $(M+H)^+$=337.80.

N-(7-bromo-4-chloro-1-methyl-1H-indazol-3-yl)-N-(4-methoxybenzyl)methanesulfonamide

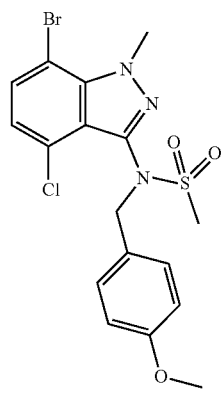 [SMILES: COc1ccc(CN(c2nn(C)c3c(Br)ccc(Cl)c23)S(C)(=O)=O)cc1]

To a mixture of N-(7-bromo-4-chloro-1-methyl-1H-indazol-3-yl)methanesulfonamide (1.3 g, 3.84 mmol) and 1-(chloromethyl)-4-methoxybenzene (0.625 mL, 4.61 mmol) in DMF (30 mL) was added cesium carbonate (1.626 g, 4.99 mmol) and the mixture was heated at 80° C. for 2 h. The mixture was poured into water (100 mL) and extracted with EtOAc (50 ml, 2×). The combined organic layer was washed with brine, dried over $MgSO_4$, filtered and concentrated in vacuo. The residue was purified by Biotage (0~35% EtOAc-hexanes) to afford the title product (1.5 g) as a white foam. $^1$H NMR (500 MHz, $CDCl_3$) δ7.44 (d, J=7.9 Hz, 1H), 7.31 (d, J=8.5 Hz, 2H), 6.99 (d, J=7.9 Hz, 1H), 6.84 (d, J=8.5 Hz, 2H), 4.99 (br s, 1H), 4.76 (br s, 1H), 4.40 (s, 3H), 3.80 (s, 3H), 3.01 (s, 3H).

N-(7-amino-4-chloro-1-methyl-1H-indazol-3-yl)-N-(4-methoxybenzyl)methanesulfonamide

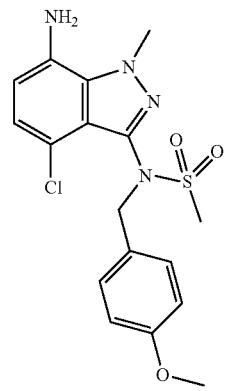 [SMILES: COc1ccc(CN(c2nn(C)c3c(N)ccc(Cl)c23)S(C)(=O)=O)cc1]

Following the reference: Andersen, Jacob et al, *Synlett* 2005 (14), 2209-2213. To a mixture of N-(7-bromo-4-chloro-1-methyl-1H-indazol-3-yl)-N-(4-methoxybenzyl)methane sulfonamide (600.0 mg, 1.308 mmol), copper(I) iodide (49.8 mg, 0.262 mmol), sodium ascorbate (518 mg, 2.62 mmol) and (1R,2R)-N1,N2-dimethylcyclohexane-1,2-diamine (46.5 mg, 0.327 mmol) in NMP (10 mL) was added a solution of sodium azide (255 mg, 3.92 mmol) in Water (2.0 mL). The mixture was then sealed and heated in a microwave system at 120° C. for 2.5 h. The mixture was then filtered through a pad of Celite and the pad was washed with EtOAc. The filtrate was poured into water (100 mL) and extracted with EtOAc (50 ml, 2×). The combined organic layer was washed with brine, dried over $MgSO_4$, filtered and evaporated in vacuo. The residue was purified by Biotage (5-100% EtOAc/hexanes) to afford the title product (400 mg) as an off-white solid. $^1$H NMR (400 MHz, $CDCl_3$) δ7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS $(M+H)^+$=395.00.

7-bromo-4-chloro-1H-indazol-3-amine

A solution of 3-bromo-6-chloro-2-fluorobenzonitrile (1.50 g, 6.40 mmol) in Ethanol (12.80 ml) in a microwave vial was treated with hydrazine (1.3 mL, 40.6 mmol), the mixture was heated at 120° C. in a microwave reactor for 35 min. The reaction mixture (pale yellow solid) was taken up in ethyl acetate, washed with water, brine, dried over Na$_2$SO$_4$ and concentrated. The residue taken up in methanol (just enough to dissolve it), some DCM was added, then hexanes was added till a precipitate formed. Air was blown into the mixture to remove some of the DCM. The suspension was filtered and suction dried to give an off-white fluffy solid (1.5 g). $^1$H NMR (500 MHz, DMSO-d$_6$) δ12.51-12.05 (m, 1H), 7.44 (d, J=7.9 Hz, 1H), 6.87 (d, J=7.9 Hz, 1H), 5.33 (s, 2H).

2-(7-bromo-4-chloro-1H-indazol-3-yl)isoindoline-1,3-dione

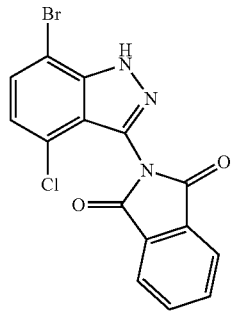 [SMILES: O=C1c2ccccc2C(=O)N1c1n[nH]c2c(Br)ccc(Cl)c12]

Phthalic anhydride (1.352 g, 9.13 mmol) was added to a solution of 7-bromo-4-chloro-1H-indazol-3-amine (1.5 g, 6.09 mmol) in Dioxane (20 mL) in a microwave vial and heated at 150° C. for 2 h in a microwave reactor. The reaction mixture was concentrated. The beige solid was purified on silica gel (220 g, Isco column) using 0-40% ethyl acetate in hexanes. The desired fractions were concentrated to give a light pink solid (1.2 g). $^1$H NMR (500 MHz, DMSO-d$_6$) δ14.57-14.29 (m, 1H), 8.14-8.08 (m, 2H), 8.05-7.99 (m, 2H), 7.76-7.72 (m, 1H), 7.26-7.21 (m, 1H). LC/MS: m/z=377.9 [M+2H]$^+$.

2-(7-bromo-4-chloro-1-cyclopropyl-1H-indazol-3-yl)isoindoline-1,3-dione

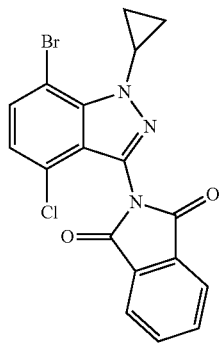 [SMILES: O=C1c2ccccc2C(=O)N1c1nn(C2CC2)c2c(Br)ccc(Cl)c12]

A round bottom flask was charged with 2-(7-bromo-4-chloro-1H-indazol-3-yl)isoindoline-1,3-dione (0.988 g, 2.62 mmol), cyclopropylboronic acid (0.676 g, 7.87 mmol), sodium carbonate (0.834 g, 7.87 mmol), copper (II) acetate (0.477 g, 2.62 mmol) and 2,2'-bipyridine (0.410 g, 2.62 mmol) which were suspended in DCE (26.2 ml), flushed with nitrogen and heated at 80° C. for 6 h. The reaction mixture was filtered and concentrated. The residue was purified on silica (220 g Isco column) using 0-40% ethyl acetate in hexanes. The desired fractions were concentrated to give a pale yellow solid (0.52 g). LC/MS: m/z=415.8 [M+H]$^+$.

7-bromo-4-chloro-1-cyclopropyl-1H-indazol-3-amine

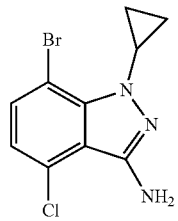 [SMILES: Nc1nn(C2CC2)c2c(Br)ccc(Cl)c12]

A mixture of 2-(7-bromo-4-chloro-1-cyclopropyl-1H-indazol-3-yl)isoindoline-1,3-dione (0.92 g, 2.208 mmol) and hydrazine hydrate (0.54 mL, 11.04 mmol) in Ethanol (18.40 mL)/THF (18.40 mL) was stirred at rt for 3 h and concentrated. The residue was dissolved in DMSO and purified on silica gel (120 g Isco column) using 10-100% ethyl acetate. The desired fraction was concentrated to give a pale yellow solid (0.5 g). $^1$H NMR (500 MHz, CDCl$_3$) δ7.47-7.36 (m, 1H), 6.83-6.70 (m, 1H), 4.62-4.40 (m, 2H), 3.89-3.74 (m, 1H), 1.35-1.30 (m, 2H), 1.16-1.11 (m, 2H).

N-(7-bromo-4-chloro-1-cyclopropyl-1H-indazol-3-yl)methanesulfonamide

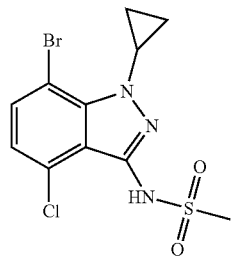 [SMILES: CS(=O)(=O)Nc1nn(C2CC2)c2c(Br)ccc(Cl)c12]

To a solution of 7-bromo-4-chloro-1-cyclopropyl-1H-indazol-3-amine (0.250 g, 0.872 mmol) in DCM (4.4 mL) was added DIPEA (0.610 ml, 3.49 mmol) then the reaction was cooled in an ice bath and methane sulfonyl chloride (0.14 ml, 1.745 mmol) was added. The reaction mixture was stirred at this temperature for 1 h (precipitate formed). Mixture was then diluted with dichloromethane (10 mL) and washed with water, 1 M HCl and brine, dried (Na$_2$SO$_4$), filtered and concentrated in vacuo to give a light yellow solid. The residue was taken up in EtOH (10 mL) and 5 ml of 20% aq. NaOH. The resulted mixture heated with a heat gun until it became a homogeneous solution and stirred at rt for 30 min. The mixture was diluted with water (20 mL) and acidified with 2 M HCl and the resultant precipitates was collected by filtration to afford the desired product as an off-white solid (0.27 g). $^1$H NMR (500 MHz, CDCl$_3$) δ7.55-7.42 (m, 1H), 7.26-7.14 (m, 1H), 7.06-6.87 (m, 1H), 4.16-3.96 (m, 1H), 3.51-3.32 (m, 3H), 1.43-1.38 (m, 2H), 1.24-1.17 (m, 2H).

N-(7-bromo-4-chloro-1-cyclopropyl-1H-indazol-3-yl)-N-(4-methoxybenzyl)methanesulfonamide

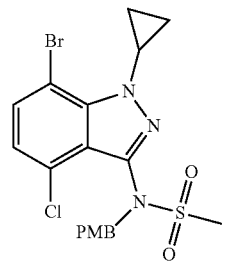

4-Methoxybenzyl chloride (0.120 ml, 0.889 mmol) was added to a mixture of N-(7-bromo-4-chloro-1-cyclopropyl-1H-indazol-3-yl)methanesulfonamide (0.27 g, 0.740 mmol) and Cs$_2$CO$_3$ (0.483 g, 1.481 mmol) in DMF (5.3 ml). The mixture was stirred at rt overnight. The mixture was diluted with ethyl acetate, washed with brine, dried over Na$_2$SO$_4$ and concentrated. The residue was purified on silica (24 g Isco column) using 0-60% ethyl acetate in hexanes. The desired fractions were concentrated to give a colorless viscous oil (0.38 g). LC/MS: m/z=484 [M+H]$^+$.

N-(4-chloro-1-cyclopropyl-7-((diphenylmethylene)amino)-1H-indazol-3-yl)-N-(4-methoxybenzyl)methanesulfonamide

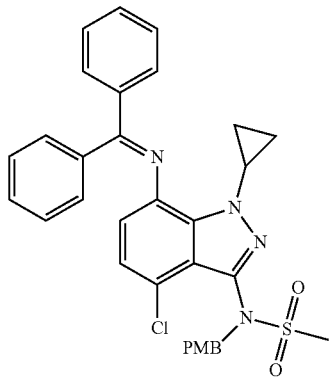

A mixture of N-(7-bromo-4-chloro-1-cyclopropyl-1H-indazol-3-yl)-N-(4-methoxybenzyl)methanesulfonamide (0.36 g, 0.743 mmol), diphenylmethanimine (0.137 ml, 0.819 mmol), PdOAc$_2$ (8.34 mg, 0.037 mmol), R-(+)-BINAP (0.069 g, 0.111 mmol) and Cs$_2$CO$_3$ (0.363 g, 1.114 mmol) in Dioxane (7.43 ml) was degassed for 5 min and heated in a microwave at 120° C. for 2 h. The reaction mixture filtered through Celite and concentrated. The residue was purified on silica gel (80 g Isco column) using 0-30% ethyl acetate, the desired fractions were concentrated to give a bright yellow solid (0.28 g). $^1$H NMR (400 MHz, CDCl$_3$) δ7.87-7.76 (m, 2H), 7.58-7.32 (m, 7H), 7.26-7.20 (m, 2H), 7.16-7.10 (m, 2H), 6.85-6.79 (m, 1H), 6.75-6.69 (m, 1H), 6.09-6.01 (m, 1H), 5.04-4.61 (m, 2H), 4.18-4.08 (m, 1H), 3.80 (s, 1H), 3.84-3.74 (m, 1H), 3.01-3.00 (m, 1H), 2.97 (s, 1H), 1.24-1.15 (m, 2H), 0.95-0.84 (m, 2H). LC/MS: m/z=585.2 [M+H]$^+$.

N-(7-amino-4-chloro-1-cyclopropyl-1H-indazol-3-yl)-N-(4-methoxybenzyl)methanesulfonamide

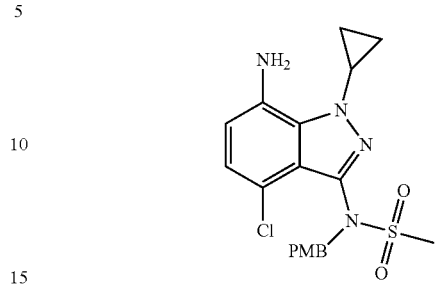

To a bright yellow solution of N-(4-chloro-1-cyclopropyl-7-((diphenylmethylene)amino)-1H-indazol-3-yl)-N-(4-methoxybenzyl)methanesulfonamide (0.284 g, 0.485 mmol) in THF (4.9 ml) was added HCl (1.2 ml, 4.85 mmol) and water (0.044 ml, 2.427 mmol)). The resulting dark orange solution was stirred at rt for 2 h and concentrated. The residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a pink foamy solid (0.1 g). $^1$H NMR (400 MHz, CDCl$_3$) δ7.26 (br d, J=2.8 Hz, 2H), 6.93-6.88 (m, 1H), 6.83-6.77 (m, 2H), 6.52-6.44 (m, 1H), 5.12-4.89 (m, 1H), 4.82-4.62 (m, 1H), 3.95-3.87 (m, 1H), 3.79 (s, 3H), 3.67-3.48 (m, 2H), 2.98 (s, 3H), 1.43-1.36 (m, 2H), 1.30-1.30 (m, 1H), 1.20 (br dd, J=7.2, 1.4 Hz, 2H). LC/MS: m/z=420.9 [M+H]$^+$.

7-bromo-4-chloro-1-isopropyl-1H-indazol-3-amine

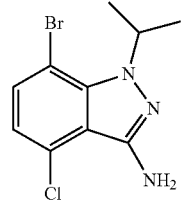

Sodium methoxide (0.54 g, 9.47 mmol) was added to a solution of 3-bromo-6-chloro-2-fluorobenzonitrile (0.5 g, 2.133 mmol) and isopropyl hydrazine hydrochloride (0.524 g, 4.73 mmol) in ethanol (5 mL), the mixture was heated at 120° C. in a microwave reactor for 35 min. The reaction mixture (pale yellow solid) was taken up in ethyl acetate, washed with water, brine, dried over Na$_2$SO$_4$ and concentrated. The residue was purified on silica gel (40 g Isco column) using 5-100% ethyl acetate in hexanes. The desired fractions were concentrated to give a light brown solid (0.29 g). $^1$H NMR (500 MHz, CDCl$_3$) δ7.30 (s, 1H), 6.76-6.56 (m, 1H), 4.73-4.32 (m, 3H), 1.65 (d, J=6.8 Hz, 6H). LC/MS: m/z=290.0 [M+H]$^+$.

N-(7-bromo-4-chloro-1-isopropyl-1H-indazol-3-yl)methanesulfonamide

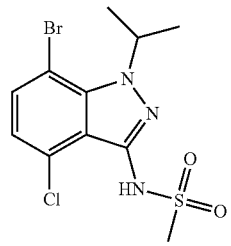 [SMILES: CC(C)n1nc(NS(C)(=O)=O)c2c(Cl)ccc(Br)c21]

To a solution of 7-bromo-4-chloro-1-isopropyl-1H-indazol-3-amine (0.159 g, 0.551 mmol) in CH$_2$Cl$_2$ (2 mL) was added DIPEA (0.385 mL, 2.204 mmol) then the reaction was cooled in an ice bath and methanesulfonyl chloride (0.19 g, 1.653 mmol) was added. The reaction mixture was stirred at this temperature for 1 h (precipitate formed). The reaction mixture was then diluted with dichloromethane (10 mL) and washed with water, 1 M HCl and brine, dried (Na$_2$SO$_4$), filtered and concentrated. The residue was purified on silica (24 g Isco column). The desired fractions were concentrated to give a light yellow solid (nmr suggests a bis-sulfonation). The residue was taken up in EtOH (4 mL) and 2 mL of 20% aq. NaOH. The resulted mixture heated with a heat gun until it became a homogeneous solution and stirred at rt for 30 min. The reaction mixture was diluted with water (5 mL) and acidified with 2 M HCl (60 mL). The resultant cloudy mixture was extracted with DCM, dried over Na$_2$SO$_4$ and concentrated to give the desired product as a pink solid (0.12 g). $^1$H NMR (500 MHz, CDCl$_3$) δ7.53-7.38 (m, 1H), 7.01 (d, J=7.7 Hz, 1H), 6.72 (s, 1H), 5.45-5.29 (m, 1H), 3.16 (s, 3H), 1.66 (d, J=6.5 Hz, 6H). LC/MS: m/z=366.0 [M+H]$^+$.

N-(7-bromo-4-chloro-1-isopropyl-1H-indazol-3-yl)-N-(4-methoxybenzyl)methanesulfonamide

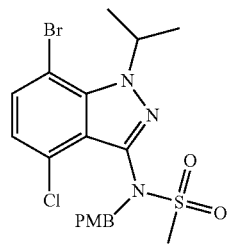

4-Methoxybenzyl chloride (0.07 ml, 0.524 mmol) was added to a mixture of N-(7-bromo-4-chloro-1-isopropyl-1H-indazol-3-yl)methanesulfonamide (0.16 g, 0.436 mmol) and Cs$_2$CO$_3$ (0.284 g, 0.873 mmol) in DMF (3.1 ml). The reaction mixture was stirred at rt overnight, then, diluted with ethyl acetate, washed with brine, dried over Na$_2$SO$_4$ and concentrated. The residue was purified on silica (24 g Isco column) using 0-60% ethyl acetate in hexanes. The desired fractions were concentrated to give a white solid (0.18 g). LC/MS: m/z=486.2 [M+H]$^+$.

N-(4-chloro-7-((diphenylmethylene)amino)-1-isopropyl-1H-indazol-3-yl)-N-(4-methoxybenzyl)methanesulfonamide

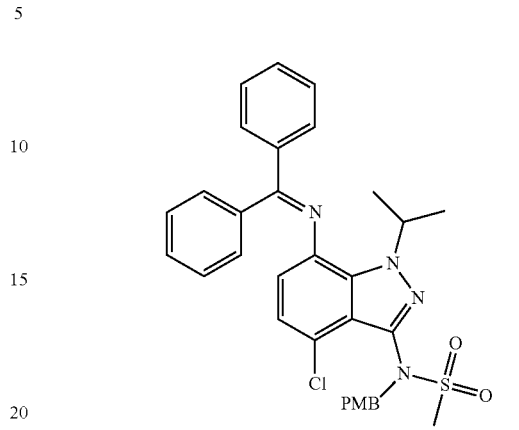

A mixture of N-(7-bromo-4-chloro-1-isopropyl-1H-indazol-3-yl)-N-(4-methoxybenzyl)methanesulfonamide (0.181 g, 0.372 mmol), diphenylmethanimine (0.074 g, 0.410 mmol), PdOAc$_2$ (4.17 mg, 0.019 mmol), R-(+)-BINAP (0.035 g, 0.056 mmol) and Cs$_2$CO$_3$ (0.182 g, 0.558 mmol) in Dioxane (3.7 mL) was degassed for 5 min and heated in the microwave at 120° C. for 2 h. The reaction mixture was purified on silica (40 g Isco column) using 0-40% ethyl acetate in hexanes. The desired fractions were concentrated to give a bright yellow solid (0.14 g). LC/MS: m/z=587.4 [M+H]$^+$.

N-(7-amino-4-chloro-1-isopropyl-1H-indazol-3-yl)-N-(4-methoxybenzyl)methanesulfonamide

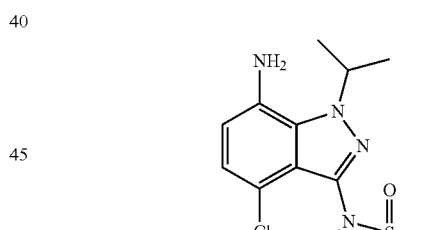

To a bright yellow solution of N-(4-chloro-7-((diphenylmethylene)amino)-1-isopropyl-1H-indazol-3-yl)-N-(4-methoxybenzyl)methanesulfonamide (0.14 g, 0.232 mmol) in THF (2.316 ml) was added HCl (0.6 ml, 2.316 mmol) and water (0.02 ml, 1.158 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K$_3$PO$_4$, dried over MgSO$_4$ and concentrated. The residue was purified on silica (24 g Isco column) using 0-40% ethyl acetate in hexanes. The desired fractions were concentrated to give an off-white sticky solid (66 mg). LC/MS: m/z=423.2 [M+H]$^+$.

N-(7-bromo-4-chloro-1-(2,2-difluoroethyl)-1H-indazol-3-yl) methanesulfonamide

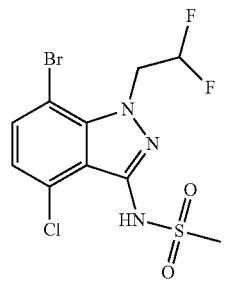 [SMILES: CS(=O)(=O)Nc1nn(CC(F)F)c2c(Br)ccc(Cl)c12]

To a 100 mL pressure bottle under N₂ was added N-(4-chloro-1-(2,2-difluoroethyl)-7-(4,4,5,5-tetramethyl-1,3,2-dioxaborolan-2-yl)-1H-indazol-3-yl)methanesulfonamide (0.4 g, 0.918 mmol) and Methanol (16.8 mL). The resulting suspension was then treated with a solution of copper(II) bromide (0.619 g, 2.77 mmol) dissolved in Water (5.1 mL). The reaction was sealed and placed in an oil bath and heated at 80° C. for 10 h. The reaction mixture was diluted with water and extracted with EtOAc, dried with MgSO₄, filtered and concentrated to produce a brown solid. The residue was purified on silica (40 g Isco column) using 0-50% ethyl acetate in hexanes. The desired fractions were concentrated to give a light pink solid (0.3 g). $^1$H NMR (500 MHz, CDCl₃) δ7.60-7.49 (m, 1H), 7.48-7.36 (m, 1H), 7.08-6.94 (m, 1H), 6.40-5.99 (m, 1H), 5.25-5.04 (m, 2H), 3.51-3.35 (m, 3H). LC/MS: m/z=387.7 [M+H]$^+$.

N-(7-bromo-4-chloro-1-(2,2-difluoroethyl)-1H-indazol-3-yl)cyclopropanesulfonamide

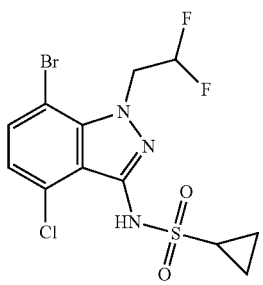 [SMILES: O=S(=O)(Nc1nn(CC(F)F)c2c(Br)ccc(Cl)c12)C1CC1]

To a 100 mL pressure bottle under N₂ was added N-(4-chloro-1-(2,2-difluoroethyl)-7-(4,4,5,5-tetramethyl-1,3,2-dioxaborolan-2-yl)-1H-indazol-3-yl)cyclopropanesulfonamide (1.9 g, 4.12 mmol) and Methanol (34 mL). The resulting suspension was then treated with a solution of copper(II) bromide (2.78 g, 12.43 mmol) dissolved in Water (10 mL). The reaction was sealed and placed in an oil bath and heated at 80° C. for 10 h. The reaction mixture was diluted with water and extracted with EtOAc, dried with MgSO₄, filtered, then concentrated give a light pink solid (1.71 g, used as is). $^1$H NMR (400 MHz, CDCl₃) δ7.61-7.49 (m, 1H), 7.44-7.35 (m, 1H), 7.02 (d, J=8.1 Hz, 1H), 6.37-5.98 (m, 1H), 5.26-5.07 (m, 2H), 3.07-2.91 (m, 1H), 1.45-1.37 (m, 2H), 1.18-1.06 (m, 2H). LC/MS: m/z=414.0 [M+H]$^+$.

N-(7-bromo-4-chloro-1-(2,2-difluoroethyl)-1H-indazol-3-yl)-N-(4-methoxybenzyl)methanesulfonamide

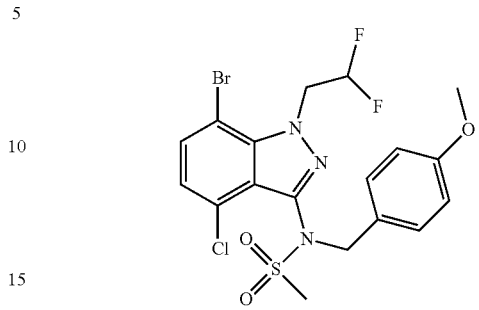

4-Methoxybenzyl chloride (0.250 ml, 1.853 mmol) was added to a mixture of N-(7-bromo-4-chloro-1-(2,2-difluoroethyl)-1H-indazol-3-yl)methanesulfonamide (0.6 g, 1.544 mmol) and Cs₂CO₃ (1.006 g, 3.09 mmol) in DMF (6.2 mL). The mixture was stirred at rt overnight. The mixture was diluted with ethyl acetate, washed with brine, dried over Na₂SO₄ and concentrated. The residue was purified on silica (80 g Isco column) using 0-60% ethyl acetate in hexanes. The desired fractions were concentrated to give a viscous yellow oil (0.73 g). LC/MS: m/z=507.9 [M+H]$^+$.

N-(7-bromo-4-chloro-1-(2,2-difluoroethyl)-1H-indazol-3-yl)-N-(4-methoxybenzyl)cyclopropanesulfonamide

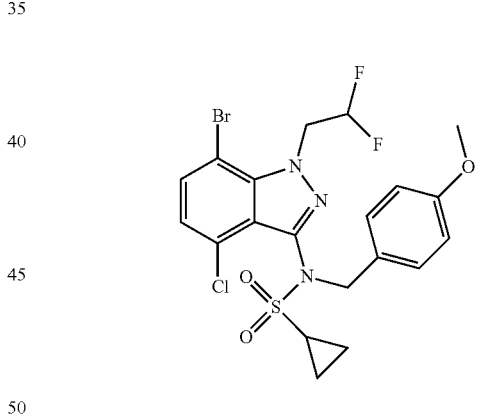

4-Methoxybenzyl chloride (0.668 ml, 4.95 mmol) was added to a mixture of N-(7-bromo-4-chloro-1-(2,2-difluoroethyl)-1H-indazol-3-yl)cyclopropanesulfonamide (1.71 g, 4.12 mmol) and Cs₂CO₃ (2.69 g, 8.25 mmol) in DMF (16.50 mL). The mixture was stirred at rt overnight. The mixture was diluted with ethyl acetate, washed with brine, dried over Na₂SO₄ and concentrated. The residue was purified on silica (220 g Isco column) using 0-60% ethyl acetate in hexanes. The desired fractions were concentrated to give a sticky white solid. $^1$H NMR (400 MHz, CDCl₃) δ7.51-7.44 (m, 1H), 7.27-7.23 (m, 2H), 7.06-7.00 (m, 1H), 6.80-6.73 (m, 2H), 6.24-5.88 (m, 1H), 5.37-4.82 (m, 4H), 3.79-3.72 (m, 3H), 2.69-2.58 (m, 1H), 1.24-1.13 (m, 2H), 1.08-0.99 (m, 2H). LC/MS: m/z=535.7 [M+2H]$^+$.

N-(4-chloro-1-(2,2-difluoroethyl)-7-((diphenylmethylene)amino)-1H-indazol-3-yl)-N-(4-methoxybenzyl)methanesulfonamide

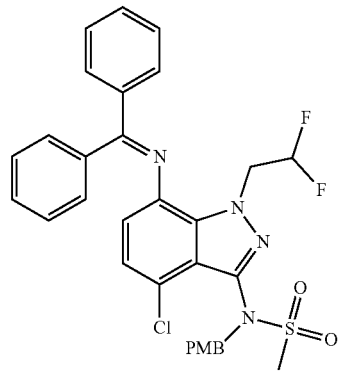

A mixture of N-(7-bromo-4-chloro-1-(2,2-difluoroethyl)-1H-indazol-3-yl)-N-(4-methoxybenzyl)methanesulfonamide (0.73 g, 1.435 mmol), diphenylmethanimine (0.27 ml, 1.583 mmol), PdOAc$_2$ (0.016 g, 0.072 mmol), R-(+)-BINAP (0.134 g, 0.215 mmol) and Cs$_2$CO$_3$ (0.701 g, 2.152 mmol) in Dioxane (14.4 mL) was degassed for 5 min and heated (heating block) at 95° C. for 2 h. The reaction mixture was purified on silica gel (220 g Isco column) using 0-40% ethyl acetate, the desired fractions were concentrated to give a bright yellow solid (0.74 g). LC/MS: m/z=609.1 [M+H]$^+$.

N-(4-chloro-1-(2,2-difluoroethyl)-7-((diphenylmethylene)amino)-1H-indazol-3-yl)-N-(4-methoxybenzyl)cyclopropanesulfonamide

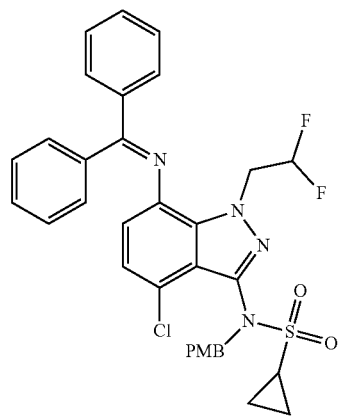

A mixture of N-(7-bromo-4-chloro-1-(2,2-difluoroethyl)-1H-indazol-3-yl)-N-(4-methoxybenzyl)cyclopropanesulfonamide (0.83 g, 1.552 mmol), diphenylmethanimine (0.287 ml, 1.712 mmol), PdOAc$_2$ (0.017 g, 0.078 mmol), R-(+)-BINAP (0.145 g, 0.233 mmol) and Cs$_2$CO$_3$ (0.758 g, 2.328 mmol) in Dioxane (13 mL) was degassed for 5 min and heated in a microwave at 120° C. for 2 h. The reaction mixture filtered through Celite and concentrated. The residue was purified on silica gel (220 g Isco column) using 0-30% ethyl acetate, the desired fractions were concentrated to give a bright yellow solid (0.85 g). LC/MS: m/z=635.3 [M+H]$^+$.

N-(7-amino-4-chloro-1-(2,2-difluoroethyl)-1H-indazol-3-yl)-N-(4-methoxybenzyl)methanesulfonamide

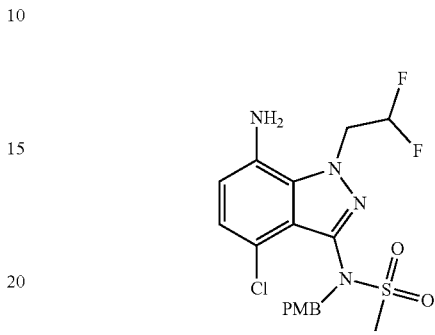

To a bright yellow solution of N-(4-chloro-1-(2,2-difluoroethyl)-7-((diphenylmethylene)amino)-1H-indazol-3-yl)-N-(4-methoxybenzyl)methanesulfonamide (0.74 g, 1.215 mmol) in THF (12.15 ml) was added HCl (3 mL, 12.15 mmol) and water (0.11 mL, 6.07 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a brown foamy solid (0.48 g).

N-(7-amino-4-chloro-1-(2,2-difluoroethyl)-1H-indazol-3-yl)-N-(4-methoxybenzyl)cyclopropanesulfonamide

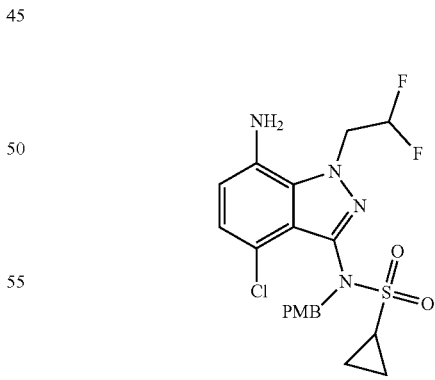

Prepared according to the general procedure described for N-(7-amino-4-chloro-1-(2,2-difluoroethyl)-1H-indazol-3-yl)-N-(4-methoxybenzyl)methanesulfonamide using N-(4-chloro-1-(2,2-difluoroethyl)-7-((diphenylmethylene)amino)-1H-indazol-3-yl)-N-(4-methoxybenzyl)cyclopropanesulfonamide. LC/MS: m/z=471.1 [M+H]$^+$.

tert-butyl (S)-(1-(7-bromo-3-(6-isopropylpyridin-3-yl)-4-oxo-3,4-dihydroquinazolin-2-yl)-2-(3,5-difluorophenyl)ethyl)carbamate

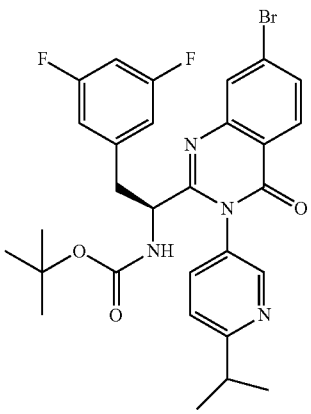 [SMILES: CC(C)c1ccc(-n2c([C@H](Cc3cc(F)cc(F)c3)NC(=O)OC(C)(C)C)nc3cc(Br)ccc3c2=O)cn1]

A mixture of (S)-2-((tert-butoxycarbonyl)amino)-3-(3,5-difluorophenyl)propanoic acid (1.00 g, 3.32 mmol), 2-amino-4-bromobenzoic acid (0.717 g, 3.32 mmol) and diphenyl phosphite (2.1 mL, 11 mmol) in pyridine (15 mL) was sealed and heated with microwave irradiation at 70° C. for 2 h. The reaction was allowed to cool to rt and then 6-isopropylpyridin-3-amine (0.497 g, 3.65 mmol) was added and the reaction solution was heated at 70° C. for 2 h. The reaction mixture was concentrated and the residue was partitioned between water (250 mL) and EtOAc (50 mL). The organic component was washed with 1.5 M $K_3PO_4$ and brine, dried ($MgSO_4$), filtered and concentrated. The residue was purified by FCC (120 g silica gel cartridge, 0~35% EtOAc-hexanes) to afford the title compound (940 mg) as an off-white foam. LC/MS retention time=1.57 min; m/z=599.3, 601.3 (1:1) [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

tert-butyl (S)-(1-(7-cyano-3-(6-isopropylpyridin-3-yl)-4-oxo-3,4-dihydroquinazolin-2-yl)-2-(3,5-difluorophenyl)ethyl)carbamate

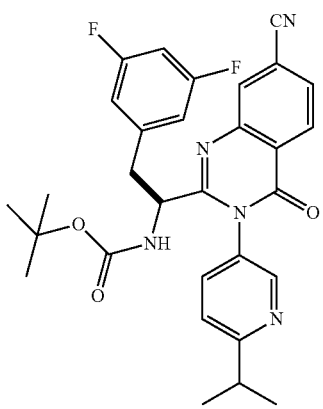 [SMILES: CC(C)c1ccc(-n2c([C@H](Cc3cc(F)cc(F)c3)NC(=O)OC(C)(C)C)nc3cc(C#N)ccc3c2=O)cn1]

A mixture of tert-butyl (S)-(1-(7-bromo-3-(6-isopropylpyridin-3-yl)-4-oxo-3,4-dihydroquinazolin-2-yl)-2-(3,5-difluorophenyl)ethyl)carbamate (300 mg, 0.500 mmol), zinc cyanide (41 mg, 0.35 mmol), t-BuXPhos Pd G3 (20 mg, 0.025 mmol), THF (2 mL) and water (8 mL) was vacuum flushed with nitrogen (3×), sealed and heated with microwave irradiation at 60° C. for 2 h. The reaction mixture was partitioned between water (50 mL) and EtOAc (25 mL). The organic component was washed with brine, ($MgSO_4$), filtered, and concentrated under reduced pressure. The residue was purified by FCC (80 g silica gel cartridge, 0~40% EtOAc-hexanes) to afford the title compound (152 mg) as a white foam and recovered starting material (110 mg). LC/MS retention time=1.47 min; m/z=546.35 [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-7-bromo-3-(6-isopropylpyridin-3-yl)quinazolin-4(3H)-one

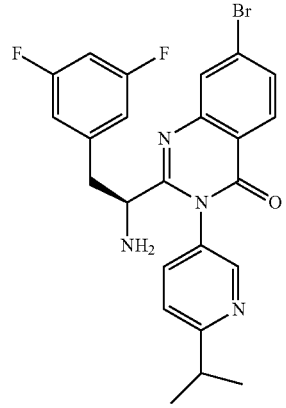 [SMILES: CC(C)c1ccc(-n2c([C@@H](N)Cc3cc(F)cc(F)c3)nc3cc(Br)ccc3c2=O)cn1]

To a solution of tert-butyl (S)-(1-(7-bromo-3-(6-isopropylpyridin-3-yl)-4-oxo-3,4-dihydroquinazolin-2-yl)-2-(3,5-difluorophenyl)ethyl)carbamate (50 mg, 0.083 mmol) in DCM (2.5 mL) was added 4 M HCl in 1,4-dioxane (0.42 mL, 1.7 mmol). The resulting light yellow solution was stirred at rt for 2 h. The reaction mixture was concentrated to afford an HCl salt of the title compound (48 mg) as a white solid. This material was used without additional purification. LC/MS retention time=1.11 min; m/z=499.2, 501.2 (1:1) [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile:water; Temperature: 40° C.; Gradient: 0-100% B over 1.5 min, then a 0.5 min hold at 100% B; Flow rate: 1.0 mL/min; Detection: UV at 220 nm.

N-((S)-1-(7-bromo-3-(6-isopropylpyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

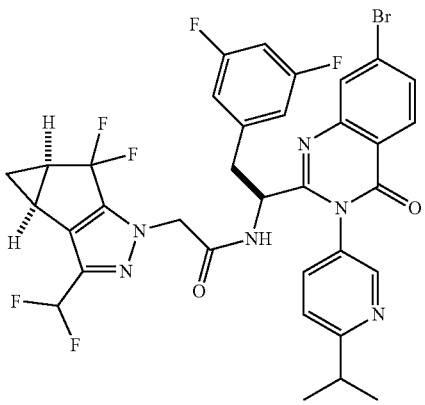 [SMILES: CC(C)c1ccc(-n2c([C@H](Cc3cc(F)cc(F)c3)NC(=O)Cn3nc(C(F)F)c4c3C(F)(F)[C@@H]3C[C@H]43)nc3cc(Br)ccc3c2=O)cn1]

To a solution of an HCl salt of (S)-2-(1-amino-2-(3,5-difluorophenyl)ethyl)-7-bromo-3-(6-isopropylpyridin-3-yl)quinazolin-4(3H)-one (48 mg, 0.084 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (26.6 mg, 0.101 mmol) and HATU (47.8 mg, 0.126 mmol) in DMF (1.4 mL) was added N,N-diisopropylethylamine (0.088 mL, 0.50 mmol) and the reaction mixture was stirred at rt for 2 h. The crude material was purified via preparative LC/MS (XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 43-83% B over 20 minutes, then a 5-minute hold at 100% B; Flow: 20 mL/min) to afford the title compound (47.5 mg) as a mixture of stereoisomers. QC-ACN-AA-XB (Purity: 100.0%; RT: 2.41 min; Obs. Adducts: [M+H]; Obs. Masses: 745.05).

tert-butyl (S)-(2-(3,5-difluorophenyl)-1-(3-(6-isopropylpyridin-3-yl)-4-oxo-7-(1H-tetrazol-5-yl)-3,4-dihydroquinazolin-2-yl)ethyl)carbamate

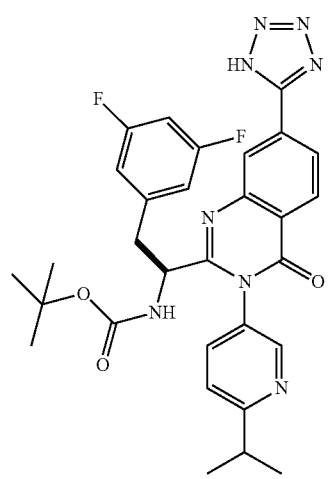 [SMILES: CC(C)c1ccc(-n2c([C@H](Cc3cc(F)cc(F)c3)NC(=O)OC(C)(C)C)nc3cc(-c4nnn[nH]4)ccc3c2=O)cn1]

A reaction mixture of tert-butyl (S)-(1-(7-cyano-3-(6-isopropylpyridin-3-yl)-4-oxo-3,4-dihydroquinazolin-2-yl)-2-(3,5-difluorophenyl)ethyl)carbamate (28 mg, 0.051 mmol) and tributyltin azide (0.03 mL, 0.1 mmol) in toluene (1.5 mL) was sealed and heated with microwave irradiation at 130° C. for 2 h. and then at 150° C. another 2 h. The reaction mixture was concentrated and the residue was used without additional purification. LC/MS retention time=1.33 min; m/z=589.35 [M+H]$^+$. Column: Acquity BEH 2.1×50 mm, 1.7 µm; Mobile Phase A: 0.1% TFA in 10:90 acetonitrile: water; Mobile Phase B: 0.1% TFA in 90:10 acetonitrile: water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-3-(6-isopropylpyridin-3-yl)-7-(1H-tetrazol-5-yl)quinazolin-4(3H)-one

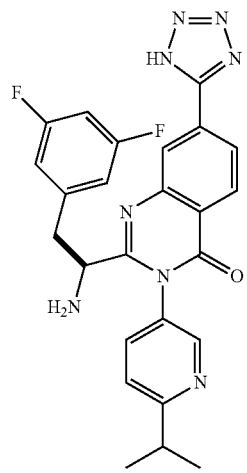 [SMILES: CC(C)c1ccc(-n2c([C@@H](N)Cc3cc(F)cc(F)c3)nc3cc(-c4nnn[nH]4)ccc3c2=O)cn1]

To a solution of tert-butyl (S)-(2-(3,5-difluorophenyl)-1-(3-(6-isopropylpyridin-3-yl)-4-oxo-7-(1H-tetrazol-5-yl)-3,4-dihydroquinazolin-2-yl)ethyl)carbamate (30 mg, 0.051 mmol) in DCM (0.5 mL) was added TFA (0.16 mL, 2.0 mmol) and the reaction mixture was stirred at rt overnight. The reaction mixture was concentrated and the residue was treated with 2 M HCl in ether and reconcentrated (2×). The resulting solids were triturated with Et$_2$O, dried under vacuum to afford and HCl salt of the title compound (29 mg) as a bright yellow solid. This material was used for the without further purification. LC/MS retention time=1.02 min; m/z=489.35 [M+H]$^+$. Column: Acquity BEH 2.1×50 mm, 1.7 µm; Mobile Phase A: 0.1% TFA in 10:90 acetonitrile:water; Mobile Phase B: 0.1% TFA in 90:10 acetonitrile: water; Temperature: 40° C.; Gradient: 0-100% B over 1.5 min, then a 0.5 min hold at 100% B; Flow rate: 1.0 mL/min; Detection: UV at 220 nm.

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(6-isopropylpyridin-3-yl)-4-oxo-7-(1H-tetrazol-5-yl)-3,4-dihydroquinazolin-2-yl)ethyl)acetamide (Example 7)

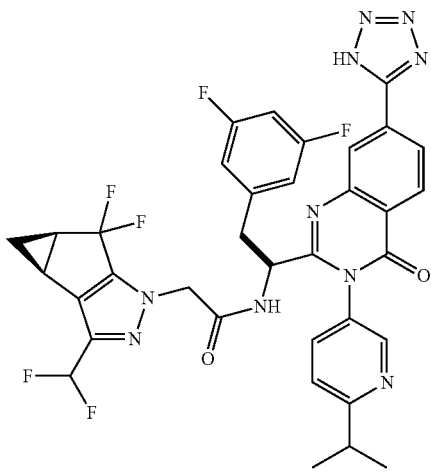 [SMILES: CC(C)c1ccc(-n2c([C@H](Cc3cc(F)cc(F)c3)NC(=O)Cn3nc(C(F)F)c4c3C(F)(F)[C@@H]3C[C@H]43)nc3cc(-c4nnn[nH]4)ccc3c2=O)cn1]

To a solution of an HCl salt of (S)-2-(1-amino-2-(3,5-difluorophenyl)ethyl)-3-(6-isopropylpyridin-3-yl)-7-(1H-tetrazol-5-yl)quinazolin-4(3H)-one (29 mg, 0.052 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid (16 mg, 0.062 mmol) and HATU (30 mg, 0.077 mmol) in DMF (1 mL) was added N,N-diisopropylethylamine (0.054 mL, 0.31 mmol), and the reaction mixture was stirred at rt for 2 h. The crude material was purified via preparative LC/MS (Column: XBridge C18, 19×200 mm, 5 μm particles; Mobile Phase A: 5:95 acetonitrile: water with 10 mM ammonium acetate; Mobile Phase B: 95:5 acetonitrile: water with 10 mM ammonium acetate; Gradient: 28-68% B over 20 minutes, then a 4-minute hold at 100% B; Flow: 20 mL/min.) to afford the title compound (13.9 mg) as a tan solid. QC-ACN-TFA-XB (Purity: 98.2%; RT: 1.96 min; Obs. Adducts: [M+H]; Obs. Masses: 735.18).

tert-butyl (S)-(1-(7-bromo-3-(4-cyclopropylphenyl)-4-oxo-3,4-dihydroquinazolin-2-yl)-2-(3,5-difluorophenyl)ethyl)carbamate

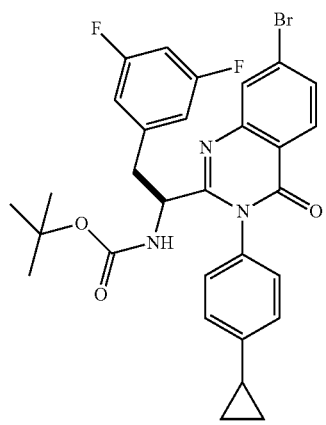 [SMILES: CC(C)(C)OC(=O)N[C@@H](Cc1cc(F)cc(F)c1)c1nc2cc(Br)ccc2c(=O)n1-c1ccc(C2CC2)cc1]

A mixture of (S)-2-((tert-butoxycarbonyl)amino)-3-(3,5-difluorophenyl)propanoic acid (1.00 g, 3.32 mmol), 2-amino-4-bromobenzoic acid (0.717 g, 3.32 mmol) and diphenyl phosphite (2.12 mL, 11.0 mmol) in pyridine (15 mL) was sealed and heated with microwave irradiation at 70° C. for 2 h. The reaction mixture was allowed to cool to rt, treated with 4-cyclopropylaniline (0.486 g, 3.65 mmol) and then resealed and heated at 70° C. for 2 h. The reaction mixture was concentrated and the residue was partitioned between water (250 mL) and EtOAc (50 mL). The organic component was washed with 5% citric acid and brine, dried it over MgSO$_4$, filtered, and concentrated in vacuo. The residue was purified by FCC (120 g silica gel cartridge, 0~20% EtOAc-hexanes) to afford the crude title compound (1.98 g) as a white solid which was used without additional purification. LC/MS retention time=1.74 min; m/z=596.30, 598.25 (1:1) [M+H]$^+$. Column: Acquity BEH 2.1×50 mm, 1.7 μm; Mobile Phase A: 0.1% TFA in 10:90 acetonitrile: water; Mobile Phase B: 0.1% TFA in 90:10 acetonitrile: water; Temperature: 40° C.; Gradient: 0-100% B over 1.5 min, then a 0.5 min hold at 100% B; Flow rate: 1.0 mL/min; Detection: UV at 220 nm.

(S)-2-(1-amino-2-(3,5-difluorophenyl)ethyl)-7-bromo-3-(4-cyclopropylphenyl)quinazolin-4(3H)-one

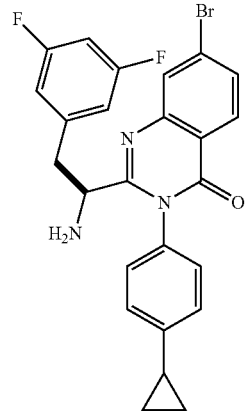 [SMILES: N[C@@H](Cc1cc(F)cc(F)c1)c1nc2cc(Br)ccc2c(=O)n1-c1ccc(C2CC2)cc1]

A solution of crude tert-butyl (S)-(1-(7-bromo-3-(4-cyclopropylphenyl)-4-oxo-3,4-dihydroquinazolin-2-yl)-2-(3,5-difluorophenyl)ethyl)carbamate (1.98 g) and 4 M hydrogen chloride in 1,4-dioxane (16.6 ml, 66.4 mmol) was stirred at rt overnight. The reaction mixture was concentrated in vacuo and azeotroped with DCM to afford an off-white solid. This white solid was triturated it with Et$_2$O and dried in vacuo to afford an HCl salt of the title compound (687 mg) as a white powder. This material was used without additional purification. LC/MS retention time=1.30 min; m/z=496.20, 498.25 (1:1) [M+H]$^+$. Column: Acquity BEH 2.1×50 mm, 1.7 μm; Mobile Phase A: 0.1% TFA in 10:90 acetonitrile: water; Mobile Phase B: 0.1% TFA in 90:10 acetonitrile: water; Temperature: 40° C.; Gradient: 0-100% B over 1.5 min, then a 0.5 min hold at 100% B; Flow rate: 1.0 mL/min; Detection: UV at 220 nm.

N-((S)-1-(7-bromo-3-(4-cyclopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

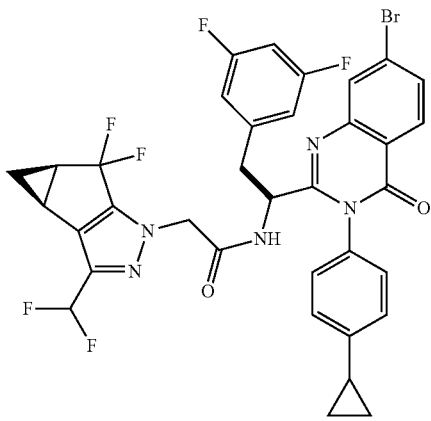 [SMILES: O=C(Cn1nc(C(F)F)c2c1C(F)(F)[C@@H]1C[C@H]21)N[C@@H](Cc1cc(F)cc(F)c1)c1nc2cc(Br)ccc2c(=O)n1-c1ccc(C2CC2)cc1]

To a solution of an HCl salt of (S)-2-(1-amino-2-(3,5-difluorophenyl)ethyl)-7-bromo-3-(4-cyclopropylphenyl)quinazolin-4(3H)-one (23 mg, 0.040 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (13 mg, 0.048 mmol) and HATU (23 mg, 0.061 mmol) in DMF (0.8 mL) was added N,N-diisopropylethylamine (0.042 mL, 0.242 mmol), and the reaction mixture was stirred at rt for 2 h. The crude material was purified via preparative LC/MS (Column: XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 53-93% B over 20 minutes, then a 4-minute hold at 100% B; Flow: 20 mL/min.) to afford the title compound (23.7 mg) as solid. QC-ACN-AA-XB (Purity: 100.0%; RT: 2.52 min; Obs. Adducts: [M+H]; Obs. Masses: 742.04). $^1$H NMR (500 MHz, MeOH-$d_4$) δ8.11 (d, J=8.5 Hz, 1H), 8.00 (d, J=1.8 Hz, 1H), 7.74 (dd, J=8.4, 1.7 Hz, 1H), 7.35-7.27 (m, 3H), 7.09 (dd, J=7.9, 1.8 Hz, 1H), 6.79-6.73 (m, 1H), 6.70 (t, $J_{HF}$=54.6 Hz, 1H), 6.40 (br d, J=6.1 Hz, 2H), 4.84 (d, J=16.5 Hz, 1H), 4.76 (d, J=16.5 Hz, 1H), 3.21 (dd, J=13.9, 4.7 Hz, 1H), 2.88 (dd, J=14.0, 9.2 Hz, 1H), 2.50-2.41 (m, 2H), 2.12-2.03 (m, 1H), 1.39 (q, J=6.9 Hz, 1H), 1.13-1.01 (m, 3H), 0.82 (td, J=4.9, 2.1 Hz, 2H). Note: One aliphatic proton unaccounted for. $^{19}$F NMR (471 MHz, MeOH-$d_4$) δ −82.3 (d, J=256.1 Hz, 1F), −105.2 (d, J=256.1 Hz, 1F), −111.8 (s, 2F), −113.1 (d, J=313.3 Hz, 1F), −114.5 (d, J=313.3 Hz, 1F).

N-(4-chloro-1-(2,2-difluoroethyl)-7-(4,4,5,5-tetramethyl-1,3,2-dioxaborolan-2-yl)-1H-indazol-3-yl)methanesulfonamide Overall Synthetic Scheme:

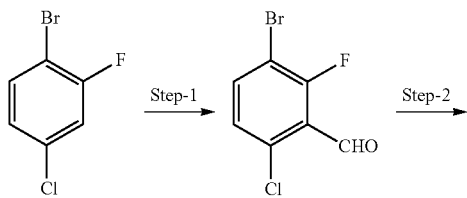

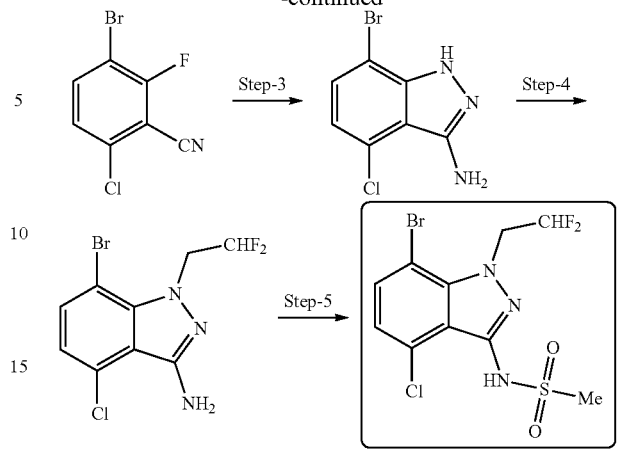

Step-1: Synthesis of 3-bromo-6-chloro-2-fluorobenzaldehyde 2

Reaction Scheme:

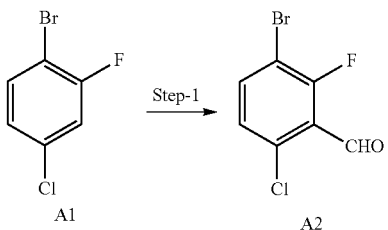

To a stirred solution of 1-Bromo-4-chloro-2-fluorobenzene (200 g, 0.955 mol, 1.0 equiv.) in anhydrous THF (2.0 L) was added 2.0 M lithium diisopropylamide (LDA) in THF (620 mL, 1.24 mol, 1.3 equiv.) at −50° C., the reaction mixture was allowed to −20° C. and stirred for 1 h. Then it was re-cooled to −50° C. and slowly added DMF (184.8 mL, 2.48 mol, 2.6 equiv.) at the same temperature. The mixture was allowed to 0° C. and stirred for 30-45 min. After completion of the reaction (monitored by TLC), it was quenched with the slow addition of ice cold water (2.0 L); then diluted with ethyl acetate (2.0 L) and stirred for 15 min at room temperature. The organic layer was separated and aqueous layer was extracted with ethyl acetate (2×1.0 L). The combined organic layers were washed with water (2×1.0 L); 1.0 N HCl (1.0 L) and 15% NaCl solution (2.0 L). The organic layer was dried over anhydrous Na$_2$SO$_4$, concentrated under vacuum. The resultant crude solid was directly used for next step without further purification. Yield: 210.0 g, 93% (reported 78%). $^1$H NMR (400 MHz, CDCl$_3$): δ10.39 (d, J=0.8 Hz, 1H), 7.69 (dd, J$_1$=7.2 Hz, J$_2$=8.8 Hz, 1H), 7.19 (dd, J$_1$=1.2 Hz, J$_2$=8.4 Hz, 1H).

Step-2: Synthesis of 3-bromo-6-chloro-2-fluorobenzonitrile

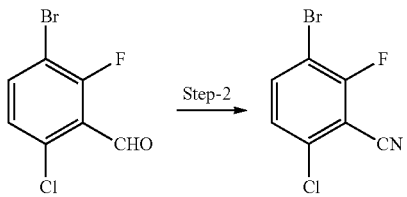 [SMILES: O=Cc1c(Cl)ccc(Br)c1F ; N#Cc1c(Cl)ccc(Br)c1F]

To a solution of 3-Bromo-6-chloro-2-fluorobenzaldehyde (210.0 g, 0.89 mol, 1.0 equiv.) in water (2.1 L) was charged with Hydroxylamine-O-sulfonic acid (175.15 g, 1.55 mol, 1.75 equiv.) at room temperature. The reaction mixture was heated to 50° C. and stirred for 18 h. After reaction completion (the reaction progress was monitored by TLC), it was cooled to room temperature and stirred for 1-1.5 h. The solids were filtered and washed with water. The wet solid was dried at 50° C. under vacuum for 12-15 h to afford the crude 3-Bromo-6-chloro-2-fluorobenzonitrile as a solid; which can be directly used for the next reaction without further purification. Yield: 190.0 g, 91% (reported 92%). $^1$H NMR (400 MHz, CDCl$_3$): δ7.50 (dd, J$_1$=7.1 Hz, J$_2$=8.6 Hz, 1H), 7.15 (dd, J$_1$=1.4 Hz, J$_2$=8.7 Hz, 1H).

Step-3: Synthesis of 7-bromo-4-chloro-1H-indazol-3-amine

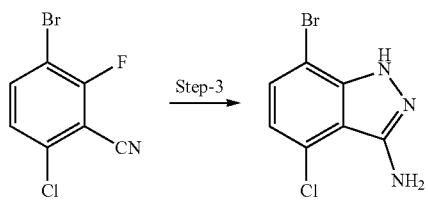 [SMILES: N#Cc1c(Cl)ccc(Br)c1F ; Nc1n[nH]c2c(Br)ccc(Cl)c12]

To a stirred solution of 3-Bromo-6-chloro-2-fluorobenzonitrile (10.0 g, 0.043 mol, 1.0 equiv.) in ethanol (50 mL) was added hydrazine hydrate (10.42 mL, 0.21 mol, 5.0 equiv.) at room temperature. The reaction mixture was heated to 110° C. and stirred for 15 h. After completion of the reaction (monitored by TLC), it was cooled to room temperature and water (100 mL) was added and stirred for 1 h at room temperature. The obtained solids were filtered and washed with water (100 mL). The wet solid was dried under vacuum at 50° C. for 12-15 hours. The crude solid was purified by column chromatography (eluting with 10% EA/Hexanes to 40% EA/Hexanes) to afford 7-Bromo-4-chloro-1H-indazol-3-amine as a dull white solid. Yield: 8.4 g, 80%; $^1$H NMR (400 MHz, DMSO-d$_6$): δ12.21 (bs, 1H), 7.41 (d, J=7.8 Hz, 1H), 6.84 (d, J=7.8 Hz, 1H), 5.34 (bs, 2H) ppm.

Step-4: Synthesis of 7-bromo-4-chloro-1-(2,2-difluoroethyl)-1H-indazol-3-amine

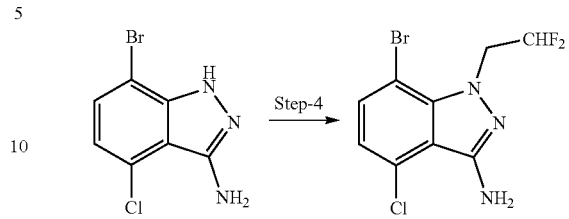

To a stirred solution of 7-Bromo-4-chloro-1H-indazol-3-amine (2.0 g, 8.16 mmol, 1.0 equiv.) in dry THF (20 mL) at 0° C. was added $^t$BuOK (1.20 g, 10.61 mmol, 1.3 equiv.) in portions. After being stirred for 10 min at 0° C., 2,2-Difluoroethyl trifluoromethanesulfonate (1.92 g, 8.98 mmol, 1.10 equiv.) was added slowly at the same temperature. Then it was slowly raised to room temperature and stirred for 2 h. After completion of the reaction (monitored by TLC), it was diluted with ice cold water (20 mL) and MTBE (40 mL). The organic layer was separated, washed with water (2×20 mL), dried over Na$_2$SO$_4$, filtered and concentrated in vacuum. Column chromatographic purification (eluting with 5% EA/hexanes to 10% EA/hexanes) of this crude led to 7-Bromo-4-chloro-1-(2,2-difluoroethyl)-1H-indazol-3-amine as a light yellow solid. Yield: 1.8 g, 71%; $^1$H NMR (400 MHz, DMSO-d$_6$): δ7.53 (d, J=8.0 Hz, 1H), 6.94 (d, J=8.0 Hz, 1H), 6.30 (tt, J$_1$=3.9 Hz, J$_2$=7.7 Hz, J$_3$=55.2 Hz, 1H), 5.61 (s, 2H), 4.92 (td, J$_1$=3.8 Hz, J$_2$=14.1 Hz, 2H).

Step-5: Synthesis of N-(7-bromo-4-chloro-1-(2,2-difluoroethyl)-1H-indazol-3-yl)methane Sulphonamide

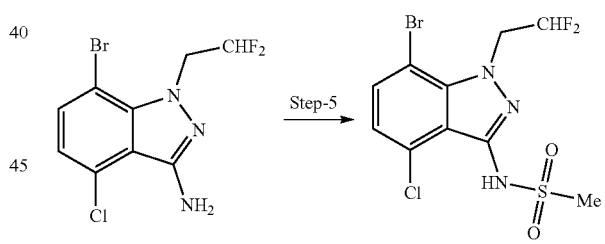

To a stirred solution of 7-Bromo-4-chloro-1-(2,2-difluoroethyl)-1H-indazol-3-amine (0.5 g, 1.61 mmol, 1.0 equiv.) in dry DCM (5 mL) was added DIPEA (0.84 mL, 4.83 mmol, 3.0 equiv.) and DMAP (0.98 mg, 0.08 mmol, 0.05 equiv.). After being stirred for 10-15 min, the reaction mixture was cooled to 0° C. and methanesulfonyl chloride (0.38 mL, 4.83 mmol, 3.0 equiv.) was added slowly. Then it was stirred at room temperature for 2 h. After completion of the reaction (monitored by TLC), it was diluted with DCM (2×10 mL) and water (10 mL). The organic layer was separated and washed with water (2×10 mL), brine (5 mL), dried over Na$_2$SO$_4$, filtered and concentrated in vacuum. The residue obtained was dissolved in ethanol (8 mL) and added with 10 N NaOH (10 mL) solution. The reaction mixture was stirred at room temperature for 2 h. After the removal of one of two mesyl groups (monitored by TLC), it was diluted with water (10 mL) and acidified with 1.0 N HCl (pH~2-3). The obtained solids were filtered, washed with water and dried under vacuum. Column chromatographic purification (eluting with 20% EA/hexanes to 40% EA/hexanes) of this crude material afforded the pure N-(7-Bromo-4-chloro-1-(2,2-difluoroethyl)-1H-indazol-3-yl)methane sulfonamide as a light yellow solid. Yield: 0.40 g, 64%

N-(7-bromo-4-chloro-1-(2,2-difluoroethyl)-1H-indazol-3-yl)-N-(4-methoxybenzyl)methanesulfonamide

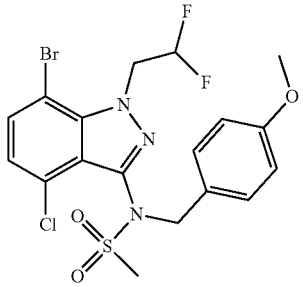 [SMILES: COc1ccc(CN(c2nn(CC(F)F)c3c(Br)ccc(Cl)c23)S(C)(=O)=O)cc1]

4-methoxybenzyl chloride (0.250 ml, 1.853 mmol) was added to a mixture of N-(7-bromo-4-chloro-1-(2,2-difluoroethyl)-1H-indazol-3-yl)methanesulfonamide (0.600 g, 1.54 mmol) and Cs$_2$CO$_3$ (1.006 g, 3.09 mmol) in DMF (6.2 ml). The mixture was stirred at rt overnight. The mixture was diluted with ethyl acetate, washed with brine, dried over Na$_2$SO$_4$ and concentrated. The residue was purified on silica (80 g Isco column) using 0-60% ethyl acetate in hexanes to give a viscous yellow oil (0.73 g). $^1$H NMR (400 MHz, CDCl$_3$) δ7.54-7.48 (m, 1H), 7.25-7.21 (m, 2H), 7.10-7.04 (m, 1H), 6.83-6.77 (m, 2H), 6.26-5.92 (m, 1H), 5.43-5.28 (m, 1H), 5.08-4.91 (m, 2H), 4.83-4.69 (m, 1H), 3.80-3.76 (m, 3H), 3.03-2.98 (m, 3H). LC/MS: m/z=531.9 [M+Na]$^+$.

N-(4-chloro-1-(2,2-difluoroethyl)-7-((diphenylmethylene)amino)-1H-indazol-3-yl)-N-(4-methoxybenzyl)methanesulfonamide

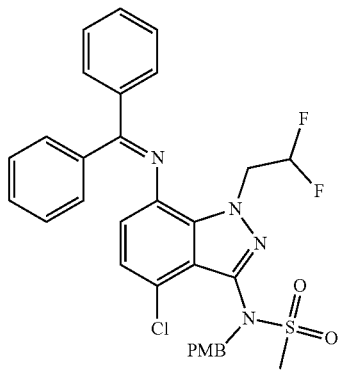

A mixture of N-(7-bromo-4-chloro-1-(2,2-difluoroethyl)-1H-indazol-3-yl)-N-(4-methoxybenzyl)methanesulfonamide (0.73 g, 1.435 mmol), diphenylmethanimine (0.266 mL, 1.583 mmol), PdOAc$_2$ (0.016 g, 0.072 mmol), R-(+)-BINAP (0.134 g, 0.215 mmol) and Cs$_2$CO$_3$ (0.701 g, 2.152 mmol) in Dioxane (14.4 mL) was degassed for 5 min and heated (heating block) at 95° C. for 2 h, filtered through a plug of Celite and concentrated. The residue was purified on silica gel (220 g Isco column) using 0-40% ethyl acetate, the desired fractions were concentrated to give a bright yellow solid (0.74 g). LC/MS: m/z=609.1 [M+H]$^+$.

N-(7-amino-4-chloro-1-(2,2-difluoroethyl)-1H-indazol-3-yl)-N-(4-methoxybenzyl)methanesulfonamide

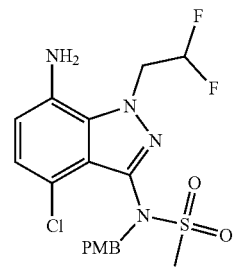

To a bright yellow solution of N-(4-chloro-1-(2,2-difluoroethyl)-7-((diphenylmethylene)amino)-1H-indazol-3-yl)-N-(4-methoxybenzyl)methanesulfonamide (0.74 g, 1.215 mmol) in THF (12 mL) was added HCl (3.0 mL, 12 mmol) and water (0.11 mL) (it was slightly exothermic at rt). The resulting dark orange solution was stirred at rt for 2 h, at which point it turned into a light-yellow solution. The reaction mixture was concentrated and the residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a brown foamy solid (0.48 g). LC/MS: m/z=445.1 [M+H]$^+$.

N-(7-amino-4-chloro-1-(2,2-difluoroethyl)-1H-indazol-3-yl)-N-(4-methoxybenzyl)methanesulfonamide

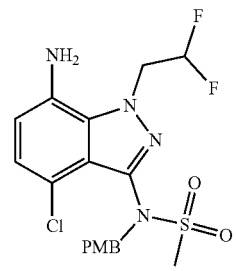

To a bright yellow solution of N-(4-chloro-1-(2,2-difluoroethyl)-7-((diphenylmethylene)amino)-1H-indazol-3-yl)-N-(4-methoxybenzyl)methanesulfonamide (0.74 g, 1.215 mmol) in THF (12.15 ml) was added HCl (3 mL, 12.15 mmol) and water (0.11 mL, 6.07 mmol) (it was slightly exothermic at rt). The resulting dark orange solution was stirred at rt for 2 h (it turned into a light yellow solution). The reaction mixture was concentrated and the residue was taken up in ethyl acetate, washed with 2 M K$_3$PO$_4$, dried over MgSO$_4$ and concentrated. The residue was purified on silica (80 g Isco column) using 0-60% ethyl acetate in hexanes. The desired fractions were concentrated to give a brown foamy solid (0.48 g).

N-(7-bromo-4-chloro-1-(2,2-difluoroethyl)-1H-indazol-3-yl)methanesulfonamide

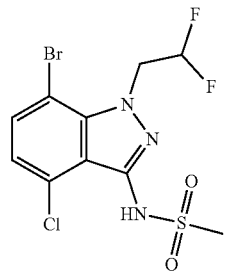 [SMILES: CS(=O)(=O)Nc1nn(CC(F)F)c2c(Br)ccc(Cl)c12]

To a 100 mL pressure bottle under $N_2$ was added N-(4-chloro-1-(2,2-difluoroethyl)-7-(4,4,5,5-tetramethyl-1,3,2-dioxaborolan-2-yl)-1H-indazol-3-yl)methane sulfonamide (0.4 g, 0.918 mmol) and Methanol (16.8 mL). The resulting suspension was then treated with a solution of copper(II) bromide (0.619 g, 2.77 mmol) dissolved in Water (5.1 mL). The reaction was sealed and placed in an oil bath and heated at 80° C. for 10 h. The reaction mixture was diluted with water and extracted with EtOAc, dried with $MgSO_4$, filtered and concentrated to produce a brown solid. The residue was purified on silica (40 g Isco column) using 0-50% ethyl acetate in hexanes. The desired fractions were concentrated to give a light pink solid (0.3 g). $^1$H NMR (500 MHz, $CDCl_3$) δ7.60-7.49 (m, 1H), 7.48-7.36 (m, 1H), 7.08-6.94 (m, 1H), 6.40-5.99 (m, 1H), 5.25-5.04 (m, 2H), 3.51-3.35 (m, 3H). LC/MS: m/z=387.7[M+H]$^+$.

N-(7-bromo-4-chloro-1-(2,2-difluoroethyl)-1H-indazol-3-yl)cyclopropanesulfonamide

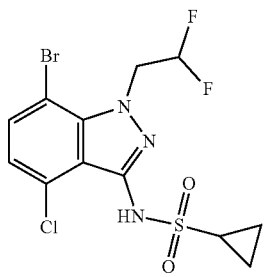 [SMILES: O=S(=O)(Nc1nn(CC(F)F)c2c(Br)ccc(Cl)c12)C1CC1]

To a 100 mL pressure bottle under $N_2$ was added N-(4-chloro-1-(2,2-difluoroethyl)-7-(4,4,5,5-tetramethyl-1,3,2-dioxaborolan-2-yl)-1H-indazol-3-yl)cyclopropanesulfonamide (1.9 g, 4.12 mmol) and Methanol (34 mL). The resulting suspension was then treated with a solution of copper(II) bromide (2.78 g, 12.43 mmol) dissolved in Water (10 mL). The reaction was sealed and placed in an oil bath and heated at 80° C. for 10 h. The reaction mixture was diluted with water and extracted with EtOAc, dried with $MgSO_4$, filtered, then concentrated give a light pink solid (1.71 g, used as is). $^1$H NMR (400 MHz, $CDCl_3$) δ7.61-7.49 (m, 1H), 7.44-7.35 (m, 1H), 7.02 (d, J=8.1 Hz, 1H), 6.37-5.98 (m, 1H), 5.26-5.07 (m, 2H), 3.07-2.91 (m, 1H), 1.45-1.37 (m, 2H), 1.18-1.06 (m, 2H). LC/MS: m/z=414.0 [M+H]$^+$.

N-(7-bromo-4-chloro-1-(2,2-difluoroethyl)-1H-indazol-3-yl)-N-(4-methoxybenzyl)methanesulfonamide

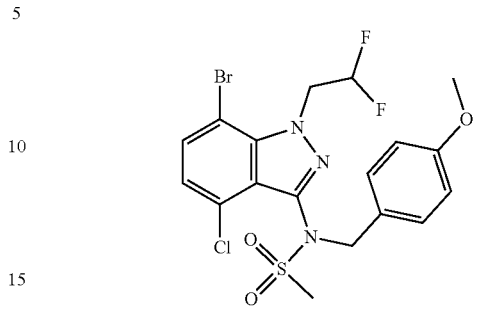

4-Methoxybenzyl chloride (0.250 ml, 1.853 mmol) was added to a mixture of N-(7-bromo-4-chloro-1-(2,2-difluoroethyl)-1H-indazol-3-yl)methanesulfonamide (0.6 g, 1.544 mmol) and $Cs_2CO_3$ (1.006 g, 3.09 mmol) in DMF (6.2 mL). The mixture was stirred at rt overnight. The mixture was diluted with ethyl acetate, washed with brine, dried over $Na_2SO_4$ and concentrated. The residue was purified on silica (80 g Isco column) using 0-60% ethyl acetate in hexanes. The desired fractions were concentrated to give a viscous yellow oil (0.73 g). LC/MS: m/z=507.9 [M+H]$^+$.

N-(7-bromo-4-chloro-1-(2,2-difluoroethyl)-1H-indazol-3-yl)-N-(4-methoxybenzyl)cyclopropanesulfonamide

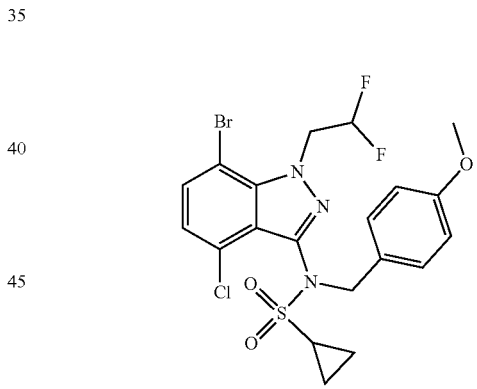

4-Methoxybenzyl chloride (0.668 ml, 4.95 mmol) was added to a mixture of N-(7-bromo-4-chloro-1-(2,2-difluoroethyl)-1H-indazol-3-yl)cyclopropanesulfonamide (1.71 g, 4.12 mmol) and $Cs_2CO_3$ (2.69 g, 8.25 mmol) in DMF (16.50 mL). The mixture was stirred at rt overnight. The mixture was diluted with ethyl acetate, washed with brine, dried over $Na_2SO_4$ and concentrated. The residue was purified on silica (220 g Isco column) using 0-60% ethyl acetate in hexanes. The desired fractions were concentrated to give a sticky white solid. $^1$H NMR (400 MHz, $CDCl_3$) δ7.51-7.44 (m, 1H), 7.27-7.23 (m, 2H), 7.06-7.00 (m, 1H), 6.80-6.73 (m, 2H), 6.24-5.88 (m, 1H), 5.37-4.82 (m, 4H), 3.79-3.72 (m, 3H), 2.69-2.58 (m, 1H), 1.24-1.13 (m, 2H), 1.08-0.99 (m, 2H). LC/MS: m/z=535.7 [M+2H]$^+$.

61

N-(4-chloro-1-(2,2-difluoroethyl)-7-((diphenylmethylene)amino)-1H-indazol-3-yl)-N-(4-methoxybenzyl)methanesulfonamide

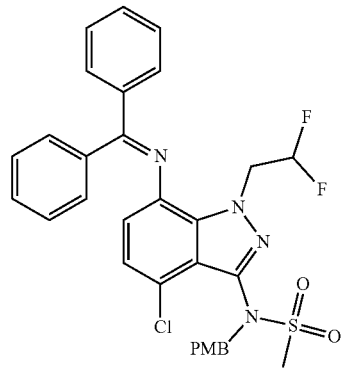

A mixture of N-(7-bromo-4-chloro-1-(2,2-difluoroethyl)-1H-indazol-3-yl)-N-(4-methoxybenzyl)methanesulfonamide (0.73 g, 1.435 mmol), diphenylmethanimine (0.27 ml, 1.583 mmol), PdOAc₂ (0.016 g, 0.072 mmol), R-(+)-BINAP (0.134 g, 0.215 mmol) and Cs₂CO₃ (0.701 g, 2.152 mmol) in Dioxane (14.4 mL) was degassed for 5 min and heated (heating block) at 95° C. for 2 h. The reaction mixture was purified on silica gel (220 g Isco column) using 0-40% ethyl acetate, the desired fractions were concentrated to give a bright yellow solid (0.74 g). LC/MS: m/z=609.1 [M+H]⁺.

N-(4-chloro-1-(2,2-difluoroethyl)-7-((diphenylmethylene)amino)-1H-indazol-3-yl)-N-(4-methoxybenzyl)cyclopropanesulfonamide

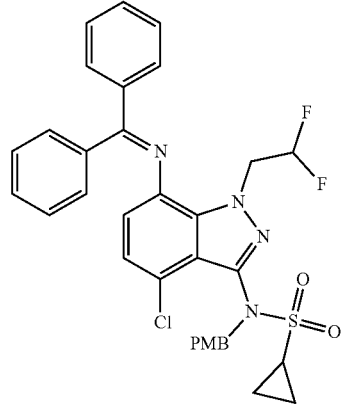

A mixture of N-(7-bromo-4-chloro-1-(2,2-difluoroethyl)-1H-indazol-3-yl)-N-(4-methoxybenzyl)cyclopropanesulfonamide (0.83 g, 1.552 mmol), diphenylmethanimine (0.287 ml, 1.712 mmol), PdOAc₂ (0.017 g, 0.078 mmol), R-(+)-BINAP (0.145 g, 0.233 mmol) and Cs₂CO₃ (0.758 g, 2.328 mmol) in Dioxane (13 mL) was degassed for 5 min and heated in a microwave at 120° C. for 2 h. The reaction mixture filtered through Celite and concentrated. The residue was purified on silica gel (220 g Isco column) using 0-30% ethyl acetate, the desired fractions were concentrated to give a bright yellow solid (0.85 g). LC/MS: m/z=635.3 [M+H]⁺.

62

N-(7-amino-4-chloro-1-(2,2-difluoroethyl)-1H-indazol-3-yl)-N-(4-methoxybenzyl)cyclopropanesulfonamide

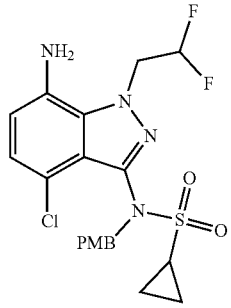

Prepared according to the general procedure described for the preparation of N-(7-amino-4-chloro-1-(2,2-difluoroethyl)-1H-indazol-3-yl)-N-(4-methoxybenzyl)methanesulfonamide using N-(4-chloro-1-(2,2-difluoroethyl)-7-((diphenylmethylene)amino)-1H-indazol-3-yl)-N-(4-methoxybenzyl)cyclopropanesulfonamide. LC/MS: m/z=471.1 [M+H]⁺.

Example 8

Preparation of N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

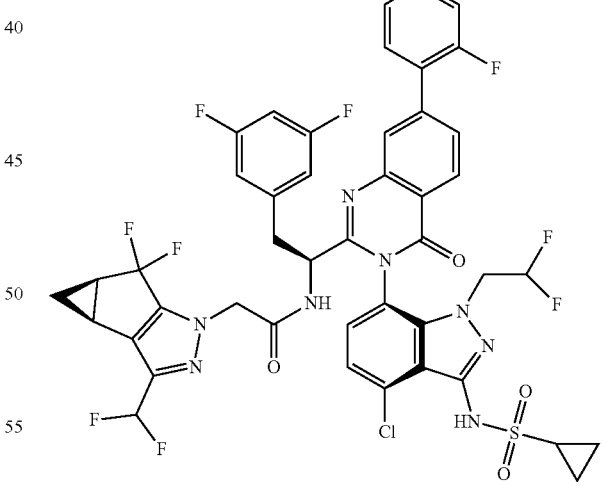

Synthetic Scheme for Preparation of Example 8

Experimental Procedure 3-amino-2'-fluoro-[1,1'-biphenyl]-4-carboxylic acid

To a solution of 2-amino-4-bromobenzoic acid (10 g, 46.3 mmol) in DME (200 mL) was added (2-fluorophenyl)

boronic acid (7.77 g, 55.5 mmol), sodium carbonate (1M Aq. solution) (94 mL, 94 mmol) at 26° C. in a sealed tube under Nitrogen atmosphere. The reaction mixture was degassed with N2 bubbling for 10 min, followed by addition Pd(PPh3)4 (5.35 g, 4.63 mmol) and later heated at 90° C. for 16 h. The progress of the reaction was monitored by TLC (SiO2, 10% MeOH/DCM, Rf=0.2). On completion, the reaction mixture was diluted with water (200 mL) and extracted with EtOAc (2×250 mL). The combined organic layers were dried over Na2SO4, filtered and concentrated under reduced pressure to afford the crude compound as a brown liquid. The above crude compound was purified by grace column chromatography with 50-75% EtOAC/Pet. The fractions containing product were collected and concentrated under reduced pressure to afford 3-amino-2'-fluoro-[1,1'-biphenyl]-4-carboxylic acid, 6 g, Yield: 55%, Off white solid). 1H NMR (400 MHz, DMSO-d6) δ=9.06-8.23 (m, 2H), 7.77 (d, J=8.2 Hz, 1H), 7.53-7.40 (m, 2H), 7.34-7.26 (m, 2H), 6.95-6.90 (m, 1H), 6.73-6.64 (m, 1H), LCMS: RT=2.29 min, (M+H)=232.21, LCMS Purity=99%.

(S)-tert-butyl(1-(3-(4-chloro-1-(2,2-difluoroethyl)-3-(N-(4-methoxybenzyl) cyclopropanesulfonamido)-1H-indazol-7-yl)-7-(2-fluorophenyl)-4-oxo-3,4-dihydroquinazolin-2-yl)-2-(3,5-difluorophenyl)ethyl) carbamate To a stirred solution of (S)-2-((tert-butoxycarbonyl) amino)-3-(3,5-difluorophenyl)propanoic acid (1.2 g, 3.98 mmol), 3-amino-2'-fluoro-[1,1'-biphenyl]-4-carboxylic acid (0.936 g, 3.99 mmol) and N-(7-amino-4-chloro-1-(2,2-difluoroethyl)-1H-indazol-3-yl)-N-(4-methoxybenzyl) cyclopropanesulfonamide (2.080 g, 4.38 mmol) in pyridine (10 mL) was added diphenyl phosphite (2.70 mL, 13.94 mmol) at 26° C. The reaction mixture was degassed with N2 bubbling before each addition of reagents. The reaction was heated at 70° C. for 16 h. The progress of the reaction was monitored by TLC (SiO2, 50% EtOAc/Pet. Rf=0.5). After the completion, the reaction mixture was evaporated under reduced pressure to get crude Compound. The crude compound was purified by column chromatography using silica gel (100-200 mesh), eluted with 18-20% EtOAc/pet ether. The fraction containing the product were collected and evaporated under reduced pressure to afford the compound as a yellow solid (LCMS: 59%). The compound was further purified by Prep-HPLC. MOBILE PHASE A: 0.01 m ammonium bicarbonate (aq). MOBILE PHASE B: Acetonitrile. Column: xbridge C18 (150*19) mm, 5u, Method: (T/% B): 0/60, 2/60, 10/70 Flow: 16 ml/Min, Solubility: ACN+THF+Water Temp: Ambient Collected pure fractions were evaporated under reduced pressure to afford tert-butyl (S)-(1-(3-(4-chloro-1-(2,2-difluoroethyl)-3-(N-(4-methoxybenzyl)cyclopropanesulfonamido)-1H-indazol-7-yl)-7-(2-fluorophenyl)-4-oxo-3,4-dihydroquinazolin-2-yl)-2-(3,5-difluorophenyl)ethyl) carbamate (N66156-54-A3, 0.9 g, yield: 23%) as a pale yellow solid. 1H NMR (400 MHz, DMSO-d6) δ=8.34-8.23 (m, 1H), 8.10-7.93 (m, 1H), 7.87-7.74 (m, 2H), 7.70-7.65 (m, 1H), 7.60-7.49 (m, 2H), 7.46-7.37 (m, 2H), 7.32-7.22 (m, 1H), 7.11-6.97 (m, 2H), 6.87-6.70 (m, 1H), 6.65-6.48 (m, 3H), 6.40-6.00 (m, 1H), 4.94-4.76 (m, 2H), 4.57-4.42 (m, 1H), 4.26-3.96 (m, 3H), 3.75-3.61 (m, 2H), 3.49-3.41 (m, 1H), 3.17 (d, J=5.2 Hz, 2H), 3.06-2.80 (m, 2H), 1.20 (s, 7H), 1.09-0.89 (m, 4H), 0.60-0.51 (m, 1H) LCMS: RT=2.66 min, (M+H)=949.14, LCMS Purity=97%.

(S)-N-(7-(2-(1-amino-2-(3,5-difluorophenyl) ethyl)-7-(2-fluorophenyl)-4-oxoquinazolin-3(4H)-yl)-4-chloro-1-(2,2-difluoroethyl)-1H-indazol-3-yl)cyclopropanesulfonamide To a stirred solution of tert-butyl (S)-(1-(3-(4-chloro-1-(2,2-difluoroethyl)-3-(N-(4-methoxybenzyl)cyclopropanesulfonamido)-1H-indazol-7-yl)-7-(2-fluorophenyl)-4-oxo-3,4-dihydroquinazolin-2-yl)-2-(3,5-difluorophenyl)ethyl) carbamate (0.9 g, 0.936 mmol) in DCM (20 mL) was added TFA (10 mL, 130 mmol) at 25° C. under N2 atmosphere and stirred for 10 min, followed by addition of trifluoromethanesulfonic acid (0.5 mL, 5.63 mmol). The reaction mixture was stirred for 1 h at 25° C. The progress of the reaction was monitored by TLC (SiO2, 10% MeOH/DCM, Rf=0.2). The solvent was removed under a gentle stream of nitrogen. The residue was dissolved in EtOAc (10 mL) and was washed with aq sat.NaHCO3 (2×5 mL), brine (5 mL), dried over Na2SO4, filtered and evaporated to dryness to afford crude compound as an off white solid (700 mg). The crude was purified by prep HPLC. Mobile phase A: 10 mM Ammonium bicarbonate (aq); Mobile phase B: Acetonitrile; COLUMN: Puritasc18 (150*25) mm, 10u; FLOW: 25 ml/min; METHOD: (T/% B): 0/60,20/60,20.1/98,23/98,23.1/60,25/60; SOLUBILITY: ACN+THF+H20; TEMPERATURE: AMBIENT Collected pure fractions were evaporated under reduced pressure to afford the desired material (390 mg, LCMS: 98.72%) which was submitted for prep-SFC for the separation of isomers Column/dimensions: Chiralpak OJ-H (30×250 mm), 5µ
% CO2: 85.0%
% Co solvent: 15.0% (100% Methanol)
Total Flow: 90.0 g/min
Back Pressure: 100.0 bar
UV: 250 nm
Stock time: 10.5 min
Load/Inj: 17 mg
Solubility: 35 mL Methanol
No of injections: 26
Instrument details: Make/Model: SFC-PIC-002
Two peaks were collected separately and evaporated under reduced pressure.

The major peak was evaporated under reduced pressure to afford (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (N66157-58-A3, 170 mg, yield: 24.47%) as an off white solid.

1H NMR (400 MHz, DMSO-d6) δ=8.29-8.25 (m, 1H), 8.00-7.98 (m, 1H), 7.84-7.80 (m, 1H), 7.78-7.71 (m, 1H), 7.59-7.39 (m, 5H), 7.04-6.94 (m, 1H), 6.73 (br d, J=6.7 Hz, 2H), 6.48-6.15 (m, 1H), 4.54-4.25 (m, 2H), 3.59-3.49 (m, 1H), 3.30-3.26 (m, 1H), 2.98-2.90 (m, 1H), 2.88-2.81 (m, 1H), 1.28-1.20 (m, 2H), 1.07-0.98 (m, 4H). LCMS: RT=2.32 min, (M+H)=729.35, LCMS Purity=98%, HPLC Purity=98%, Chiral HPLC Purity=99%.

N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide To a solution of ((S)-N-(7-(2-(1-amino-2-(3,5-difluorophenyl)ethyl)-7-(2-fluorophenyl)-4-oxoquinazolin-3(4H)- yl)-4-chloro-1-(2,2-difluoroethyl)-1H-indazol-3-yl)cyclopropanesulfonamide (150 mg, 0.206 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (54.3 mg, 0.206 mmol) and HOBt (12.60 mg, 0.082 mmol) in N,N-Dimethylformamide (DMF) (10 mL), were added N-Methylmorpholine (0.045 mL, 0.411 mmol) and N-(3-Dimethylaminopropyl)-N'-ethylcarbodiimide hydrochloride (71.0 mg, 0.370 mmol) at 27° C. The reaction mixture was degassed for 10 mins with N2 and later stirred at 27° C. for 16 h. The progress of the reaction was monitored by TLC (SiO2, 50% EtOAc/Pet. Rf=0.3). The reaction mixture was diluted with ice cold water (50 mL), stirred for 30 min at 27° C. The precipitated solid was filtered and dried under vacuum to get crude Compound as an off white solid. Which was further purified by prep-SFC
Column/dimensions: R, R WHELK (30×250 mm), 5μ
% CO2: 60.0%
% Co solvent: 40.0% (100% Methanol)
Total Flow: 100.0 g/min
Back Pressure: 100.0 bar
UV: 214 nm
Stock time: 26 min
Load/Inj: 25 mg
Solubility: Methanol
Of injections: 7
Instrument details: Make/Model: SFC-PIC-002

Collected pure fractions were evaporated under reduced pressure to get the product as an off white solid (we observed solvent peaks in 1H NMR). To remove the residual solvent peaks the product was lyophilized to afford pure N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (110 mg, yield: 54.7%, off white solid).

1H NMR (400 MHz, DMSO-d6) δ=10.00-9.87 (m, 1H), 9.23-9.18 (m, 1H), 8.30 (d, J=8.1 Hz, 1H), 7.99-7.97 (m, 1H), 7.86-7.83 (m, 1H), 7.76-7.71 (m, 2H), 7.59-7.54 (m, 1H), 7.51-7.40 (m, 3H), 7.07-6.89 (m, 2H), 6.66-6.57 (m, 2H), 6.29-5.95 (m, 1H), 4.76-4.69 (m, 1H), 4.64-4.57 (m, 1H), 4.48-4.41 (m, 1H), 4.31-4.17 (m, 1H), 4.01-3.87 (m, 1H), 3.41-3.34 (m, 1H), 3.03-2.95 (m, 1H), 2.91-2.83 (m, 1H), 2.48-2.41 (m, 2H), 1.38-1.29 (m, 1H), 0.98-0.83 (m, 5H). LCMS: RT=6.72 min, (M+H)=975.0, LCMS Purity=99%, HPLC Purity=99%, Chiral HPLC Purity=99%.

The general procedures and general purification methods used to prepare examples 9-114 follow and the experimental procedure supplied for each specific example identifies the general method used to prepare and purify that compound.

General Procedure A:

To a vial equipped with a stir bar was added N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 25-50 mg), tribasic potassium phosphate (3 equiv), dichloro[9,9-dimethyl-4,5-bis(diphenylphosphino)xanthene]palladium(II) (0.05-0.10 equiv), and the appropriate boronic acid/boronic ester (1.5-3 equiv). The vial was sealed with a septum cap, and then was purged with argon. To the vial was added THF:water (4:1) to afford a reaction volume 0.05M in bromide. The reaction was stirred at either ambient temperature (16-48 h) or 55-60° C. (16 h). Upon cooling to ambient temperature, the reaction mixture was concentrated in vacuo and the resulting residue was subjected to HPLC purification to afford the indicated product. Alternately, the reaction may be run under ambient atmosphere. Alternately, the reagents may be combined using stock solutions of THF and water to achieve the final concentrations indicated. Alternately, (R)-N-(1-(7-bromo-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide or N-((R)-1-(7-bromo-3-(4-(morpholinosulfonyl)phenyl)-4-oxo-3,4-dihydroquinazolin-2-yl)-2-(3,5-difluorophenyl)ethyl)-2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamide may be substituted for N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

General Procedure B:

To a vial equipped with a stir bar was added N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 25-50 mg), tribasic potassium phosphate (3 equiv), dichloro[9,9-dimethyl-4,5-bis(diphenylphosphino)xanthene]palladium(II) (0.05 equiv), and the appropriate aryl/heteroaryl halide (2-3 equiv). The vial was sealed with a septum cap and then was purged with argon. To the vial was added THF:water (4:1) to afford a reaction volume 0.05M in boronic ester. The reaction mixture was stirred at room 20-60° C. for 16-24 h. Upon cooling to ambient temperature, the reaction mixture was concentrated in vacuo and the resulting residue was subjected to HPLC purification to afford the indicated product. Alternately, the reaction may be run under ambient atmosphere. Alternately, the reagents may be combined using stock solutions of THF and water to achieve the final concentrations indicated. Alternately, (S)-2-(3-cyclopropyl-1H-pyrazol-1-yl)-N-(2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide or 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide may be substituted for N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

General Procedure C:

To vial equipped with a stir bar and placed under argon atmosphere was added N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 25-50 mg), the appropriate aryl halide/heteroaryl halide (3 equiv), potassium acetate (2.6 equiv) and Pd(PPh$_3$)$_4$ (0.2 equiv). The vial was sealed with a septum capped. To the vial was added 1,4-dioxane:water (4:1) to afford a reaction volume 0.05M in boronic ester. The reaction solution was degassed with argon. The reaction mixture was stirred at 90° C. for 5 h or 16 h. Upon cooling to ambient temperature, the reaction mixture was concentrated in vacuo and the resulting residue was subjected to HPLC purification to afford the indicated product. Alternately, (S)-2-(3-cyclopropyl-1H-pyrazol-1-yl)-N-(2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide or 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide may be substituted for N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

General Procedure D:

To a vial equipped with a stir bar and placed under argon atmosphere was added Pd(OAc)$_2$ (0.1 equiv), dicyclohexyl(2',6'-dimethoxy-[1,1'-biphenyl]-2-yl)phosphane (0.2 equiv), tribasic potassium phosphate (3 equiv), N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 25-50 mg), and the appropriate aryl/heteroaryl halide (3 equiv). The vial was sealed with a septum cap. To the vial was added THF:water (4:1) to afford a reaction volume 0.05M in boronic ester. The reaction mixture was degassed with argon, then the reaction mixture was stirred at either ambient temperature or 45° C. for 16 to 48 h. Upon cooling to ambient temperature, the reaction mixture was concentrated in vacuo and the resulting residue was subjected to HPLC purification to afford the indicated product. Alternately, (S)-2-(3-cyclopropyl-1H-pyrazol-1-yl)-N-(2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide or 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide may be substituted for N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

HPLC Purification:

HPLC purification was performed using one of the conditions indicated below, optionally followed by a second HPLC purification using a different condition indicated below. Based on analytical HPLC data obtained on the crude reaction mixture, the purification condition was optimized for each target compound by modifying the initial Solvent A:Solvent B ratio, the gradient time, the final Solvent A:Solvent B ratio, and the hold time at the final Solvent A:Solvent B concentration.

HPLC Condition A: Column: Zorbax Eclipse Plus C18, 21.2×100 mm, 5 μm particles; Solvent A=0.1% Formic Acid in 100% Water. Solvent B=Acetonitrile. Flow Rate=40 mL/min. Wavelength=215 and 254 nm. ESI+Range: 150 to 1500 dalton.

HPLC Condition B: Column: Sunfire prep C18 OBD, 30×100 mm, 5 μm particles; Solvent A: water:MeCN 95:5 w/0.1% TFA, Solvent B: MeCN:water 95:5 w/0.1% TFA. Flow Rate=42 mL/min. Wavelength=220 and 254 nm.

HPLC Condition C: Column: Waters Xterra C18, 19×100 mm, 10 μm particles; Solvent A=0.1% NH4OH in 100% Water. Solvent B=Acetonitrile. Flow Rate=40 mL/min. Wavelength=215 and 254 nm. ESI+Range: 150 to 1500 dalton.

General LCMS Analysis Methods:

LCMS Method A:

Wavelength1: 220 nm, Wavelength2: 254 nm, Injection Vol.: 5.00 Stop Time: 4.00, Grad. Time: 3.0, Start % B: 0, End % B: 100, Total Flow: 0.80 ml/min, Solvent A: 95:5 Water:MeCN 0.1% TFA, Solvent B: 5:95 Water:MeCN 0.1% TFA, Column: Acquity UPLC BEH C18, 2.1×50 mm, 1.7 μm particles.

LCMS Method B:

Wavelength1: 220 nm, Wavelength2: 254 nm, Injection Vol.: 5.00 Stop Time: 4.00, Grad. Time: 3.0, Start % B: 20, End % B: 100, Total Flow: 1.20 ml/min, Solvent A: 95:5 Water:MeCN 0.1% TFA, Solvent B: 5:95 Water:MeCN 0.1% TFA, Column: Acquity UPLC BEH C18, 2.1×50 mm, 1.7 μm particles.

LCMS Method C:

Column: Acquity UPLC BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.6 min, then a 0.25 min hold at 95% B. Wavelength=215 nm.

LCMS Method D:

Column: Waters XTerra C18, 4.6×50 mm, 5 μm particles; Solvent A=0.1% NH4OH in 100% Water. Solvent B=Acetonitrile. Flow Rate=2.5 mL/min. Start % B=5. Final % B=95. Gradient Time=4 min, then a 1 min hold at 95% B. Wavelength=215 nm and 254 nm.

Preparation of tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate

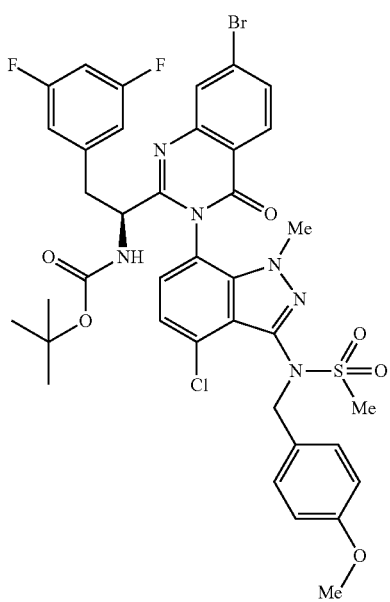 [SMILES: COc1ccc(CN(c2nn(C)c3c(-n4c([C@H](Cc5cc(F)cc(F)c5)NC(=O)OC(C)(C)C)nc5cc(Br)ccc5c4=O)ccc(Cl)c23)S(C)(=O)=O)cc1]

To a solution of (S)-2-((tert-butoxycarbonyl)amino)-3-(3,5-difluorophenyl)propanoic acid (3.82 g, 12.66 mmol), 2-amino-4-bromobenzoic acid (3.01 g, 13.93 mmol) and N-(7-amino-4-chloro-1-methyl-1H-indazol-3-yl)-N-(4-methoxybenzyl)methanesulfonamide (5 g, 12.66 mmol) in pyridine (50 mL) was added diphenyl phosphite (9.80 mL, 50.6 mmol). The resulting mixture was placed on a preheated oil bath (70° C.) and heated at 70° C. for 16 h. The mixture was cooled to room temperature and then concentrated under reduced pressure. The mixture was then diluted with EtOAc (approximately 500 mL) and washed with aqueous citric acid (0.5M, 2×50 mL), then aqueous NaOH (1M, 3×50 mL), dried over $Na_2SO_4$, filtered, and concentrated. The residue was then purified via silica gel chromatography (330 g silica gel column, gradient of hexanes:EtOAc 0:100→0:50) to afford tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (6.2 g, 7.22 mmol, 57.1% yield) as pale yellow solid foam (inseparable mixture of atropisomers). LC/MS: m/z=801.10 [M-tBu].

Preparation of (S) N (7 (2 (1 amino-2-(3,5-difluorophenyl)ethyl)-7-bromo-4-oxoquinazolin-3(4H)-yl)-4-chloro-1-methyl-1H-indazol-3-yl)methanesulfonamide

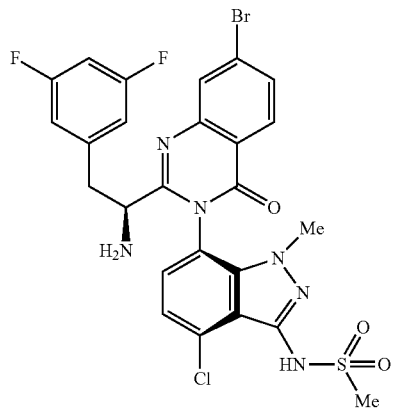

To a stirred solution of tert-butyl (S)-(1-(7-bromo-3-(4-chloro-3-(N-(4-methoxybenzyl)methylsulfonamido)-1-methyl-1H-indazol-7-yl)-4-oxo-3,4-dihydroquinazolin-2-yl)-2-(3,5-difluorophenyl)ethyl)carbamate (6.2 g, 7.22 mmol) in dichloromethane (DCM) (50 mL) was added trifluoroacetic acid (20 mL, 260 mmol) followed by trifluoromethanesulfonic acid (0.770 mL, 8.67 mmol). The resulting dark red solution was stirred at room temperature for 1 h. LCMS at this point indicates two peaks containing the desired product mass, consistent with the presence of two diastereomeric atropisomers (ratio of approximately 30:70). The mixture was concentrated in vacuo and the resulting residue was partitioned between EtOAc (300 mL) and aq. NaOH (1M, 30 mL). The aq. phase was tested and determined to be pH>=8.0. The organic phase was isolated and dried over $Na_2SO_4$, filtered, and then concentrated in vacuo. The residue was purified in three approximately equal portions via C18 chromatography (275 g RediSep Gold Column, Mobile Phase A: 5:95 acetonitrile:water with 0.1% TFA; Mobile Phase B: 95:5 acetonitrile:water with 0.1% TFA; gradient of 10-60% B over 30 min). Fractions containing the major atropisomer (second eluting) were combined, adjusted to pH 8 via addition of aq. 1M NaOH; extracted with ethyl acetate; washed with brine (sat. aq. NaCl); dried over $Na_2SO_4$; filtered; and then concentrated to afford the desired major atropisomer (S)-N-(7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (2.4 g, 3.76 mmol, 52% yield). $^1$H NMR (500 MHz, DMSO-$d_6$) δ ppm 8.11 (d, J=8.55 Hz, 1H), 8.06 (d, J=1.53 Hz, 1H), 7.81 (dd, J=8.55, 1.83 Hz, 1H), 7.33 (s, 2H), 6.96-7.05 (m, 1H), 6.75 (br d, J=7.02 Hz, 2H), 3.67 (s, 3H), 3.56 (dd, J=7.63, 5.19 Hz, 1H), 3.25-3.29 (m, 1H), 3.21 (s, 3H), 2.81 (dd, J=13.43, 8.24 Hz, 1H). LCMS: m/z=637.05 [M+H]$^+$.

Preparation of N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

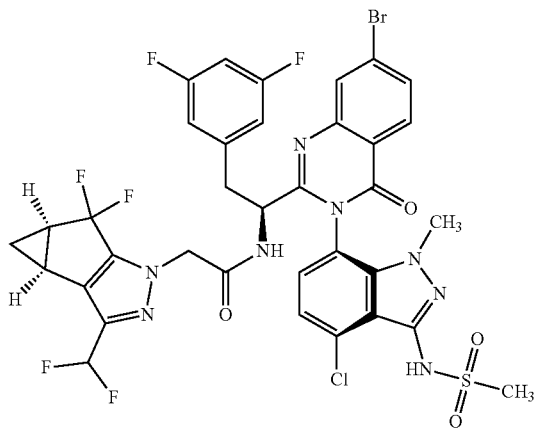

To a solution of (S)-N-(7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (2.08 g, 3.26 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.861 g, 3.26 mmol) and diisopropylethylamine ("DIPEA") (1.709 mL, 9.78 mmol) in tetrahydrofuran (THF) (30 mL) was added HATU (1.364 g, 3.59 mmol). The resulting mixture was stirred at room temp for 3 h. To the mixture was added ammonia in methanol (2M, 3 mL). The mixture was stirred at room temp for 30 min. Water was then added and the mixture was extracted with ethyl acetate; washed with brine; dried over $Na_2SO_4$, filtered; and concentrated in vacuo. The resulting residue was subjected to silica gel chromatography (hexanes:EtOAc 100:→30:70) to afford N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (2.5 g, 2.83 mmol, 87% yield). $^1$H NMR (500 MHz, $CDCl_3$) δ ppm 8.18 (d, J=8.24 Hz, 1H), 7.88 (d, J=1.53 Hz, 1H), 7.72 (dd, J=8.55, 1.83 Hz, 1H), 7.33 (s, 1H), 7.16 (d, J=7.63 Hz, 1H), 6.57-6.83 (m, 4H), 6.38 (br d, J=5.80 Hz, 2H), 4.71-4.80 (m, 1H), 4.63 (d, J=6.71 Hz, 2H), 3.56 (s, 3H), 3.40 (s, 3H), 3.18 (dd, J=13.73, 6.10 Hz, 1H), 2.86 (dd, J=13.58, 7.48 Hz, 1H), 2.52-2.61 (m, 1H), 2.41-2.50 (m, 1H), 1.42-1.50 (m, 1H), 1.09-1.16 (m, 1H). LCMS: m/z=883.05 [M+H]$^+$.

Preparation of N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

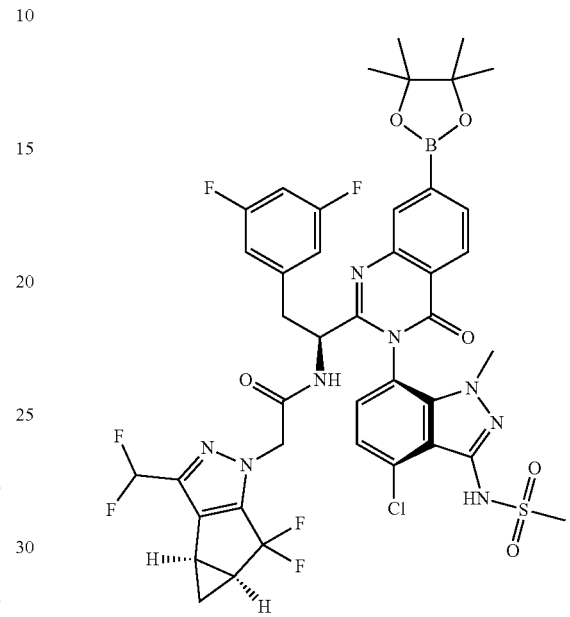

To a round bottom flask equipped with a stir bar was added N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.00 g, 1.13 mmol), 4,4,4',4',5,5,5',5'-octamethyl-2,2'-bi(1,3,2-dioxaborolane) (431 mg, 1.70 mmol), potassium acetate (333 mg, 3.39 mmol), and [1,1'-bis(diphenylphosphino)ferrocene]dichloropalladium(II) ("Pd(dppf)Cl$_2$") (83 mg, 0.113 mmol). The flask was sealed with a rubber septum, and then was placed under an argon atmosphere. To the flask was added dioxane (23 mL). The reaction mixture was degassed with argon, then the reaction mixture was stirred at 60° C. for 16 h. The reaction mixture was concentrated in vacuo and adsorbed onto Celite. The resulting powder was subjected to silica gel chromatography (hexanes:EtOAc 100:0→0:100 over 10 column volumes) to afford N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1.2 g, quantitative yield). LCMS: During LCMS analysis both the boronic acid and boronate were observed. Conditions: Wavelength1: 220 nm, Wavelength2: 254 nm, Injection Vol.: 5.00 μl, Stop Time: 4.00, Grad. Time: 3.0, Start % B: 0, End % B: 100, Total Flow: 0.80 ml/min, Solvent A: 95:5 Water:MeCN 0.1% TFA, Solvent B: 5:95 Water:MeCN 0.1% TFA, Column: Acquity UPLC BEH C18 1.7 um; Result: retention time (boronic acid): 2.112 min., mass found: 849.15 (M+H); retention time (boronic ester): 2.733 min., mass found: 931.25 (M+H). $^1$H NMR (CDCl₃, 500 MHz) δ8.26 (d, 1H, J=7.6 Hz), 8.11 (s, 1H), 7.95 (d, 1H, J=7.6 Hz), 7.3-7.3 (m, 1H), 7.14 (d, 1H, J=7.9 Hz), 6.7-6.7 (m, 3H), 6.35 (d, 2H, J=6.8 Hz), 4.7-4.8 (m, 1H), 4.1-4.2 (m, 1H), 3.70 (s, 1H), 3.47 (s, 3H), 3.37 (s, 3H), 3.1-3.2 (m, 1H), 2.8-2.9 (m, 1H), 2.6-2.7 (m, 1H), 2.3-2.5 (m, 1H), 1.8-1.9 (m, 2H), 1.24 (s, 12H), 1.1-1.2 (m, 1H)

Preparation of (S)-tert-butyl (1-(7-bromo-3-(4-(morpholinosulfonyl)phenyl)-4-oxo-3,4-dihydroquinazolin-2-yl)-2-(3,5-difluorophenyl)ethyl)carbamate

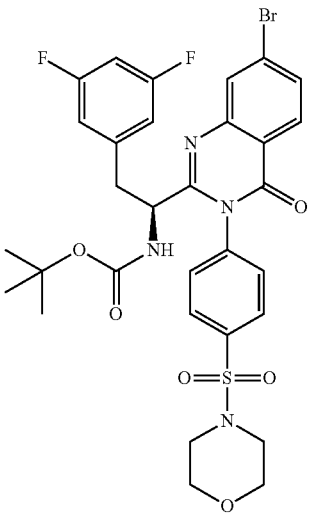 [SMILES: CC(C)(C)OC(=O)N[C@@H](Cc1cc(F)cc(F)c1)c1nc2cc(Br)ccc2c(=O)n1-c1ccc(S(=O)(=O)N2CCOCC2)cc1]

To a 100 mL r.b. flask equipped with a stir bar was added (S)-2-((tert-butoxycarbonyl)amino)-3-(3,5-difluorophenyl)propanoic acid (2.44 g, 8.10 mmol) and 2-amino-4-bromobenzoic acid (3.15 g, 14.58 mmol), then pyridine (31.1 ml), then diphenyl phosphonate (6.27 ml, 32.4 mmol). The solution was stirred at r.t. for 18 h. The reaction mixture was transferred into a 100 mL r.b. flask charged with 4-(morpholinosulfonyl)aniline (2.55 g, 10.53 mmol) and equipped with a stir bar. The amber solution was stirred at r.t. for 3.5 days. The reaction solution was concentrated in vacuo. The amber oil residue was dissolved in EtOAc (250 mL), then transferred to a 500 mL separatory funnel. The organic solution was washed with aq. HCl (1M, 150 mL); then aq. NaOH (1M, 150 mL); then brine (100 mL). The organic solution was dried over MgSO₄, then filtered. The filtrate was concentrated in vacuo. The resulting residue was dissolved in a minimum of acetone and then concentrated onto Celite in vacuo. The resulting powder was subjected to SiO₂ chromatography (220 g silica gel column, gradient=hexanes:EtOAc 100:0→50:50 over 12 column volumes, then hold at 50:50 for 8 column volumes) to afford (S)-tert-butyl (1-(7-bromo-3-(4-(morpholinosulfonyl)phenyl)-4-oxo-3,4-dihydroquinazolin-2-yl)-2-(3,5-difluorophenyl)ethyl)carbamate as a colorless solid foam (2.23 g, 39% yield). ¹H NMR (CDCl₃) δ: 8.11 (d, J=8.5 Hz, 1H), 7.93-7.99 (m, 2H), 7.85 (br d, J=7.0 Hz, 1H), 7.65 (d, J=8.3 Hz, 1H), 7.57 (br d, J=7.9 Hz, 1H), 6.86 (br d, J=7.0 Hz, 1H), 6.68 (br t, J=9.0 Hz, 1H), 6.40 (br d, J=5.8 Hz, 2H), 5.25 (br d, J=8.9 Hz, 1H), 4.56 (br d, J=7.6 Hz, 1H), 3.79 (t, J=4.6 Hz, 4H), 3.05-3.18 (m, 6H), 2.86 (br dd, J=13.1, 6.7 Hz, 1H), 1.37 (br s, 9H).

Preparation of (S)-2-(1-amino-2-(3,5-difluorophenyl)ethyl)-7-bromo-3-(4-(morpholinosulfonyl)phenyl)quinazolin-4(3H)-one

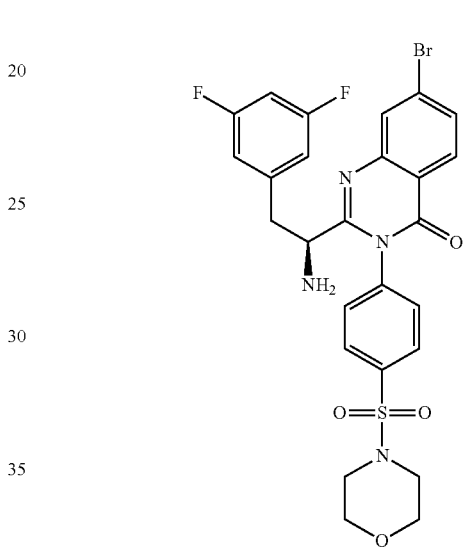

To a round bottom flask equipped with a stir bar and charged with a solution of tert-butyl (S)-(1-(7-bromo-3-(4-(morpholinosulfonyl)phenyl)-4-oxo-3,4-dihydroquinazolin-2-yl)-2-(3,5-difluorophenyl)ethyl)carbamate (1.4 g, 1.984 mmol) in dichloromethane (10 mL) was trifluoroacetic acid (3.06 ml, 39.7 mmol). The solution was stirred at room temperature for 36 h. The resultant pale yellow solution was concentrated in vacuo. The residue was dissolved in ethyl acetate and then was transferred to a separatory funnel. The solution was washed with 1N NaOH (the pH of the aqueous phase was >8); dried over Na₂SO₄; filtered; and then was concentrated in vacuo to afford (S)-2-(1-amino-2-(3,5-difluorophenyl)ethyl)-7-bromo-3-(4-(morpholinosulfonyl)phenyl)quinazolin-4(3H)-one as pale yellow solid in quantitative yield. ¹H NMR (500 MHz, CHLOROFORM-d) δ ppm 8.10-8.16 (m, 1H) 7.88-8.03 (m, 3H) 7.63-7.70 (m, 1H) 7.50-7.60 (m, 1H) 6.93-6.99 (m, 1H) 6.66-6.74 (m, 1H) 6.41-6.48 (m, 2H) 3.76-3.86 (m, 4H) 3.56-3.65 (m, 1H) 3.18-3.29 (m, 1H) 3.08-3.17 (m, 4H) 2.75-2.91 (m, 1H). The product was analyzed by LCMS Method A: retention time=1.77 min; observed mass=607.1 [M+H]⁺.

Preparation of N-((R)-1-(7-bromo-3-(4-(morpholinosulfonyl)phenyl)-4-oxo-3,4-dihydroquinazolin-2-yl)-2-(3,5-difluorophenyl)ethyl)-2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamide

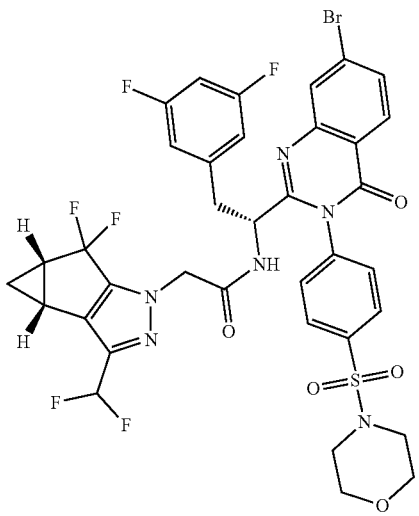 [SMILES: O=C(Cn1nc(C(F)F)c2c1C(F)(F)[C@H]1C[C@@H]21)N[C@H](Cc1cc(F)cc(F)c1)c1nc2cc(Br)ccc2c(=O)n1-c1ccc(S(=O)(=O)N2CCOCC2)cc1]

To a stirred solution of (S)-2-(1-amino-2-(3,5-difluorophenyl)ethyl)-7-bromo-3-(4-(morpholinosulfonyl)phenyl)quinazolin-4(3H)-one (1.2 g, 1.982 mmol) in N,N-Dimethylformamide (20 mL) were added 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.550 g, 2.081 mmol), 2-(3H-[1,2,3]triazolo[4,5-b]pyridin-3-yl)-1,1,3,3-tetramethylisouronium hexafluorophosphate (V) (0.904 g, 2.378 mmol) and DIPEA (0.69 ml, 3.96 mmol). The reaction mixture was stirred at room temperature for 1 h, then was diluted with water and filtered. The cream colored filter cake was taken up in ethyl acetate; dried over $Na_2SO_4$; filtered; and then concentrated in vacuo to afford of N-((R)-1-(7-bromo-3-(4-(morpholinosulfonyl)phenyl)-4-oxo-3,4-dihydroquinazolin-2-yl)-2-(3,5-difluorophenyl)ethyl)-2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamide as a light orange solid (1.55 g, 92%). LCMS Method A: retention time=2.61 min; observed mass=851.1 $[M+H]^+$.

Preparation of (R)-N-(1-(7-bromo-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

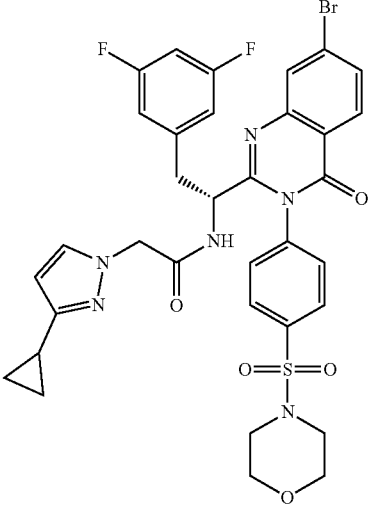 [SMILES: O=C(Cn1ccc(C2CC2)n1)N[C@H](Cc1cc(F)cc(F)c1)c1nc2cc(Br)ccc2c(=O)n1-c1ccc(S(=O)(=O)N2CCOCC2)cc1]

The title compound was prepared by the same method described for the synthesis of N-((R)-1-(7-bromo-3-(4-(morpholinosulfonyl)phenyl)-4-oxo-3,4-dihydroquinazolin-2-yl)-2-(3,5-difluorophenyl)ethyl)-2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamide, substituting 2-(3-cyclopropyl-1H-pyrazol-1-yl)acetic acid for 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid. $^1$H NMR (CDCl$_3$) δ: 8.10 (d, J=8.3 Hz, 1H), 7.93-7.97 (m, 2H), 7.85 (dd, J=8.3, 2.1 Hz, 1H), 7.65 (d, J=8.4 Hz, 1H), 7.51 (dd, J=8.3, 2.1 Hz, 1H), 7.44 (d, J=8.3 Hz, 1H), 7.27 (d, J=2.1 Hz, 1H), 6.89 (dd, J=8.2, 2.2 Hz, 1H), 6.68 (tt, J=8.9, 2.2 Hz, 1H), 6.26-6.32 (m, 2H), 6.06 (d, J=2.4 Hz, 1H), 4.75-4.83 (m, 1H), 4.59-4.68 (m, 2H), 3.79 (t, J=4.6 Hz, 4H), 3.02-3.14 (m, 5H), 2.78 (dd, J=13.4, 6.6 Hz, 1H), 1.98-2.04 (m, 1H), 1.00-1.05 (m, 2H), 0.79-0.83 (m, 2H).

Preparation of (S)-2-(3-cyclopropyl-1H-pyrazol-1-yl)-N-(2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide

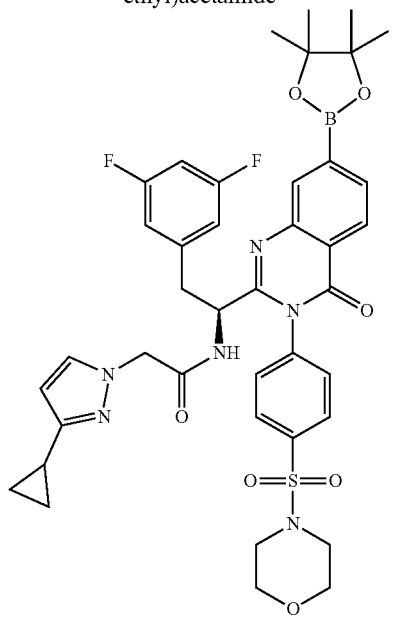

To a round bottom flask equipped with a stir bar was added (S)-N-(1-(7-bromo-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide (0.6 g, 0.796 mmol), 4,4,4',4',5,5,5',5'-octamethyl-2,2'-bi(1,3,2-dioxaborolane) (0.303 g, 1.194 mmol), potassium acetate (0.234 g, 2.388 mmol) and PdCl$_2$(dppf) (0.058 g, 0.080 mmol). The flask was sealed with a septum and then placed under argon atmosphere (vac/fill×3). To the flask was added 1,4-dioxane (16 mL). The reaction mixture was degassed with Ar (vac/fill×3). The resulting mixture was stirred at 60° C. for 16 h. The reaction mixture was concentrated in vacuo. The resulting residue was adsorbed onto Celite and then subjected to silica gel chromatography (120 g silica gel column, gradient=hexanes:EtOAc 100:0→0:100 over 10 column volumes). This purification afforded (S)-2-(3-cyclopropyl-1H-pyrazol-1-yl)-N-(2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide (0.35 g, 55% yield) as a brown solid. $^1$H NMR (500 MHz, CHLOROFORM-d) δ ppm 8.16-8.29 (m, 2H) 7.80-8.04 (m, 3H) 7.44-7.57 (m, 2H) 7.30 (d, J=2.14 Hz, 1H) 6.90-6.91 (m, 1H) 6.92 (dd, J=8.24, 1.83 Hz, 1H) 6.62-6.73 (m, 1H) 6.29-6.40 (m, 2H) 6.06 (d, J=2.14 Hz, 1H) 4.79-4.88 (m, 1H) 4.60-4.73 (m, 2H) 3.82 (t, J=4.58 Hz, 4H) 3.04-3.23 (m, 5H) 2.74-2.87 (m, 1H) 2.01-2.10 (m, 1H) 1.39-1.48 (m, 12H) 1.00-1.10 (m, 2H) 0.79-0.89 (m, 2H). LCMS Method A: retention time=2.70 min; observed mass=801.3 [M+H]$^+$.

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide

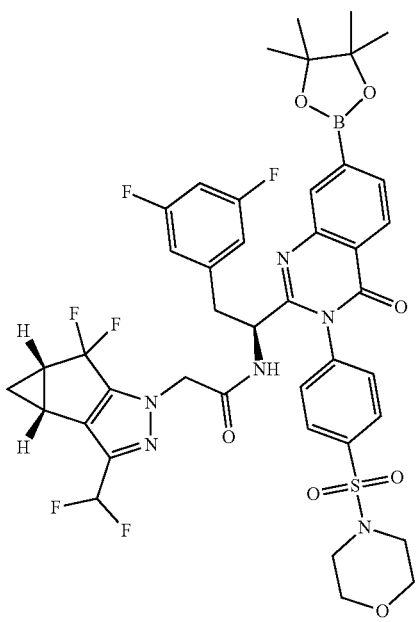 [SMILES: CC1(C)OB(c2ccc3c(=O)n(-c4ccc(S(=O)(=O)N5CCOCC5)cc4)c([C@H](Cc4cc(F)cc(F)c4)NC(=O)Cn4nc(C(F)F)c5c4C(F)(F)[C@H]4C[C@@H]54)nc3c2)OC1(C)C]

To a round bottom flask equipped with a stir bar was added N-((S)-1-(7-bromo-3-(4-(morpholinosulfonyl)phenyl)-4-oxo-3,4-dihydroquinazolin-2-yl)-2-(3,5-difluorophenyl)ethyl)-2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamide (0.8 g, 0.939 mmol), 4,4,4',4',5,5,5',5'-octamethyl-2,2'-bi(1,3,2-dioxaborolane) (0.358 g, 1.409 mmol), potassium acetate (0.277 g, 2.82 mmol) and PdCl$_2$(dppf) (0.069 g, 0.094 mmol). The flask was sealed with a septum and then placed under argon atmosphere (vac/fill×3). To the flask was added 1,4-Dioxane (19 mL). The reaction mixture was degassed with argon (vac/fill×3). The resulting mixture was stirred at 60° C. for 16 h. The reaction mixture was concentrated in vacuo and the resulting residue was then adsorbed onto Celite. The resulting powder was subjected to silica gel chromatography (120 g silica gel column, gradient=hexanes:EtOAc 100:0→0:100 over 10 column volumes) to afford 2-((3bR,4aS)-3-(difluoromethyl)-5,5-difluoro-3b,4,4a,5-tetrahydro-1H-cyclopropa[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide (0.47 g, 56% yield) as a beige solid. LCMS Method A: retention time=2.79 min; observed mass=899.3 [M+H]$^+$.

Example 9

Preparation of N-((S)-1-(7-([1,1'-biphenyl]-2-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

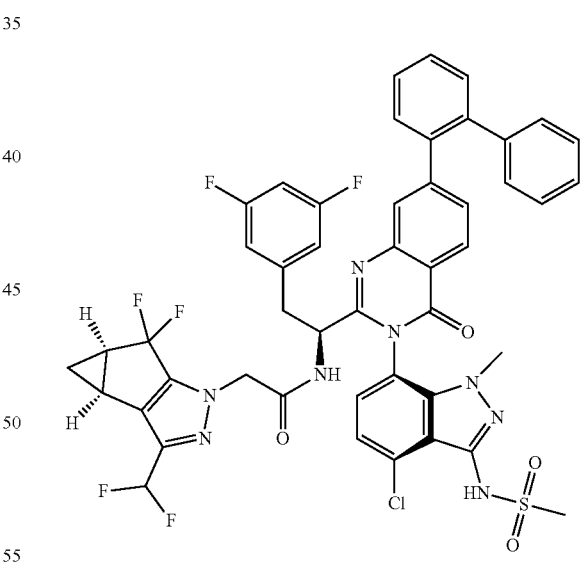

The title compound was prepared according to General Procedure A using [1,1'-biphenyl]-2-ylboronic acid as the coupling partner. Specific details are provided as a representative example of this general procedure. To a solution of N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.057 mmol), [1,1'-biphenyl]-2-ylboronic acid (16.80 mg, 0.085 mmol) and K$_3$PO$_4$ (36.0 mg, 0.170 mmol) in THF (1 mL):water (0.25 mL) was added dichloro[9,9-dimethyl-4,5-bis(diphenylphosphino)xanthene]palladium(II) (4.28 mg, 5.66 µmol) and the resulting mixture was stirred at room temp for 2 days. The contents of the vial were transferred to a 20 mL scintillation vial and was then concentrated a Biotage V10 concentrator. The residue was then taken up in DMF (2 mL) and then filtered through a syringe filter. The filtrated was purified using the following HPLC conditions: Column=Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=66 Final % B=86. Gradient Time=7 min, then a 2 min hold at 98% B. Wavelength=215 and 254 nm. ESI+Range: 150 to 1500 dalton. Sample was loaded at 66% B. This purification afforded N-((S)-1-(7-([1,1'-biphenyl]-2-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (24 mg, 42% yield, 100% purity). The sample was analyzed using LCMS Method D: retention time=3.04 min.; observed ion=957.2 (M+H). 1H NMR (500 MHz, METHANOL-d4) δ ppm 8.10 (d, J=8.24 Hz, 1H), 7.68 (s, 1H), 7.50-7.61 (m, 4H), 7.39 (br d, J=8.85 Hz, 1H), 7.25-7.32 (m, 4H), 7.19-7.24 (m, 2H), 7.12 (d, J=7.63 Hz, 1H), 6.77-6.83 (m, 1H), 6.50-6.71 (m, 3H), 4.86-4.90 (m, 1H), 4.53 (s, 2H), 3.60 (s, 3H), 3.41 (br dd, J=13.58, 5.04 Hz, 1H), 3.24 (s, 3H), 3.03 (br dd, J=13.89, 9.00 Hz, 1H), 2.37-2.47 (m, 2H), 1.34-1.40 (m, 1H), 1.01 (br d, J=1.83 Hz, 1H).

Example 10

Preparation of N-((S)-1-(3-(4-chloro-1-methyl-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

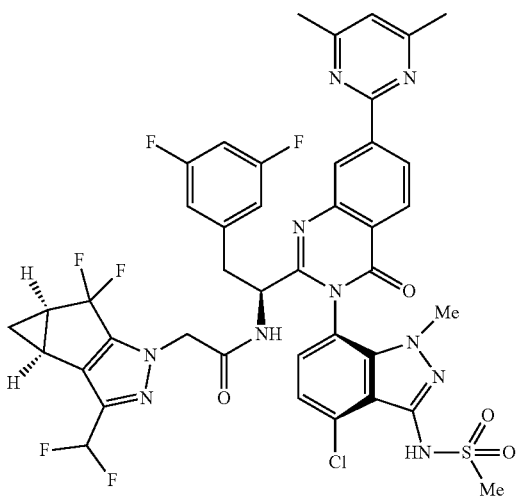

The title compound was prepared according to General Procedure D using 2-chloro-4,6-dimethylpyrimidine as the coupling partner. Specific details are provided as a representative example of this general procedure. To a 5 mL microwave vial containing a stir bar and 2-chloro-4,6-dimethylpyrimidine (23.0 mg, 0.161 mmol) was added PdOAc$_2$ (1.2 mg, 5.4 µmol), dicyclohexyl(2',6'-dimethoxy-[1,1'-biphenyl]-2-yl)phosphane (4.41 mg, 10.74 µmol) tribasic potassium phosphate (34.2 mg, 0.161 mmol), and N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (50 mg, 0.054 mmol). The vial was capped and then degassed with argon (vac/fill×3). To the vial was added THF (859 µl) and Water (215 µl). The vial was degassed again with argon (vac/fill×3, the solvent boils slightly under vacuum). The reaction mixture was stirred at room temperature for 16 h. The contents of the vial were transferred to a 20 mL scintillation vial with the aid of DCM and then evaporated using a Biotage V10 concentrator. The residue was then taken up in DMF (1.5 mL) and filtered through a syringe filter. The filtrate was purified by HPLC as follows: Column=Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=59 Final % B=79. Gradient Time=7 min, then a 2 min hold at 98% B. Wavelength=215 and 254 nm. ESI+Range: 150 to 1500 dalton. Sample was loaded at 59% B. This purification afforded the title compound, N-((S)-1-(3-(4-chloro-1-methyl-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (16.7 mg, 32% yield, 100% purity). The sample was analyzed using LCMS Method C: retention time=1.46 min.; observed ion=911.8 (M+H). 1H NMR (METHANOL-d4, 500 MHz) δ8.92 (d, 1H, J=1.2 Hz), 8.68 (dd, 1H, J=1.5, 8.3 Hz), 8.39 (d, 1H, J=8.3 Hz), 7.33 (d, 1H, J=7.7 Hz), 7.29 (s, 1H), 7.23 (d, 1H, J=7.7 Hz), 6.6-6.8 (m, 4H), 4.9-4.9 (m, 1H), 4.5-4.6 (m, 2H), 3.70 (s, 1H), 3.65 (s, 3H), 3.5-3.5 (m, 1H), 3.3-3.3 (m, 3H), 3.12 (dd, 1H, J=9.2, 14.0 Hz), 2.64 (s, 6H), 2.4-2.5 (m, 1H), 1.3-1.4 (m, 1H), 1.0-1.0 (m, 1H)

Example 11

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(isopropylsulfonyl)phenyl)-3-(4-(morpholinosulfonyl)phenyl)-4-oxo-3,4-dihydroquinazolin-2-yl)ethyl)acetamide (2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(isopropylsulfonyl)phenyl)-3-(4-(morpholinosulfonyl)phenyl)-4-oxo-3,4-dihydroquinazolin-2-yl)ethyl)acetamide

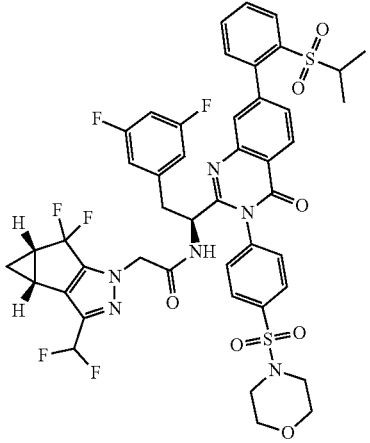 [SMILES: CC(C)S(=O)(=O)c1ccccc1-c1ccc2c(=O)n(-c3ccc(S(=O)(=O)N4CCOCC4)cc3)c([C@H](Cc3cc(F)cc(F)c3)NC(=O)Cn3nc(C(F)F)c4c3C(F)(F)[C@H]3C[C@@H]43)nc2c1]

The title compound was prepared according to General Procedure B using 1-bromo-2-(isopropylsulfonyl)benzene as the coupling partner. Specific details are provided as a representative example of this general procedure. To a 1 dram vial equipped with a stir bar and charged with 1-bromo-2-(isopropylsulfonyl)benzene (0.027 g, 0.102 mmol was added 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(4,4,5,5-tetramethyl-1,3,2-dioxaborolan-2-yl)-3,4-dihydroquinazolin-2-yl)ethyl)acetamide (0.046 g, 0.051 mmol) in THF (1 mL), then potassium phosphate (0.033 g, 0.154 mmol) in water (0.25 mL), then dichloro[9,9-dimethyl-4,5-bis(diphenylphosphino)xanthene]palladium(II) (1.94 mg, 2.56 µmol) in THF (0.1 mL). The reaction was stirred at 55° C. for 16 h. The contents of the vial were transferred to a 20 mL scintillation vial and then concentrated in vacuo using a Biotage V10 concentrator. The residue was then taken up in DMF (2 mL) and then filtered through a syringe filter. The filtrate was subjected to HPLC purification as follows: Column=Zorbax Eclipse Plus C18, 21.2×100 mm, 5 µm particles; Solvent A=0.1% Formic Acid in 100% Water. Solvent B=Acetonitrile. Flow Rate=40 mL/min. Start % B=58.2 Final % B=78.2. Gradient Time=7 min, then a 2 min hold at 98% B. Wavelength=215 and 254 nm. ESI+Range: 150 to 1500 dalton. Sample was loaded at 35% B. This purification afforded 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(isopropylsulfonyl)phenyl)-3-(4-(morpholinosulfonyl)phenyl)-4-oxo-3,4-dihydroquinazolin-2-yl)ethyl)acetamide (2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(isopropylsulfonyl)phenyl)-3-(4-(morpholinosulfonyl)phenyl)-4-oxo-3,4-dihydroquinazolin-2-yl)ethyl)acetamide (4.3 mg, 8% yield, 99% purity). The sample was analyzed using LCMS Method C: retention time=1.45 min.; observed ion=955.4 (M+H). 1H NMR (500 MHz, DMSO-d6) δ ppm 8.05-8.13 (m, 2H) 7.70-7.86 (m, 5H) 7.45-7.52 (m, 2H) 6.74-7.13 (m, 5H) 5.68-5.77 (m, 1H) 4.58-4.80 (m, 2H) 3.97-4.07 (m, 1H) 3.57-3.61 (m, 4H) 3.02-3.10 (m, 1H) 2.84-2.89 (m, 4H) 2.52-2.53 (m, 2H) 2.45-2.49 (m, 2H) 1.34-1.40 (m, 1H) 0.97-1.07 (m, 6H) 0.84-0.88 (m, 1H).

Example 12

Preparation of (S)-2-(3-cyclopropyl-1H-pyrazol-1-yl)-N-(2-(3,5-difluorophenyl)-1-(7-(2,4-difluorophenyl)-3-(4-(morpholinosulfonyl)phenyl)-4-oxo-3,4-dihydroquinazolin-2-yl)ethyl)acetamide

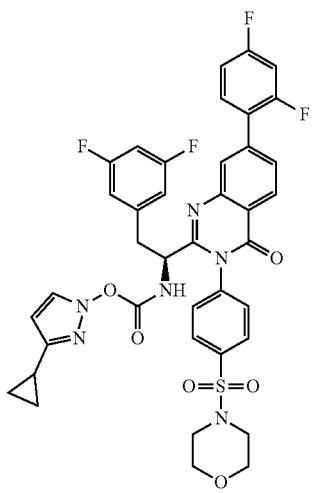 [SMILES: O=C(N[C@@H](Cc1cc(F)cc(F)c1)c1nc2cc(-c3ccc(F)cc3F)ccc2c(=O)n1-c1ccc(S(=O)(=O)N2CCOCC2)cc1)On1ccc(C2CC2)n1]

The title compound was prepared according to General Procedure A using (2,4-difluorophenyl)boronic acid (10.80 mg, 0.068 mmol) as the coupling partner. The experiment afforded the title compound, (S)-2-(3-cyclopropyl-1H-pyrazol-1-yl)-N-(2-(3,5-difluorophenyl)-1-(7-(2,4-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.48 min.; observed ion=787.5 (M+H). 1H NMR (500 MHz, METHANOL-d4) δ ppm 8.33 (d, J=8.24 Hz, 1H) 8.02 (s, 1H) 7.90-8.00 (m, 2H) 7.68-7.83 (m, 3H) 7.44 (d, J=2.14 Hz, 1H) 7.40 (dd, J=8.09, 1.98 Hz, 1H) 7.15-7.24 (m, 2H) 6.80 (t, J=8.49 Hz, 1H) 6.64 (br d, J=5.80 Hz, 2H) 5.98 (d, J=2.44 Hz, 1H) 4.80-4.82 (m, 1H) 4.63-4.78 (m, 2H) 3.74 (t, J=4.73 Hz, 4H) 3.36-3.42 (m, 1H) 3.00-3.11 (m, 5H) 1.87-1.95 (m, 1H) 0.87-0.93 (m, 2H) 0.67-0.71 (m, 2H)

Example 13

Preparation of N-((S)-1-(3-(4-chloro-1-methyl-3-(methylsulfonamido)-1H-indazol-7-yl)-7-(3,6-dimethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

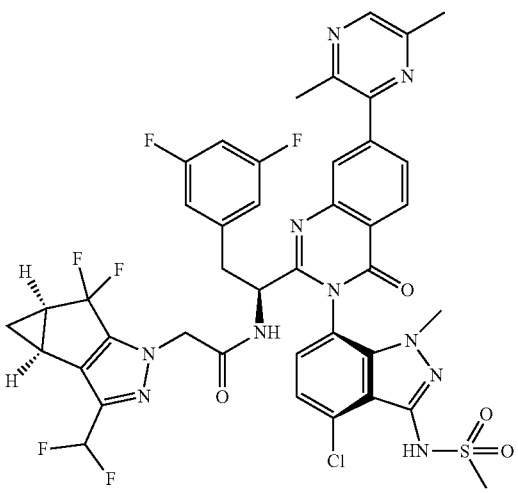

The title compound was prepared according to General Procedure B using 3-chloro-2,5-dimethylpyrazine as the coupling partner. The experiment afforded the title compound, N-((S)-1-(3-(4-chloro-1-methyl-3-(methylsulfonamido)-1H-indazol-7-yl)-7-(3,6-dimethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.34 min.; observed ion=911.4 (M+H). 1H NMR (METHANOL-d4, 500 MHz) δ8.52 (s, 1H), 8.43 (d, 1H, J=8.2 Hz), 8.10 (d, 1H, J=1.3 Hz), 7.89 (dd, 1H, J=1.6, 8.2 Hz), 7.33 (d, 1H, J=7.9 Hz), 7.24 (d, 1H, J=7.9 Hz), 6.79 (tt, 1H, J=2.3, 9.2 Hz), 6.6-6.7 (m, 2H), 6.69 (br t, 1H, J=54.7 Hz), 4.5-4.6 (m, 2H), 3.65 (s, 3H), 3.4-3.5 (m, 2H), 3.2-3.3 (m, 3H), 3.12 (dd, 1H, J=9.3, 14.0 Hz), 2.66 (d, 6H, J=6.0 Hz), 2.4-2.5 (m, 2H), 1.3-1.4 (m, 1H), 1.0-1.0 (m, 1H)

Example 14

Preparation of N-((S)-1-(3-(4-chloro-1-methyl-3-(methylsulfonamido)-1H-indazol-7-yl)-4-oxo-7-(4-phenoxyphenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Example 15

Preparation of N-((S)-1-(7-(4-chloro-2-methylphenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

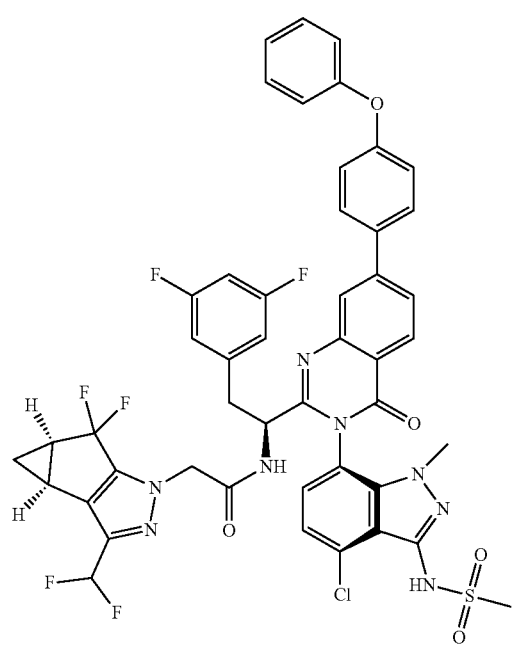

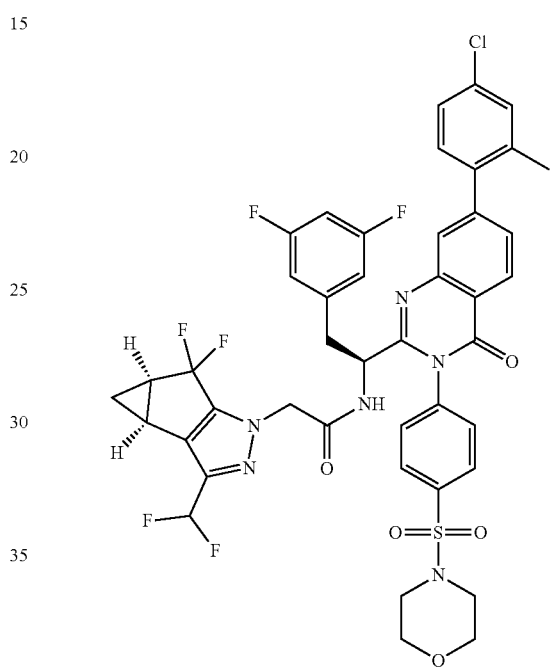

The title compound was prepared according to General Procedure A using (4-phenoxyphenyl)boronic acid as the coupling partner. The experiment afforded the title compound, N-((S)-1-(3-(4-chloro-1-methyl-3-(methylsulfonamido)-1H-indazol-7-yl)-4-oxo-7-(4-phenoxyphenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.13 min.; observed ion=973.2 (M+H). 1H NMR (500 MHz, METHANOL-d4) δ ppm 8.35 (d, J=8.24 Hz, 1H), 8.11 (s, 1H), 7.92-7.99 (m, 1H), 7.85 (br d, J=8.55 Hz, 2H), 7.44 (br t, J=7.93 Hz, 2H), 7.31 (br d, J=7.63 Hz, 1H), 7.16-7.24 (m, 4H), 7.12 (br d, J=7.93 Hz, 2H), 6.77-6.83 (m, 1H), 6.56-6.73 (m, 3H), 4.87-4.91 (m, 1H), 4.54 (br d, J=3.05 Hz, 2H), 3.63 (s, 3H), 3.46-3.52 (m, 1H), 3.25 (s, 3H), 3.10-3.16 (m, 1H), 2.37-2.48 (m, 2H), 1.36 (q, J=6.92 Hz, 1H), 1.01 (br d, J=0.61 Hz, 1H).

The title compound was prepared according to General Procedure A using (4-chloro-2-methylphenyl)boronic acid as the coupling partner. The experiment afforded the title compound, N-((S)-1-(7-(4-chloro-2-methylphenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=2.48 min.; observed ion=898.3 (M+H). 1H NMR (500 MHz, METHANOL-d4) δ ppm 8.27-8.34 (m, 1H) 7.91-7.99 (m, 2H) 7.80 (d, J=1.26 Hz, 1H) 7.68 (dt, J=7.96, 1.22 Hz, 1H) 7.61 (s, 1H) 7.42-7.46 (m, 1H) 7.32-7.39 (m, 3H) 6.59-6.86 (m, 4H) 4.69-4.84 (m, 3H) 3.71-3.77 (m, 4H) 3.38-3.43 (m, 1H) 3.00-3.11 (m, 5H) 2.44-2.50 (m, 2H) 2.34-2.36 (m, 3H) 1.36-1.43 (m, 1H) 1.02-1.06 (m, 1H).

Example 17

Preparation of 3-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid

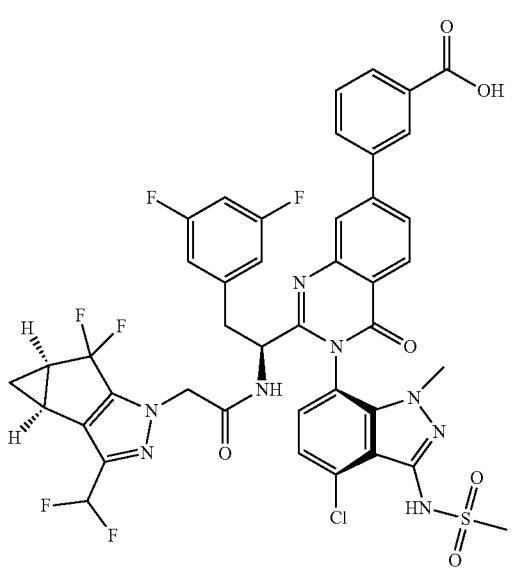

The title compound was prepared according to General Procedure A using 3-boronobenzoic acid as the coupling partner. The experiment afforded the title compound, 3-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid. The sample was analyzed using LCMS Method D: retention time=1.67 min.; observed ion=925.2 (M+H). 1H NMR (500 MHz, METHANOL-d4) δ ppm 8.48 (s, 1H), 8.40 (d, J=8.24 Hz, 1H), 8.13-8.21 (m, 2H), 8.05-8.09 (m, 1H), 8.00 (br d, J=8.24 Hz, 1H), 7.69 (t, J=7.78 Hz, 1H), 7.33 (d, J=7.63 Hz, 1H), 7.23 (d, J=7.63 Hz, 1H), 6.77-6.82 (m, 1H), 6.51-6.72 (m, 3H), 4.87-4.91 (m, 1H), 4.56 (d, J=5.19 Hz, 2H), 3.65 (s, 3H), 3.46-3.54 (m, 1H), 3.26 (s, 3H), 3.12 (br dd, J=14.19, 9.00 Hz, 1H), 2.38-2.49 (m, 2H), 1.33-1.40 (m, 1H), 0.97-1.04 (m, 1H).

Example 18

Preparation of N-((S)-1-(3-(4-chloro-1-methyl-3-(methylsulfonamido)-1H-indazol-7-yl)-7-(4-(2-hydroxypropan-2-yl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

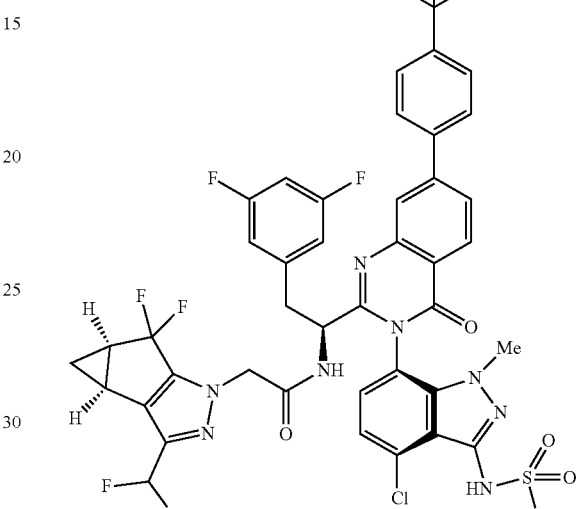

The title compound was prepared according to General Procedure C using 2-(4-bromophenyl)propan-2-ol as the coupling partner. Specific details are provided as a representative example of this general procedure. To a 1 dram vial equipped with a stir bar was added N-((S)-1-(3-(4-chloro-1-methyl-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (40 mg, 0.043 mmol), 2-(4-bromophenyl)propan-2-ol (27.7 mg, 0.129 mmol), potassium acetate (10.96 mg, 0.112 mmol) and Pd(Ph₃P)₄ (9.93 mg, 8.59 μmol). The vial was capped with a septum cap and then placed under argon atmosphere (vac/fill×3). To the vial was added dioxane (687 μl) and water (172 μl). The reaction mixture was degassed (vac/fill with argon×3, the solvent boils slightly under brief vacuum). The reaction mixture was stirred at 90° C. for 5 hr. Upon cooling to room temperature, the contents of the vial were transferred to a 20 mL scintillation vial with the aid of DCM and then was concentrated in vacuo using a Biotage V10 evaporator. The residue was then taken up in DMF (1.5 mL) and then filtered through a syringe filter. The filtrate was subjected to HPLC purification with the following conditions: Column=Zorbax Eclipse Plus C18, 21.2×100 mm, 5 μm particles; Solvent A=0.1% Formic Acid in 100% Water. Solvent B=Acetonitrile. Flow Rate=40 mL/min. Start % B=53.2 Final % B=73.2. Gradient Time=7 min, then a 2 min hold at 98% B. Wavelength=215 and 254 nm. ESI+Range: 150 to 1500 dalton. Sample was loaded at 30% B. This purification afforded N-((S)-1-(3-(4-chloro-1-methyl-3-(methylsulfonamido)-1H-indazol-7-yl)-7-(4-(2-hydroxypropan-2-yl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (9.9 mg, 25% yield, 100% purity). The sample was analyzed using LCMS Method D: retention time=2.45 min.; observed ion=939.2 (M+H). 1H NMR (METHANOL-d4, 500 MHz) δ8.35 (d, 1H, J=7.9 Hz), 8.13 (s, 1H), 7.96 (br d, 1H, J=8.2 Hz), 7.81 (br d, 2H, J=7.9 Hz), 7.71 (d, 2H, J=8.2 Hz), 7.31 (br d, 1H, J=7.6 Hz), 7.20 (d, 1H, J=7.6 Hz), 6.8-6.8 (m, 1H), 6.63 (br d, 2H, J=6.7 Hz), 4.9-4.9 (m, 1H), 4.55 (d, 2H, J=4.0 Hz), 3.63 (s, 3H), 3.5-3.5 (m, 1H), 3.4-3.4 (m, 1H), 3.2-3.3 (m, 3H), 3.12 (br dd, 1H, J=9.2, 14.0 Hz), 2.4-2.5 (m, 2H), 1.63 (s, 6H), 1.36 (br d, 1H, J=6.1 Hz), 1.01 (br s, 1H)

Example 19

Preparation of (S)-2-(3-cyclopropyl-1H-pyrazol-1-yl)-N-(2-(3,5-difluorophenyl)-1-(7-(2,5-difluorophenyl)-3-(4-(morpholinosulfonyl)phenyl)-4-oxo-3,4-dihydroquinazolin-2-yl)ethyl)acetamide

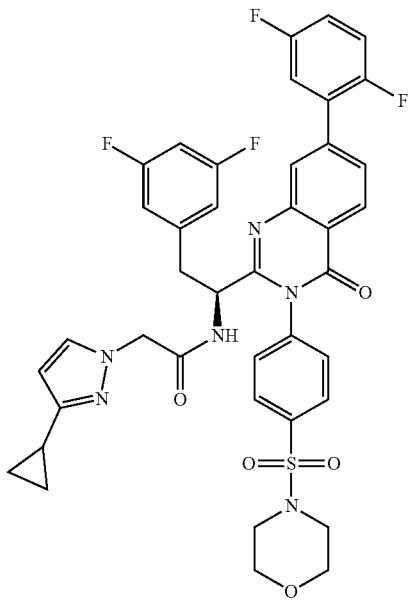 [SMILES: O=C(Cn1ccc(C2CC2)n1)N[C@@H](Cc1cc(F)cc(F)c1)c1nc2cc(-c3cc(F)ccc3F)ccc2c(=O)n1-c1ccc(S(=O)(=O)N2CCOCC2)cc1]

The title compound was prepared according to General Procedure A using (2,5-difluorophenyl)boronic acid as the coupling partner. The experiment afforded the title compound, (S)-2-(3-cyclopropyl-1H-pyrazol-1-yl)-N-(2-(3,5-difluorophenyl)-1-(7-(2,5-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.45 min.; observed ion=787.4 (M+H). 1H NMR (500 MHz, METHANOL-d4) δ ppm 8.30-8.37 (m, 1H) 8.06 (s, 1H) 7.95 (ddd, J=16.94, 8.24, 1.98 Hz, 2H) 7.82 (d, J=8.24 Hz, 1H) 7.72 (dd, J=8.24, 2.14 Hz, 1H) 7.40-7.49 (m, 3H) 7.36 (td, J=9.61, 4.58 Hz, 1H) 7.24-7.30 (m, 1H) 6.74-6.84 (m, 1H) 6.60-6.68 (m, 2H) 5.96-6.02 (m, 1H) 4.80-4.82 (m, 1H) 4.63-4.79 (m, 2H) 3.74 (t, J=4.58 Hz, 4H) 3.36-3.41 (m, 1H) 3.00-3.11 (m, 5H) 1.88-1.96 (m, 1H) 0.87-0.92 (m, 2H) 0.67-0.72 (m, 2H)

Example 20

Preparation of (S)-2-(3-cyclopropyl-1H-pyrazol-1-yl)-N-(2-(3,5-difluorophenyl)-1-(3-(4-(morpholinosulfonyl)phenyl)-4-oxo-7-(pyridin-3-yl)-3,4-dihydroquinazolin-2-yl)ethyl)acetamide

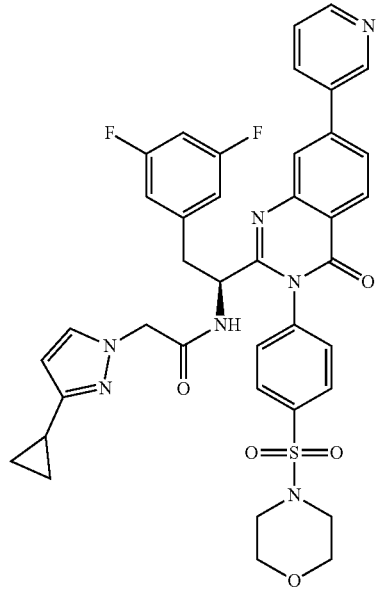 [SMILES: O=C(Cn1ccc(C2CC2)n1)N[C@@H](Cc1cc(F)cc(F)c1)c1nc2cc(-c3cccnc3)ccc2c(=O)n1-c1ccc(S(=O)(=O)N2CCOCC2)cc1]

The title compound was prepared according to General Procedure A using pyridin-3-ylboronic acid as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-(pyridin-3-yl)-3,4-dihydroquinazolin-2-yl)ethyl)acetamide. The sample was analyzed using LCMS Method C: retention time=1.13 min.; observed ion=752.7 (M+H). 1H NMR (500 MHz, METHANOL-d4) δ ppm 8.60 (dd, J=2.52, 0.63 Hz, 1H) 8.30 (d, J=8.07 Hz, 1H) 8.13-8.16 (m, 1H) 8.06 (d, J=1.89 Hz, 1H) 7.69 (dd, J=8.20, 2.21 Hz, 1H) 7.42 (d, J=2.21 Hz, 1H) 7.36 (dd, J=8.20, 2.21 Hz, 1H) 6.99 (dd, J=8.51, 0.63 Hz, 1H) 6.78 (t, J=8.48 Hz, 1H) 6.60-6.65 (m, 2H) 5.97 (d, J=2.21 Hz, 1H) 4.86-4.93 (m, 1H) 3.97-4.00 (m, 1H) 3.72 (t, J=4.73 Hz, 4H) 2.98-3.07 (m, 5H) 1.88-1.92 (m, 1H) 0.86-0.91 (m, 2H) 0.68 (dtd, J=6.46, 2.68, 2.68, 1.73 Hz, 2H).

Example 21

Preparation of N-((S)-1-(3-(4-chloro-1-methyl-3-(methylsulfonamido)-1H-indazol-7-yl)-7-(6-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

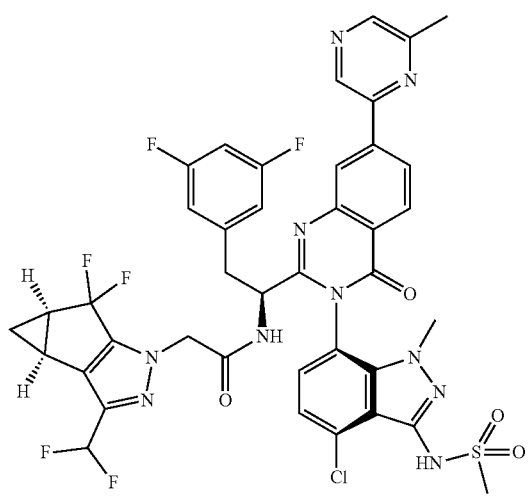

The title compound was prepared according to General Procedure B using 2-chloro-6-methylpyrazine as the coupling partner. The experiment afforded the title compound, N-((S)-1-(3-(4-chloro-1-methyl-3-(methylsulfonamido)-1H-indazol-7-yl)-7-(6-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=897.4 (M+H). 1H NMR (METHANOL-d4, 500 MHz) Shift 9.13 (s, 1H), 8.62 (d, 1H, J=1.3 Hz), 8.60 (s, 1H), 8.4-8.4 (m, 1H), 8.4-8.4 (m, 1H), 7.32 (d, 1H, J=7.9 Hz), 7.23 (d, 1H, J=7.6 Hz), 6.8-6.8 (m, 1H), 6.64 (dd, 2H, J=2.0, 8.0 Hz), 6.70 (t, 1H, J=54.7 Hz), 4.5-4.6 (m, 2H), 3.64 (s, 3H), 3.4-3.5 (m, 2H), 3.3-3.3 (m, 3H), 3.13 (dd, 1H, J=9.1, 14.2 Hz), 2.73 (s, 3H), 2.44 (br dd, 2H, J=4.1, 8.2 Hz), 1.3-1.4 (m, 1H), 1.0-1.0 (m, 1H)

Example 22

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,4-difluorophenyl)-3-(4-(morpholinosulfonyl)phenyl)-4-oxo-3,4-dihydroquinazolin-2-yl)ethyl)acetamide

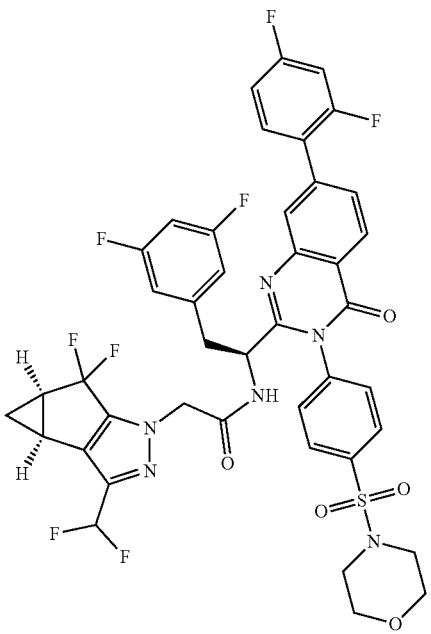 [SMILES: O=C(Cn1nc(C(F)F)c2c1C(F)(F)[C@@H]1C[C@H]21)N[C@@H](Cc1cc(F)cc(F)c1)c1nc2cc(-c3ccc(F)cc3F)ccc2c(=O)n1-c1ccc(S(=O)(=O)N2CCOCC2)cc1]

The title compound was prepared according to General Procedure A using (2,4-difluorophenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,4-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.5 min.; observed ion=885.3 (M+H). 1H NMR (500 MHz, METHANOL-d4) δ ppm 8.30-8.37 (m, 1H) 8.01-8.06 (m, 1H) 7.92-7.98 (m, 2H) 7.76-7.82 (m, 1H) 7.64-7.76 (m, 2H) 7.33-7.40 (m, 1H) 7.16-7.24 (m, 2H) 6.61-6.85 (m, 4H) 4.69-4.85 (m, 3H) 3.71-3.76 (m, 4H) 3.38-3.44 (m, 1H) 2.99-3.10 (m, 5H) 2.43-2.51 (m, 2H) 1.36-1.42 (m, 1H) 1.01-1.06 (m, 1H).

Example 24

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-3-yl)-3,4-dihydroquinazolin-2-yl)ethyl)acetamide

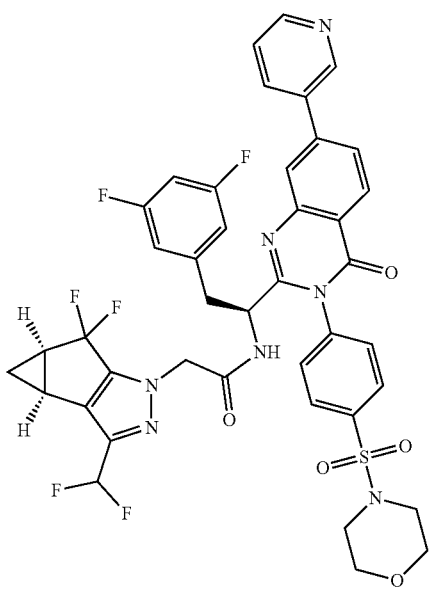 [SMILES: O=C(Cn1nc(C(F)F)c2c1C(F)(F)[C@@H]1C[C@H]21)N[C@@H](Cc1cc(F)cc(F)c1)c1nc2cc(-c3cccnc3)ccc2c(=O)n1-c1ccc(S(=O)(=O)N2CCOCC2)cc1]

The title compound was prepared according to General Procedure A using pyridin-3-ylboronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-3-yl)-3,4-dihydroquinazolin-2-yl)ethyl)acetamide. The sample was analyzed using LCMS Method C: retention time=1.21 min.; observed ion=850.4 (M+H). 1H NMR (500 MHz, METHANOL-d4) δ ppm 8.96-9.00 (m, 1H) 8.61-8.65 (m, 1H) 8.25-8.30 (m, 2H) 7.92-8.02 (m, 2H) 7.85-7.88 (m, 1H) 7.81 (d, J=8.83 Hz, 2H) 7.61 (ddd, J=8.04, 4.89, 0.95 Hz, 1H) 6.54-6.98 (m, 5H) 5.81-5.86 (m, 1H) 4.70-4.84 (m, 2H) 3.58 (t, J=4.73 Hz, 4H) 3.25 (d, J=4.41 Hz, 1H) 2.99-3.12 (m, 1H) 2.77-2.89 (m, 4H) 2.42-2.50 (m, 2H) 1.33-1.41 (m, 1H) 0.99-1.05 (m, 1H).

Example 25

Preparation of N-((S)-1-(3-(4-chloro-1-methyl-3-(methylsulfonamido)-1H-indazol-7-yl)-7-(5,6-difluoropyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

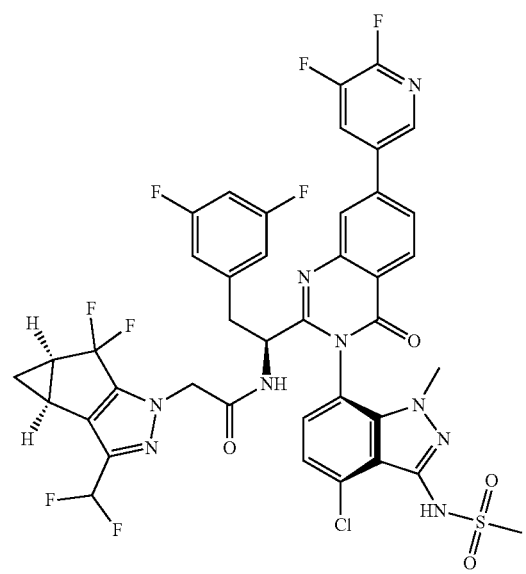

The title compound was prepared according to General Procedure A using (5,6-difluoropyridin-3-yl)boronic acid as the coupling partner. The experiment afforded the title compound, N-((S)-1-(3-(4-chloro-1-methyl-3-(methylsulfonamido)-1H-indazol-7-yl)-7-(5,6-difluoropyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.58 min.; observed ion=918.2 (M+H). 1H NMR (500 MHz, METHANOL-d4) δ ppm 8.49 (s, 1H), 8.42 (d, J=8.55 Hz, 1H), 8.34 (br t, J=9.61 Hz, 1H), 8.19 (s, 1H), 7.98 (br d, J=8.24 Hz, 1H), 7.31 (br d, J=7.93 Hz, 1H), 7.20 (d, J=8.24 Hz, 1H), 6.77-6.83 (m, 1H), 6.54-6.72 (m, 3H), 4.88-4.92 (m, 1H), 4.53 (s, 2H), 3.63 (s, 3H), 3.46-3.54 (m, 1H), 3.25 (s, 3H), 3.12 (br dd, J=14.19, 9.61 Hz, 1H), 2.36-2.50 (m, 2H), 1.33-1.40 (m, 1H), 1.01 (br dd, J=3.81, 1.68 Hz, 1H).

Example 26

Preparation of N-((S)-1-(3-(4-chloro-1-methyl-3-(methylsulfonamido)-1H-indazol-7-yl)-7-(2,6-dimethylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

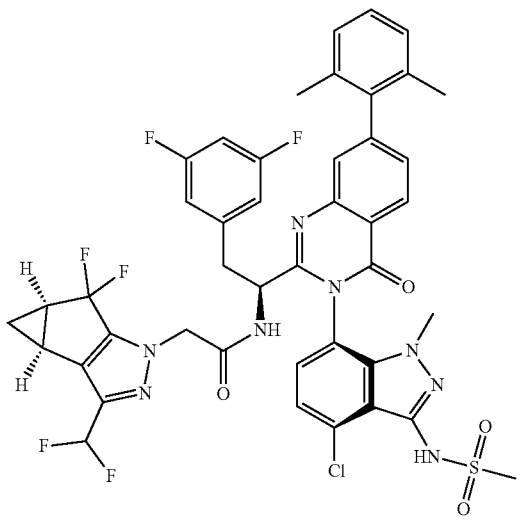

The title compound was prepared according to General Procedure A using (2,6-dimethylphenyl)boronic acid as the coupling partner. The experiment afforded the title compound, N-((S)-1-(3-(4-chloro-1-methyl-3-(methylsulfonamido)-1H-indazol-7-yl)-7-(2,6-dimethylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=2.79 min.; observed ion=909.2 (M+H). 1H NMR (500 MHz, METHANOL-d4) δ ppm 8.27 (d, J=7.94 Hz, 1H), 7.55 (s, 1H), 7.31-7.40 (m, 1H), 7.22 (d, J=7.93 Hz, 1H), 7.11-7.17 (m, 2H), 7.05-7.10 (m, 2H), 6.64-6.70 (m, 1H), 6.42-6.60 (m, 3H), 4.75-4.78 (m, 1H), 4.44 (d, J=7.63 Hz, 2H), 3.56 (s, 3H), 3.33-3.39 (m, 1H), 3.15 (s, 3H), 2.99 (br dd, J=13.73, 9.77 Hz, 1H), 2.26-2.34 (m, 2H), 2.00 (s, 3H), 1.97 (s, 3H), 1.21-1.27 (m, 1H), 0.84-0.91 (m, 1H)

Example 27

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrimidin-2-yl)-3,4-dihydroquinazolin-2-yl)ethyl)acetamide

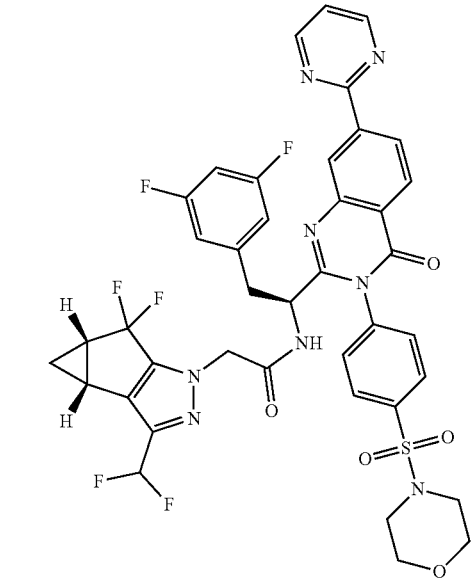 [SMILES: O=C(Cn1nc(C(F)F)c2c1C(F)(F)[C@H]1C[C@@H]21)N[C@@H](Cc1cc(F)cc(F)c1)c1nc2cc(-c3ncccn3)ccc2c(=O)n1-c1ccc(S(=O)(=O)N2CCOCC2)cc1]

The title compound was prepared according to General Procedure B using 2-chloropyrimidine as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrimidin-2-yl)-3,4-dihydroquinazolin-2-yl)ethyl)acetamide. The sample was analyzed using LCMS Method C: retention time=1.41 min.; observed ion=851.4 (M+H). 1H NMR (500 MHz, METHANOL-d4) δ ppm 8.94 (d, J=5.04 Hz, 2H) 8.67-8.74 (m, 1H) 8.51-8.62 (m, 1H) 8.26 (d, J=8.20 Hz, 1H) 7.73-7.85 (m, 2H) 7.66 (br d, J=8.20 Hz, 2H) 7.46 (t, J=4.89 Hz, 1H) 6.60-7.01 (m, 5H) 5.81-5.93 (m, 1H) 4.77 (s, 2H) 3.64-3.83 (m, 2H) 3.51 (br t, J=4.41 Hz, 4H) 2.76-2.83 (m, 2H) 2.66-2.74 (m, 2H) 2.43-2.50 (m, 2H) 1.34-1.41 (m, 1H) 1.00-1.06 (m, 1H).

Example 28

Preparation of N-((S)-1-(3-(4-chloro-1-methyl-3-(methylsulfonamido)-1H-indazol-7-yl)-7-(chroman-6-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

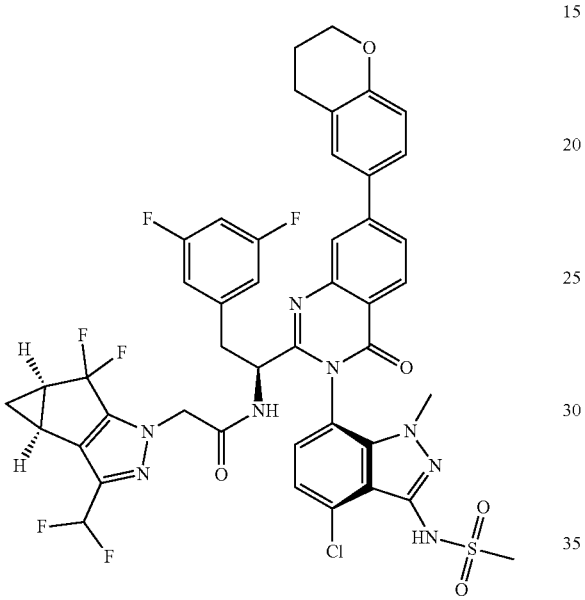

The title compound was prepared according to General Procedure A using 2-(chroman-6-yl)-4,4,5,5-tetramethyl-1,3,2-dioxaborolane as the coupling partner. The experiment afforded the title compound, N-((S)-1-(3-(4-chloro-1-methyl-3-(methylsulfonamido)-1H-indazol-7-yl)-7-(chroman-6-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.51 min.; observed ion=937.1 (M+H). 1H NMR (500 MHz, METHANOL-d4) δ ppm 8.29 (d, J=8.20 Hz, 1H), 8.04 (d, J=1.89 Hz, 1H), 7.89 (dd, J=8.35, 1.73 Hz, 1H), 7.51-7.59 (m, 2H), 7.29 (d, J=7.88 Hz, 1H), 7.18 (d, J=7.88 Hz, 1H), 6.91 (d, J=9.14 Hz, 1H), 6.52-6.82 (m, 4H), 4.81-4.85 (m, 1H), 4.54 (d, J=4.41 Hz, 2H), 4.23-4.28 (m, 2H), 3.62 (s, 3H), 3.48 (dd, J=13.56, 4.73 Hz, 1H), 3.24 (s, 3H), 3.10 (dd, J=13.87, 9.14 Hz, 1H), 2.93 (t, J=6.46 Hz, 2H), 2.41 (ddd, J=11.27, 7.65, 4.10 Hz, 2H), 2.04-2.13 (m, 2H), 1.32-1.39 (m, 1H), 0.97-1.05 (m, 1H)

Example 29

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,5-difluorophenyl)-3-(4-(morpholinosulfonyl)phenyl)-4-oxo-3,4-dihydroquinazolin-2-yl)ethyl)acetamide

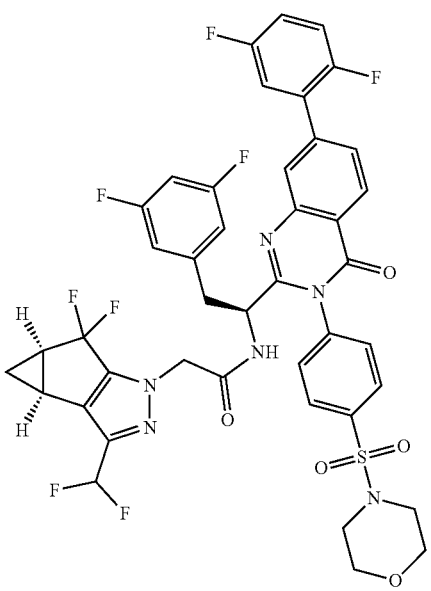 [SMILES: O=C(Cn1nc(C(F)F)c2c1C(F)(F)[C@@H]1C[C@H]21)N[C@@H](Cc1cc(F)cc(F)c1)c1nc2cc(-c3cc(F)ccc3F)ccc2c(=O)n1-c1ccc(S(=O)(=O)N2CCOCC2)cc1]

The title compound was prepared according to General Procedure A using (2,5-difluorophenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,5-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.49 min.; observed ion=885.1 (M+H). 1H NMR (500 MHz, METHANOL-d4) δ ppm 8.26-8.36 (m, 1H) 7.89-8.00 (m, 2H) 7.76-7.83 (m, 1H) 7.64-7.70 (m, 1H) 7.54-7.61 (m, 1H) 7.30-7.44 (m, 4H) 6.57-6.86 (m, 4H) 4.69-4.84 (m, 3H) 3.72-3.76 (m, 4H) 3.38-3.44 (m, 1H) 2.99-3.11 (m, 5H) 2.43-2.51 (m, 2H) 2.33-2.36 (m, 3H) 1.35-1.43 (m, 1H) 1.01-1.07 (m, 1H).

Example 30

Preparation of N-((S)-1-(3-(4-chloro-1-methyl-3-(methylsulfonamido)-1H-indazol-7-yl)-7-(3-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Example 31

Preparation of N-((S)-1-(3-(4-chloro-1-methyl-3-(methylsulfonamido)-1H-indazol-7-yl)-7-(4-chloro-3-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

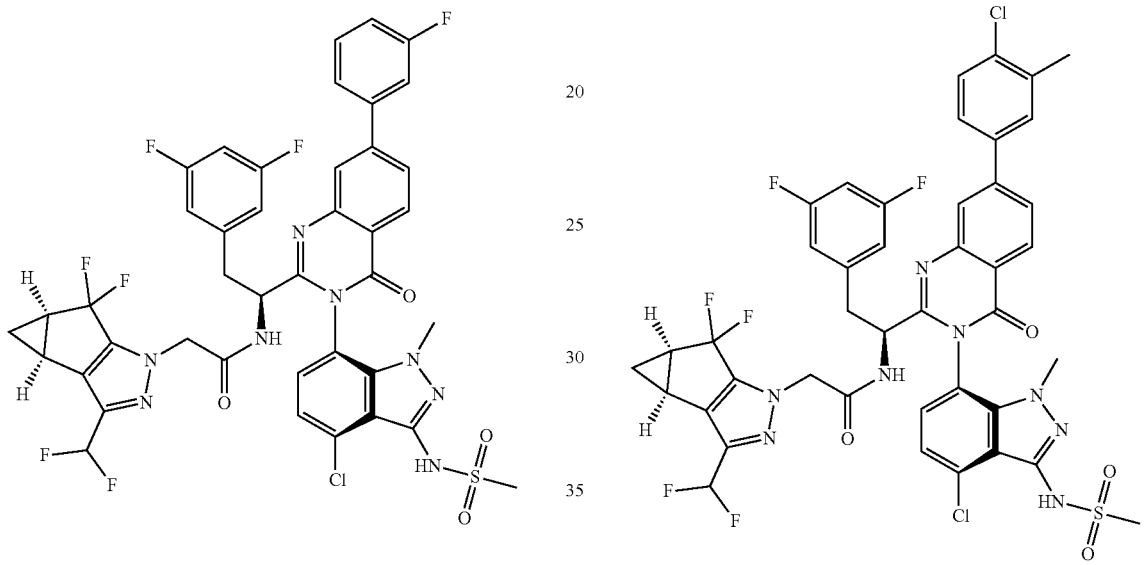

The title compound was prepared according to General Procedure A using (3-fluorophenyl)boronic acid as the coupling partner. The experiment afforded the title compound, N-((S)-1-(3-(4-chloro-1-methyl-3-(methylsulfonamido)-1H-indazol-7-yl)-7-(3-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.67 min.; observed ion=899.2 (M+H). 1H NMR (500 MHz, METHANOL-d4) δ ppm 8.38 (d, J=8.24 Hz, 1H), 8.14 (s, 1H), 7.96 (br d, J=8.55 Hz, 1H), 7.67 (br d, J=7.63 Hz, 1H), 7.55-7.64 (m, 2H), 7.32 (br d, J=7.63 Hz, 1H), 7.26 (td, J=8.32, 2.29 Hz, 1H), 7.21 (d, J=7.63 Hz, 1H), 6.77-6.82 (m, 1H), 6.55-6.71 (m, 3H), 4.87-4.90 (m, 1H), 4.48-4.62 (m, 2H), 3.63 (s, 3H), 3.46-3.56 (m, 1H), 3.26 (s, 3H), 3.12 (br dd, J=14.19, 9.00 Hz, 1H), 2.36-2.49 (m, 2H), 1.33-1.42 (m, 1H), 1.01 (br d, J=3.36 Hz, 1H).

The title compound was prepared according to General Procedure A using (4-chloro-3-methylphenyl)boronic acid as the coupling partner. The experiment afforded the title compound, N-((S)-1-(3-(4-chloro-1-methyl-3-(methylsulfonamido)-1H-indazol-7-yl)-7-(4-chloro-3-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.63 min.; observed ion=929.2 (M+H). 1H NMR (500 MHz, METHANOL-d4) δ ppm 8.34-8.40 (m, 1H), 8.25 (dd, J=5.99, 2.21 Hz, 1H), 8.18 (ddd, J=8.75, 4.97, 2.36 Hz, 1H), 8.14 (d, J=1.58 Hz, 1H), 7.94 (dd, J=8.20, 1.89 Hz, 1H), 7.57 (t, J=8.83 Hz, 1H), 7.29 (d, J=7.88 Hz, 1H), 7.18 (d, J=7.88 Hz, 1H), 6.53-6.81 (m, 4H), 4.78-4.83 (m, 1H), 4.51 (d, J=1.89 Hz, 2H), 3.60 (s, 3H), 3.48 (dd, J=14.03, 4.89 Hz, 1H), 3.23 (s, 3H), 3.10 (dd, J=13.87, 9.14 Hz, 1H), 2.33-2.47 (m, 2H), 1.30-1.40 (m, 1H), 0.94-1.04 (m, 1H).

Example 32

(S)-2-(3-cyclopropyl-1H-pyrazol-1-yl)-N-(2-(3,5-difluorophenyl)-1-(7-(6-methoxypyridin-3-yl)-3-(4-(morpholinosulfonyl)phenyl)-4-oxo-3,4-dihydroquinazolin-2-yl)ethyl)acetamide

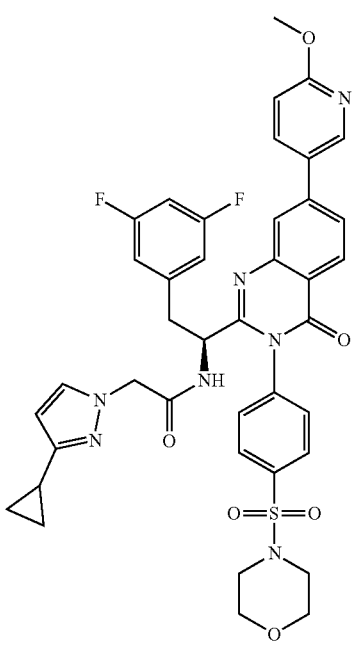 [SMILES: COc1ccc(-c2ccc3c(=O)n(-c4ccc(S(=O)(=O)N5CCOCC5)cc4)c([C@H](Cc4cc(F)cc(F)c4)NC(=O)Cn4ccc(C5CC5)n4)nc3c2)cn1]

The title compound was prepared according to General Procedure A using (6-methoxypyridin-3-yl)boronic acid as the coupling partner. The experiment afforded the title compound, (S)-2-(3-cyclopropyl-1H-pyrazol-1-yl)-N-(2-(3,5-difluorophenyl)-1-(7-(6-methoxypyridin-3-yl)-3-(4-(morpholinosulfonyl)phenyl)-4-oxo-3,4-dihydroquinazolin-2-yl)ethyl)acetamide. The sample was analyzed using LCMS Method C: retention time=1.35 min.; observed ion=782.5 (M+H). 1H NMR (500 MHz, METHANOL-d4) δ ppm 8.60 (dd, J=2.52, 0.63 Hz, 1H) 8.30 (d, J=8.07 Hz, 1H) 8.13-8.16 (m, 1H) 8.06 (d, J=1.89 Hz, 1H) 7.69 (dd, J=8.20, 2.21 Hz, 1H) 7.42 (d, J=2.21 Hz, 1H) 7.36 (dd, J=8.20, 2.21 Hz, 1H) 6.99 (dd, J=8.51, 0.63 Hz, 1H) 6.78 (t, J=8.48 Hz, 1H) 6.60-6.65 (m, 2H) 5.97 (d, J=2.21 Hz, 1H) 4.86-4.93 (m, 1H) 3.97-4.00 (m, 1H) 3.72 (t, J=4.73 Hz, 4H) 2.98-3.07 (m, 5H) 1.88-1.92 (m, 1H) 0.86-0.91 (m, 2H) 0.68 (dtd, J=6.46, 2.68, 2.68, 1.73 Hz, 2H)

Example 33

Preparation of N-((S)-1-(3-(4-chloro-1-methyl-3-(methylsulfonamido)-1H-indazol-7-yl)-7-(5-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

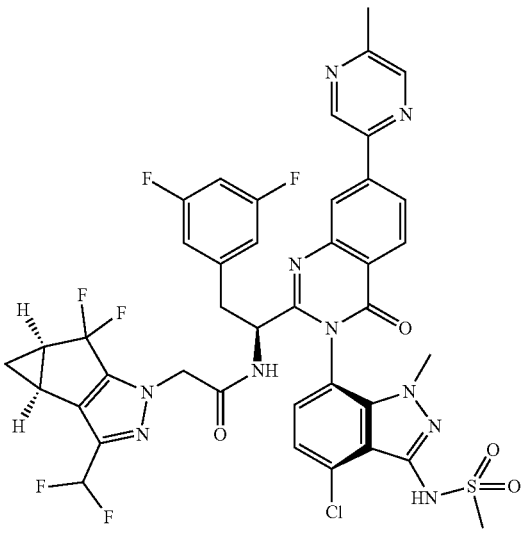

The title compound was prepared according to General Procedure B using 2-chloro-5-methylpyrazine as the coupling partner. The experiment afforded the title compound, N-((S)-1-(3-(4-chloro-1-methyl-3-(methylsulfonamido)-1H-indazol-7-yl)-7-(5-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.34 min.; observed ion=897.4 (M+H). 1H NMR (METHANOL-d4, 500 MHz) Shift 9.21 (d, 1H, J=1.6 Hz), 8.74 (s, 1H), 8.59 (d, 1H, J=1.3 Hz), 8.4-8.4 (m, 1H), 8.4-8.4 (m, 1H), 7.32 (d, 1H, J=7.9 Hz), 7.22 (d, 1H, J=7.9 Hz), 6.8-6.8 (m, 1H), 6.64 (dd, 2H, J=2.4, 8.0 Hz), 6.70 (t, 1H, J=54.9 Hz), 4.5-4.6 (m, 2H), 3.64 (s, 3H), 3.5-3.5 (m, 1H), 3.26 (s, 3H), 3.1-3.2 (m, 2H), 2.69 (s, 3H), 2.4-2.5 (m, 2H), 1.3-1.4 (m, 1H), 1.0-1.0 (m, 1H)

Example 34

Preparation of N-((S)-1-(3-(4-chloro-1-methyl-3-(methylsulfonamido)-1H-indazol-7-yl)-4-oxo-7-(4-(piperidine-1-carbonyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

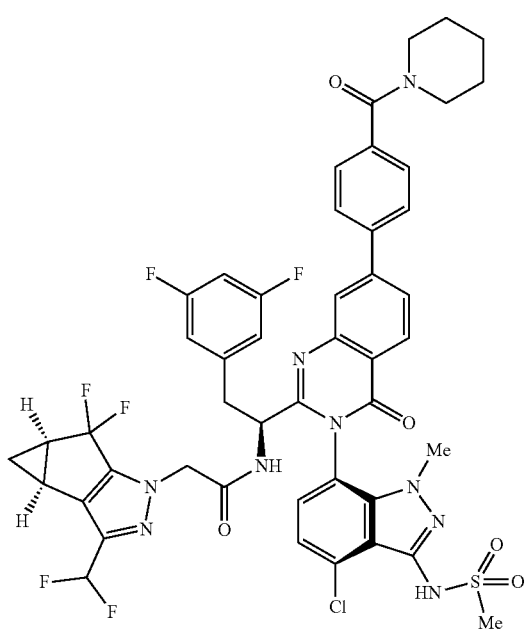

The title compound was prepared according to General Procedure C using (4-bromophenyl)(piperidin-1-yl)methanone as the coupling partner. The experiment afforded the title compound, N-((S)-1-(3-(4-chloro-1-methyl-3-(methylsulfonamido)-1H-indazol-7-yl)-4-oxo-7-(4-(piperidine-1-carbonyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.46 min.; observed ion=992.3 (M+H). 1H NMR (METHANOL-d4, 500 MHz) δ8.39 (d, 1H, J=8.2 Hz), 8.17 (s, 1H), 7.9-8.0 (m, 3H), 7.62 (d, 2H, J=8.2 Hz), 7.31 (br d, 1H, J=7.6 Hz), 7.21 (d, 1H, J=7.9 Hz), 6.6-6.8 (m, 4H), 4.9-5.0 (m, 2H), 4.55 (d, 2H, J=3.7 Hz), 3.7-3.8 (m, 2H), 3.64 (s, 3H), 3.5-3.6 (m, 3H), 3.2-3.3 (m, 4H), 3.12 (br dd, 1H, J=9.3, 13.9 Hz), 2.4-2.5 (m, 2H), 1.7-1.8 (m, 4H), 1.63 (br d, 2H, J=2.4 Hz)

Example 36

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-difluorophenyl)-3-(4-(morpholinosulfonyl)phenyl)-4-oxo-3,4-dihydroquinazolin-2-yl)ethyl)acetamide

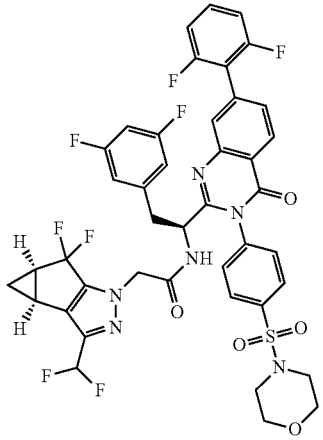 [SMILES: O=C(Cn1nc(C(F)F)c2c1C(F)(F)[C@@H]1C[C@H]21)N[C@@H](Cc1cc(F)cc(F)c1)c1nc2cc(-c3c(F)cccc3F)ccc2c(=O)n1-c1ccc(S(=O)(=O)N2CCOCC2)cc1]

The title compound was prepared according to General Procedure A using (2,6-difluorophenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.49 min.; observed ion=885.5 (M+H). 1H NMR (500 MHz, METHANOL-d4) δ ppm 8.24-8.29 (m, 1H) 7.79-7.83 (m, 3H) 7.60-7.63 (m, 1H) 7.46-7.54 (m, 2H) 7.13-7.19 (m, 2H) 6.60-6.88 (m, 5H) 5.81-5.87 (m, 1H) 4.70-4.83 (m, 3H) 3.61-3.66 (m, 4H) 3.23-3.31 (m, 1H) 2.87-2.92 (m, 4H) 2.43-2.48 (m, 2H) 1.34-1.40 (m, 1H) 0.97-1.04 (m, 1H)

Example 37

Preparation of (S)-2-(3-cyclopropyl-1H-pyrazol-1-yl)-N-(2-(3,5-difluorophenyl)-1-(7-(2,6-difluorophenyl)-3-(4-(morpholinosulfonyl)phenyl)-4-oxo-3,4-dihydroquinazolin-2-yl)ethyl)acetamide

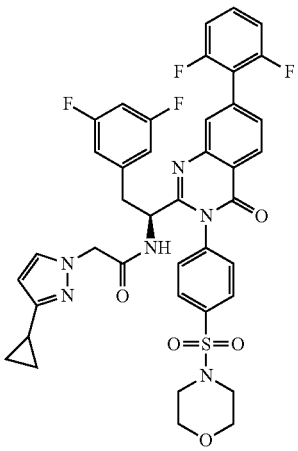 [SMILES: O=C(Cn1ccc(C2CC2)n1)N[C@@H](Cc1cc(F)cc(F)c1)c1nc2cc(-c3c(F)cccc3F)ccc2c(=O)n1-c1ccc(S(=O)(=O)N2CCOCC2)cc1]

The title compound was prepared according to General Procedure A using (2,6-difluorophenyl)boronic acid as the coupling partner. The experiment afforded the title compound, (S)-2-(3-cyclopropyl-1H-pyrazol-1-yl)-N-(2-(3,5-difluorophenyl)-1-(7-(2,6-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.45 min.; observed ion=787.4 (M+H). 1H NMR (500 MHz, METHANOL-d4) δ ppm 8.30-8.38 (m, 1H) 7.90-8.02 (m, 3H) 7.67-7.76 (m, 2H) 7.50-7.59 (m, 1H) 7.40-7.47 (m, 2H) 7.16-7.25 (m, 2H) 6.75-6.83 (m, 1H) 6.58-6.68 (m, 2H) 5.95-6.02 (m, 1H) 4.63-4.77 (m, 2H) 3.74 (t, J=4.73 Hz, 4H) 3.36-3.41 (m, 1H) 3.00-3.11 (m, 5H) 1.87-1.95 (m, 1H) 0.87-0.92 (m, 2H) 0.66-0.73 (m, 2H).

Example 38

Preparation of 5-(3-(4-chloro-1-methyl-3-(methylsulfonamido)-1H-indazol-7-yl)-2-(S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)-2-fluorobenzoic acid

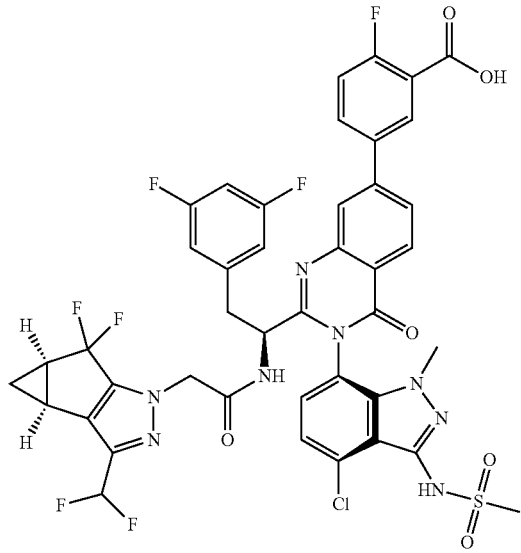

The title compound was prepared according to General Procedure A using 5-borono-2-fluorobenzoic acid as the coupling partner. The experiment afforded the title compound, 5-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)-2-fluorobenzoic acid. The sample was analyzed using LCMS Method D: retention time=1.62 min.; observed ion=943.2 (M+H). 1H NMR (500 MHz, METHANOL-d4) δ ppm 8.38 (d, J=8.24 Hz, 1H), 8.32-8.36 (m, 1H), 8.14 (s, 1H), 8.01-8.07 (m, 1H), 7.96 (dd, J=8.09, 1.07 Hz, 1H), 7.41 (dd, J=10.07, 8.85 Hz, 1H), 7.32 (d, J=7.63 Hz, 1H), 7.22 (d, J=7.63 Hz, 1H), 6.76-6.83 (m, 1H), 6.57-6.73 (m, 3H), 4.87-4.90 (m, 1H), 4.50-4.61 (m, 2H), 3.64 (s, 3H), 3.46-3.53 (m, 1H), 3.26 (s, 3H), 3.08-3.15 (m, 1H), 2.35-2.51 (m, 2H), 1.34-1.40 (m, 1H), 0.97-1.06 (m, 1H).

Example 39

Preparation of N-((S)-1-(3-(4-chloro-1-methyl-3-(methylsulfonamido)-1H-indazol-7-yl)-4-oxo-7-(pyrazin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

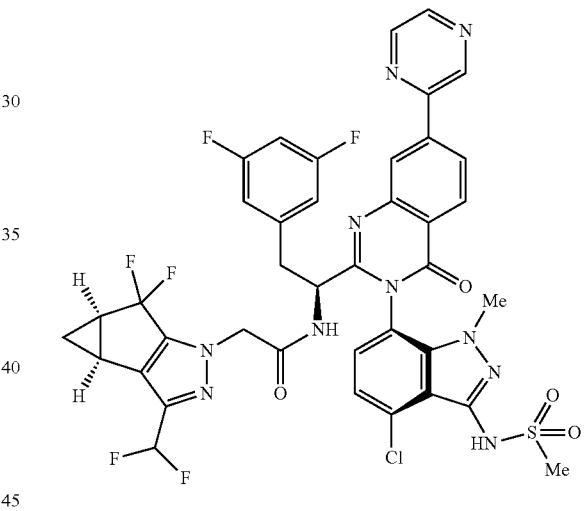

The title compound was prepared according to General Procedure B using 2-chloropyrazine as the coupling partner. The experiment afforded the title compound, N-((S)-1-(3-(4-chloro-1-methyl-3-(methylsulfonamido)-1H-indazol-7-yl)-4-oxo-7-(pyrazin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.23 min.; observed ion=883.2 (M+H). 1H NMR (METHANOL-d4, 500 MHz) δ9.36 (s, 1H), 8.8-8.9 (m, 1H), 8.70 (d, 1H, J=2.1 Hz), 8.63 (s, 1H), 8.4-8.5 (m, 2H), 7.32 (d, 1H, J=7.9 Hz), 7.22 (d, 1H, J=7.9 Hz), 6.8-6.8 (m, 1H), 6.70 (s, 1H), 6.64 (br d, 2H, J=6.1 Hz), 6.59 (s, 1H), 4.9-5.0 (m, 2H), 4.55 (d, 2H, J=2.4 Hz), 3.64 (s, 3H), 3.4-3.6 (m, 2H), 3.4-3.4 (m, 2H), 3.1-3.2 (m, 2H), 2.4-2.5 (m, 2H), 1.3-1.4 (m, 1H), 1.0-1.0 (m, 1H)

Example 40

Preparation of N-((S)-1-(3-(4-chloro-1-methyl-3-(methylsulfonamido)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

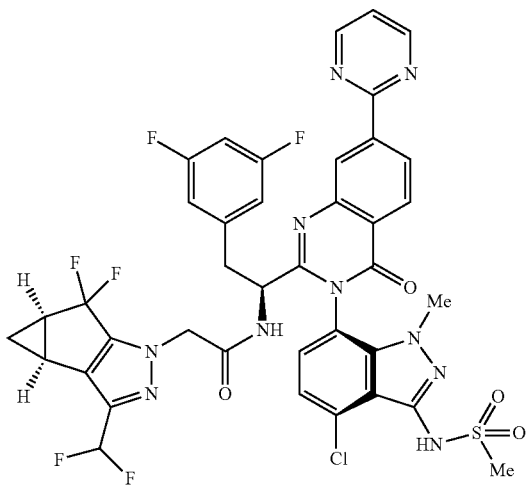

The title compound was prepared according to General Procedure B using 2-chloropyrimidine as the coupling partner. The experiment afforded the title compound, N-((S)-1-(3-(4-chloro-1-methyl-3-(methylsulfonamido)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.33 min.; observed ion=883.2 (M+H). 1H NMR (METHANOL-d4, 500 MHz) δ9.00 (d, 2H, J=4.9 Hz), 8.95 (s, 1H), 8.71 (d, 1H, J=8.2 Hz), 8.41 (d, 1H, J=8.2 Hz), 7.52 (t, 1H, J=4.9 Hz), 7.32 (br d, 1H, J=7.6 Hz), 7.22 (d, 1H, J=7.6 Hz), 6.8-6.8 (m, 1H), 6.6-6.7 (m, 2H), 4.9-4.9 (m, 2H), 4.5-4.6 (m, 2H), 3.64 (s, 3H), 3.4-3.6 (m, 2H), 3.4-3.4 (m, 2H), 3.1-3.2 (m, 2H), 2.4-2.5 (m, 2H), 1.3-1.4 (m, 1H), 1.0-1.0 (m, 1H)

Example 41

Preparation of N-((S)-1-(3-(4-chloro-1-methyl-3-(methylsulfonamido)-1H-indazol-7-yl)-7-(3-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

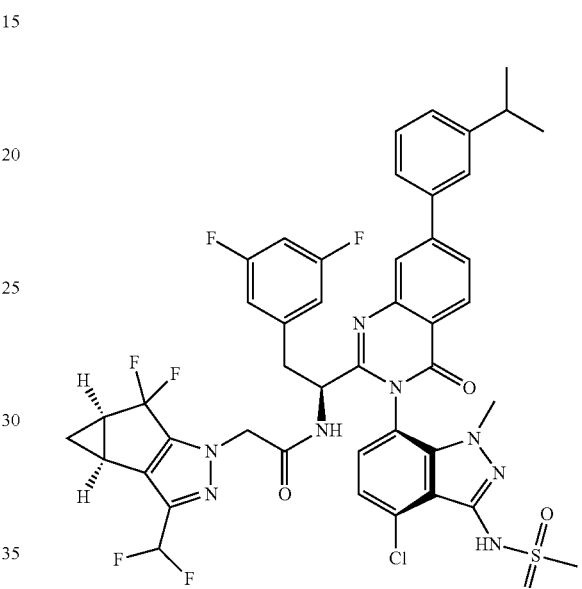

The title compound was prepared according to General Procedure A using (3-isopropylphenyl)boronic acid as the coupling partner. The experiment afforded the title compound, N-((S)-1-(3-(4-chloro-1-methyl-3-(methylsulfonamido)-1H-indazol-7-yl)-7-(3-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.03 min.; observed ion=915.1 (M+H). 1H NMR (500 MHz, METHANOL-d4) δ ppm 8.36 (d, J=8.55 Hz, 1H), 8.10 (s, 1H), 7.91-7.98 (m, 1H), 7.68 (s, 1H), 7.64 (br d, J=7.63 Hz, 1H), 7.50 (t, J=7.63 Hz, 1H), 7.35-7.42 (m, 1H), 7.32 (br d, J=7.93 Hz, 1H), 7.21 (d, J=7.93 Hz, 1H), 6.76-6.84 (m, 1H), 6.54-6.72 (m, 3H), 4.87-4.91 (m, 1H), 4.45-4.65 (m, 2H), 3.63 (s, 3H), 3.43-3.53 (m, 1H), 3.26 (s, 3H), 3.02-3.14 (m, 2H), 2.33-2.48 (m, 2H), 1.38 (d, J=6.71 Hz, 6H), 1.27-1.34 (m, 1H), 0.93-1.05 (m, 1H).

Example 42

Preparation of (S)-2-(3-cyclopropyl-1H-pyrazol-1-yl)-N-(2-(3,5-difluorophenyl)-1-(3-(4-(morpholinosulfonyl)phenyl)-4-oxo-7-(2-phenoxyphenyl)-3,4-dihydroquinazolin-2-yl)ethyl)acetamide

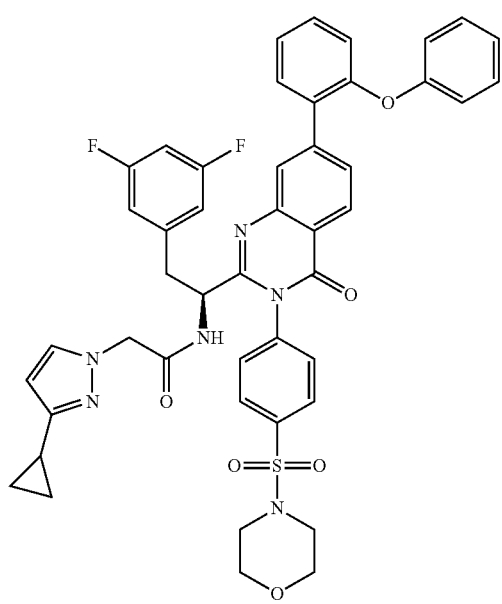 [SMILES: O=C(Cn1ccc(C2CC2)n1)N[C@@H](Cc1cc(F)cc(F)c1)c1nc2cc(-c3ccccc3Oc3ccccc3)ccc2c(=O)n1-c1ccc(S(=O)(=O)N2CCOCC2)cc1]

The title compound was prepared according to General Procedure A using (2-phenoxyphenyl)boronic acid as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-(2-phenoxyphenyl)-3,4-dihydroquinazolin-2-yl)ethyl)acetamide. The sample was analyzed using LCMS Method C: retention time=1.57 min.; observed ion=843.5 (M+H). 1H NMR (500 MHz, METHANOL-d4) δ ppm 8.18-8.29 (m, 1H) 8.01-8.06 (m, 1H) 7.92 (ddd, J=19.15, 8.32, 2.14 Hz, 2H) 7.80 (dd, J=8.24, 1.53 Hz, 1H) 7.63-7.70 (m, 2H) 7.46-7.53 (m, 1H) 7.24-7.46 (m, 6H) 7.10-7.17 (m, 1H) 7.05 (t, J=7.32 Hz, 1H) 6.88-6.96 (m, 2H) 6.75-6.82 (m, 1H) 6.59-6.68 (m, 2H) 5.94-5.99 (m, 1H) 4.78 (t, J=7.17 Hz, 1H) 4.62-4.73 (m, 2H) 3.73 (t, J=4.58 Hz, 4H) 3.36-3.39 (m, 1H) 2.97-3.09 (m, 5H) 1.87-1.94 (m, 1H) 0.86-0.92 (m, 2H) 0.66-0.71 (m, 2H).

Example 43

Preparation of N-((S)-1-(3-(4-chloro-1-methyl-3-(methylsulfonamido)-1H-indazol-7-yl)-7-(2-chlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

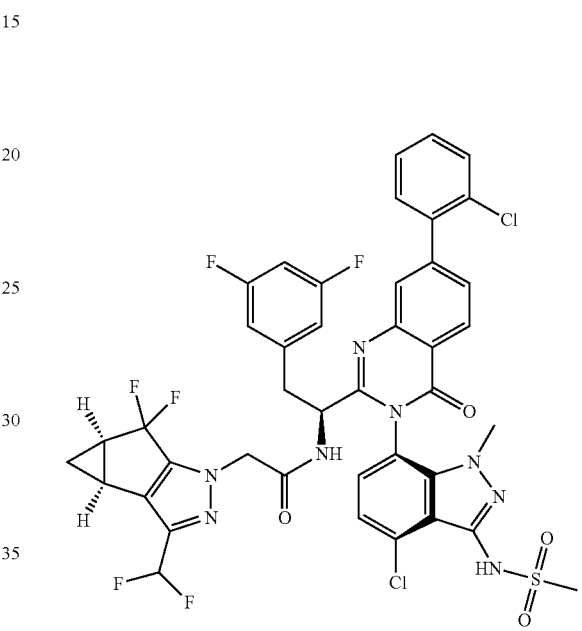

The title compound was prepared according to General Procedure A using (2-chlorophenyl)boronic acid as the coupling partner. The experiment afforded the title compound, N-((S)-1-(3-(4-chloro-1-methyl-3-(methylsulfonamido)-1H-indazol-7-yl)-7-(2-chlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=2.71 min.; observed ion=915.1 (M+H). 1H NMR (500 MHz, METHANOL-d4) δ ppm 8.73-8.84 (m, 1H), 8.37 (d, J=7.93 Hz, 1H), 7.96 (s, 1H), 7.73 (dd, J=8.24, 1.53 Hz, 1H), 7.63 (dd, J=7.17, 1.68 Hz, 1H), 7.44-7.57 (m, 3H), 7.33 (d, J=7.93 Hz, 1H), 7.23 (d, J=7.93 Hz, 1H), 6.76-6.81 (m, 1H), 6.56-6.69 (m, 3H), 4.87-4.92 (m, 1H), 4.48-4.60 (m, 2H), 3.66 (s, 3H), 3.44-3.53 (m, 1H), 3.27 (s, 3H), 3.11 (br dd, J=13.73, 8.85 Hz, 1H), 2.36-2.47 (m, 2H), 1.33-1.40 (m, 1H), 0.91-1.06 (m, 1H).

Example 44

Preparation of N-((S)-1-(3-(4-chloro-1-methyl-3-(methylsulfonamido)-1H-indazol-7-yl)-7-(3-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

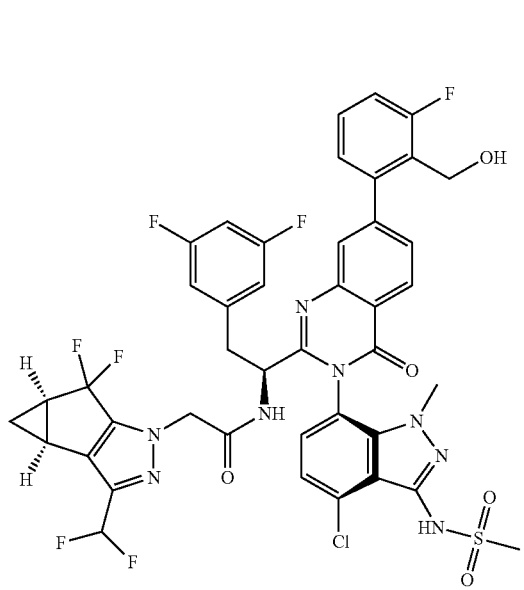

The title compound was prepared according to General Procedure A using (3-fluoro-2-(hydroxymethyl)phenyl)boronic acid as the coupling partner. The experiment afforded the title compound, N-((S)-1-(3-(4-chloro-1-methyl-3-(methylsulfonamido)-1H-indazol-7-yl)-7-(3-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.33 min.; observed ion=930.9 (M+H). 1H NMR (500 MHz, METHANOL-d4) δ ppm 8.21 (d, J=8.20 Hz, 1H), 7.74 (d, J=0.95 Hz, 1H), 7.55 (dd, J=8.20, 1.58 Hz, 1H), 7.29 (d, J=7.88 Hz, 1H), 7.15 (d, J=7.88 Hz, 1H), 6.55-6.83 (m, 4H), 4.82-4.85 (m, 1H), 4.53 (s, 2H), 3.59 (s, 3H), 3.45-3.49 (m, 1H), 3.25 (s, 3H), 3.09 (dd, J=13.87, 9.14 Hz, 1H), 2.92 (q, J=7.57 Hz, 2H), 2.39-2.50 (m, 2H), 1.35-1.43 (m, 4H), 0.96-1.06 (m, 1H).

Example 45

Preparation of N-((S)-1-(7-(3-(tert-butyl)phenyl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

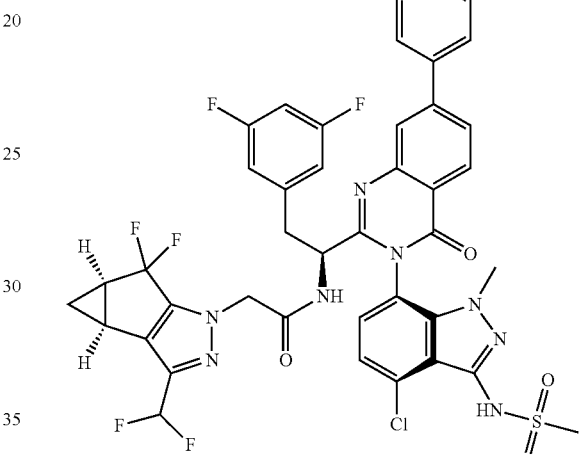

The title compound was prepared according to General Procedure A using (3-(tert-butyl)phenyl)boronic acid as the coupling partner. The experiment afforded the title compound, N-((S)-1-(7-(3-(tert-butyl)phenyl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.12 min.; observed ion=937.3 (M+H). 1H NMR (500 MHz, METHANOL-d4) δ ppm 8.37 (d, J=7.93 Hz, 1H), 8.10 (s, 1H), 7.95 (br d, J=8.85 Hz, 1H), 7.83 (s, 1H), 7.63 (br d, J=7.93 Hz, 1H), 7.58 (br d, J=7.93 Hz, 1H), 7.48-7.54 (m, 1H), 7.32 (br d, J=7.93 Hz, 1H), 7.22 (d, J=7.63 Hz, 1H), 6.77-6.82 (m, 1H), 6.56-6.71 (m, 3H), 4.87-4.91 (m, 1H), 4.48-4.64 (m, 2H), 3.63 (s, 3H), 3.46-3.53 (m, 1H), 3.26 (s, 3H), 3.09-3.16 (m, 1H), 2.35-2.48 (m, 2H), 1.46 (s, 9H), 1.30-1.39 (m, 1H), 0.93-1.04 (m, 1H)

Example 46

Preparation of N-((S)-1-(3-(4-chloro-1-methyl-3-(methylsulfonamido)-1H-indazol-7-yl)-7-(6-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

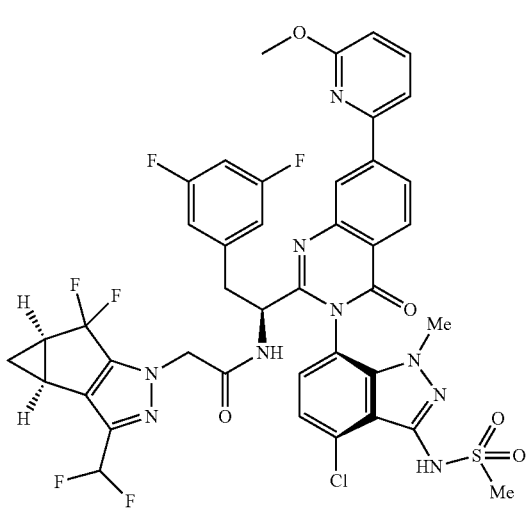

The title compound was prepared according to General Procedure B using 2-bromo-6-methoxypyridine as the coupling partner. The experiment afforded the title compound, N-((S)-1-(3-(4-chloro-1-methyl-3-(methylsulfonamido)-1H-indazol-7-yl)-7-(6-methoxypyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.69 min.; observed ion=912.2 (M+H). 1H NMR (METHANOL-d4, 500 MHz) δ8.63 (s, 1H), 8.37 (s, 2H), 7.85 (t, 1H, J=7.5 Hz), 7.72 (d, 1H, J=7.4 Hz), 7.32 (br d, 1H, J=7.9 Hz), 7.22 (d, 1H, J=8.2 Hz), 6.89 (d, 1H, J=8.2 Hz), 6.7-6.8 (m, 2H), 6.64 (br d, 2H, J=6.7 Hz), 4.5-4.6 (m, 2H), 4.1-4.1 (m, 3H), 3.64 (s, 3H), 3.4-3.5 (m, 2H), 3.4-3.4 (m, 1H), 3.1-3.3 (m, 5H), 2.4-2.5 (m, 2H), 1.3-1.4 (m, 1H), 1.0-1.0 (m, 1H)

Example 47

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(methylsulfonyl)phenyl)-3-(4-(morpholinosulfonyl)phenyl)-4-oxo-3,4-dihydroquinazolin-2-yl)ethyl)acetamide

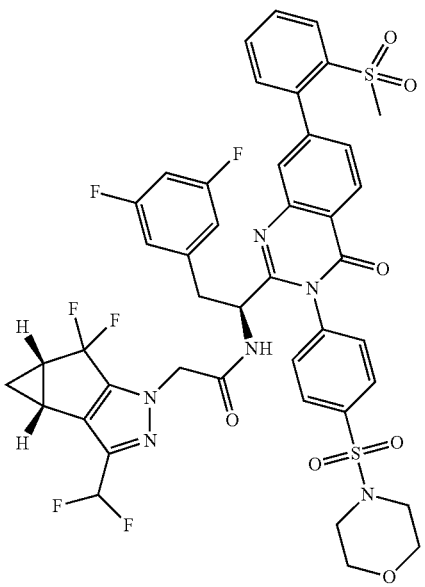 [SMILES: CS(=O)(=O)c1ccccc1-c1ccc2c(=O)n(-c3ccc(S(=O)(=O)N4CCOCC4)cc3)c([C@H](Cc3cc(F)cc(F)c3)NC(=O)Cn3nc(C(F)F)c4c3C(F)(F)[C@H]3C[C@@H]43)nc2c1]

The title compound was prepared according to General Procedure B using 1-bromo-2-(methylsulfonyl)benzene as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2-(methylsulfonyl)phenyl)-3-(4-(morpholinosulfonyl)phenyl)-4-oxo-3,4-dihydroquinazolin-2-yl)ethyl)acetamide. The sample was analyzed using LCMS Method C: retention time=1.38 min.; observed ion=927.3 (M+H). 1H NMR (500 MHz, DMSO-d6) δ ppm 8.04-8.21 (m, 3H) 7.67-7.87 (m, 7H) 7.46-7.58 (m, 2H) 6.72-7.15 (m, 4H) 5.69-5.80 (m, 1H) 4.55-4.79 (m, 2H) 3.99-4.07 (m, 2H) 3.56-3.67 (m, 5H) 2.94-2.98 (m, 3H) 2.84-2.89 (m, 4H) 1.34-1.40 (m, 1H) 0.81-0.87 (m, 1H).

Example 48

Preparation of (S)-2-(3-cyclopropyl-1H-pyrazol-1-yl)-N-(2-(3,5-difluorophenyl)-1-(7-(2-(methylsulfonyl)phenyl)-3-(4-(morpholinosulfonyl)phenyl)-4-oxo-3,4-dihydroquinazolin-2-yl)ethyl)acetamide

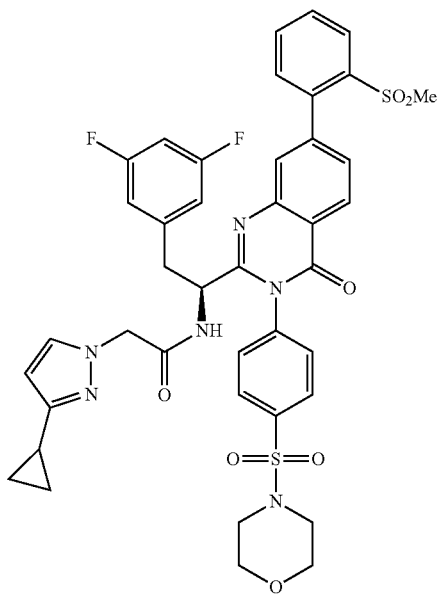 [SMILES: CS(=O)(=O)c1ccccc1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure B using 1-bromo-2-(methylsulfonyl)benzene as the coupling partner. The experiment afforded the title compound, (S)-2-(3-cyclopropyl-1H-pyrazol-1-yl)-N-(2-(3,5-difluorophenyl)-1-(7-(2-(methylsulfonyl)phenyl)-3-(4-(morpholinosulfonyl)phenyl)-4-oxo-3,4-dihydroquinazolin-2-yl)ethyl)acetamide. The sample was analyzed using LCMS Method C: retention time=1.28 min.; observed ion=829.5 (M+H). 1H NMR (500 MHz, METHANOL-d4) δ ppm 8.21-8.32 (m, 2H) 7.91-7.99 (m, 1H) 7.70-7.88 (m, 4H) 7.49-7.68 (m, 3H) 7.28-7.46 (m, 2H) 6.83-6.90 (m, 1H) 6.76-6.83 (m, 1H) 6.61-6.69 (m, 1H) 5.86-5.98 (m, 2H) 4.63-4.84 (m, 2H) 3.64-3.76 (m, 4H) 3.36-3.42 (m, 1H) 3.22-3.28 (m, 1H) 2.92-3.10 (m, 4H) 2.84-2.92 (m, 3H) 1.85-1.96 (m, 1H) 0.86-0.93 (m, 2H) 0.64-0.70 (m, 2H).

Example 49

Preparation of (S)-2-(3-cyclopropyl-1H-pyrazol-1-yl)-N-(2-(3,5-difluorophenyl)-1-(7-(2,6-dimethylphenyl)-3-(4-(morpholinosulfonyl)phenyl)-4-oxo-3,4-dihydroquinazolin-2-yl)ethyl)acetamide

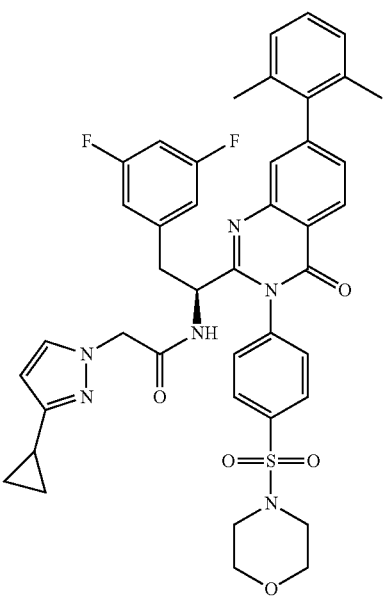 [SMILES: Cc1cccc(C)c1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure A using (2,6-dimethylphenyl)boronic acid as the coupling partner. The experiment afforded the title compound, (S)-2-(3-cyclopropyl-1H-pyrazol-1-yl)-N-(2-(3,5-difluorophenyl)-1-(7-(2,6-dimethylphenyl)-3-(4-(morpholinosulfonyl)phenyl)-4-oxo-3,4-dihydroquinazolin-2-yl)ethyl)acetamide. The sample was analyzed using LCMS Method C: retention time=1.53 min.; observed ion=779.6 (M+H). 1H NMR (500 MHz, METHANOL-d4) δ ppm 8.29-8.37 (m, 1H) 7.87-8.00 (m, 2H) 7.66-7.74 (m, 1H) 7.61 (dd, J=1.58, 0.63 Hz, 1H) 7.37-7.51 (m, 3H) 7.12-7.28 (m, 4H) 6.74-6.83 (m, 2H) 6.59-6.68 (m, 2H) 4.79-4.83 (m, 1H) 4.60-4.76 (m, 2H) 3.71-3.75 (m, 4H) 2.98-3.09 (m, 5H) 1.85-1.93 (m, 1H) 0.83-0.88 (m, 2H) 0.64-0.68 (m, 2H)

115

Example 50

Preparation of (S)-N-(1-(7-(4-chloro-2-methylphenyl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

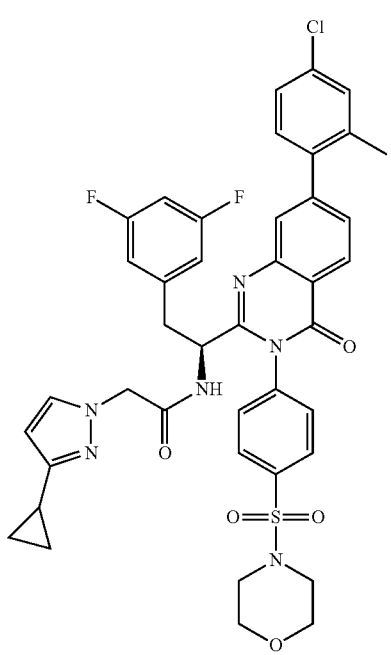 [SMILES: Cc1cc(Cl)ccc1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure A using (4-chloro-2-methylphenyl)boronic acid as the coupling partner. The experiment afforded the title compound, (S)-N-(1-(7-(4-chloro-2-methylphenyl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide. The sample was analyzed using LCMS Method C: retention time=1.57 min.; observed ion=799.4 (M+H). 1H NMR (500 MHz, METHANOL-d4) δ ppm 8.31 (d, J=8.24 Hz, 1H) 7.92-7.99 (m, 2H) 7.78 (d, J=1.22 Hz, 1H) 7.71 (dd, J=8.09, 1.98 Hz, 1H) 7.59 (dd, J=8.24, 1.53 Hz, 1H) 7.32-7.45 (m, 5H) 6.80 (br t, J=9.16 Hz, 1H) 6.64 (br d, J=6.10 Hz, 2H) 5.98 (d, J=2.44 Hz, 1H) 4.81 (br s, 1H) 4.65-4.72 (m, 2H) 3.74 (t, J=4.73 Hz, 4H) 3.35-3.40 (m, 1H) 2.99-3.11 (m, 5H) 2.34 (s, 3H) 1.88-1.93 (m, 1H) 0.84-0.93 (m, 2H) 0.65-0.71 (m, 2H)

116

Example 51

Preparation of N-((S)-1-(3-(4-chloro-1-methyl-3-(methylsulfonamido)-1H-indazol-7-yl)-7-(4-chlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

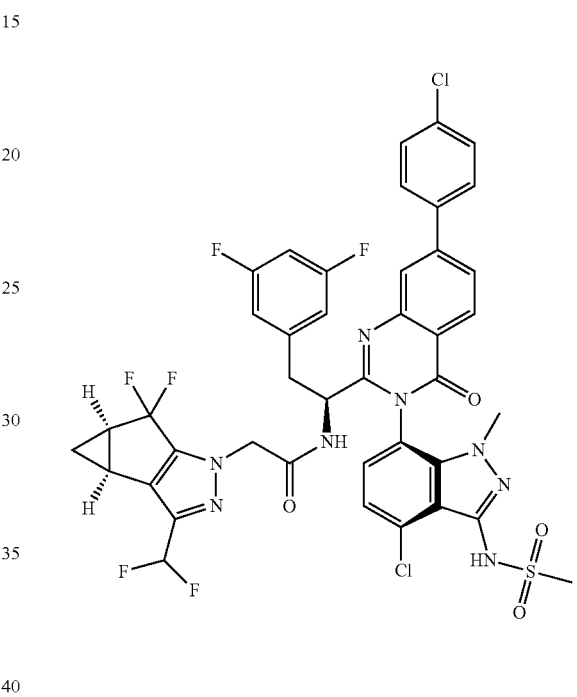

The title compound was prepared according to General Procedure A using (4-chlorophenyl)boronic acid as the coupling partner. The experiment afforded the title compound, N-((S)-1-(3-(4-chloro-1-methyl-3-(methylsulfonamido)-1H-indazol-7-yl)-7-(4-chlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.83 min.; observed ion=915.1 (M+H). 1H NMR (500 MHz, METHANOL-d4) δ ppm 8.37 (d, J=8.55 Hz, 1H), 8.13 (d, J=1.53 Hz, 1H), 7.95 (dd, J=8.09, 1.68 Hz, 1H), 7.84 (d, J=8.24 Hz, 2H), 7.60 (d, J=8.55 Hz, 2H), 7.31 (br d, J=7.94 Hz, 1H), 7.20 (d, J=7.63 Hz, 1H), 6.76-6.84 (m, 1H), 6.55-6.72 (m, 3H), 4.87-4.91 (m, 1H), 4.54 (d, J=2.44 Hz, 2H), 3.63 (s, 3H), 3.45-3.54 (m, 1H), 3.25 (s, 3H), 3.09-3.15 (m, 1H), 2.36-2.51 (m, 2H), 1.32-1.41 (m, 1H), 0.95-1.07 (m, 1H).

Example 52

Preparation of N-((S)-1-(3-(4-chloro-1-methyl-3-(methylsulfonamido)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

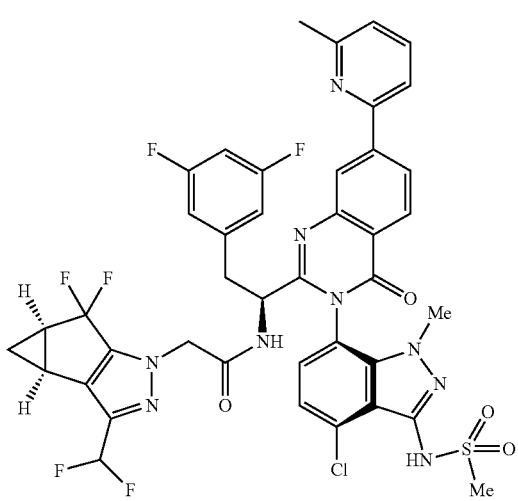

The title compound was prepared according to General Procedure D using 2-bromo-6-methylpyridine as the coupling partner. The experiment afforded the title compound, N-((S)-1-(3-(4-chloro-1-methyl-3-(methylsulfonamido)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=896.7 (M+H). 1H NMR (METHANOL-d4, 500 MHz) δ8.51 (s, 1H), 8.39 (d, 1H, J=8.2 Hz), 8.28 (dd, 1H, J=1.8, 8.3 Hz), 7.9-7.9 (m, 2H), 7.38 (d, 1H, J=6.9 Hz), 7.32 (d, 1H, J=8.0 Hz), 7.21 (d, 1H, J=7.7 Hz), 6.6-6.8 (m, 4H), 4.9-4.9 (m, 1H), 4.5-4.6 (m, 2H), 3.64 (s, 3H), 3.5-3.5 (m, 1H), 3.3-3.3 (m, 3H), 3.13 (dd, 1H, J=9.2, 14.0 Hz), 2.69 (s, 3H), 2.44 (br dd, 2H, J=3.9, 8.0 Hz), 1.3-1.4 (m, 1H), 1.0-1.0 (m, 1H)

Example 53

Preparation of N-((S)-1-(3-(4-chloro-1-methyl-3-(methylsulfonamido)-1H-indazol-7-yl)-7-(8-fluoro-5-methylchroman-6-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

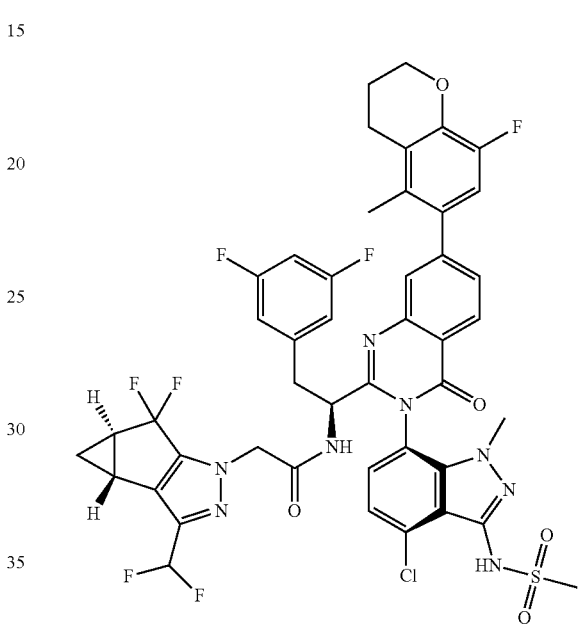

The title compound was prepared according to General Procedure A using 2-(8-fluoro-5-methylchroman-6-yl)-4,4,5,5-tetramethyl-1,3,2-dioxaborolane as the coupling partner. The experiment afforded the title compound, N-((S)-1-(3-(4-chloro-1-methyl-3-(methylsulfonamido)-1H-indazol-7-yl)-7-(8-fluoro-5-methylchroman-6-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide. The sample was analyzed using LCMS Method C: retention time=1.52 min.; observed ion=969.2 (M+H). 1H NMR (500 MHz, METHANOL-d4) δ ppm 8.30 (d, J=8.20 Hz, 1H), 7.75 (d, J=1.58 Hz, 1H), 7.56 (dd, J=8.20, 1.58 Hz, 1H), 7.29 (d, J=7.88 Hz, 1H), 7.20 (d, J=7.88 Hz, 1H), 6.93 (d, J=11.35 Hz, 1H), 6.52-6.80 (m, 4H), 4.79-4.84 (m, 1H), 4.52 (d, J=5.36 Hz, 2H), 4.23-4.27 (m, 2H), 3.62 (s, 3H), 3.44 (dt, J=3.39, 1.62 Hz, 1H), 3.23 (s, 3H), 3.08 (dd, J=14.19, 9.14 Hz, 1H), 2.80 (t, J=6.62 Hz, 2H), 2.40 (ddd, J=11.51, 7.72, 4.10 Hz, 2H), 2.16 (s, 3H), 2.11-2.15 (m, 2H), 1.32-1.37 (m, 1H), 0.94-1.01 (m, 1H).

Example 54

Preparation of N-((S)-1-(3-(4-chloro-1-methyl-3-(methylsulfonamido)-1H-indazol-7-yl)-7-(3-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

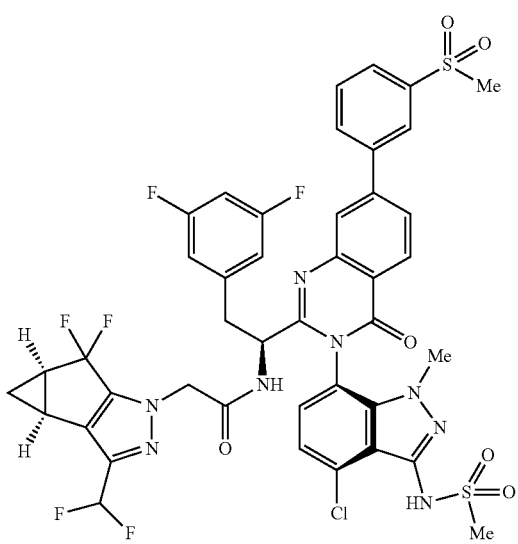

The title compound was prepared according to General Procedure C using 1-bromo-3-(methylsulfonyl)benzene as the coupling partner. The experiment afforded the title compound, N-((S)-1-(3-(4-chloro-1-methyl-3-(methylsulfonamido)-1H-indazol-7-yl)-7-(3-(methyl sulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.29 min.; observed ion=959.2 (M+H). 1H NMR (METHANOL-d4, 500 MHz) δ 8.43 (d, 1H, J=8.2 Hz), 8.40 (s, 1H), 8.21 (br s, 2H), 8.11 (br d, 1H, J=7.9 Hz), 8.03 (br d, 1H, J=8.2 Hz), 7.87 (t, 1H, J=7.8 Hz), 7.32 (br d, 1H, J=7.9 Hz), 7.22 (d, 1H, J=8.2 Hz), 6.8-6.8 (m, 1H), 6.70 (s, 1H), 6.6-6.7 (m, 2H), 4.89 (br s, 4H), 4.55 (br d, 2H, J=4.3 Hz), 3.64 (s, 3H), 3.4-3.5 (m, 1H), 3.1-3.2 (m, 2H), 2.4-2.5 (m, 2H), 1.37 (br d, 1H, J=7.0 Hz), 1.0-1.0 (m, 1H)

Example 55

Preparation of (S)-2-(3-cyclopropyl-1H-pyrazol-1-yl)-N-(2-(3,5-difluorophenyl)-1-(7-(6-methoxypyridin-2-yl)-3-(4-(morpholinosulfonyl)phenyl)-4-oxo-3,4-dihydroquinazolin-2-yl)ethyl)acetamide

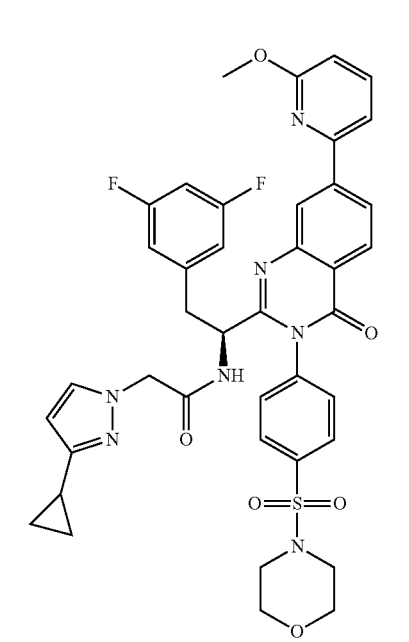 [SMILES: COc1cccc(-c2ccc3c(=O)n(-c4ccc(S(=O)(=O)N5CCOCC5)cc4)c([C@H](Cc4cc(F)cc(F)c4)NC(=O)Cn4ccc(C5CC5)n4)nc3c2)n1]

The title compound was prepared according to General Procedure B using 2-bromo-6-methoxypyridine as the coupling partner. The experiment afforded the title compound, (S)-2-(3-cyclopropyl-1H-pyrazol-1-yl)-N-(2-(3,5-difluorophenyl)-1-(7-(6-methoxypyridin-2-yl)-3-(4-(morpholinosulfonyl)phenyl)-4-oxo-3,4-dihydroquinazolin-2-yl)ethyl)acetamide. The sample was analyzed using LCMS Method C: retention time=1.44 min.; observed ion=782.7 (M+H). 1H NMR (500 MHz, METHANOL-d4) δ ppm 8.56-8.62 (m, 1H) 8.29-8.37 (m, 2H) 7.90-7.99 (m, 2H) 7.83-7.88 (m, 1H) 7.69-7.74 (m, 2H) 7.42-7.46 (m, 1H) 7.37-7.42 (m, 1H) 6.77-6.86 (m, 2H) 6.62-6.69 (m, 2H) 5.96-6.01 (m, 1H) 4.64-4.78 (m, 3H) 4.10-4.15 (m, 3H) 3.71-3.78 (m, 4H) 3.39-3.44 (m, 1H) 2.99-3.10 (m, 5H) 1.88-1.95 (m, 1H) 0.89-0.92 (m, 2H) 0.68-0.71 (m, 2H).

Example 56

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrimidin-5-yl)-3,4-dihydroquinazolin-2-yl)ethyl)acetamide

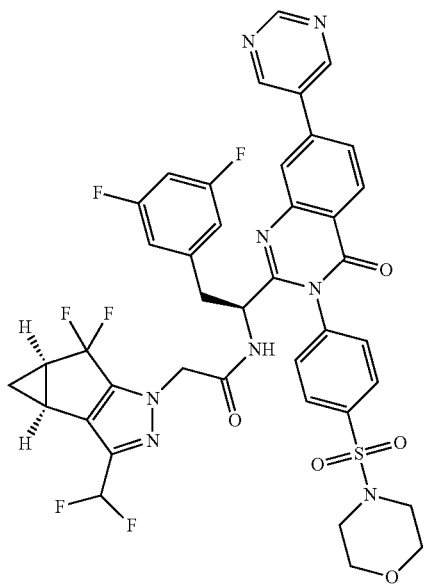 [SMILES: O=C(Cn1nc(C(F)F)c2c1C(F)(F)[C@@H]1C[C@H]21)N[C@@H](Cc1cc(F)cc(F)c1)c1nc2cc(-c3cncnc3)ccc2c(=O)n1-c1ccc(S(=O)(=O)N2CCOCC2)cc1]

The title compound was prepared according to General Procedure A using pyrimidin-5-ylboronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrimidin-5-yl)-3,4-dihydroquinazolin-2-yl)ethyl)acetamide. The sample was analyzed using LCMS Method C: retention time=1.26 min.; observed ion=851 (M+H). 1H NMR (500 MHz, METHANOL-d4) δ ppm 8.88-9.14 (m, 3H) 8.12-8.22 (m, 1H) 7.83-7.95 (m, 1H) 7.47-7.79 (m, 5H) 6.43-6.91 (m, 4H) 5.59-5.79 (m, 1H) 4.62-4.67 (m, 1H) 3.52-3.69 (m, 1H) 3.41-3.49 (m, 4H) 3.13-3.20 (m, 1H) 2.58-2.79 (m, 4H) 2.30-2.45 (m, 2H) 1.22-1.31 (m, 1H) 0.84-0.97 (m, 1H)

Example 57

Preparation of 2-chloro-5-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid)

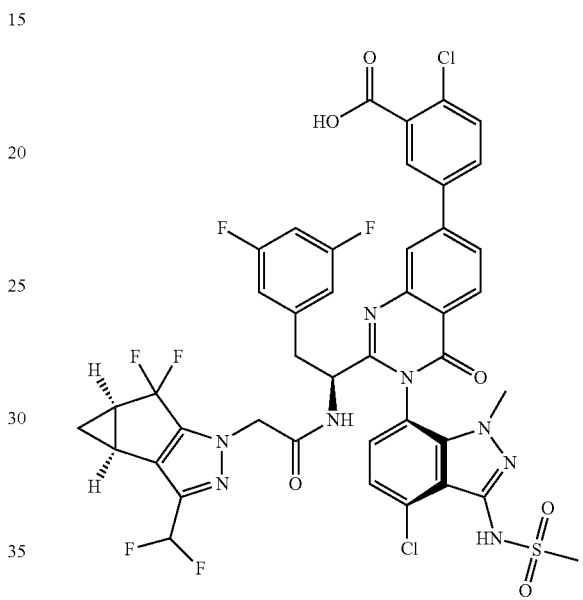

The title compound was prepared according to General Procedure A using 5-borono-2-chlorobenzoic acid as the coupling partner. The experiment afforded the title compound, 2-chloro-5-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid). The sample was analyzed using LCMS Method D: retention time=1.69 min.; observed ion=959.1 (M+H). 1H NMR (500 MHz, METHANOL-d4) δ ppm 8.39 (d, J=8.24 Hz, 1H), 8.23 (s, 1H), 8.16 (s, 1H), 7.97 (br d, J=8.24 Hz, 1H), 7.93 (br d, J=7.93 Hz, 1H), 7.69 (d, J=8.24 Hz, 1H), 7.32 (d, J=7.63 Hz, 1H), 7.22 (d, J=7.93 Hz, 1H), 6.77-6.83 (m, 1H), 6.54-6.73 (m, 3H), 4.88-4.91 (m, 1H), 4.56 (d, J=5.19 Hz, 2H), 3.64 (s, 3H), 3.46-3.53 (m, 1H), 3.26 (s, 3H), 3.12 (br dd, J=14.34, 9.16 Hz, 1H), 2.38-2.49 (m, 2H), 1.33-1.41 (m, 1H), 1.01 (br d, J=1.83 Hz, 1H).

123

Example 58

Preparation of N-((S)-1-(3-(4-chloro-1-methyl-3-(methylsulfonamido)-1H-indazol-7-yl)-7-(6-methoxypyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

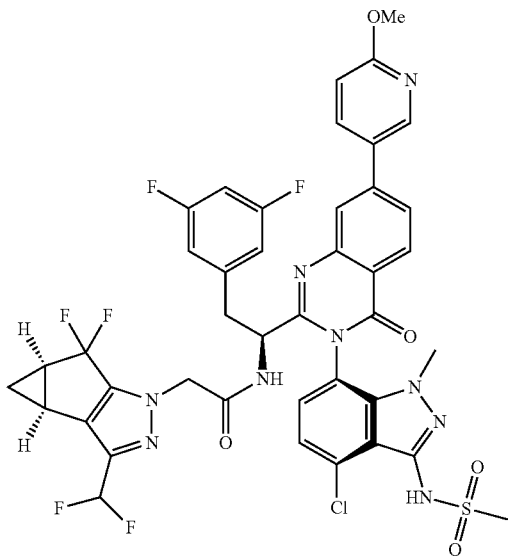

The title compound was prepared according to General Procedure A using (6-methoxypyridin-3-yl)boronic acid as the coupling partner. The experiment afforded the title compound, N-((S)-1-(3-(4-chloro-1-methyl-3-(methylsulfonamido)-1H-indazol-7-yl)-7-(6-methoxypyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.54 min.; observed ion=912.2 (M+H). 1H NMR (500 MHz, METHANOL-d4) δ ppm 8.63 (s, 1H), 8.37 (d, J=8.24 Hz, 1H), 8.17 (dd, J=8.85, 2.44 Hz, 1H), 8.11 (s, 1H), 7.94 (br d, J=8.24 Hz, 1H), 7.31 (br d, J=7.63 Hz, 1H), 7.20 (d, J=7.63 Hz, 1H), 7.01 (d, J=8.55 Hz, 1H), 6.75-6.85 (m, 1H), 6.53-6.72 (m, 3H), 4.87-4.91 (m, 1H), 4.55 (br d, J=2.44 Hz, 2H), 4.03 (s, 3H), 3.63 (s, 3H), 3.45-3.53 (m, 1H), 3.25 (s, 3H), 3.08-3.15 (m, 1H), 2.39-2.48 (m, 2H), 1.33-1.41 (m, 1H), 0.94-1.06 (m, 1H).

124

Example 59

Preparation of N-((S)-1-(3-(4-chloro-1-methyl-3-(methylsulfonamido)-1H-indazol-7-yl)-7-(4-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

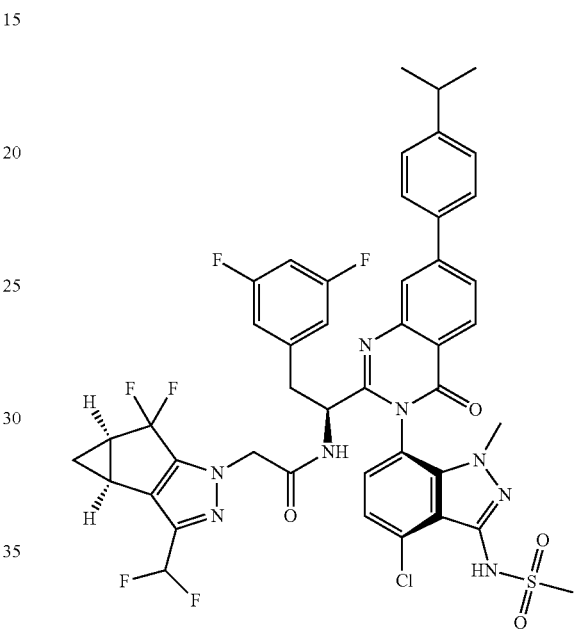

The title compound was prepared according to General Procedure A using (4-isopropylphenyl)boronic acid as the coupling partner. The experiment afforded the title compound, N-((S)-1-(3-(4-chloro-1-methyl-3-(methylsulfonamido)-1H-indazol-7-yl)-7-(4-isopropylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.06 min.; observed ion=923.2 (M+H). 1H NMR (500 MHz, METHANOL-d4) δ ppm 8.35 (d, J=8.24 Hz, 1H), 8.11 (s, 1H), 7.93-7.99 (m, 1H), 7.77 (d, J=8.24 Hz, 2H), 7.46 (d, J=7.93 Hz, 2H), 7.31 (br d, J=7.63 Hz, 1H), 7.20 (d, J=7.63 Hz, 1H), 6.76-6.82 (m, 1H), 6.56-6.71 (m, 3H), 4.87-4.90 (m, 1H), 4.47-4.60 (m, 2H), 3.63 (s, 3H), 3.44-3.51 (m, 1H), 3.25 (s, 3H), 3.12 (dd, J=13.73, 9.16 Hz, 1H), 2.99-3.07 (m, 1H), 2.42 (td, J=7.10, 3.20 Hz, 2H), 1.36-1.39 (m, 1H), 1.35 (d, J=6.71 Hz, 6H), 1.01 (br d, J=3.36 Hz, 1H).

Example 60

Preparation of N-((S)-1-(3-(4-chloro-1-methyl-3-(methylsulfonamido)-1H-indazol-7-yl)-4-oxo-7-(1,3,5-trimethyl-1H-pyrazol-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

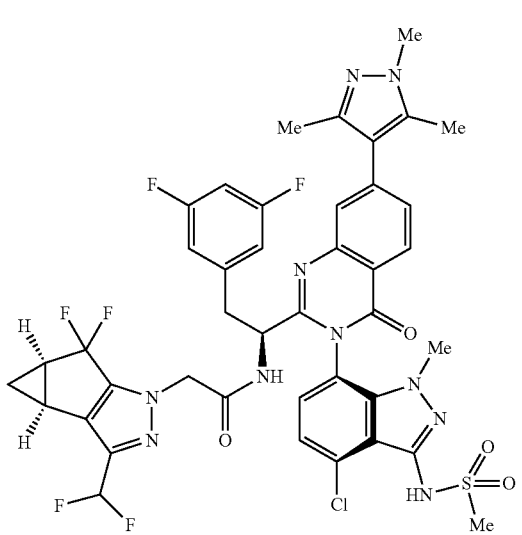

The title compound was prepared according to General Procedure C using 4-bromo-1,3,5-trimethyl-1H-pyrazole as the coupling partner. The experiment afforded the title compound, N-((S)-1-(3-(4-chloro-1-methyl-3-(methylsulfonamido)-1H-indazol-7-yl)-4-oxo-7-(1,3,5-trimethyl-1H-pyrazol-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.18 min.; observed ion=913.2 (M+H). 1H NMR (METHANOL-d4, 500 MHz) δ 8.57 (s, 1H), 8.33 (d, 1H, J=8.2 Hz), 7.76 (s, 1H), 7.60 (br d, 1H, J=7.9 Hz), 7.31 (br d, 1H, J=8.2 Hz), 7.20 (br d, 1H, J=7.9 Hz), 6.8-6.8 (m, 1H), 6.68 (s, 1H), 6.6-6.7 (m, 2H), 4.5-4.6 (m, 2H), 3.85 (s, 2H), 3.6-3.7 (m, 3H), 3.4-3.5 (m, 1H), 3.2-3.3 (m, 4H), 3.19 (br s, 1H), 3.11 (br dd, 1H, J=8.7, 14.2 Hz), 2.41 (s, 3H), 2.34 (s, 3H), 1.3-1.4 (m, 2H), 0.9-1.0 (m, 1H)

Example 61

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrazin-2-yl)-3,4-dihydroquinazolin-2-yl)ethyl)acetamide

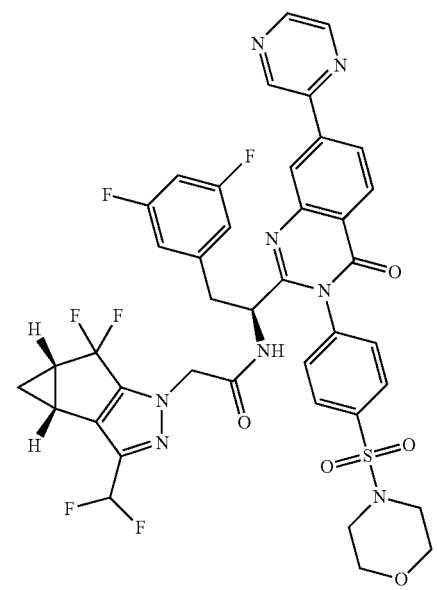 [SMILES: O=C(Cn1nc(C(F)F)c2c1C(F)(F)[C@H]1C[C@@H]21)N[C@@H](Cc1cc(F)cc(F)c1)c1nc2cc(-c3cnccn3)ccc2c(=O)n1-c1ccc(S(=O)(=O)N2CCOCC2)cc1]

The title compound was prepared according to General Procedure B using 2-chloropyrazine as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyrazin-2-yl)-3,4-dihydroquinazolin-2-yl)ethyl)acetamide. The sample was analyzed using LCMS Method C: retention time=1.32 min.; observed ion=851.4 (M+H). 1H NMR (500 MHz, DMSO-d6) δ ppm 9.39-9.51 (m, 1H) 8.67-8.88 (m, 2H) 8.39-8.47 (m, 1H) 8.15-8.31 (m, 1H) 8.10-8.33 (m, 1H) 7.73-7.92 (m, 3H) 6.76-7.13 (m, 4H) 5.65-5.79 (m, 1H) 4.60-4.78 (m, 2H) 3.69-3.69 (m, 1H) 3.43-3.56 (m, 5H) 3.05-3.14 (m, 1H) 2.72-2.85 (m, 4H) 2.52-2.53 (m, 2H) 1.31-1.44 (m, 1H) 0.88-0.89 (m, 1H) 0.77-0.92 (m, 1H)

Example 62

Preparation of 4-(3-(4-chloro-1-methyl-3-(methyl-sulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)-N-methylbenzamide

Example 63

Preparation of N-((S)-1-(3-(4-chloro-1-methyl-3-(methylsulfonamido)-1H-indazol-7-yl)-7-(2,4-dichlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

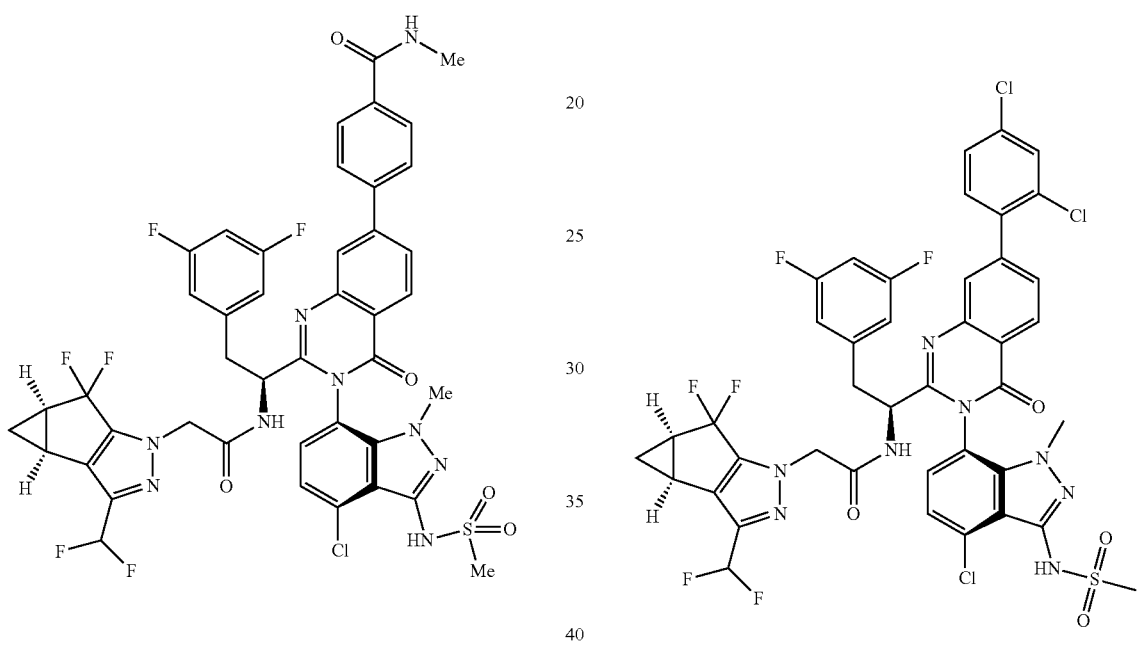

The title compound was prepared according to General Procedure C using 4-bromo-N-methylbenzamide as the coupling partner. The experiment afforded the title compound, 4-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)-N-methylbenzamide. The sample was analyzed using LCMS Method D: retention time=2.22 min.; observed ion=938.2 (M+H). 1H NMR (METHANOL-d4, 500 MHz) δ8.39 (d, 1H, J=8.5 Hz), 8.18 (s, 1H), 7.9-8.1 (m, 5H), 7.3-7.4 (m, 1H), 7.21 (d, 1H, J=7.9 Hz), 6.8-6.8 (m, 1H), 6.6-6.7 (m, 2H), 4.9-4.9 (m, 1H), 4.55 (d, 2H, J=3.7 Hz), 3.63 (s, 3H), 3.4-3.6 (m, 1H), 3.2-3.3 (m, 3H), 3.1-3.2 (m, 2H), 2.99 (s, 3H), 2.4-2.5 (m, 2H), 1.3-1.4 (m, 1H), 1.01 (br d, 1H, J=0.9 Hz)

The title compound was prepared according to General Procedure A using (2,4-dichlorophenyl)boronic acid as the coupling partner. The experiment afforded the title compound, N-((S)-1-(3-(4-chloro-1-methyl-3-(methylsulfonamido)-1H-indazol-7-yl)-7-(2,4-dichlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.95 min.; observed ion=949.1 (M+H). 1H NMR (500 MHz, METHANOL-d4) δ ppm 8.37 (d, J=8.54 Hz, 1H), 7.96 (s, 1H), 7.68-7.75 (m, 2H), 7.54 (s, 2H), 7.32 (br d, J=7.93 Hz, 1H), 7.22 (br d, J=7.32 Hz, 1H), 6.75-6.84 (m, 1H), 6.53-6.71 (m, 3H), 4.88-4.92 (m, 1H), 4.48-4.59 (m, 2H), 3.65 (s, 3H), 3.45-3.51 (m, 1H), 3.26 (s, 3H), 3.11 (br dd, J=14.04, 8.85 Hz, 1H), 2.35-2.52 (m, 2H), 1.32-1.42 (m, 1H), 1.00 (br dd, J=2.90, 1.98 Hz, 1H).

Example 64

Preparation of N-((S)-1-(7-(2,6-dichlorophenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

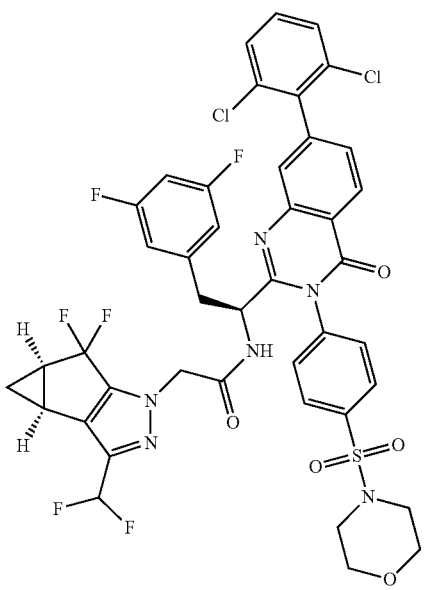 [SMILES: O=C(Cn1nc(C(F)F)c2c1C(F)(F)[C@@H]1C[C@H]21)N[C@@H](Cc1cc(F)cc(F)c1)c1nc2cc(-c3c(Cl)cccc3Cl)ccc2c(=O)n1-c1ccc(S(=O)(=O)N2CCOCC2)cc1]

The title compound was prepared according to General Procedure A using (2,6-dichlorophenyl)boronic acid as the coupling partner. The experiment afforded the title compound, N-((S)-1-(7-(2,6-dichlorophenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.65 min.; observed ion=919.1 (M+H). 1H NMR (500 MHz, METHANOL-d4) δ ppm 8.21-8.27 (m, 1H) 7.78-7.83 (m, 2H) 7.73-7.77 (m, 1H) 7.66 (dd, J=1.58, 0.95 Hz, 1H) 7.64 (br d, J=0.63 Hz, 1H) 7.59 (dd, J=8.35, 1.73 Hz, 1H) 7.48-7.51 (m, 2H) 6.60-6.90 (m, 4H) 5.81-5.86 (m, 1H) 4.69-4.84 (m, 3H) 3.63-3.67 (m, 4H) 3.24-3.30 (m, 2H) 2.91 (br d, J=2.52 Hz, 4H) 2.42-2.48 (m, 2H) 1.34-1.39 (m, 1H) 0.98-1.03 (m, 1H).

Example 65

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-2-yl)-3,4-dihydroquinazolin-2-yl)ethyl)acetamide

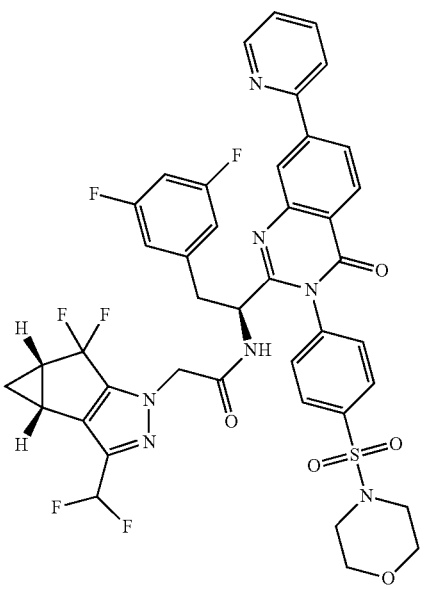 [SMILES: O=C(Cn1nc(C(F)F)c2c1C(F)(F)[C@H]1C[C@@H]21)N[C@@H](Cc1cc(F)cc(F)c1)c1nc2cc(-c3ccccn3)ccc2c(=O)n1-c1ccc(S(=O)(=O)N2CCOCC2)cc1]

The title compound was prepared according to General Procedure B using 2-bromopyridine as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-2-yl)-3,4-dihydroquinazolin-2-yl)ethyl)acetamide. The sample was analyzed using LCMS Method C: retention time=1.42 min.; observed ion=850.4 (M+H). 1H NMR (500 MHz, METHANOL-d4) δ ppm 8.69-8.77 (m, 1H) 8.23-8.34 (m, 2H) 7.95-8.17 (m, 3H) 7.77-7.85 (m, 2H) 7.61-7.71 (m, 2H) 7.43-7.51 (m, 1H) 6.57-6.93 (m, 4H) 5.80-5.88 (m, 1H) 4.71-4.83 (m, 2H) 3.63-3.73 (m, 1H) 3.52-3.60 (m, 4H) 3.26-3.31 (m, 1H) 2.76-2.87 (m, 4H) 2.41-2.50 (m, 2H) 1.33-1.41 (m, 1H) 0.99-1.04 (m, 1H).

Example 66

Preparation of N-((S)-1-(3-(4-chloro-1-methyl-3-(methylsulfonamido)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Example 67

Preparation of N-((S)-1-(3-(4-chloro-1-methyl-3-(methylsulfonamido)-1H-indazol-7-yl)-7-(2-cyanophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

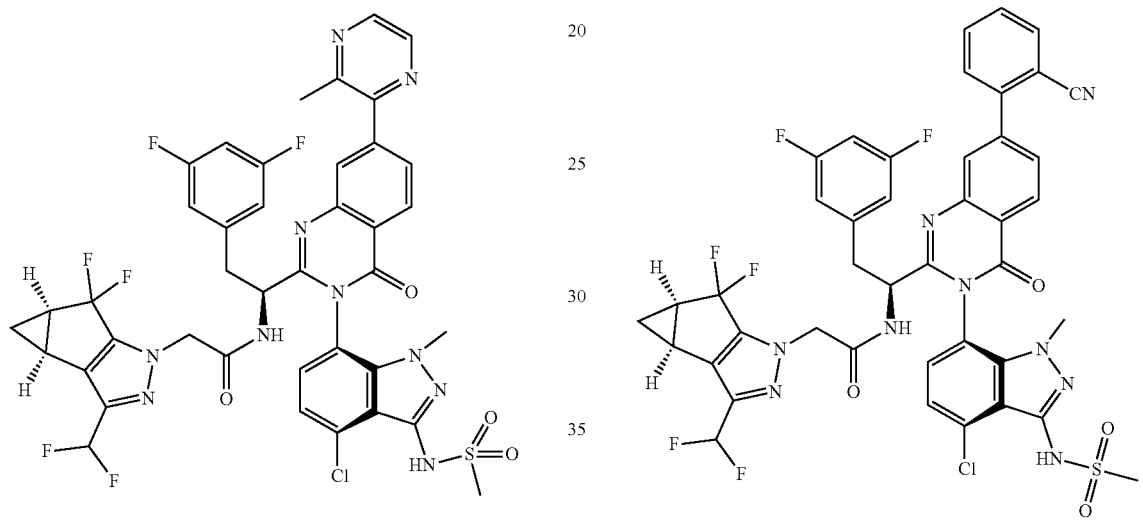

The title compound was prepared according to General Procedure B using 2-chloro-3-methylpyrazine as the coupling partner. The experiment afforded the title compound, N-((S)-1-(3-(4-chloro-1-methyl-3-(methylsulfonamido)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.3 min.; observed ion=897.1 (M+H). 1H NMR (METHANOL-d4, 500 MHz) δ8.65 (s, 1H), 8.62 (d, 1H, J=2.5 Hz), 8.44 (dd, 1H, J=0.6, 8.2 Hz), 8.12 (dd, 1H, J=0.6, 1.6 Hz), 7.91 (dd, 1H, J=1.6, 8.2 Hz), 7.33 (d, 1H, J=7.9 Hz), 7.24 (d, 1H, J=7.9 Hz), 6.8-6.8 (m, 1H), 6.64 (dd, 2H, J=2.2, 8.2 Hz), 6.69 (br t, 2H, J=54.7 Hz), 4.5-4.6 (m, 2H), 3.66 (s, 3H), 3.5-3.5 (m, 1H), 3.2-3.3 (m, 3H), 3.12 (dd, 1H, J=9.3, 14.0 Hz), 2.72 (s, 3H), 2.4-2.5 (m, 2H), 1.3-1.4 (m, 1H), 1.0-1.0 (m, 1H)

The title compound was prepared according to General Procedure A using (2-cyanophenyl)boronic acid as the coupling partner. The experiment afforded the title compound, N-((S)-1-(3-(4-chloro-1-methyl-3-(methylsulfonamido)-1H-indazol-7-yl)-7-(2-cyanophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=1.41 min.; observed ion=906.1 (M+H). 1H NMR (500 MHz, METHANOL-d4) δ ppm 8.32 (d, J=8.20 Hz, 1H), 7.99 (d, J=2.21 Hz, 1H), 7.83-7.88 (m, 1H), 7.70-7.79 (m, 2H), 7.66 (dd, J=7.72, 0.79 Hz, 1H), 7.53-7.60 (m, 1H), 7.21 (d, J=7.88 Hz, 1H), 7.12 (d, J=7.88 Hz, 1H), 6.45-6.72 (m, 4H), 4.76-4.81 (m, 1H), 4.41 (d, J=2.21 Hz, 2H), 3.54 (s, 3H), 3.38 (dd, J=14.03, 4.89 Hz, 1H), 3.15 (s, 3H), 3.01 (dd, J=14.03, 9.30 Hz, 1H), 2.26-2.34 (m, 2H), 1.21-1.27 (m, 1H), 0.89 (ddt, J=5.60, 3.86, 2.05, 2.05 Hz, 1H).

Example 68

Preparation of N-((S)-1-(3-(4-chloro-1-methyl-3-(methylsulfonamido)-1H-indazol-7-yl)-7-(2,3-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

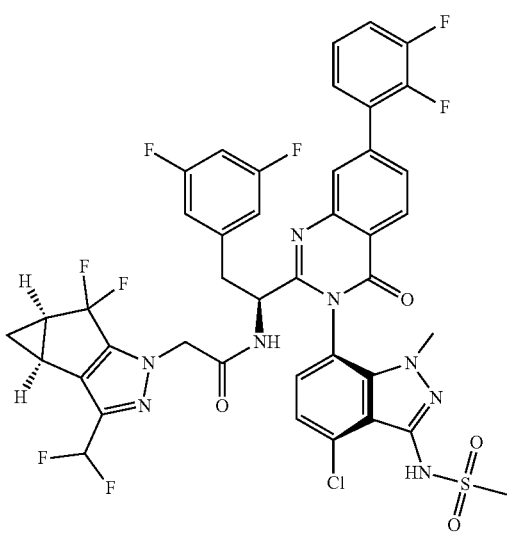

The title compound was prepared according to General Procedure A using 2,3-difluorophenyl)boronic acid as the coupling partner. The experiment afforded the title compound, N-((S)-1-(3-(4-chloro-1-methyl-3-(methylsulfonamido)-1H-indazol-7-yl)-7-(2,3-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.68 min.; observed ion=917.2 (M+H). 1H NMR (500 MHz, METHANOL-d4) δ ppm 8.40 (d, J=8.24 Hz, 1H), 8.09 (s, 1H), 7.86 (br d, J=8.24 Hz, 1H), 7.48 (br t, J=7.32 Hz, 1H), 7.35-7.45 (m, 2H), 7.32 (d, J=7.63 Hz, 1H), 7.23 (d, J=7.63 Hz, 1H), 6.77-6.81 (m, 1H), 6.54-6.71 (m, 3H), 4.87-4.93 (m, 1H), 4.47-4.61 (m, 2H), 3.64 (s, 3H), 3.45-3.53 (m, 1H), 3.26 (s, 3H), 3.12 (br dd, J=14.04, 9.16 Hz, 1H), 2.39-2.48 (m, 2H), 1.32-1.41 (m, 1H), 0.96-1.05 (m, 1H).

Example 69

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-4-yl)-3,4-dihydroquinazolin-2-yl)ethyl)acetamide

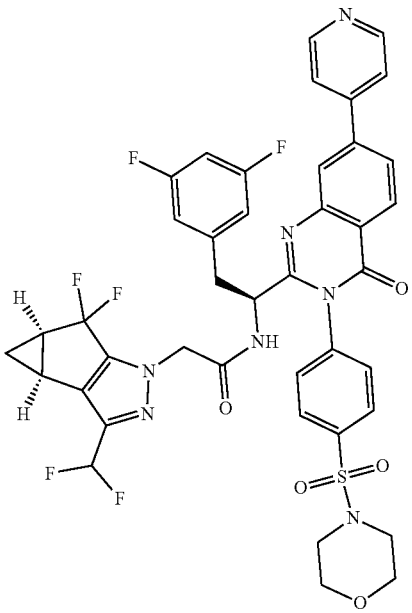 [SMILES: O=C(Cn1nc(C(F)F)c2c1C(F)(F)[C@@H]1C[C@H]21)N[C@@H](Cc1cc(F)cc(F)c1)c1nc2cc(-c3ccncc3)ccc2c(=O)n1-c1ccc(S(=O)(=O)N2CCOCC2)cc1]

The title compound was prepared according to General Procedure A using pyridin-4-ylboronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(3-(4-(morpholinosulfonyl)phenyl)-4-oxo-7-(pyridin-4-yl)-3,4-dihydroquinazolin-2-yl)ethyl)acetamide. The sample was analyzed using LCMS Method C: retention time=1.13 min.; observed ion=850.3 (M+H). 1H NMR (500 MHz, METHANOL-d4) δ ppm 8.72-8.79 (m, 2H) 8.36-8.43 (m, 1H) 7.99-8.05 (m, 1H) 7.91-7.98 (m, 4H) 7.67-7.70 (m, 1H) 7.35-7.43 (m, 2H) 6.62-6.85 (m, 4H) 4.70-4.84 (m, 3H) 3.72-3.76 (m, 4H) 3.40-3.46 (m, 1H) 3.00-3.11 (m, 5H) 2.43-2.50 (m, 2H) 1.36-1.42 (m, 1H) 1.01-1.06 (m, 1H)

Example 70

Preparation of N-((S)-1-(3-(4-chloro-1-methyl-3-(methylsulfonamido)-1H-indazol-7-yl)-7-(3,5-difluoro-4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

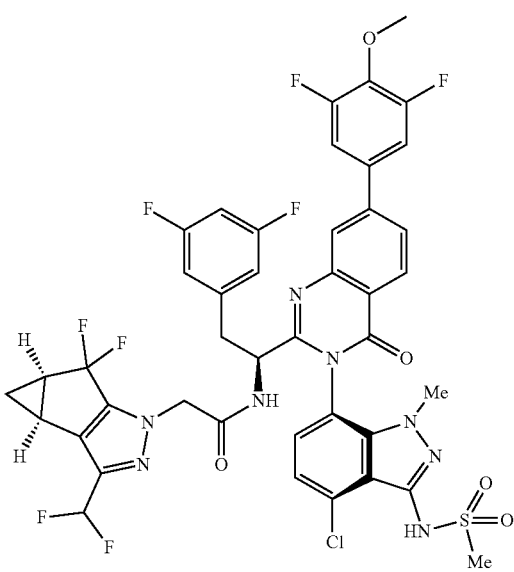

The title compound was prepared according to General Procedure B using 5-bromo-1,3-difluoro-2-methoxybenzene as the coupling partner. The experiment afforded the title compound, N-((S)-1-(3-(4-chloro-1-methyl-3-(methylsulfonamido)-1H-indazol-7-yl)-7-(3,5-difluoro-4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=2.683 min.; observed ion=947.15 (M+H). 1H NMR (METHANOL-d4, 500 MHz) δ 8.65 (br d, 1H, J=8.9 Hz), 8.24 (d, 1H, J=8.2 Hz), 7.99 (s, 1H), 7.81 (d, 1H, J=8.0 Hz), 7.4-7.4 (m, 2H), 7.20 (d, 1H, J=7.9 Hz), 7.08 (d, 1H, J=7.7 Hz), 6.6-6.8 (m, 2H), 6.51 (br d, 2H, J=7.0 Hz), 4.4-4.5 (m, 2H), 3.97 (s, 3H), 3.51 (s, 3H), 3.3-3.4 (m, 2H), 3.07 (br s, 1H), 3.0-3.0 (m, 1H), 2.31 (ddd, 2H, J=3.7, 7.5, 10.8 Hz), 1.2-1.3 (m, 2H), 1.12 (s, 1H), 0.8-0.9 (m, 2H)

Example 71

Preparation of N-((S)-1-(3-(4-chloro-1-methyl-3-(methylsulfonamido)-1H-indazol-7-yl)-4-oxo-7-(pyridin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

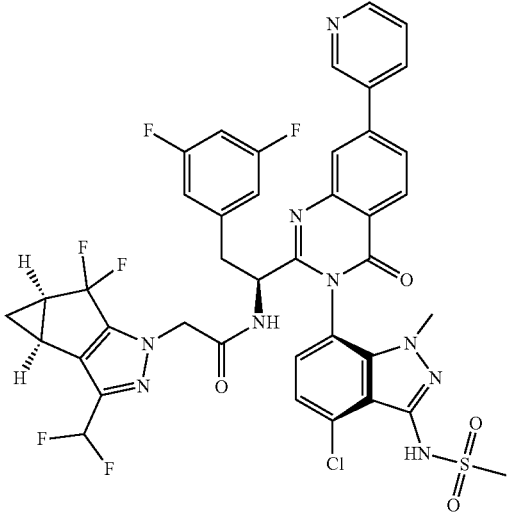

The title compound was prepared according to General Procedure A using pyridin-3-ylboronic acid as the coupling partner. The experiment afforded the title compound, N-((S)-1-(3-(4-chloro-1-methyl-3-(methylsulfonamido)-1H-indazol-7-yl)-4-oxo-7-(pyridin-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.24 min.; observed ion=882.2 (M+H). 1H NMR (500 MHz, METHANOL-d4) δ ppm 9.03 (s, 1H), 8.62-8.75 (m, 1H), 8.43 (d, J=8.24 Hz, 1H), 8.32 (br d, J=7.94 Hz, 1H), 8.19 (s, 1H), 7.95-8.05 (m, 1H), 7.67 (dd, J=8.09, 5.04 Hz, 1H), 7.32 (d, J=7.63 Hz, 1H), 7.22 (d, J=7.63 Hz, 1H), 6.77-6.84 (m, 1H), 6.55-6.72 (m, 3H), 4.87-4.90 (m, 1H), 4.55 (d, J=2.75 Hz, 2H), 3.64 (s, 3H), 3.46-3.53 (m, 1H), 3.26 (s, 3H), 3.13 (dd, J=14.19, 9.31 Hz, 1H), 2.35-2.49 (m, 2H), 1.33-1.42 (m, 1H), 1.01 (br d, J=3.05 Hz, 1H).

Example 72

Preparation of N-((S)-1-(7-(2-(tert-butyl)pyrimidin-5-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

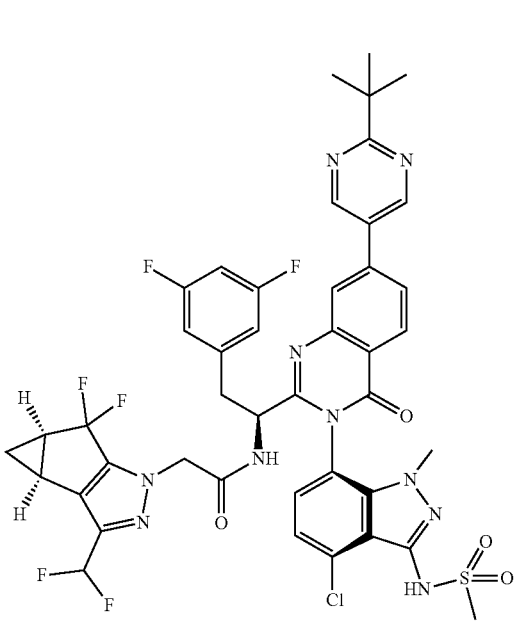

The title compound was prepared according to General Procedure C using 5-bromo-2-(tert-butyl)pyrimidine as the coupling partner. The experiment afforded the title compound, N-((S)-1-(7-(2-(tert-butyl)pyrimidin-5-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.51 min.; observed ion=940.5 (M+H). 1H NMR (METHANOL-d4, 500 MHz) Shift 9.18 (s, 2H), 8.44 (d, 1H, J=8.2 Hz), 8.22 (d, 1H, J=1.9 Hz), 8.02 (dd, 1H, J=1.7, 8.4 Hz), 7.32 (d, 1H, J=7.9 Hz), 7.21 (d, 1H, J=7.9 Hz), 6.8-6.8 (m, 1H), 6.64 (dd, 2H, J=2.0, 8.0 Hz), 6.69 (t, 2H, J=54.7 Hz), 4.54 (d, 2H, J=1.9 Hz), 3.63 (s, 3H), 3.51 (dd, 1H, J=5.0, 14.2 Hz), 3.2-3.3 (m, 3H), 3.1-3.2 (m, 1H), 2.44 (ddd, 2H, J=3.9, 7.6, 11.4 Hz), 1.51 (s, 9H), 1.3-1.4 (m, 1H), 1.0-1.0 (m, 1H)

Example 74

Preparation of (S)-2-(3-cyclopropyl-1H-pyrazol-1-yl)-N-(2-(3,5-difluorophenyl)-1-(7-(2,3-difluorophenyl)-3-(4-(morpholinosulfonyl)phenyl)-4-oxo-3,4-dihydroquinazolin-2-yl)ethyl)acetamide

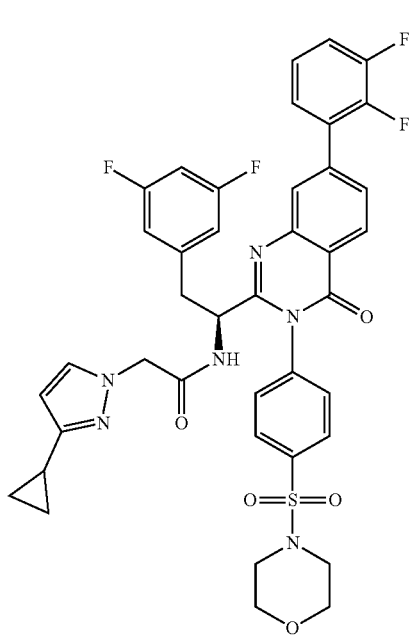 [SMILES: O=C(Cn1ccc(C2CC2)n1)N[C@@H](Cc1cc(F)cc(F)c1)c1nc2cc(-c3cccc(F)c3F)ccc2c(=O)n1-c1ccc(S(=O)(=O)N2CCOCC2)cc1]

The title compound was prepared according to General Procedure A using (2,3-difluorophenyl)boronic acid as the coupling partner. The experiment afforded the title compound, (S)-2-(3-cyclopropyl-1H-pyrazol-1-yl)-N-(2-(3,5-difluorophenyl)-1-(7-(2,3-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.45 min.; observed ion=787.5 (M+H). 1H NMR (500 MHz, METHANOL-d4) δ ppm 8.35 (d, J=8.24 Hz, 1H) 8.06 (s, 1H) 7.92-7.98 (m, 2H) 7.77-7.84 (m, 1H) 7.72 (dd, J=8.39, 1.98 Hz, 1H) 7.29-7.49 (m, 5H) 6.80 (br t, J=8.56 Hz, 1H) 6.64 (br d, J=6.41 Hz, 2H) 5.98 (d, J=2.44 Hz, 1H) 4.78-4.81 (m, 1H) 4.65-4.78 (m, 2H) 3.74 (t, J=4.58 Hz, 4H) 3.61 (br s, 1H) 3.35-3.41 (m, 2H) 3.00-3.10 (m, 4H) 2.86 (br d, J=5.19 Hz, 1H) 1.88-1.94 (m, 1H) 0.86-0.95 (m, 2H) 0.69 (br d, J=3.36 Hz, 2H)

Example 75

Preparation of 2-chloro-4-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid

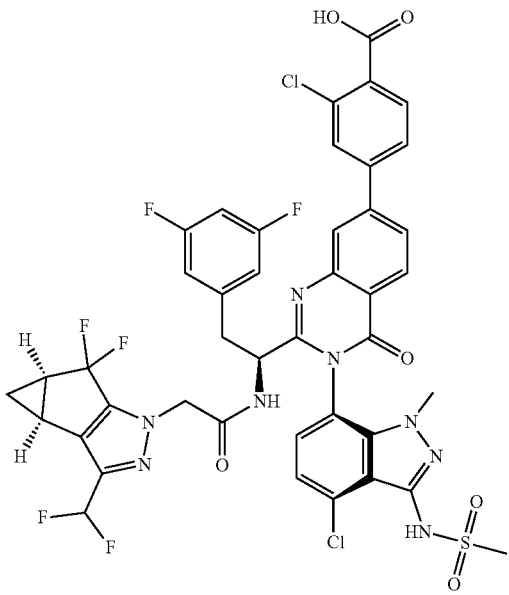

The title compound was prepared according to General Procedure A using 4-borono-2-chlorobenzoic acid as the coupling partner. The experiment afforded the title compound, 2-chloro-4-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid. The sample was analyzed using LCMS Method D: retention time=1.33 min.; observed ion=959.1 (M+H). 1H NMR (500 MHz, METHANOL-d4) δ ppm 8.38 (d, J=8.24 Hz, 1H), 8.14 (s, 1H), 7.93-8.00 (m, 1H), 7.87 (s, 1H), 7.71-7.80 (m, 2H), 7.33 (d, J=7.32 Hz, 1H), 7.22 (d, J=7.93 Hz, 1H), 6.76-6.83 (m, 1H), 6.54-6.72 (m, 3H), 4.86-4.91 (m, 1H), 4.57 (br d, J=4.88 Hz, 2H), 3.64 (s, 3H), 3.46-3.53 (m, 1H), 3.26 (s, 3H), 3.12 (br dd, J=13.89, 9.31 Hz, 1H), 2.39-2.48 (m, 2H), 1.34-1.40 (m, 1H), 0.96-1.05 (m, 1H).

Example 76

Preparation of N-((S)-1-(3-(4-chloro-1-methyl-3-(methylsulfonamido)-1H-indazol-7-yl)-7-(isoxazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

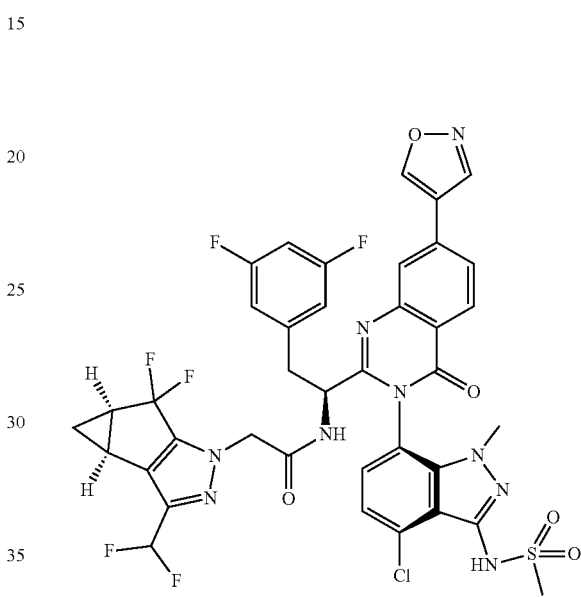

The title compound was prepared according to General Procedure C using 4-bromoisoxazole as the coupling partner. The experiment afforded the title compound, N-((S)-1-(3-(4-chloro-1-methyl-3-(methylsulfonamido)-1H-indazol-7-yl)-7-(isoxazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method C: retention time=1.32 min.; observed ion=872.5 (M+H). 1H NMR (METHANOL-d4, 500 MHz) Shift 9.39 (s, 1H), 9.08 (s, 1H), 8.3-8.4 (m, 1H), 8.16 (d, 1H, J=1.3 Hz), 7.9-8.0 (m, 1H), 7.30 (d, 1H, J=7.9 Hz), 7.18 (d, 1H, J=7.9 Hz), 6.8-6.8 (m, 1H), 6.64 (br dd, 2H, J=2.2, 8.2 Hz), 6.70 (br t, 1H, J=54.9 Hz), 4.5-4.5 (m, 2H), 3.6-3.6 (m, 3H), 3.4-3.5 (m, 1H), 3.3-3.4 (m, 1H), 3.25 (s, 3H), 3.12 (dd, 1H, J=9.1, 14.2 Hz), 2.43 (ddd, 2H, J=4.1, 7.6, 11.3 Hz), 1.3-1.4 (m, 1H), 1.0-1.0 (m, 1H)

Example 77

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-dimethylphenyl)-3-(4-(morpholinosulfonyl)phenyl)-4-oxo-3,4-dihydroquinazolin-2-yl)ethyl)acetamide

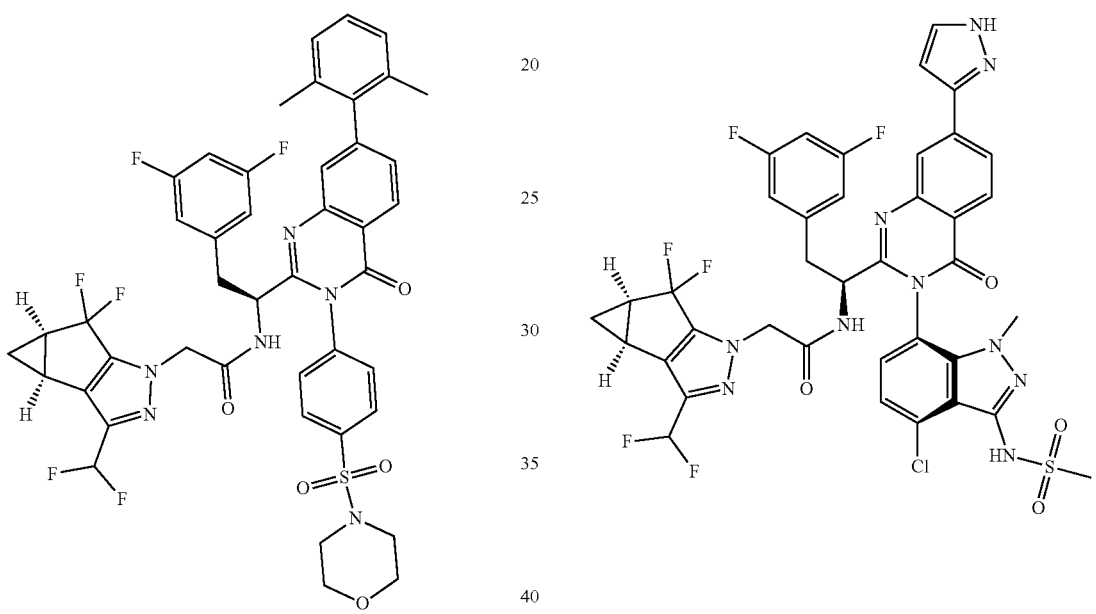

The title compound was prepared according to General Procedure A using (2,6-dimethylphenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-dimethylphenyl)-3-(4-(morpholinosulfonyl)phenyl)-4-oxo-3,4-dihydroquinazolin-2-yl)ethyl)acetamide. The sample was analyzed using LCMS Method C: retention time=1.59 min.; observed ion=878.1 (M+H). 1H NMR (500 MHz, METHANOL-d4) δ ppm 8.30-8.38 (m, 1H) 7.92-7.99 (m, 2H) 7.61-7.73 (m, 2H) 7.39-7.45 (m, 2H) 7.14-7.28 (m, 3H) 6.61-6.83 (m, 4H) 4.66-4.85 (m, 3H) 3.70-3.76 (m, 4H) 3.37-3.42 (m, 1H) 3.00-3.11 (m, 5H) 2.42-2.51 (m, 2H) 2.07-2.11 (m, 6H) 1.35-1.42 (m, 1H) 1.00-1.06 (m, 1H).

Preparation of Example 78

N-((S)-1-(3-(4-chloro-1-methyl-3-(methylsulfonamido)-1H-indazol-7-yl)-4-oxo-7-(1H-pyrazol-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

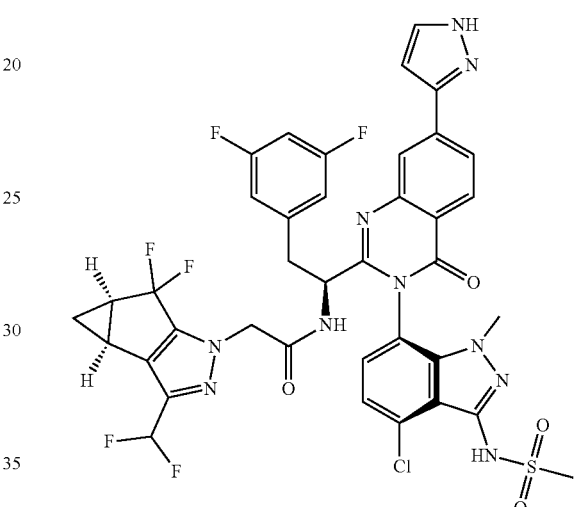

The title compound was prepared according to General Procedure A using (1H-pyrazol-3-yl)boronic acid as the coupling partner. The experiment afforded the title compound, N-((S)-1-(3-(4-chloro-1-methyl-3-(methylsulfonamido)-1H-indazol-7-yl)-4-oxo-7-(1H-pyrazol-3-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.25 min.; observed ion=871.3 (M+H). 1H NMR (500 MHz, METHANOL-d4) δ ppm 8.25-8.38 (m, 2H), 8.13 (br d, J=8.83 Hz, 1H), 7.84 (br d, J=1.58 Hz, 1H), 7.31 (d, J=7.88 Hz, 1H), 7.19 (d, J=7.88 Hz, 1H), 6.95 (d, J=2.21 Hz, 1H), 6.57-6.84 (m, 4H), 4.88-4.91 (m, 1H), 4.54 (s, 2H), 3.64 (s, 3H), 3.49-3.52 (m, 1H), 3.25 (s, 3H), 3.12 (dd, J=13.87, 9.14 Hz, 1H), 2.35-2.50 (m, 2H), 1.31-1.43 (m, 1H), 0.88-1.06 (m, 1H).

Example 79

Preparation of (S)-2-(3-cyclopropyl-1H-pyrazol-1-yl)-N-(2-(3,5-difluorophenyl)-1-(3-(4-(morpholinosulfonyl)phenyl)-4-oxo-7-(pyrimidin-5-yl)-3,4-dihydroquinazolin-2-yl)ethyl)acetamide

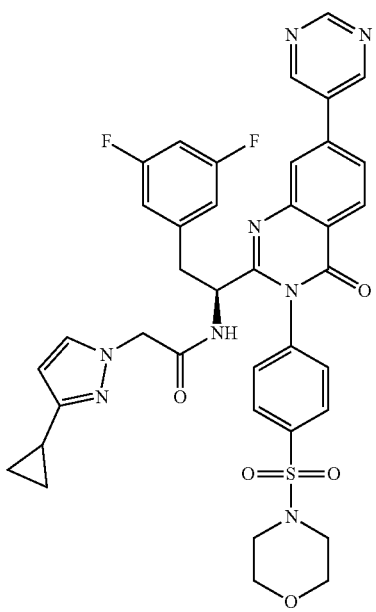 [SMILES: O=C(Cn1ccc(C2CC2)n1)N[C@@H](Cc1cc(F)cc(F)c1)c1nc2cc(-c3cncnc3)ccc2c(=O)n1-c1ccc(S(=O)(=O)N2CCOCC2)cc1]

The title compound was prepared according to General Procedure A using pyrimidin-5-ylboronic acid as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-(pyrimidin-5-yl)-3,4-dihydroquinazolin-2-yl)ethyl)acetamide. The sample was analyzed using LCMS Method C: retention time=1.12 min.; observed ion=753.3 (M+H). 1H NMR (500 MHz, METHANOL-d4) δ ppm 8.35-8.43 (m, 1H) 8.20-8.24 (m, 1H) 7.86-8.03 (m, 3H) 7.67-7.74 (m, 1H) 7.35-7.46 (m, 2H) 6.76-6.83 (m, 1H) 6.61-6.68 (m, 2H) 4.78-4.82 (m, 1H) 4.64-4.74 (m, 1H) 3.70-3.74 (m, 4H) 3.44-3.46 (m, 2H) 3.16-3.18 (m, 2H) 2.98-3.07 (m, 7H) 1.87-1.94 (m, 1H) 0.87-0.91 (m, 2H) 0.66-0.70 (m, 2H).

Example 80

Preparation of N-((S)-1-(7-(2,4-dichlorophenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

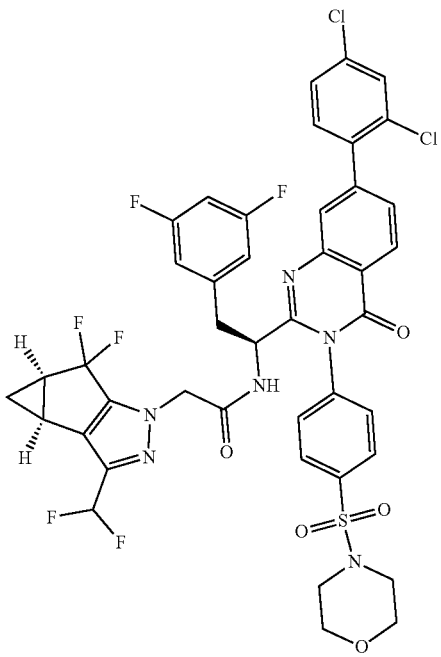 [SMILES: O=C(Cn1nc(C(F)F)c2c1C(F)(F)[C@@H]1C[C@H]21)N[C@@H](Cc1cc(F)cc(F)c1)c1nc2cc(-c3ccc(Cl)cc3Cl)ccc2c(=O)n1-c1ccc(S(=O)(=O)N2CCOCC2)cc1]

The title compound was prepared according to General Procedure A using (2,4-dichlorophenyl)boronic acid as the coupling partner. The experiment afforded the title compound, N-((S)-1-(7-(2,4-dichlorophenyl)-3-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method A: retention time=2.35 min.; observed ion=917.2 (M+H). 1H NMR (500 MHz, METHANOL-d4) δ ppm 8.33-8.38 (m, 1H) 7.91-8.00 (m, 2H) 7.74-7.78 (m, 1H) 7.70 (dd, J=8.36, 2.05 Hz, 1H) 7.59-7.63 (m, 2H) 7.39-7.53 (m, 3H) 6.63-6.87 (m, 4H) 4.68-4.84 (m, 3H) 3.72-3.76 (m, 4H) 3.38-3.43 (m, 1H) 3.00-3.11 (m, 5H) 2.42-2.51 (m, 2H) 1.35-1.42 (m, 1H) 1.01-1.06 (m, 1H).

Example 81

Preparation of (S)-2-(3-cyclopropyl-1H-pyrazol-1-yl)-N-(1-(7-(2,4-dichlorophenyl)-3-(4-(morpholinosulfonyl)phenyl)-4-oxo-3,4-dihydroquinazolin-2-yl)-2-(3,5-difluorophenyl)ethyl)acetamide

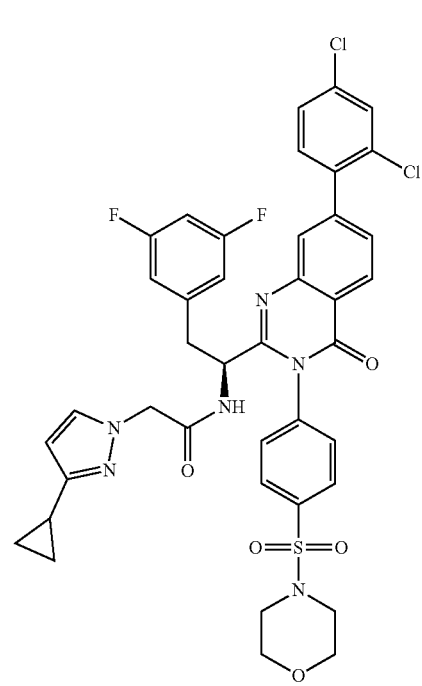 [SMILES: O=C(Cn1ccc(C2CC2)n1)N[C@@H](Cc1cc(F)cc(F)c1)c1nc2cc(-c3ccc(Cl)cc3Cl)ccc2c(=O)n1-c1ccc(S(=O)(=O)N2CCOCC2)cc1]

The title compound was prepared according to General Procedure A using (2,4-dichlorophenyl)boronic acid as the coupling partner. The experiment afforded the title compound, (S)-2-(3-cyclopropyl-1H-pyrazol-1-yl)-N-(1-(7-(2,4-dichlorophenyl)-3-(4-(morpholinosulfonyl)phenyl)-4-oxo-3,4-dihydroquinazolin-2-yl)-2-(3,5-difluorophenyl)ethyl)acetamide. The sample was analyzed using LCMS Method C: retention time=1.59 min.; observed ion=819.7 (M+H). 1H NMR (500 MHz, METHANOL-d4) δ ppm 8.32 (d, J=8.24 Hz, 1H) 7.91-7.99 (m, 3H) 7.65-7.75 (m, 3H) 7.54 (d, J=0.92 Hz, 2H) 7.44 (d, J=2.14 Hz, 1H) 7.42 (dd, J=8.09, 1.98 Hz, 1H) 6.80 (br t, J=9.16 Hz, 1H) 6.64 (br d, J=6.71 Hz, 2H) 5.98 (d, J=2.44 Hz, 1H) 4.81 (s, 1H) 4.68-4.75 (m, 2H) 3.74 (t, J=4.58 Hz, 4H) 3.35-3.40 (m, 6H) 3.15-3.30 (m, 2H) 2.98-3.11 (m, 6H) 1.88-1.94 (m, 1H) 0.84-0.93 (m, 2H) 0.64-0.71 (m, 2H)

Example 82

Preparation of N-((S)-1-(3-(4-chloro-1-methyl-3-(methylsulfonamido)-1H-indazol-7-yl)-7-(2,3-dihydropyrano[4,3,2-de]quinolin-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

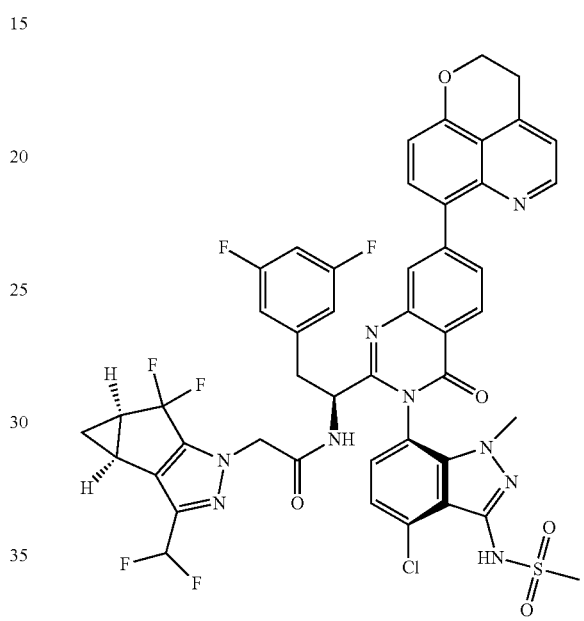

The title compound was prepared according to General Procedure A using (2,3-dihydropyrano[4,3,2-de]quinolin-7-yl)boronic acid as the coupling partner. The experiment afforded the title compound, N-((S)-1-(3-(4-chloro-1-methyl-3-(methylsulfonamido)-1H-indazol-7-yl)-7-(2,3-dihydropyrano[4,3,2-de]quinolin-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.

The sample was analyzed using LCMS Method C: retention time=1.43 min.; observed ion=974.3 (M+H). 1H NMR (500 MHz, METHANOL-d4) δ ppm 8.79 (d, J=4.41 Hz, 1H), 8.34 (d, J=8.20 Hz, 1H), 8.15 (d, J=1.26 Hz, 1H), 7.91 (dd, J=8.20, 1.89 Hz, 1H), 7.84 (d, J=8.20 Hz, 1H), 7.36 (d, J=4.41 Hz, 1H), 7.27 (br d, J=7.57 Hz, 1H), 7.17 (d, J=7.88 Hz, 1H), 7.12 (d, J=7.88 Hz, 1H), 6.53-6.81 (m, 4H), 4.87-4.90 (m, 1H), 4.50-4.56 (m, 4H), 3.62 (s, 3H), 3.48 (dd, J=13.87, 5.36 Hz, 1H), 3.37 (t, J=5.67 Hz, 2H), 3.22 (s, 3H), 3.09 (dd, J=13.87, 8.83 Hz, 1H), 2.34-2.44 (m, 2H), 1.31-1.37 (m, 1H), 0.95-1.02 (m, 1H).

Example 83

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-dimethoxyphenyl)-3-(4-(morpholinosulfonyl)phenyl)-4-oxo-3,4-dihydroquinazolin-2-yl)ethyl)acetamide

Example 84

Preparation of N-((S)-1-(3-(4-chloro-1-methyl-3-(methylsulfonamido)-1H-indazol-7-yl)-4-oxo-7-(pyrimidin-5-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

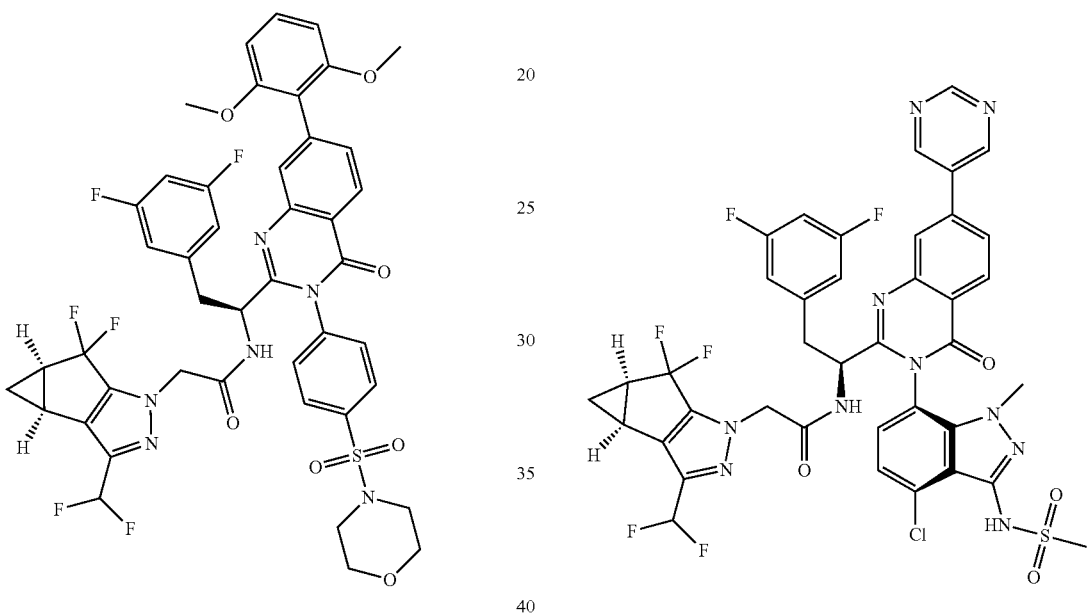

The title compound was prepared according to General Procedure A using (2,6-dimethoxyphenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,6-dimethoxyphenyl)-3-(4-(morpholinosulfonyl)phenyl)-4-oxo-3,4-dihydroquinazolin-2-yl)ethyl)acetamide. The sample was analyzed using LCMS Method C: retention time=1.46 min.; observed ion=909.3 (M+H). 1H NMR (500 MHz, METHANOL-d4) δ ppm 8.19-8.22 (m, 1H) 7.91-7.97 (m, 2H) 7.76-7.82 (m, 3H) 7.65-7.69 (m, 2H) 7.52-7.55 (m, 1H) 7.34-7.43 (m, 2H) 6.59-6.90 (m, 4H) 4.79-4.83 (m, 2H) 4.68-4.73 (m, 1H) 3.77-3.81 (m, 6H) 3.72-3.75 (m, 4H) 3.39-3.44 (m, 1H) 3.00-3.10 (m, 5H) 2.43-2.50 (m, 2H) 1.35-1.44 (m, 1H) 0.99-1.07 (m, 1H).

The title compound was prepared according to General Procedure A using pyrimidin-5-ylboronic acid as the coupling partner. The experiment afforded the title compound, N-((S)-1-(3-(4-chloro-1-methyl-3-(methylsulfonamido)-1H-indazol-7-yl)-4-oxo-7-(pyrimidin-5-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.11 min.; observed ion=883.2 (M+H). 1H NMR (500 MHz, METHANOL-d4) δ ppm 9.19-9.32 (m, 3H), 8.46 (d, J=8.24 Hz, 1H), 8.26 (s, 1H), 8.01-8.10 (m, 1H), 7.32 (br d, J=7.93 Hz, 1H), 7.21 (d, J=7.63 Hz, 1H), 6.75-6.84 (m, 1H), 6.55-6.73 (m, 3H), 4.87-4.90 (m, 1H), 4.54 (s, 2H), 3.63 (s, 3H), 3.44-3.55 (m, 1H), 3.26 (s, 3H), 3.07-3.17 (m, 1H), 2.37-2.49 (m, 2H), 1.33-1.40 (m, 1H), 0.97-1.03 (m, 1H).

Example 85

Preparation of 4-(2-((S)-1-(2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-3-(4-(morpholinosulfonyl)phenyl)-4-oxo-3,4-dihydroquinazolin-7-yl)-N-methylbenzamide

Preparation of Example 86

N-((S)-1-(3-(4-chloro-1-methyl-3-(methylsulfonamido)-1H-indazol-7-yl)-7-(2,6-dimethoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

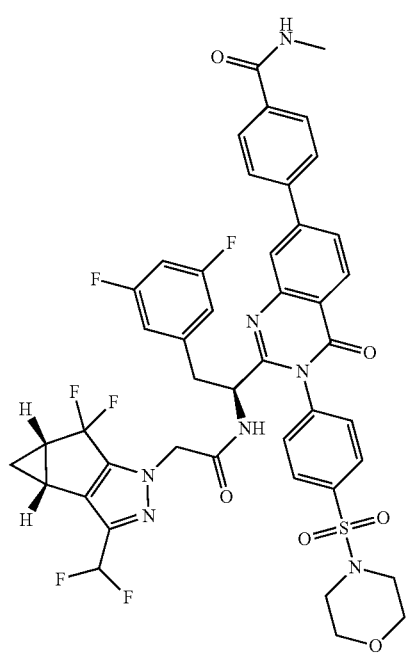 [SMILES: CNC(=O)c1ccc(-c2ccc3c(=O)n(-c4ccc(S(=O)(=O)N5CCOCC5)cc4)c([C@H](Cc4cc(F)cc(F)c4)NC(=O)Cn4nc(C(F)F)c5c4C(F)(F)[C@H]4C[C@@H]54)nc3c2)cc1]

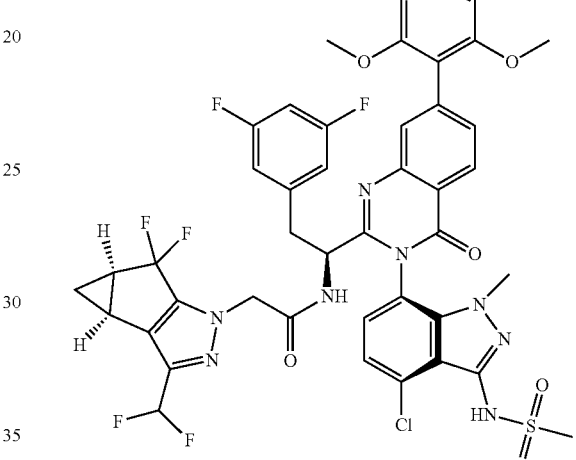

The title compound was prepared according to General Procedure B using 4-bromo-N-methylbenzamide as the coupling partner. The experiment afforded the title compound, 4-(2-((S)-1-(2-((3bR,4aS)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-3-(4-(morpholinosulfonyl)phenyl)-4-oxo-3,4-dihydroquinazolin-7-yl)-N-methylbenzamide. The sample was analyzed using LCMS Method C: retention time=1.39 min.; observed ion=906.3 (M+H). 1H NMR (500 MHz, METHANOL-d4) δ ppm 8.23-8.27 (m, 1H) 7.97-8.00 (m, 3H) 7.84-7.91 (m, 3H) 7.81 (d, J=8.83 Hz, 2H) 6.60-6.93 (m, 5H) 5.80-5.86 (m, 1H) 4.69-4.83 (m, 3H) 3.59 (t, J=4.73 Hz, 4H) 3.26-3.31 (m, 1H) 3.02-3.10 (m, 1H) 2.98 (s, 3H) 2.78-2.90 (m, 4H) 2.41-2.50 (m, 3H) 1.32-1.42 (m, 1H) 0.97-1.06 (m, 1H)

The title compound was prepared according to General Procedure A using (2,6-dimethoxyphenyl)boronic acid as the coupling partner. The experiment afforded the title compound, N-((S)-1-(3-(4-chloro-1-methyl-3-(methylsulfonamido)-1H-indazol-7-yl)-7-(2,6-dimethoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.67 min.; observed ion=941.2 (M+H). 1H NMR (500 MHz, METHANOL-d4) δ ppm 8.25 (d, J=8.24 Hz, 1H), 7.80 (s, 1H), 7.57 (d, J=8.24 Hz, 1H), 7.42 (t, J=8.55 Hz, 1H), 7.31 (br d, J=7.93 Hz, 1H), 7.18 (br d, J=7.93 Hz, 1H), 6.83 (d, J=8.55 Hz, 2H), 6.75-6.81 (m, 1H), 6.56-6.70 (m, 3H), 4.89-4.91 (m, 1H), 4.53 (d, J=4.88 Hz, 2H), 3.79 (s, 6H), 3.65 (s, 3H), 3.46-3.52 (m, 1H), 3.25 (s, 3H), 3.10 (br dd, J=13.43, 8.85 Hz, 1H), 2.39-2.49 (m, 2H), 1.32-1.40 (m, 1H), 0.97-1.06 (m, 1H).

Example 87

Preparation of N-((S)-1-(3-(4-chloro-1-methyl-3-(methylsulfonamido)-1H-indazol-7-yl)-4-oxo-7-(pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

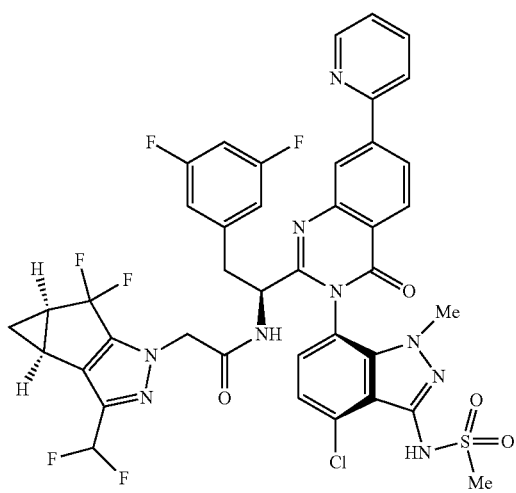

The title compound was prepared according to General Procedure B using 2-bromopyridine as the coupling partner. The experiment afforded the title compound, N-((S)-1-(3-(4-chloro-1-methyl-3-(methylsulfonamido)-1H-indazol-7-yl)-4-oxo-7-(pyridin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.39 min.; observed ion=882.2 (M+H). 1H NMR (METHANOL-d4, 500 MHz) δ8.78 (br d, 1H, J=5.2 Hz), 8.51 (s, 1H), 8.41 (d, 1H, J=7.9 Hz), 8.29 (d, 1H, J=8.2 Hz), 8.11 (d, 1H, J=8.2 Hz), 8.0-8.1 (m, 1H), 7.52 (t, 1H, J=6.3 Hz), 7.31 (br d, 1H, J=8.2 Hz), 7.20 (d, 1H, J=7.9 Hz), 6.8-6.8 (m, 1H), 6.64 (br d, 2H, J=5.8 Hz), 4.9-4.9 (m, 1H), 4.80 (br s, 1H), 4.54 (s, 2H), 3.64 (s, 3H), 3.5-3.5 (m, 1H), 3.4-3.4 (m, 1H), 3.2-3.3 (m, 3H), 3.1-3.2 (m, 2H), 2.4-2.5 (m, 2H), 1.3-1.4 (m, 1H), 1.01 (br d, 1H, J=4.0 Hz)

Example 88

Preparation of N-((S)-1-(3-(4-chloro-1-methyl-3-(methylsulfonamido)-1H-indazol-7-yl)-4-oxo-7-(o-tolyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

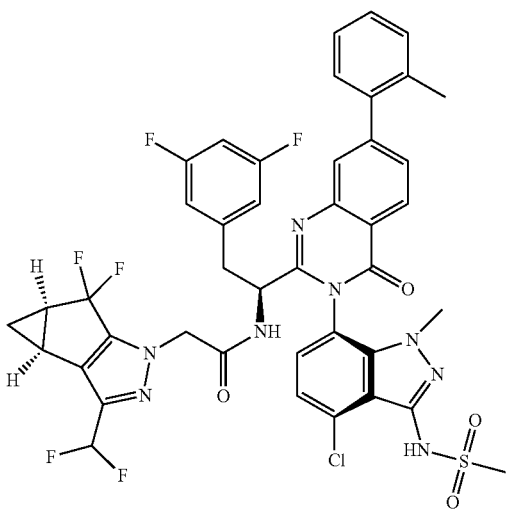

The title compound was prepared according to General Procedure A using o-tolylboronic acid as the coupling partner. The experiment afforded the title compound, N-((S)-1-(3-(4-chloro-1-methyl-3-(methylsulfonamido)-1H-indazol-7-yl)-4-oxo-7-(o-tolyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.75 min.; observed ion=895.2 (M+H). 1H NMR (500 MHz, METHANOL-d4) δ ppm 8.35 (d, J=8.24 Hz, 1H), 7.83 (s, 1H), 7.64 (dd, J=8.24, 1.53 Hz, 1H), 7.32-7.41 (m, 4H), 7.31-7.42 (m, 1H), 7.23 (d, J=7.63 Hz, 1H), 6.77-6.83 (m, 1H), 6.53-6.72 (m, 3H), 4.86-4.89 (m, 1H), 4.49-4.61 (m, 2H), 3.65 (s, 3H), 3.43-3.53 (m, 1H), 3.26 (s, 3H), 3.11 (br dd, J=14.19, 9.00 Hz, 1H), 2.39-2.45 (m, 2H), 2.36 (s, 3H), 1.32-1.40 (m, 1H), 0.97-1.05 (m, 1H).

Example 89

Preparation of N-((S)-1-(3-(4-chloro-1-methyl-3-(methylsulfonamido)-1H-indazol-7-yl)-7-(3,5-dimethyl-1H-pyrazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

Example 90

Preparation of N-((S)-1-(3-(4-chloro-1-methyl-3-(methylsulfonamido)-1H-indazol-7-yl)-7-(4-chloro-2-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide)

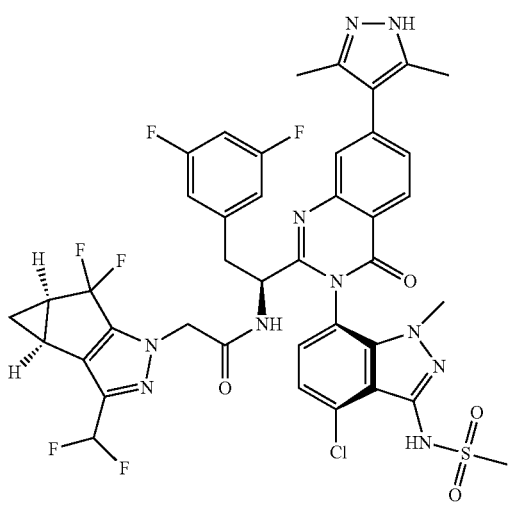

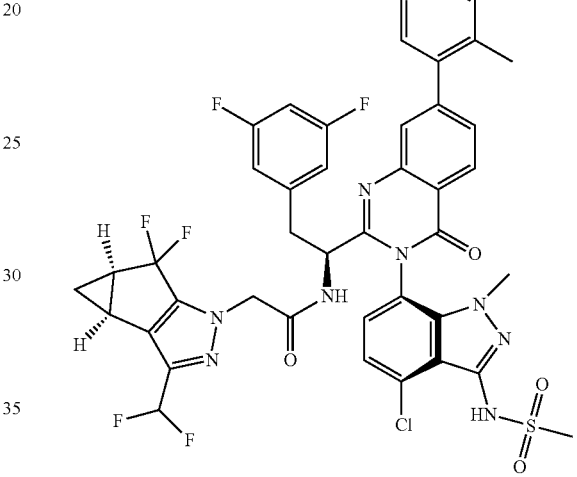

The title compound was prepared according to General Procedure A using (3,5-dimethyl-1H-pyrazol-4-yl)boronic acid as the coupling partner. The experiment afforded the title compound, N-((S)-1-(3-(4-chloro-1-methyl-3-(methylsulfonamido)-1H-indazol-7-yl)-7-(3,5-dimethyl-1H-pyrazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=1.85 min.; observed ion=899.2 (M+H). 1H NMR (500 MHz, METHANOL-d4) δ ppm 8.33 (d, J=8.24 Hz, 1H), 7.79 (s, 1H), 7.64 (br d, J=8.24 Hz, 1H), 7.24-7.31 (m, 1H), 7.18 (br d, J=7.63 Hz, 1H), 6.76-6.83 (m, 1H), 6.52-6.72 (m, 3H), 4.87-4.92 (m, 1H), 4.55 (br d, J=5.49 Hz, 2H), 3.62 (s, 3H), 3.45-3.50 (m, 1H), 3.23 (s, 3H), 3.06-3.14 (m, 1H), 2.36-2.49 (m, 2H), 2.41 (br s, 6H), 1.34-1.40 (m, 1H), 0.93-1.04 (m, 1H).

The title compound was prepared according to General Procedure A using (4-chloro-2-methylphenyl)boronic acid as the coupling partner. The experiment afforded the title compound, N-((S)-1-(3-(4-chloro-1-methyl-3-(methylsulfonamido)-1H-indazol-7-yl)-7-(4-chloro-2-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide). The sample was analyzed using LCMS Method D: retention time=2.93 min.; observed ion=929.2 (M+H). 1H NMR (500 MHz, METHANOL-d4) δ ppm 8.36 (d, J=8.24 Hz, 1H), 7.83 (s, 1H), 7.61-7.67 (m, 1H), 7.44 (s, 1H), 7.29-7.39 (m, 3H), 7.22 (d, J=7.93 Hz, 1H), 6.77-6.82 (m, 1H), 6.55-6.71 (m, 3H), 4.86-4.91 (m, 1H), 4.49-4.59 (m, 2H), 3.65 (s, 3H), 3.44-3.52 (m, 1H), 3.26 (s, 3H), 3.11 (br dd, J=14.19, 9.00 Hz, 1H), 2.40-2.46 (m, 2H), 2.36 (s, 3H), 1.31-1.42 (m, 1H), 1.00 (br dd, J=4.73, 2.29 Hz, 1H).

Example 91

Preparation of N-((S)-1-(3-(4-chloro-1-methyl-3-(methylsulfonamido)-1H-indazol-7-yl)-7-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

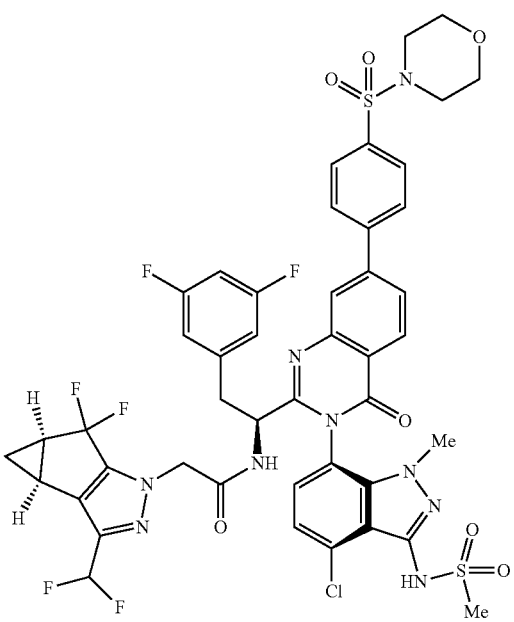

The title compound was prepared according to General Procedure C using 4-((4-bromophenyl)sulfonyl)morpholine as the coupling partner. The experiment afforded the title compound, N-((S)-1-(3-(4-chloro-1-methyl-3-(methylsulfonamido)-1H-indazol-7-yl)-7-(4-(morpholinosulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.4 min.; observed ion=1030.2 (M+H). 1H NMR (METHANOL-d4, 500 MHz) δ8.42 (d, 1H, J=8.2 Hz), 8.22 (s, 1H), 8.11 (d, 2H, J=7.9 Hz), 8.0-8.0 (m, 3H), 7.31 (br d, 1H, J=7.9 Hz), 7.21 (d, 1H, J=7.9 Hz), 6.8-6.8 (m, 1H), 6.69 (s, 1H), 6.64 (br d, 2H, J=6.4 Hz), 4.9-4.9 (m, 1H), 4.54 (d, 2H, J=2.4 Hz), 3.7-3.8 (m, 4H), 3.64 (s, 3H), 3.5-3.5 (m, 1H), 3.2-3.3 (m, 3H), 3.1-3.2 (m, 5H), 2.42 (br d, 2H, J=4.9 Hz), 1.36 (br d, 1H, J=6.7 Hz), 1.01 (br d, 1H, J=2.7 Hz)

Example 92

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(4-fluoropyridin-3-yl)-3-(4-(morpholinosulfonyl)phenyl)-4-oxo-3,4-dihydroquinazolin-2-yl)ethyl)acetamide

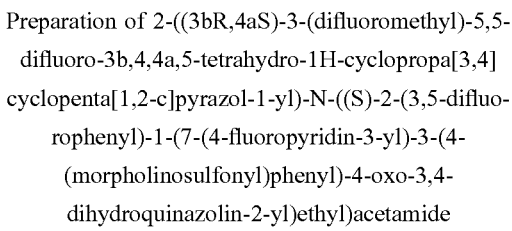

The title compound was prepared according to General Procedure B using 3-bromo-4-fluoropyridine as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(4-fluoropyridin-3-yl)-3-(4-(morpholinosulfonyl)phenyl)-4-oxo-3,4-dihydroquinazolin-2-yl)ethyl)acetamide. The sample was analyzed using LCMS Method C: retention time=1.36 min.; observed ion=868.3 (M+H). 1H NMR (500 MHz, METHANOL-d4) δ ppm 8.77-8.90 (m, 1H) 8.62-8.68 (m, 1H) 8.25-8.32 (m, 1H) 7.91-7.97 (m, 1H) 7.75-7.84 (m, 3H) 7.61-7.73 (m, 2H) 7.40-7.47 (m, 1H) 6.58-6.93 (m, 4H) 5.79-5.88 (m, 1H) 4.70-4.83 (m, 2H) 3.56-3.67 (m, 5H) 3.23-3.31 (m, 1H) 2.78-2.92 (m, 4H) 2.40-2.52 (m, 2H) 1.32-1.41 (m, 1H) 0.98-1.05 (m, 1H).

Example 93

Preparation of (S)-2-(3-cyclopropyl-1H-pyrazol-1-yl)-N-(2-(3,5-difluorophenyl)-1-(3-(4-(morpholinosulfonyl)phenyl)-4-oxo-7-(pyridin-2-yl)-3,4-dihydroquinazolin-2-yl)ethyl)acetamide

Example 94

Preparation of N-((S)-1-(3-(4-chloro-1-methyl-3-(methylsulfonamido)-1H-indazol-7-yl)-7-(3,5-dimethylisoxazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

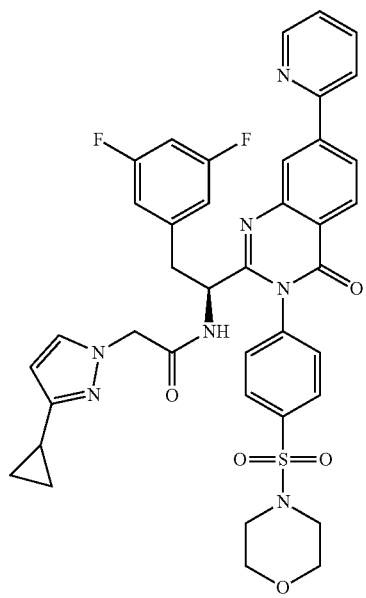 [SMILES: O=C(Cn1ccc(C2CC2)n1)N[C@@H](Cc1cc(F)cc(F)c1)c1nc2cc(-c3ccccn3)ccc2c(=O)n1-c1ccc(S(=O)(=O)N2CCOCC2)cc1]

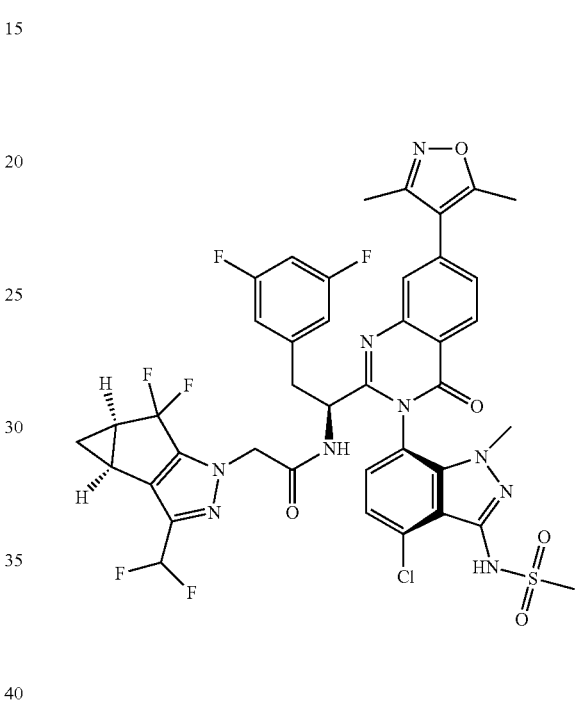

The title compound was prepared according to General Procedure B using 2-bromopyridine as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-(pyridin-2-yl)-3,4-dihydroquinazolin-2-yl)ethyl)acetamide. The sample was analyzed using LCMS Method C: retention time=1.28 min.; observed ion=752.5 (M+H). 1H NMR (500 MHz, METHANOL-d4) δ ppm 8.75-8.80 (m, 1H) 8.47-8.51 (m, 1H) 8.34-8.38 (m, 1H) 8.23-8.27 (m, 1H) 8.09-8.13 (m, 1H) 8.01-8.06 (m, 1H) 7.91-7.99 (m, 2H) 7.69-7.74 (m, 1H) 7.49-7.53 (m, 1H) 7.43-7.45 (m, 1H) 7.37-7.42 (m, 1H) 6.77-6.84 (m, 1H) 6.63-6.69 (m, 2H) 5.97-6.00 (m, 1H) 4.80-4.84 (m, 1H) 4.66-4.77 (m, 2H) 3.71-3.77 (m, 4H) 3.39-3.45 (m, 2H) 3.02-3.09 (m, 4H) 1.88-1.96 (m, 1H) 0.89-0.94 (m, 2H) 0.68-0.73 (m, 2H)

The title compound was prepared according to General Procedure A using (3,5-dimethylisoxazol-4-yl)boronic acid as the coupling partner. The experiment afforded the title compound, N-((S)-1-(3-(4-chloro-1-methyl-3-(methylsulfonamido)-1H-indazol-7-yl)-7-(3,5-dimethylisoxazol-4-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.33 min.; observed ion=900.2 (M+H). 1H NMR (500 MHz, METHANOL-d4) δ ppm 8.39 (d, J=7.94 Hz, 1H), 7.86 (s, 1H), 7.68 (br d, J=8.24 Hz, 1H), 7.32 (br d, J=7.63 Hz, 1H), 7.22 (d, J=8.24 Hz, 1H), 6.76-6.83 (m, 1H), 6.54-6.71 (m, 3H), 4.86-4.91 (m, 1H), 4.54 (br d, J=2.75 Hz, 2H), 3.64 (s, 3H), 3.44-3.53 (m, 1H), 3.26 (s, 3H), 3.11 (br dd, J=13.89, 9.31 Hz, 1H), 2.56 (s, 3H), 2.42-2.47 (m, 2H), 2.40 (s, 3H), 1.35-1.41 (m, 1H), 0.97-1.05 (m, 1H).

Example 96

Preparation of N-((S)-1-(3-(4-chloro-1-methyl-3-(methylsulfonamido)-1H-indazol-7-yl)-7-(4-fluoropyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

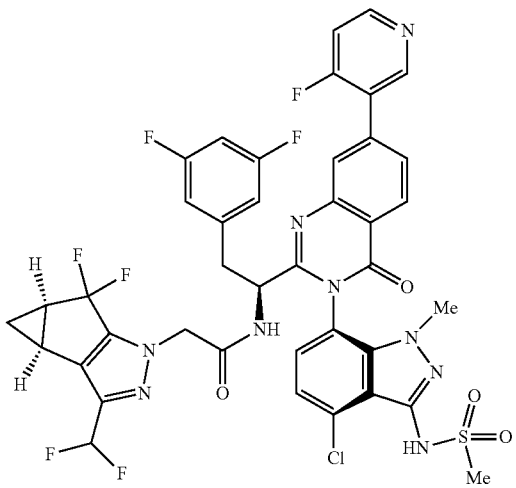

The title compound was prepared according to General Procedure B using 3-bromo-4-fluoropyridine as the coupling partner. The experiment afforded the title compound, N-((S)-1-(3-(4-chloro-1-methyl-3-(methylsulfonamido)-1H-indazol-7-yl)-7-(4-fluoropyridin-3-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.29 min.; observed ion=900.2 (M+H). 1H NMR (METHANOL-d4, 500 MHz) δ8.88 (d, 1H, J=10.4 Hz), 8.70 (t, 1H, J=6.6 Hz), 8.43 (d, 1H, J=8.2 Hz), 8.14 (s, 1H), 7.90 (br d, 1H, J=8.2 Hz), 7.5-7.5 (m, 1H), 7.32 (br d, 1H, J=7.9 Hz), 7.23 (d, 1H, J=7.6 Hz), 6.8-6.8 (m, 1H), 6.69 (s, 1H), 6.6-6.7 (m, 1H), 6.6-6.6 (m, 1H), 4.9-4.9 (m, 1H), 4.54 (d, 2H, J=4.3 Hz), 3.64 (s, 3H), 3.5-3.5 (m, 1H), 3.2-3.3 (m, 4H), 3.19 (br s, 1H), 3.1-3.2 (m, 1H), 2.4-2.5 (m, 2H), 1.3-1.4 (m, 1H), 1.0-1.0 (m, 1H)

Example 97

Preparation of N-((S)-1-(3-(4-chloro-1-methyl-3-(methylsulfonamido)-1H-indazol-7-yl)-7-(3-cyano-4-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

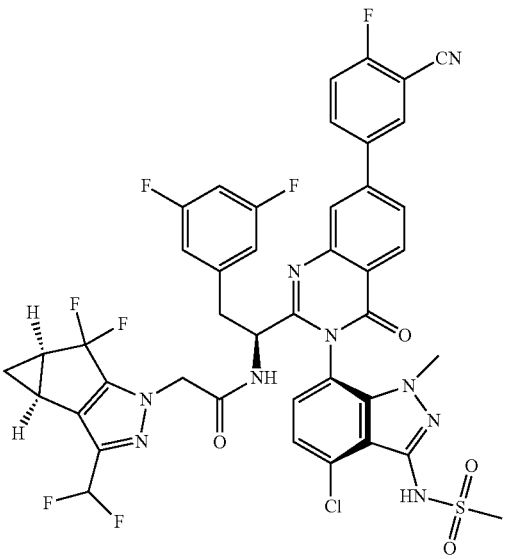

The title compound was prepared according to General Procedure A using (3-cyano-4-fluorophenyl)boronic acid as the coupling partner. The experiment afforded the title compound, N-((S)-1-(3-(4-chloro-1-methyl-3-(methylsulfonamido)-1H-indazol-7-yl)-7-(3-cyano-4-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.43 min.; observed ion=924.4 (M+H). 1H NMR (500 MHz, METHANOL-d4) δ ppm 8.34-8.40 (m, 1H), 8.25 (dd, J=5.99, 2.21 Hz, 1H), 8.18 (ddd, J=8.75, 4.97, 2.36 Hz, 1H), 8.14 (d, J=1.58 Hz, 1H), 7.94 (dd, J=8.20, 1.89 Hz, 1H), 7.57 (t, J=8.83 Hz, 1H), 7.29 (d, J=7.88 Hz, 1H), 7.18 (d, J=7.88 Hz, 1H), 6.53-6.81 (m, 4H), 4.78-4.83 (m, 1H), 4.51 (d, J=1.89 Hz, 2H), 3.60 (s, 3H), 3.48 (dd, J=14.03, 4.89 Hz, 1H), 3.23 (s, 3H), 3.10 (dd, J=13.87, 9.14 Hz, 1H), 2.33-2.47 (m, 2H), 1.30-1.40 (m, 1H), 0.94-1.04 (m, 1H).

161
Preparation of Example 98

N-((S)-1-(3-(4-chloro-1-methyl-3-(methylsulfonamido)-1H-indazol-7-yl)-7-(4-fluoro-3-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

162
Example 99

Preparation of N-((S)-1-(3-(4-chloro-1-methyl-3-(methylsulfonamido)-1H-indazol-7-yl)-7-(2,5-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

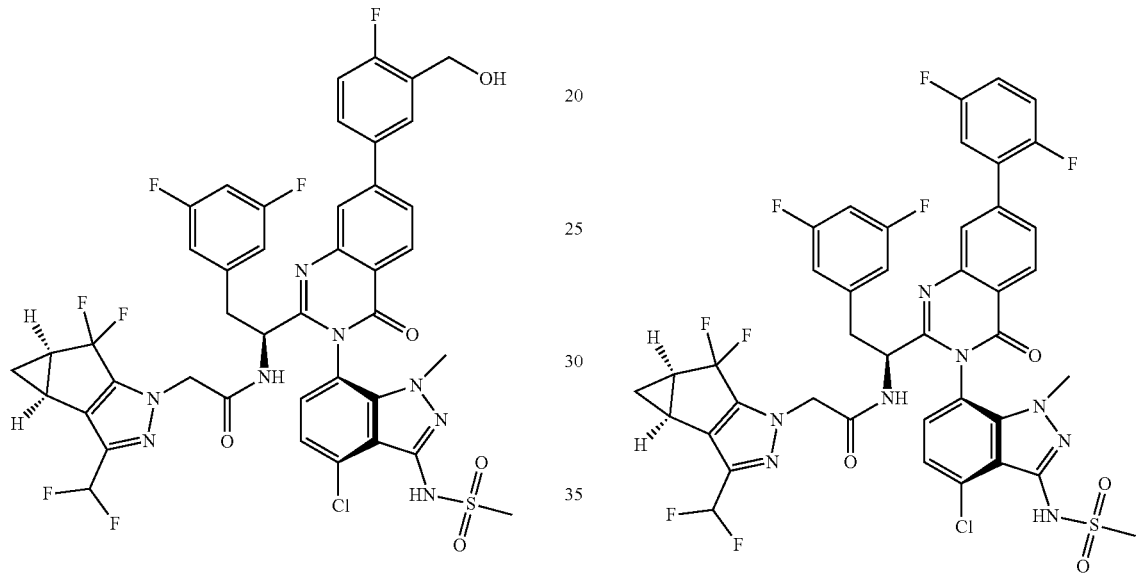

The title compound was prepared according to General Procedure A using (4-fluoro-3-(hydroxymethyl)phenyl)boronic acid as the coupling partner. The experiment afforded the title compound, N-((S)-1-(3-(4-chloro-1-methyl-3-(methylsulfonamido)-1H-indazol-7-yl)-7-(4-fluoro-3-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.29 min.; observed ion=929.2 (M+H). 1H NMR (500 MHz, METHANOL-d4) δ ppm 8.37 (d, J=8.24 Hz, 1H), 8.14 (s, 1H), 7.97 (br d, J=8.55 Hz, 1H), 7.66-7.73 (m, 2H), 7.59 (br d, J=10.99 Hz, 1H), 7.31 (br d, J=8.24 Hz, 1H), 7.21 (d, J=7.93 Hz, 1H), 6.76-6.85 (m, 1H), 6.51-6.72 (m, 3H), 4.87-4.89 (m, 1H), 4.79 (s, 2H), 4.49-4.60 (m, 2H), 3.63 (s, 3H), 3.46-3.54 (m, 1H), 3.25 (s, 3H), 3.12 (br dd, J=14.19, 9.00 Hz, 1H), 2.34-2.51 (m, 2H), 1.32-1.42 (m, 1H), 1.01 (br d, J=3.97 Hz, 1H).

The title compound was prepared according to General Procedure A using (2,5-difluorophenyl)boronic acid as the coupling partner. The experiment afforded the title compound, N-((S)-1-(3-(4-chloro-1-methyl-3-(methylsulfonamido)-1H-indazol-7-yl)-7-(2,5-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.71 min.; observed ion=917.2 (M+H). 1H NMR (500 MHz, METHANOL-d4) δ ppm 8.39 (d, J=8.24 Hz, 1H), 8.10 (s, 1H), 7.81-7.89 (m, 1H), 7.47 (ddd, J=8.77, 5.87, 3.05 Hz, 1H), 7.25-7.40 (m, 3H), 7.22 (d, J=7.93 Hz, 1H), 6.76-6.82 (m, 1H), 6.49-6.71 (m, 3H), 4.87-4.91 (m, 1H), 4.54 (d, J=5.19 Hz, 2H), 3.63 (s, 3H), 3.45-3.52 (m, 1H), 3.26 (s, 3H), 3.12 (dd, J=14.04, 9.46 Hz, 1H), 2.36-2.48 (m, 2H), 1.31-1.41 (m, 1H), 1.01 (br dd, J=1.83, 1.22 Hz, 1H).

163

Preparation of Example 100

4-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid

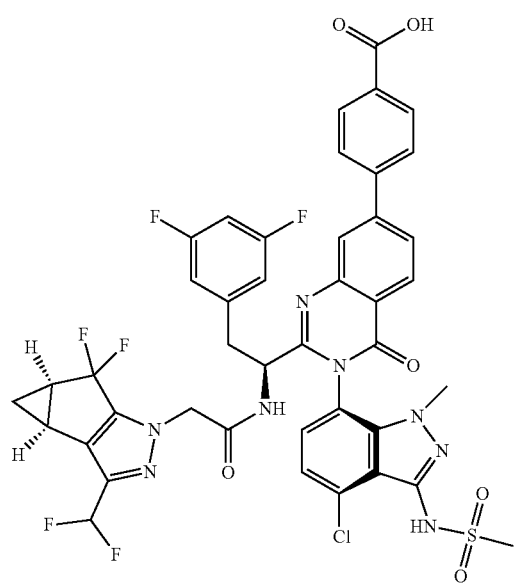

The title compound was prepared according to General Procedure A using 4-boronobenzoic acid as the coupling partner. The experiment afforded the title compound, 4-(3-(4-chloro-1-methyl-3-(methylsulfonamido)-1H-indazol-7-yl)-2-((S)-1-(2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)-4-oxo-3,4-dihydroquinazolin-7-yl)benzoic acid. The sample was analyzed using LCMS Method D: retention time=1.62 min.; observed ion=925.2 (M+H). 1H NMR (500 MHz, METHANOL-d4) δ ppm 8.40 (d, J=8.24 Hz, 1H), 8.17-8.28 (m, 3H), 8.01 (br d, J=8.54 Hz, 1H), 7.94 (br d, J=8.24 Hz, 2H), 7.33 (d, J=7.93 Hz, 1H), 7.22 (d, J=7.93 Hz, 1H), 6.77-6.83 (m, 1H), 6.53-6.71 (m, 3H), 4.88-4.91 (m, 1H), 4.55 (d, J=3.05 Hz, 2H), 3.64 (s, 3H), 3.44-3.54 (m, 1H), 3.26 (s, 3H), 3.13 (br dd, J=13.89, 9.31 Hz, 1H), 2.39-2.48 (m, 2H), 1.33-1.40 (m, 1H), 1.01 (br s, 1H).

164

Example 101

Preparation of N-((S)-1-(7-([1,1'-biphenyl]-4-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

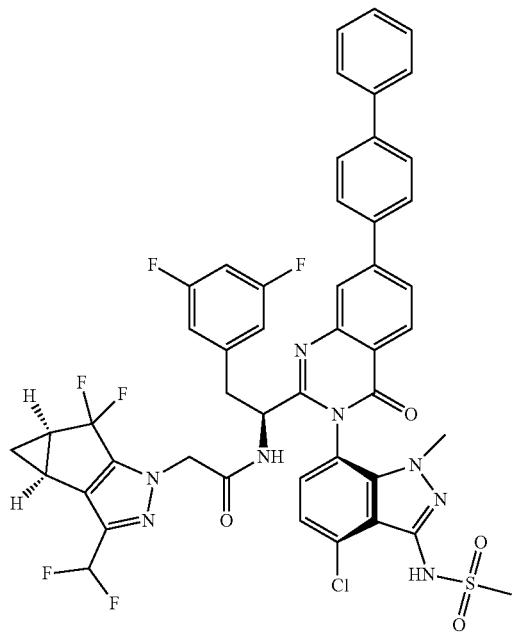

The title compound was prepared according to General Procedure A using [1,1'-biphenyl]-4-ylboronic acid as the coupling partner. The experiment afforded the title compound, N-((S)-1-(7-([1,1'-biphenyl]-4-yl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.15 min.; observed ion=957.2 (M+H). 1H NMR (500 MHz, METHANOL-d4) δ ppm 8.38 (d, J=8.24 Hz, 1H), 8.19 (d, J=0.61 Hz, 1H), 8.02 (br d, J=9.46 Hz, 1H), 7.95 (d, J=8.24 Hz, 2H), 7.86 (d, J=8.24 Hz, 2H), 7.75 (br d, J=7.63 Hz, 2H), 7.51 (t, J=7.48 Hz, 2H), 7.37-7.45 (m, 1H), 7.31 (br d, J=7.32 Hz, 1H), 7.21 (d, J=7.93 Hz, 1H), 6.77-6.84 (m, 1H), 6.55-6.74 (m, 3H), 4.86-4.93 (m, 1H), 4.56 (d, J=3.66 Hz, 2H), 3.64 (s, 3H), 3.46-3.55 (m, 1H), 3.26 (s, 3H), 3.13 (br dd, J=13.73, 9.16 Hz, 1H), 2.39-2.50 (m, 2H), 1.36 (br d, J=6.71 Hz, 1H), 0.97-1.06 (m, 1H).

Example 102

Preparation of (S)-2-(3-cyclopropyl-1H-pyrazol-1-yl)-N-(2-(3,5-difluorophenyl)-1-(7-(4-fluoro-2-methylphenyl)-3-(4-(morpholinosulfonyl)phenyl)-4-oxo-3,4-dihydroquinazolin-2-yl)ethyl)acetamide

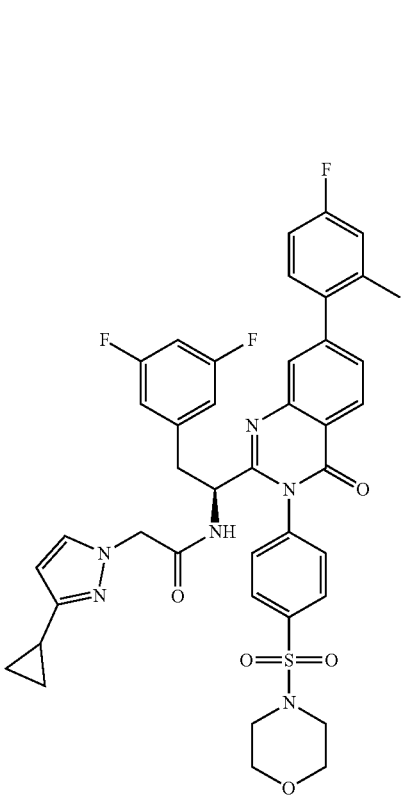 [SMILES: Cc1cc(F)ccc1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure A using (4-fluoro-2-methylphenyl)boronic acid (10.53 mg, 0.068 mmol) as the coupling partner. The experiment afforded the title compound, (S)-2-(3-cyclopropyl-1H-pyrazol-1-yl)-N-(2-(3,5-difluorophenyl)-1-(7-(4-fluoro-2-methylphenyl)-3-(4-(morpholinosulfonyl)phenyl)-4-oxo-3,4-dihydroquinazolin-2-yl)ethyl)acetamide. The sample was analyzed using LCMS Method C: retention time=1.49 min.; observed ion=783.5 (M+H). 1H NMR (500 MHz, METHANOL-d4) δ ppm 8.18-8.29 (m, 1H) 8.01-8.06 (m, 1H) 7.92 (ddd, J=19.15, 8.32, 2.14 Hz, 2H) 7.80 (dd, J=8.24, 1.53 Hz, 1H) 7.63-7.70 (m, 2H) 7.46-7.53 (m, 1H) 7.24-7.46 (m, 6H) 7.10-7.17 (m, 1H) 7.05 (t, J=7.32 Hz, 1H) 6.88-6.96 (m, 2H) 6.75-6.82 (m, 1H) 6.59-6.68 (m, 2H) 5.94-5.99 (m, 1H) 4.78 (t, J=7.17 Hz, 1H) 4.62-4.73 (m, 2H) 3.73 (t, J=4.58 Hz, 4H) 3.36-3.39 (m, 1H) 2.97-3.09 (m, 5H) 1.87-1.94 (m, 1H) 0.86-0.92 (m, 2H) 0.66-0.71 (m, 2H)

Example 103

Preparation of N-((S)-1-(3-(4-chloro-1-methyl-3-(methylsulfonamido)-1H-indazol-7-yl)-7-(3,5-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

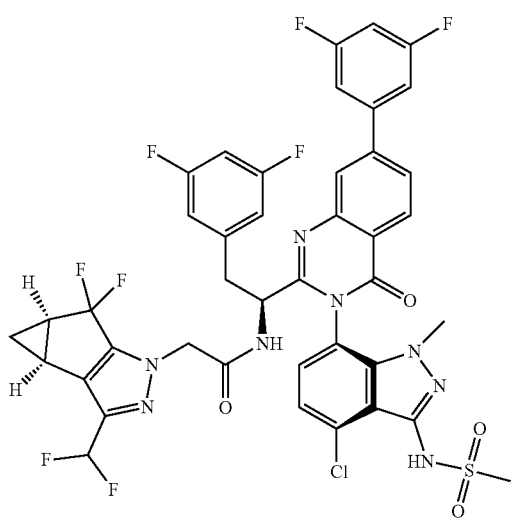

The title compound was prepared according to General Procedure A using (3,5-difluorophenyl)boronic acid as the coupling partner. The experiment afforded the title compound, N-((S)-1-(3-(4-chloro-1-methyl-3-(methylsulfonamido)-1H-indazol-7-yl)-7-(3,5-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.77 min.; observed ion=917.2 (M+H). 1H NMR (500 MHz, METHANOL-d4) δ ppm 8.39 (d, J=8.24 Hz, 1H), 8.15 (s, 1H), 7.96 (br d, J=7.93 Hz, 1H), 7.49 (br d, J=6.71 Hz, 2H), 7.31 (br d, J=8.24 Hz, 1H), 7.21 (d, J=7.93 Hz, 1H), 7.12 (br t, J=8.85 Hz, 1H), 6.76-6.83 (m, 1H), 6.54-6.73 (m, 3H), 4.87-4.90 (m, 1H), 4.55 (d, J=3.66 Hz, 2H), 3.63 (s, 3H), 3.45-3.54 (m, 1H), 3.25 (s, 3H), 3.12 (br dd, J=14.04, 9.16 Hz, 1H), 2.38-2.49 (m, 2H), 1.33-1.40 (m, 1H), 0.96-1.05 (m, 1H).

Example 104

Preparation of N-((S)-1-(3-(4-chloro-1-methyl-3-(methylsulfonamido)-1H-indazol-7-yl)-7-(2,6-dichlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

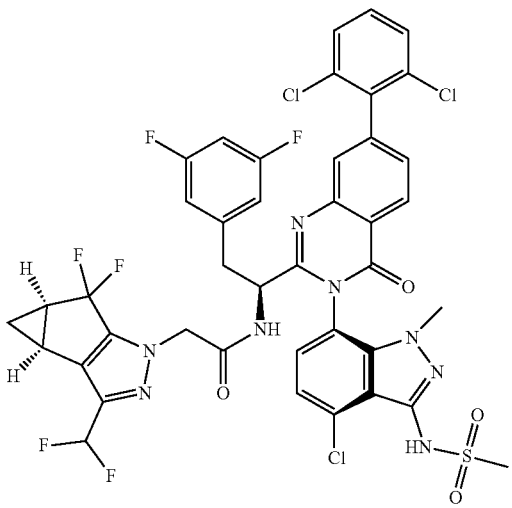

The title compound was prepared according to General Procedure A using (2,6-dichlorophenyl)boronic acid as the coupling partner. The experiment afforded the title compound, N-((S)-1-(3-(4-chloro-1-methyl-3-(methylsulfonamido)-1H-indazol-7-yl)-7-(2,6-dichlorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.38 min.; observed ion=951.1 (M+H). 1H NMR (500 MHz, METHANOL-d4) δ ppm 8.40 (d, J=7.93 Hz, 1H), 7.78 (s, 1H), 7.60 (d, J=7.93 Hz, 2H), 7.54 (br d, J=7.63 Hz, 1H), 7.45-7.51 (m, 1H), 7.19-7.33 (m, 2H), 6.75-6.81 (m, 1H), 6.54-6.71 (m, 3H), 4.87-4.91 (m, 1H), 4.55 (br d, J=10.07 Hz, 2H), 3.66 (s, 3H), 3.45-3.52 (m, 1H), 3.23 (s, 3H), 3.04-3.15 (m, 1H), 2.42 (ddd, J=11.22, 7.55, 4.12 Hz, 2H), 1.33-1.40 (m, 1H), 0.94-1.02 (m, 1H).

Example 105

Preparation of N-((S)-1-(3-(4-chloro-1-methyl-3-(methylsulfonamido)-1H-indazol-7-yl)-7-(4-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

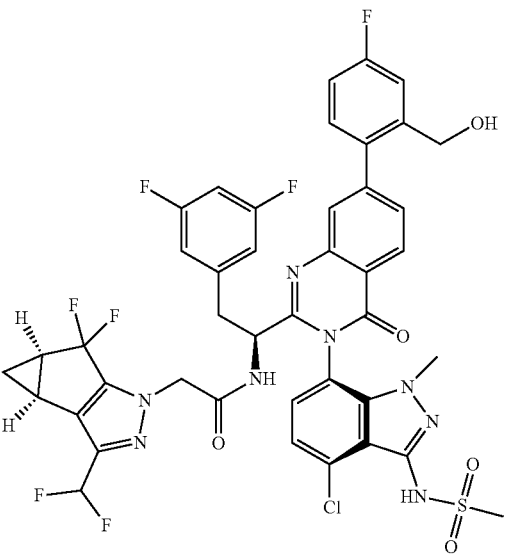

The title compound was prepared according to General Procedure A using (4-fluoro-2-(hydroxymethyl)phenyl)boronic acid as the coupling partner. The experiment afforded the title compound, N-((S)-1-(3-(4-chloro-1-methyl-3-(methylsulfonamido)-1H-indazol-7-yl)-7-(4-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.43 min.; observed ion=929.2 (M+H). 1H NMR (500 MHz, METHANOL-d4) δ ppm 8.35 (d, J=8.24 Hz, 1H), 7.87 (s, 1H), 7.66 (d, J=8.55 Hz, 1H), 7.40-7.49 (m, 2H), 7.32 (br d, J=7.63 Hz, 1H), 7.15-7.24 (m, 2H), 6.77-6.82 (m, 1H), 6.53-6.71 (m, 3H), 4.86-4.89 (m, 1H), 4.61 (s, 2H), 4.54 (d, J=4.88 Hz, 2H), 3.65 (s, 3H), 3.46-3.51 (m, 1H), 3.26 (s, 3H), 3.06-3.15 (m, 1H), 2.32-2.49 (m, 2H), 1.31-1.41 (m, 1H), 1.01 (br d, J=2.75 Hz, 1H).

Example 106

Preparation of (S)-2-(3-cyclopropyl-1H-pyrazol-1-yl)-N-(2-(3,5-difluorophenyl)-1-(7-(2,6-dimethoxyphenyl)-3-(4-(morpholinosulfonyl)phenyl)-4-oxo-3,4-dihydroquinazolin-2-yl)ethyl)acetamide

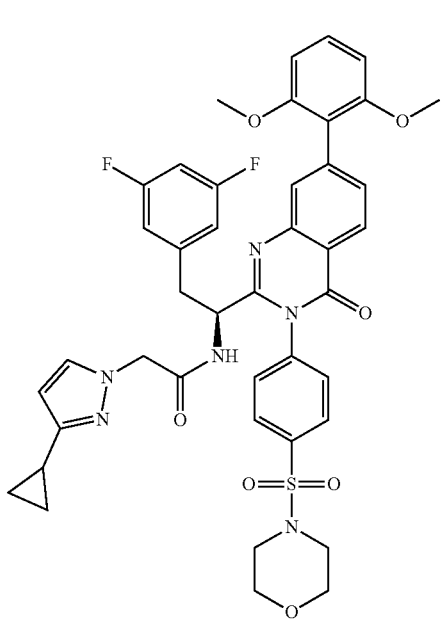 [SMILES: COc1cccc(OC)c1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure A using (2,6-dimethoxyphenyl)boronic acid as the coupling partner. The experiment afforded the title compound, (S)-2-(3-cyclopropyl-1H-pyrazol-1-yl)-N-(2-(3,5-difluorophenyl)-1-(7-(2,6-dimethoxyphenyl)-3-(4-(morpholinosulfonyl)phenyl)-4-oxo-3,4-dihydroquinazolin-2-yl)ethyl)acetamide. The sample was analyzed using LCMS Method C: retention time=1.14 min.; observed ion=811.3 (M+H). 1H NMR (500 MHz, METHANOL-d4) δ ppm 8.19 (d, J=8.20 Hz, 1H) 7.95 (dd, J=8.04, 2.05 Hz, 1H) 7.91 (dd, J=8.20, 1.89 Hz, 1H) 7.75 (d, J=1.58 Hz, 1H) 7.68 (dd, J=8.20, 1.89 Hz, 1H) 7.51 (dd, J=8.20, 1.58 Hz, 1H) 7.38-7.44 (m, 3H) 6.61-6.66 (m, 2H) 5.96 (d, J=2.21 Hz, 1H) 4.79 (dd, J=7.57, 6.62 Hz, 1H) 4.64-4.67 (m, 1H) 4.61-4.74 (m, 1H) 3.73 (t, J=4.73 Hz, 4H) 2.97-3.08 (m, 5H) 1.87-1.91 (m, 1H) 0.83-0.92 (m, 2H) 0.64-0.70 (m, 2H).

Example 107

Preparation of N-((S)-1-(3-(4-chloro-1-methyl-3-(methylsulfonamido)-1H-indazol-7-yl)-4-oxo-7-(2-phenoxyphenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

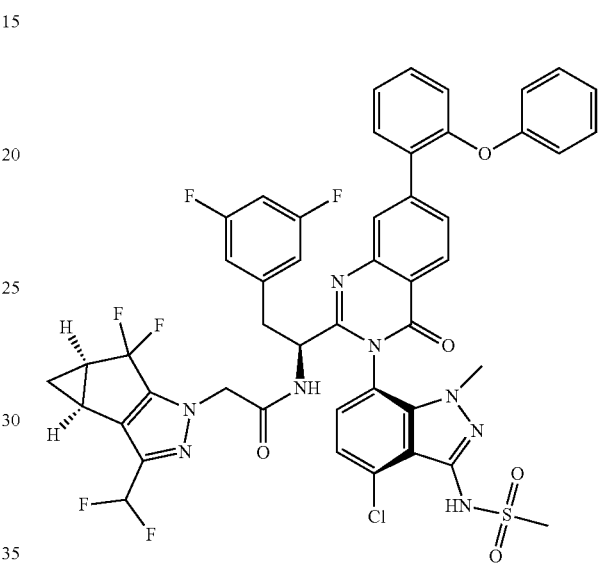

The title compound was prepared according to General Procedure A using (2-phenoxyphenyl)boronic acid as the coupling partner. The experiment afforded the title compound, N-((S)-1-(3-(4-chloro-1-methyl-3-(methylsulfonamido)-1H-indazol-7-yl)-4-oxo-7-(2-phenoxyphenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=3.05 min.; observed ion=973.2 (M+H). 1H NMR (500 MHz, METHANOL-d4) δ ppm 8.27 (d, J=8.54 Hz, 1H), 8.08 (s, 1H), 7.84 (br d, J=8.55 Hz, 1H), 7.65 (br d, J=7.63 Hz, 1H), 7.49 (br t, J=7.93 Hz, 1H), 7.35-7.41 (m, 1H), 7.27-7.34 (m, 3H), 7.17 (br d, J=7.93 Hz, 1H), 7.11 (d, J=7.93 Hz, 1H), 7.06 (t, J=7.32 Hz, 1H), 6.94 (br d, J=8.55 Hz, 2H), 6.75-6.80 (m, 1H), 6.54-6.70 (m, 3H), 4.85-4.92 (m, 1H), 4.52 (s, 2H), 3.60 (s, 3H), 3.42-3.49 (m, 1H), 3.24 (s, 3H), 3.03-3.12 (m, 1H), 2.36-2.49 (m, 2H), 1.31-1.41 (m, 1H), 1.00 (br d, J=0.92 Hz, 1H).

Preparation of Example 108

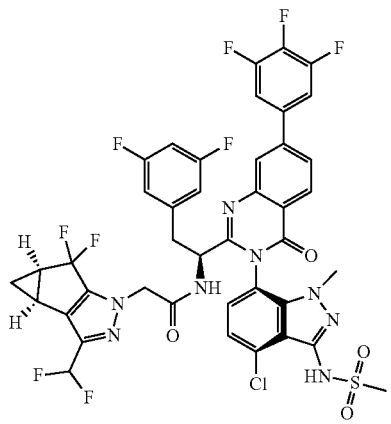

The title compound was prepared according to General Procedure A using (3,4,5-trifluorophenyl)boronic acid as the coupling partner. The experiment afforded the title compound, N-((S)-1-(3-(4-chloro-1-methyl-3-(methylsulfonamido)-1H-indazol-7-yl)-4-oxo-7-(3,4,5-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.83 min.; observed ion=935.2 (M+H). 1H NMR (500 MHz, METHANOL-d4) δ ppm 8.38 (d, J=8.24 Hz, 1H), 8.13 (s, 1H), 7.88-7.98 (m, 1H), 7.62-7.72 (m, 2H), 7.31 (br d, J=7.93 Hz, 1H), 7.20 (d, J=8.24 Hz, 1H), 6.77-6.84 (m, 1H), 6.55-6.72 (m, 3H), 4.87-4.89 (m, 1H), 4.54 (s, 2H), 3.62 (s, 3H), 3.46-3.52 (m, 1H), 3.25 (s, 3H), 3.12 (br dd, J=14.19, 9.31 Hz, 1H), 2.37-2.49 (m, 2H), 1.32-1.40 (m, 1H), 0.97-1.04 (m, 1H).

Example 109

Preparation of N-((S)-1-(3-(4-chloro-1-methyl-3-(methylsulfonamido)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

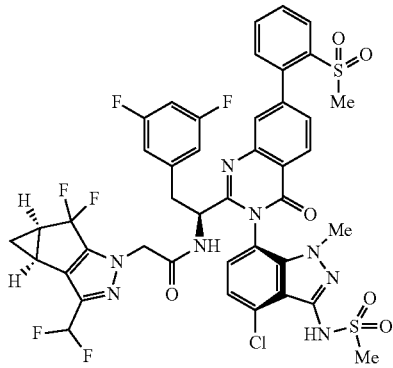

The title compound was prepared according to General Procedure C using 1-bromo-2-(methylsulfonyl)benzene as the coupling partner. The experiment afforded the title compound, N-((S)-1-(3-(4-chloro-1-methyl-3-(methylsulfonamido)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method D: retention time=2.38 min.; observed ion=959.2 (M+H). 1H NMR (METHANOL-d4, 500 MHz) δ8.3-8.4 (m, 1H), 8.27 (d, 1H, J=7.9 Hz), 7.9-8.0 (m, 1H), 7.86 (t, 1H, J=7.5 Hz), 7.77 (t, 1H, J=7.8 Hz), 7.71 (br d, 1H, J=7.9 Hz), 7.54 (br d, 1H, J=7.0 Hz), 7.3-7.4 (m, 1H), 7.22 (br d, 1H, J=7.6 Hz), 6.8-6.8 (m, 1H), 6.6-6.7 (m, 2H), 4.9-5.0 (m, 1H), 4.5-4.6 (m, 2H), 3.66 (s, 3H), 3.5-3.5 (m, 1H), 3.2-3.3 (m, 3H), 3.19 (br d, 1H, J=1.5 Hz), 3.1-3.2 (m, 1H), 2.94 (s, 3H), 2.4-2.5 (m, 2H), 1.3-1.4 (m, 1H), 1.01 (br d, 1H, J=1.8 Hz)

Example 110

Preparation of N-((S)-1-(3-(4-chloro-1-methyl-3-(methylsulfonamido)-1H-indazol-7-yl)-7-(3,5-dimethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

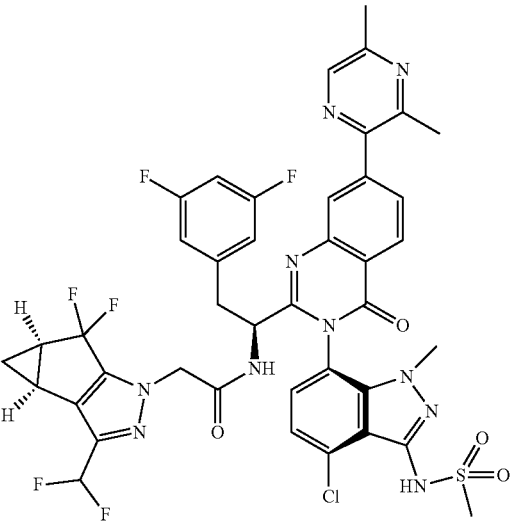

The title compound was prepared according to General Procedure B using 2-chloro-3,5-dimethylpyrazine as the coupling partner. The experiment afforded the title compound, N-((S)-1-(3-(4-chloro-1-methyl-3-(methylsulfonamido)-1H-indazol-7-yl)-7-(3,5-dimethylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.34 min.; observed ion=911.4 (M+H). 1H NMR (METHANOL-d4, 500 MHz) Shift 8.53 (s, 1H), 8.42 (d, 1H, J=8.2 Hz), 8.09 (s, 1H), 7.89 (dd, 1H, J=1.6, 8.2 Hz), 7.3-7.3 (m, 1H), 7.23 (d, 1H, J=7.9 Hz), 6.6-6.8 (m, 4H), 4.5-4.6 (m, 2H), 3.65 (s, 3H), 3.4-3.5

(m, 2H), 3.2-3.3 (m, 3H), 3.11 (dd, 1H, J=9.1, 13.9 Hz), 2.6-2.7 (m, 6H), 2.4-2.5 (m, 2H), 1.3-1.4 (m, 1H), 1.0-1.0 (m, 1H)

Example 112

Preparation of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(6-methoxypyridin-3-yl)-3-(4-(morpholinosulfonyl)phenyl)-4-oxo-3,4-dihydroquinazolin-2-yl)ethyl)acetamide

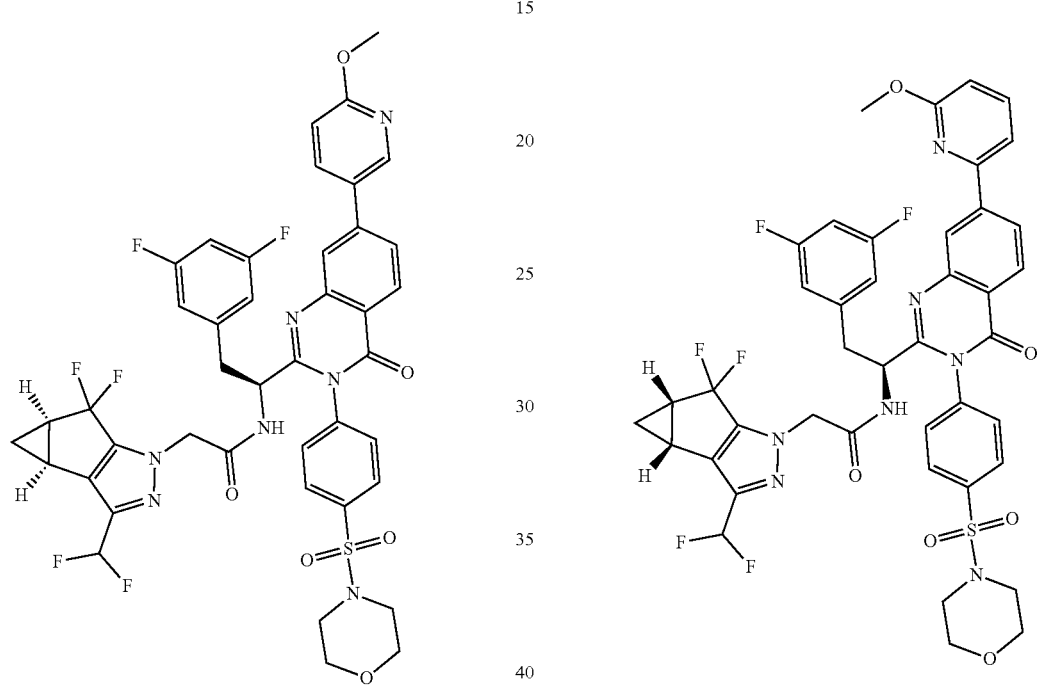

The title compound was prepared according to General Procedure A using (6-methoxypyridin-3-yl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(6-methoxypyridin-3-yl)-3-(4-(morpholinosulfonyl)phenyl)-4-oxo-3,4-dihydroquinazolin-2-yl)ethyl)acetamide. The sample was analyzed using LCMS Method C: retention time=1.42 min.; observed ion=880.5 (M+H). 1H NMR (500 MHz, METHANOL-d4) δ ppm 8.61-8.64 (m, 1H) 8.30-8.34 (m, 1H) 8.14-8.19 (m, 1H) 8.07-8.09 (m, 1H) 7.89-7.98 (m, 3H) 7.88-7.97 (m, 4H) 7.78-7.82 (m, 1H) 7.65-7.69 (m, 1H) 7.33-7.38 (m, 1H) 7.01 (dd, J=8.51, 0.63 Hz, 1H) 6.82-6.85 (m, 1H) 6.83 (br d, J=19.23 Hz, 1H) 6.62-6.69 (m, 2H) 4.77-4.85 (m, 3H) 4.02-4.05 (m, 3H) 3.74 (t, J=4.73 Hz, 4H) 3.39-3.45 (m, 1H) 3.00-3.10 (m, 5H) 2.39-2.47 (m, 2H) 1.36-1.42 (m, 1H) 1.00-1.07 (m, 1H) 0.98-0.98 (m, 1H)

Example 113

Preparation of 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(6-methoxypyridin-2-yl)-3-(4-(morpholinosulfonyl)phenyl)-4-oxo-3,4-dihydroquinazolin-2-yl)ethyl)acetamide

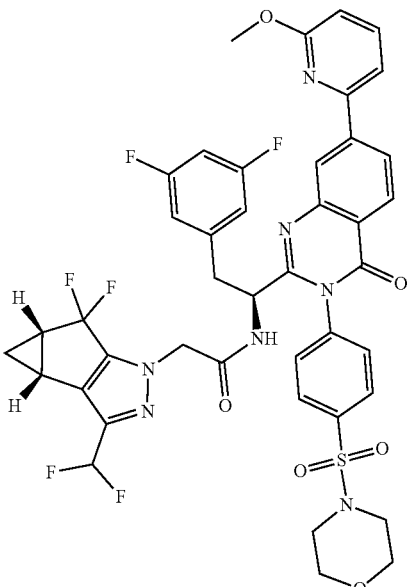

The title compound was prepared according to General Procedure B using 2-bromo-6-methoxypyridine as the coupling partner. The experiment afforded the title compound, 2-((3bR,4aS)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(6-methoxypyridin-2-yl)-3-(4-(morpholinosulfonyl)phenyl)-4-oxo-3,4-dihydroquinazolin-2-yl)ethyl)acetamide. The sample was analyzed using LCMS Method C: retention time=1.55 min.; observed ion=880.5 (M+H). 1H NMR (500 MHz, METHANOL-d4) δ ppm 8.33-8.40 (m, 1H) 8.20-8.28 (m, 2H) 7.76-7.85 (m, 3H) 7.59-7.68 (m, 3H) 6.58-6.95 (m, 5H) 5.81-5.90 (m, 1H) 4.75-4.80 (m, 2H) 4.06-4.10 (m, 3H) 3.67-3.76 (m, 1H) 3.52-3.60 (m, 4H) 3.34-3.36 (m, 1H) 2.72-2.86 (m, 4H) 2.41-2.52 (m, 2H) 1.33-1.41 (m, 1H) 0.98-1.06 (m, 1H).

Example 114

Preparation of (S)-2-(3-cyclopropyl-1H-pyrazol-1-yl)-N-(1-(7-(2,6-dichlorophenyl)-3-(4-(morpholinosulfonyl)phenyl)-4-oxo-3,4-dihydroquinazolin-2-yl)-2-(3,5-difluorophenyl)ethyl)acetamide

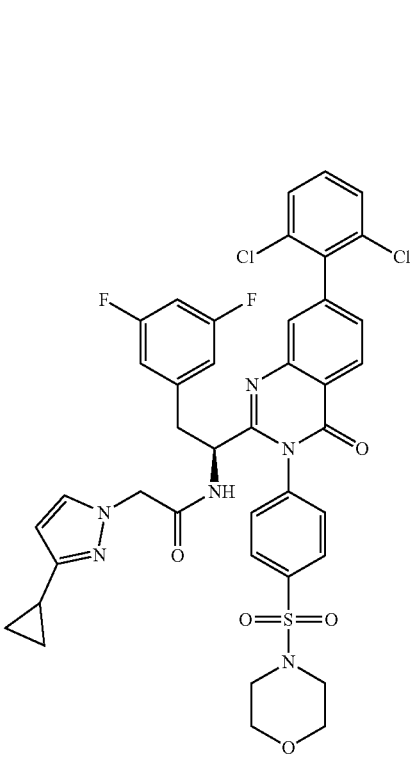 [SMILES: O=C(Cn1ccc(C2CC2)n1)N[C@@H](Cc1cc(F)cc(F)c1)c1nc2cc(-c3c(Cl)cccc3Cl)ccc2c(=O)n1-c1ccc(S(=O)(=O)N2CCOCC2)cc1]

The title compound was prepared according to General Procedure A using (2,6-dichlorophenyl)boronic acid as the coupling partner. The experiment afforded the title compound, (S)-2-(3-cyclopropyl-1H-pyrazol-1-yl)-N-(1-(7-(2,6-dichlorophenyl)-3-(4-(morpholinosulfonyl)phenyl)-4-oxo-3,4-dihydroquinazolin-2-yl)-2-(3,5-difluorophenyl)ethyl)acetamide. The sample was analyzed using LCMS Method C: retention time=1.5 min.; observed ion=821.4 (M+H). 1H NMR (500 MHz, METHANOL-d4) δ ppm 8.34 (d, J=8.20 Hz, 1H) 7.97 (dd, J=8.20, 1.89 Hz, 1H) 7.92 (dd, J=8.35, 2.05 Hz, 1H) 7.73 (d, J=0.95 Hz, 1H) 7.71 (dd, J=8.20, 2.21 Hz, 1H) 7.60 (s, 1H) 7.58 (q, J=1.16 Hz, 1H) 7.40-7.53 (m, 4H) 6.75-6.82 (m, 1H) 6.62 (br d, J=6.31 Hz, 2H) 5.95 (d, J=2.21 Hz, 1H) 4.79-4.84 (m, 1H) 4.63-4.74 (m, 2H) 3.73 (t, J=4.73 Hz, 4H) 3.15-3.19 (m, 1H) 2.98-3.07 (m, 5H) 1.86-1.92 (m, 1H) 0.83-0.89 (m, 2H) 0.67 (td, J=4.57, 2.52 Hz, 2H).

Example 115

Preparation of N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-43bS,4aR)-3-(difluoromethyl)-5,5-difluoro-3b,4,4a,5-tetrahydro-1H-cyclopropa[3,4]cyclopenta[1,2-c]pyrazol-1-yl)acetamide

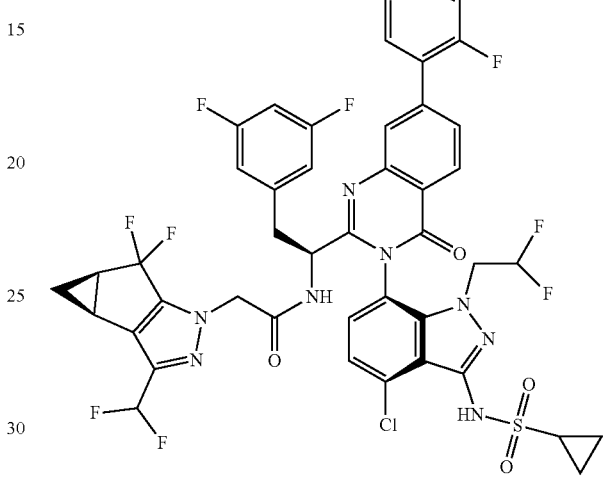

The preparation of Example 115 is described in the series of procedures which follow:

Experimental Procedure: 3-amino-2'-fluoro-[1,1'-biphenyl]-4-carboxylic acid

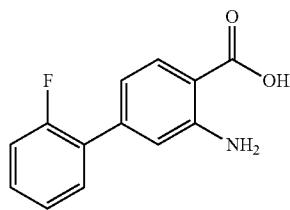 [SMILES: Nc1cc(-c2ccccc2F)ccc1C(=O)O]

To a solution of 2-amino-4-bromobenzoic acid (10 g, 46.3 mmol) in DME (200 mL) was added (2-fluorophenyl)boronic acid (7.77 g, 55.5 mmol), sodium carbonate (1M Aq. solution) (94 mL, 94 mmol) at 26° C. in a sealed tube under Nitrogen atmosphere. The reaction mixture was degassed with N$_2$ bubbling for 10 min, followed by addition Pd(PPh$_3$)$_4$ (5.35 g, 4.63 mmol) and later heated at 90° C. for 16 h. The progress of the reaction was monitored by TLC (SiO$_2$, 10% MeOH/DCM, Rf=0.2). On completion, the reaction mixture was diluted with water (200 mL) and extracted with EtOAc (2×250 mL). The combined organic layers were dried over Na$_2$SO$_4$, filtered and concentrated under reduced pressure to afford the crude compound as a brown liquid. The above crude compound was purified by grace column chromatography with 50-75% EtOAC/Pet. The fractions containing product were collected and concentrated under reduced pressure to afford 3-amino-2'- fluoro-[1,1'-biphenyl]-4-carboxylic acid, 6 g, Yield: 55%, Off white solid). $^1$H NMR (400 MHz, DMSO-$d_6$) δ=9.06-8.23 (m, 2H), 7.77 (d, J=8.2 Hz, 1H), 7.53-7.40 (m, 2H), 7.34-7.26 (m, 2H), 6.95-6.90 (m, 1H), 6.73-6.64 (m, 1H), LCMS: RT=2.29 min, (M+H)=232.21, LCMS Purity=99%.

(S)-tert-butyl(1-(3-(4-chloro-1-(2,2-difluoroethyl)-3-(N-(4-methoxybenzyl) cyclopropanesulfonamido)-1H-indazol-7-yl)-7-(2-fluorophenyl)-4-oxo-3,4-dihydroquinazolin-2-yl)-2-(3,5-difluorophenyl)ethyl) carbamate

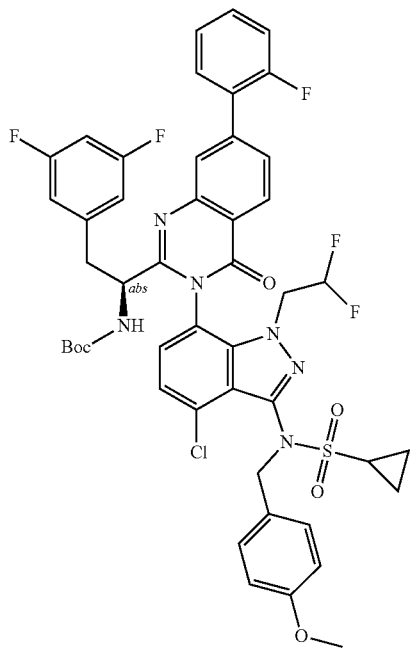 [SMILES: COc1ccc(CN(c2nn(CC(F)F)c3c(-n4c([C@H](Cc5cc(F)cc(F)c5)NC(=O)OC(C)(C)C)nc5cc(-c6ccccc6F)ccc5c4=O)ccc(Cl)c23)S(=O)(=O)C2CC2)cc1]

To a stirred solution of (S)-2-((tert-butoxycarbonyl)amino)-3-(3,5-difluorophenyl)propanoic acid (1.2 g, 3.98 mmol), 3-amino-2'-fluoro-[1,1'-biphenyl]-4-carboxylic acid (0.936 g, 3.99 mmol) and N-(7-amino-4-chloro-1-(2,2-difluoroethyl)-1H-indazol-3-yl)-N-(4-methoxybenzyl) cyclopropanesulfonamide (2.080 g, 4.38 mmol) in pyridine (10 mL) was added diphenyl phosphite (2.70 mL, 13.94 mmol) at 26° C. The reaction mixture was degassed with $N_2$ bubbling before each addition of reagents. The reaction was heated at 70° C. for 16 h. The progress of the reaction was monitored by TLC (SiO$_2$, 50% EtOAc/Pet. Rf=0.5). After the completion, the reaction mixture was evaporated under reduced pressure to get crude compound. The crude compound was purified by column chromatography using silica gel (100-200 mesh), eluted with 18-20% EtOAc/pet ether. The fraction containing the product were collected and evaporated under reduced pressure to afford the compound as a yellow solid (LCMS: 59%).
The compound was further purified by Prep-HPLC.
MOBILE PHASE A: 0.01 m ammonium bicarbonate (aq)
MOBILE PHASE B: Acetonitrile
Column: xbridge C18 (150*19) mm, 5u,
Method: (T/% B): 0/60, 2/60, 10/70
Flow: 16 ml/Min,
Solubility: ACN+THF+Water
Temp: Ambient Collected pure fractions were evaporated under reduced pressure to afford tert-butyl (S)-(1-(3-(4-chloro-1-(2,2-difluoroethyl)-3-(N-(4-methoxybenzyl)cyclopropanesulfonamido)-1H-indazol-7-yl)-7-(2-fluorophenyl)-4-oxo-3,4-dihydroquinazolin-2-yl)-2-(3,5-difluorophenyl)ethyl)carbamate (0.9 g, yield: 23%) as a pale yellow solid.
$^1$H NMR (400 MHz, DMSO-$d_6$) δ=8.34-8.23 (m, 1H), 8.10-7.93 (m, 1H), 7.87-7.74 (m, 2H), 7.70-7.65 (m, 1H), 7.60-7.49 (m, 2H), 7.46-7.37 (m, 2H), 7.32-7.22 (m, 1H), 7.11-6.97 (m, 2H), 6.87-6.70 (m, 1H), 6.65-6.48 (m, 3H), 6.40-6.00 (m, 1H), 4.94-4.76 (m, 2H), 4.57-4.42 (m, 1H), 4.26-3.96 (m, 3H), 3.75-3.61 (m, 2H), 3.49-3.41 (m, 1H), 3.17 (d, J=5.2 Hz, 2H), 3.06-2.80 (m, 2H), 1.20 (s, 7H), 1.09-0.89 (m, 4H), 0.60-0.51 (m, 1H) LCMS: RT=2.66 min, (M+H)=949.14, LCMS Purity=97%.

(S)-N-(7-(2-(1-amino-2-(3,5-difluorophenyl) ethyl)-7-(2-fluorophenyl)-4-oxoquinazolin-3(4H)-yl)-4-chloro-1-(2,2-difluoroethyl)-1H-indazol-3-yl)cyclopropanesulfonamide

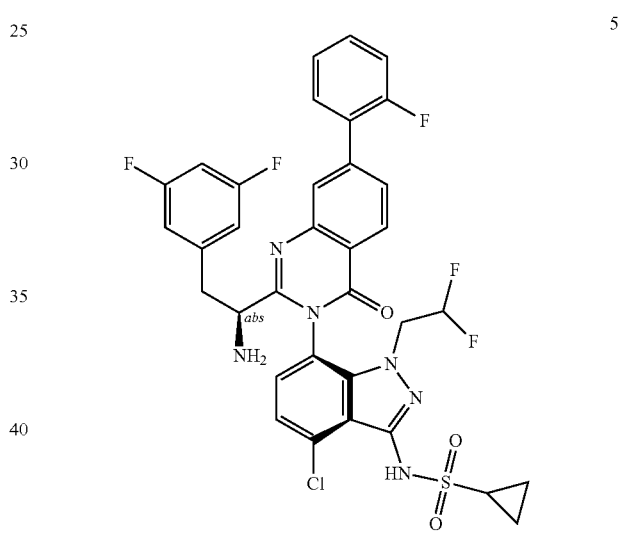

To a stirred solution of tert-butyl (S)-(1-(3-(4-chloro-1-(2,2-difluoroethyl)-3-(N-(4-methoxybenzyl)cyclopropanesulfonamido)-1H-indazol-7-yl)-7-(2-fluorophenyl)-4-oxo-3,4-dihydroquinazolin-2-yl)-2-(3,5-difluorophenyl)ethyl) carbamate (0.9 g, 0.936 mmol) in DCM (20 mL) was added TFA (10 mL, 130 mmol) at 25° C. under $N_2$ atmosphere and stirred for 10 min, followed by addition of trifluoromethanesulfonic acid (0.5 mL, 5.63 mmol). The reaction mixture was stirred for 1 h at 25° C. The progress of the reaction was monitored by TLC (SiO$_2$, 10% MeOH/DCM, Rf=0.2). The solvent was removed under a gentle stream of nitrogen. The residue was dissolved in EtOAc (10 mL) and was washed with aq sat.NaHCO$_3$ (2×5 mL), brine (5 mL), dried over Na$_2$SO$_4$, filtered and evaporated to dryness to afford crude compound as an off white solid (700 mg).
The crude was purified by prep HPLC
Mobile phase A: 10 mM Ammonium bicarbonate (aq)
Mobile phase B: Acetonitrile
COLUMN: Puritasc18 (150*25) mm, 10u,
FLOW: 25 ml/min,
METHOD: (T/% B): 0/60,20/60,20.1/98,23/98,23.1/60,25/60

SOLUBILITY: ACN+THF+H20
TEMPERATURE: AMBIENT
Collected pure fractions were evaporated under reduced pressure to afford the initial product (390 mg, LCMS: 98.72%) which was submitted to prep-SFC for the separation of isomers
Column/dimensions: Chiralpak OJ-H (30×250 mm), 5μ
% CO2: 85.0%
% Co solvent: 15.0% (100% Methanol)
Total Flow: 90.0 g/min
Back Pressure: 100.0 bar
UV: 250 nm
Stock time: 10.5 min
Load/Inj: 17 mg
Solubility: 35 mL Methanol
No of injections: 26
Instrument details: Make/Model: SFC-PIC-002
Two peaks were collected separately and evaporated under reduced pressure.
Major peak was evaporated under reduced pressure to afford (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (170 mg, yield: 24.47%) as an off white solid.

$^1$H NMR (400 MHz, DMSO-$d_6$) δ=8.29-8.25 (m, 1H), 8.00-7.98 (m, 1H), 7.84-7.80 (m, 1H), 7.78-7.71 (m, 1H), 7.59-7.39 (m, 5H), 7.04-6.94 (m, 1H), 6.73 (br d, J=6.7 Hz, 2H), 6.48-6.15 (m, 1H), 4.54-4.25 (m, 2H), 3.59-3.49 (m, 1H), 3.30-3.26 (m, 1H), 2.98-2.90 (m, 1H), 2.88-2.81 (m, 1H), 1.28-1.20 (m, 2H), 1.07-0.98 (m, 4H). LCMS: RT=2.32 min, (M+H)=729.35, LCMS Purity=98%, HPLC Purity=98%, Chiral HPLC Purity=99%.

N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (Example 115)

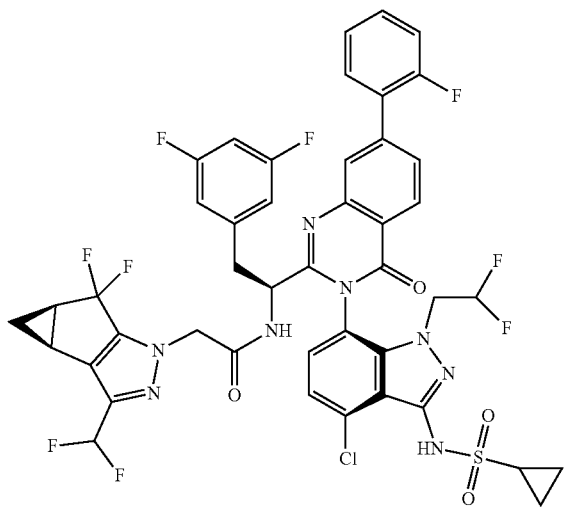

To a solution of ((S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (150 mg, 0.206 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (54.3 mg, 0.206 mmol) and HOBt (12.60 mg, 0.082 mmol) in N,N-Dimethylformamide (DMF) (10 mL), were added N-Methylmorpholine (0.045 mL, 0.411 mmol) and N-(3-Dimethylaminopropyl)-N'-ethylcarbodiimide hydrochloride (71.0 mg, 0.370 mmol) at 27° C. The reaction mixture was degassed for 10 mins with $N_2$ and later stirred at 27° C. for 16 h. The progress of the reaction was monitored by TLC ($SiO_2$, 50% EtOAc/Pet. Rf=0.3). The reaction mixture was diluted with ice cold water (50 mL), stirred for 30 min at 27° C. The precipitated solid was filtered and dried under vacuum to get crude product as an off white solid which was further purified by prep-SFC
Column/dimensions: R, R WHELK (30×250 mm), 5μ
% CO2: 60.0%
% Co solvent: 40.0% (100% Methanol)
Total Flow: 100.0 g/min
Back Pressure: 100.0 bar
UV: 214 nm
Stock time: 26 min
Load/Inj: 25 mg
Solubility: Methanol
No Of injections: 7
Instrument details: Make/Model: SFC-PIC-002
Collected pure fractions were evaporated under reduced pressure to get the desired product as an off white solid (we observed solvent peaks in 1H NMR). To remove the residual solvent peaks the material was lyophilized to afford pure N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (110 mg, yield: 54.7%, off white solid).

$^1$H NMR (400 MHz, DMSO-$d_6$) δ=10.00-9.87 (m, 1H), 9.23-9.18 (m, 1H), 8.30 (d, J=8.1 Hz, 1H), 7.99-7.97 (m, 1H), 7.86-7.83 (m, 1H), 7.76-7.71 (m, 2H), 7.59-7.54 (m, 1H), 7.51-7.40 (m, 3H), 7.07-6.89 (m, 2H), 6.66-6.57 (m, 2H), 6.29-5.95 (m, 1H), 4.76-4.69 (m, 1H), 4.64-4.57 (m, 1H), 4.48-4.41 (m, 1H), 4.31-4.17 (m, 1H), 4.01-3.87 (m, 1H), 3.41-3.34 (m, 1H), 3.03-2.95 (m, 1H), 2.91-2.83 (m, 1H), 2.48-2.41 (m, 2H), 1.38-1.29 (m, 1H), 0.98-0.83 (m, 5H). LCMS: RT=6.72 min, (M+H)=975.0, LCMS Purity=99%, HPLC Purity=99%, Chiral HPLC Purity=99%.

The general procedures and general purification methods used to prepare examples 116-140 are described above or detailed below. The experimental procedure supplied for each specific example identifies the general method used to prepare and purify that compound.

General Procedure I:

To a vial equipped with a stir bar was added $Pd(OAc)_2$ (0.1 equiv), dicyclohexyl(2',6'-dimethoxy-[1,1'-biphenyl]-2-yl)phosphane (0.2 equiv), $K_3PO_4$ (3 equiv), and N-((S)-1-(3-(4-chloro-1-(2,2-difluoroethyl)-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4] cyclopenta[1,2-c]pyrazol-1-yl)acetamide (1 equiv, typically 50-100 mg). To the vial was added the appropriate aryl halide or heteroaryl halide (3 equiv). The vial was capped with a septum cap and then placed under argon atmosphere (vac/fillx3). To the vial was added THF:water (4:1) to afford a reaction volume 0.05M in boronic ester. The reaction mixture was degassed via vac/fill (x3) with argon. The reaction mixture was stirred at either ambient temperature, 45° C., or 60° C. for overnight (~18 h). Upon cooling to ambient temperature, the reaction mixture was concentrated and the residue was subjected to HPLC purification to afford the indicated product.

General Procedure J:

To a vial equipped with a stir bar was added Pd(OAc)₂ (0.1 equiv), dicyclohexyl(2',6'-dimethoxy-[1,1'-biphenyl]-2-yl)phosphane (0.2 equiv), K₃PO₄ (3 equiv), and N-((S)-1-(3-(4-chloro-3-(cyclopropanesulfonamido)-1-(2,2-difluoro-ethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 50-100 mg). To the vial was added the appropriate aryl halide or heteroaryl halide (3 equiv). The vial was capped with a septum cap and then placed under argon atmosphere (vac/fill×3). To the vial was added THF:water (4:1) to afford a reaction volume 0.05M in boronic ester. The reaction mixture was degassed via vac/fill (×3) with argon. The reaction mixture was stirred at either ambient temperature, 45° C., or 60° C. overnight (~18 h). Upon cooling to ambient temperature, the reaction mixture was concentrated and the residue was subjected to HPLC purification to afford the indicated product.

General Procedure K:

To a vial equipped with a stir bar was added N-((S)-1-(3-(4-chloro-3-(cyclopropanesulfonamido)-1-(2,2-difluoro-ethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv, typically 50-100 mg), K₃PO₄ (3 equiv), dichloro[9,9-dimethyl-4,5-bis(diphenylphosphino)xanthene]palladium(II) (0.05 equiv). To the vial was added the appropriate aryl halide or heteroaryl halide (3 equiv). The vial was capped with a septum cap and then placed under argon atmosphere (vac/fill×3). To the vial was added THF:water (4:1) to afford a reaction volume 0.05M in boronic ester. The reaction mixture was degassed via vac/fill (×3) with argon. The reaction mixture was stirred at either ambient temperature, 45° C., or 60° C. overnight (~18 h). Upon cooling to ambient temperature, the reaction mixture was concentrated and the residue was subjected to HPLC purification to afford the indicated product.

LCMS Method E:

Column: Zorbax Eclipse Plus C18, 2.1×50 mm, 1.7 μm particles; Solvent A=0.1% Formic acid in 100% Water. Solvent B=0.1% Formic Acid in 100% Acetonitrile. Flow Rate=1 mL/min. Start % B=5. Final % B=95. Gradient Time=2.1 min, then a 0.3 min hold at 95% B. Wavelength=215 and 254 nm.

LCMS Method F:

Column: Acquity BEH C18, 2.1×30 mm, 1.7 μm particles; Solvent A=0.1% Formic acid in 100% Water. Solvent B=0.1% Formic Acid in 100% Acetonitrile. Flow Rate=0.8 mL/min. Start % B=5. Final % B=95. Gradient Time=1.7 min, then a 0.2 min hold at 95% B. Wavelength=215 and 254 nm.

Preparation of N-(7-amino-4-chloro-1-methyl-1H-indazol-3-yl)-N-(4-methoxybenzyl)methanesulfonamide

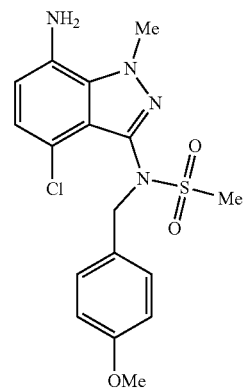 [SMILES: COc1ccc(CN(c2nn(C)c3c(N)ccc(Cl)c23)S(C)(=O)=O)cc1]

To a stirred solution of N-(7-Bromo-4-chloro-1-methyl-1H-indazol-3-yl)-N-(4-methoxybenzyl) methanesulfonamide (55 g, 0.12 mol, 1.0 equiv.) in NMP (900 mL) at room temperature was added copper (I) iodide (4.57 g, 0.024 mol, 0.2 equiv.), sodium ascorbate (47.4 g, 0.24 mol, 2 equiv.) and (1R, 2R)-N₁,N₂-dimethylcyclohexane-1,2-diamine (8.52 g, 0.06 mol, 0.5 equiv.) were added at room temperature. Then a solution of sodium azide (23.3 g, 0.36 mol, 3.0 equiv.) in water (182 mL). The mixture was heated to 100° C. and maintained at that temperature for 12 h. The reaction mixture was cooled to room temperature and diluted with ethyl acetate (1.5 L), then filtered through a pad of Celite. The filter pad was extracted with EtOAc (500 mL). The combined filtrate was diluted with water (2.0 L) and the organic layer was isolated and reserved. The aqueous phase was extracted with EtOAc (2×1.0 L). The combined organic layers were washed with water (1.0 L); brine (1.0 L); dried over Na₂SO₄; filtered; and concentrated in vacuo. The crude material was purified by silica column chromatography (hexanes:EtOAc 100:0→80:20) to afford the title compound, N-(7-Amino-4-chloro-1-methyl-1H-indazol-3-yl)-N-(4-methoxybenzyl) methanesulfonamide, as an off-white solid, 27.0 g (57%). ¹H NMR (400 MHz, CDCl₃) δ7.33-7.29 (m, 2H), 6.89 (d, J=7.8 Hz, 1H), 6.85-6.79 (m, 2H), 6.48 (d, J=7.8 Hz, 1H), 5.11 (br.s, 1H), 4.81 (br.s, 1H), 4.30 (s, 3H), 3.80 (br s, 2H), 3.79 (s, 3H), 2.99 (s, 3H). LC/MS (M+H)⁺= 395.00.

Preparation of N-(7-amino-4-chloro-1-(2,2-difluoroethyl)-1H-indazol-3-yl)-N-(4-methoxybenzyl)methanesulfonamide

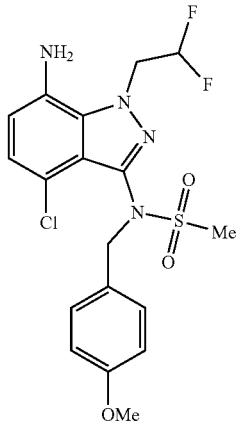 [SMILES: COc1ccc(CN(c2nn(CC(F)F)c3c(N)ccc(Cl)c23)S(C)(=O)=O)cc1]

To a stirred solution of N-(7-bromo-4-chloro-1-(2,2-difluoroethyl)-1H-indazol-3-yl)-N-(4-methoxybenzyl)methanesulfonamide (62 g, 0.12 mol, 1.0 equiv.) in NMP (745 mL) at room temperature was added copper (I) iodide (4.64 g, 0.024 mol, 0.2 equiv.), sodium ascorbate (48.3 g, 0.24 mol, 2 equiv.) and (1R, 2R)-$N_1,N_2$-dimethylcyclohexane-1,2-diamine (8.7 g, 0.06 mol, 0.5 equiv.). To the mixture was added a solution of sodium azide (23.8 g, 0.36 mol, 3.0 equiv.) in water (204 mL). The mixture was heated to 100° C. and maintained at that temperature for 15 h. The mixture was cooled to room temperature and was then diluted with ethyl acetate (1.5 L). The mixture was filtered through a pad of Celite and the filter pad was extracted with EtOAc (500 mL). The combined filtrate was diluted with water (2.0 L), organic layer was separated and aqueous layer extracted with EtOAc (2×1.0 L). The combined organic layers were washed with water (1.2 L), brine (1.0 L), dried over $Na_2SO_4$, filtered and then concentrated in vacuo. The resulting residue was subjected to silica gel column chromatography (hexanes:EtOAc 100:0→75:25) to afford the title compound, N-(7-amino-4-chloro-1-(2,2-difluoroethyl)-1H-indazol-3-yl)-N-(4-methoxybenzyl)methanesulfonamide, as an off-white solid, 23.0 g, (44%).

Preparation of N-(7-amino-4-chloro-1-(2,2-difluoroethyl)-1H-indazol-3-yl)-N-(4-methoxybenzyl)cyclopropanesulfonamide

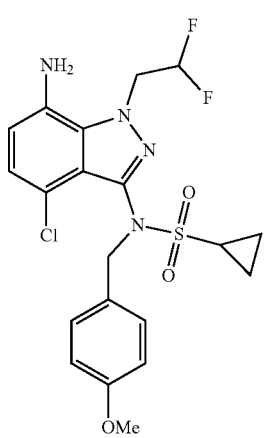 [SMILES: COc1ccc(CN(c2nn(CC(F)F)c3c(N)ccc(Cl)c23)S(=O)(=O)C2CC2)cc1]

To a stirred solution of N-(7-bromo-4-chloro-1-(2,2-difluoroethyl)-1H-indazol-3-yl)-N-(4-methoxybenzyl)cyclopropanesulfonamide (32 g, 0.059 mol, 1.0 equiv.) in NMP (512 mL) at room temperature was added copper (I) iodide (2.27 g, 0.012 mol, 0.2 equiv.), sodium ascorbate (23.7 g, 0.12 mol, 2 equiv.) and (1R, 2R)-$N_1,N_2$-dimethylcyclohexane-1,2-diamine (4.25 g, 0.03 mol, 0.5 equiv.). To the mixture was added a solution of sodium azide (11.6 g, 0.18 mol, 3.0 equiv.) in water (112 mL). The reaction was heated to 100° C. and stirred for 18 h the same temperature. The mixture was cooled to room temperature and diluted with ethyl acetate (1.2 L). The mixture was filtered through a pad of Celite, extracting with EtOAc (300 mL). The combined filtrate was poured into water (1.5 L) and the organic layer was isolated and reserved. The aqueous layer was extracted with EtOAc (2×0.8 L). The combined organic layers were washed with water (0.8 L), brine (0.8 L), dried over $Na_2SO_4$, filtered and then concentrated in vacuo. The crude residue was subjected to silica gel column chromatography (hexanes:EtOAc 100:0→80:20) to afford the title compound, N-(7-amino-4-chloro-1-(2,2-difluoroethyl)-1H-indazol-3-yl)-N-(4-methoxybenzyl)cyclopropanesulfonamide as an off-white solid, 14.2 g (50%).

Preparation of N-(7-amino-4-chloro-1-(2,2,2-trifluoroethyl)-1H-indazol-3-yl)-N-(4-methoxybenzyl)methanesulfonamide

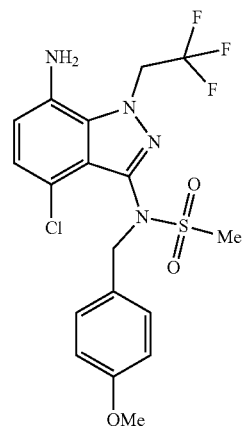 [SMILES: COc1ccc(CN(c2nn(CC(F)(F)F)c3c(N)ccc(Cl)c23)S(C)(=O)=O)cc1]

To a stirred solution of N-(7-bromo-4-chloro-1-(2,2,2-trifluoroethyl)-1H-indazol-3-yl)-N-(4-methoxybenzyl)methanesulfonamide (3 g, 5.69 mmol, 1.0 equiv.) in NMP (45 mL) was added at room temperature copper (I) iodide (0.22 g, 1.13 mmol, 0.2 equiv.), sodium ascorbate (2.25 g, 11.38 mmol, 2 equiv.) and (1R, 2R)-$N_1,N_2$-dimethylcyclohexane-1,2-diamine (0.4 g, 2.84 mmol, 0.5 equiv.). To the mixture was added a solution of sodium azide (1.1 g, 17.07 mmol) in water (15 mL). The mixture was heated to 100° C. and maintained at that temperature for 13 h. The reaction mixture was cooled to room temperature and was then diluted with ethyl acetate (50 mL). The mixture was filtered through a pad of Celite bed extracting with EtOAc (30 mL). The combined filtrate was poured into water (50 mL) and the organic layer was isolated and reserved. The aqueous phase was extracted with EtOAc (2×30 mL). The combined organics were washed with water (50 mL), brine (40 mL), dried over $Na_2SO_4$, filtered and concentrated in vacuo. The resulting residue was subjected to silica gel column chromatography (hexanes:EtOAc 100:0→75:25) to afford the title compound, N-(7-amino-4-chloro-1-(2,2,2-trifluoroethyl)-1H-indazol-3-yl)-N-(4-methoxybenzyl)methanesulfonamide as an off-white solid, 1.6 g (61%).

Preparation of tert-Butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate

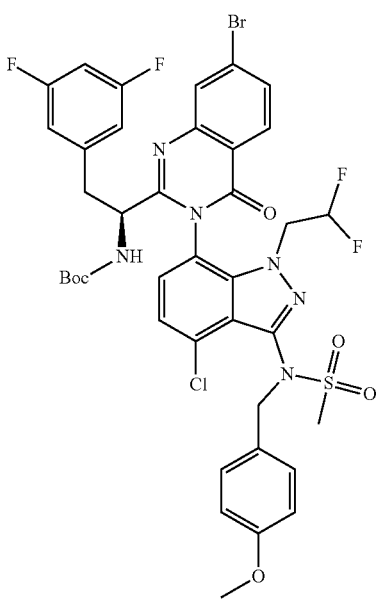 [SMILES: COc1ccc(CN(c2nn(CC(F)F)c3c(-n4c([C@H](Cc5cc(F)cc(F)c5)NC(=O)OC(C)(C)C)nc5cc(Br)ccc5c4=O)ccc(Cl)c23)S(C)(=O)=O)cc1]

To a stirred solution of (S)-2-((tert-butoxycarbonyl)amino)-3-(3,5-difluorophenyl)propanoic acid (15 g, 49.8 mmol) and 2-amino-4-bromobenzoic acid (10.76 g, 49.8 mmol) in pyridine (150 mL) was added diphenyl phosphite (9.64 mL, 49.8 mmol) at 27° C. The mixture was flushed with argon and the flask was then sealed. The reaction mixture was heated to 80° C. and stirred at that temperature for 2 hr. The reaction mixture was cooled to 27° C. and to the mixture was added N-(7-amino-4-chloro-1-(2,2-difluoroethyl)-1H-indazol-3-yl)-N-(4-methoxybenzyl)methanesulfonamide. The flask was sealed and the mixture was heated at 80° C. for 16 hr. The progress of the reaction was monitored by TLC (SiO$_2$, 30% EtOAc/Pet., Rf=0.4, UV-active). The reaction mixture was allowed to cool to 27° C. and then was concentrated under reduced pressure. The resulting residue was subjected to silica gel column chromatography (Pet.:EtOAc 80:20→70:30) to afford tert-butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate as an off-white solid, 18 g (35%). The isolated material is a mixture of stereoisomers. LCMS: M+H=907.18 and 909.12; purity=89%.

Preparation of (S) N (7-(2 (1 amino-2-(3,5-difluorophenyl)ethyl)-7-bromo-4-oxoquinazolin-3 (4H)-yl)-4-chloro-1-(2,2-difluoroethyl)-1H-indazol-3-yl)methanesulfonamide

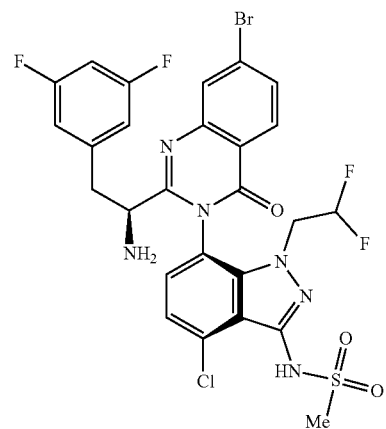

To a stirred solution of tert-butyl (S)-(1-(7-bromo-3-(4-chloro-1-(2,2-difluoroethyl)-3-(N-(4-methoxybenzyl)methylsulfonamido)-1H-indazol-7-yl)-4-oxo-3,4-dihydroquinazolin-2-yl)-2-(3,5-difluorophenyl)ethyl)carbamate (15 g, 14.70 mmol) in DCM (150 mL) at 27° C. under N$_2$ atmosphere was added TFA (150 mL, 1947 mmol). The solution was stirred for 10 min. To the reaction mixture was added triflic acid (15 mL, 169 mmol). The solution was stirred for 1 h at 27° C. The progress of the reaction was monitored by TLC (SiO$_2$, 5% MeOH/DCM, Rf=0.4, UV-active). On completion, the solvent was removed under a gentle stream of nitrogen. The residue was dissolved in EtOAc (500 mL), washed with aq saturated NaHCO$_3$ (2×250 mL), brine (150 mL), dried over Na$_2$SO$_4$ and filtered. The filtrate was concentrated under reduced pressure to afford an off-white solid. LCMS analysis of the solid found a 75.42%:21.47% ratio of diastereomers. The crude solid subjected to C18 reverse-phase column chromatography (Mobile Phase: A: 0.1% TFA in water and B: 0.1% TFA in MeCN). Pure fractions containing the major diastereomer (atropisomer) were combined concentrated under reduced pressure. The resulting aqueous solution was made basic via the addition of aq. sat. NaHCO$_3$; then was extracted with EtOAc (2×500 mL). The combined organic layers were washed with brine (200 mL), dried over Na$_2$SO$_4$, filtered and concentrated to afford (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide as an off-white solid, 8.0 g (76%). LCMS: M+H=687.34, Purity=96%. This material was further purified to isolate the major enantiomer as follows: (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide (4.5 g, 6.28 mmol) was dissolved in MeOH:MeCN (1:1, 170 mL). The solution was subjected portionwise to SFC chiral separation as follows: column=(R, R) WHELK-01, 30×250 mm, 5 micron; solvent A=super critical CO$_2$; solvent B=methanol); eluent composition=50% A:50% B; flow-rate=100 g/min; back-pressure=90 bar; injection volume=1.1 mL; detection=214 nm; Stack time=6.8 min. For each isolated enantiomer, the resulting solution was concentrated under reduced pressure to afford an off-white solid. (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide as was isolated as the peak eluting from 6 min to 8 min and afforded 2.1 g (48%). $^{1}$H NMR (400 MHz, DMSO-d$_6$) δ=8.11-8.05 (m, 2H), 7.83-7.78 (m, 1H), 7.47-7.41 (m, 2H), 7.03-6.97 (m, 1H), 6.76-6.69 (m, 2H), 6.41-6.14 (m, 1H), 4.47-4.22 (m, 2H), 3.54-3.49 (m, 1H), 3.25-3.21 (m, 4H), 2.83-2.76 (m, 1H). LCMS: M+H=687.04, Purity=99%, Chiral HPLC Purity=96%.

Preparation of N-((S)-1-(7-Bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

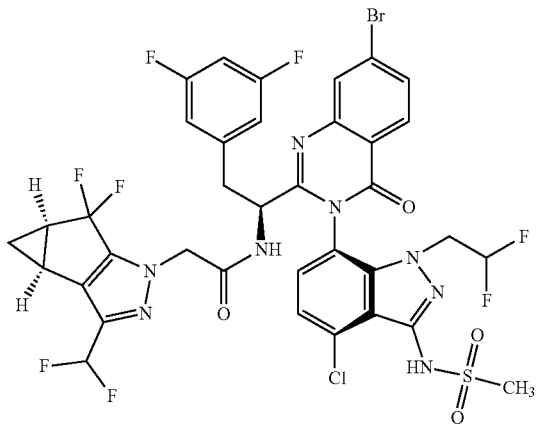

To a solution of (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)methanesulfonamide (1.75 g, 2.52 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (0.739 g, 2.77 mmol), HOBt (0.424 g, 2.77 mmol) and EDC.HCl (0.579 g, 3.02 mmol) in DMF (15 mL) at 27° C. under nitrogen atmosphere was added N-methylmorpholine (2.215 mL, 20.15 mmol). The solution was stirred at 27° C. for 36 h. The progress of the reaction was monitored by TLC (SiO$_2$, 50% EtOAc/Pet. Rf=0.5, UV-active). The reaction mixture was diluted with ice cold water (50 mL), and stirred for 15 min. The precipitated solid was isolated via filtration, washed with water (50 mL), and dried under vacuum to obtain the crude product. This material was treated with EtOAc (20 mL), stirred for 15 min, and then the solids were isolated via filtration and dried under vacuum to afford N-((S)-1-(7-bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide as an off-white solid, 1.6 g (64%). $^{1}$H NMR (400 MHz, DMSO-d$_6$) δ=10.00 (brs, 1H), 9.23 (d, J=8.1 Hz, 1H), 8.13 (d, J=8.6 Hz, 1H), 7.98 (d, J=2.0 Hz, 1H), 7.85 (dd, J=2.0, 2.1 Hz, 1H), 7.78 (d, J=7.9 Hz, 1H), 7.54 (d, J=7.9 Hz, 1H), 7.07-6.99 (m, 1H), 6.92 (t, J=51.7 Hz, 1H), 6.61 (d, J=6.3 Hz, 2H), 6.11 (t, J=54.6 Hz, 1H), 4.72-4.57 (m, 2H), 4.38 (tt, J=107, 2.9 Hz, 1H), 4.31-4.19 (m, 1H), 3.96-3.83 (m, 1H), 3.44-3.37 (m, 1H), 3.19 (s, 3H), 3.00-2.92 (m, 1H), 2.49-2.45 (m, 2H), 1.39-1.31 (m, 1H), 0.87-0.82 (m, 1H). LCMS: M+H=933.13, LCMS Purity=95%, HPLC Purity=96%, Chiral HPLC Purity=97%.

Preparation of N-((S)-1-(3-(4-chloro-1-(2,2-difluoroethyl)-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

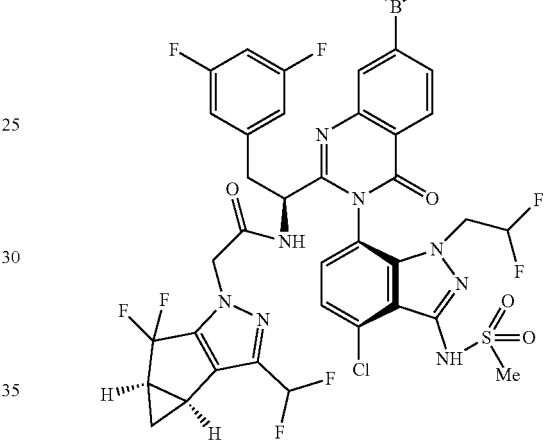

To a dry round-bottom flask equipped with a stir bar was added N-((S)-1-(7-bromo-3-(4-chloro-1-(2,2-difluoroethyl)-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide (500 mg, 0.535 mmol), 4,4,4',4',5,5,5',5'-octamethyl-2,2'-bi(1,3,2-dioxaborolane) (204 mg, 0.803 mmol), potassium acetate (158 mg, 1.606 mmol), and PdCl$_2$(dppf) (39.2 mg, 0.054 mmol). The flask was sealed with a septum and then placed under argon atmosphere (vac/fill×3). To the flask was added 1,4-dioxane (14 mL). The mixture was degassed (vac/fill with argon×3). The mixture was then stirred at 60° C. for overnight (16 h). The reaction mixture was concentrated under reduced pressure. The resulting residue was adsorbed onto Celite. The resulting powder was subjected to silica gel column chromatography (40 g silica gel column, hexanes:EtOAc 100:0→50:50 over 10 column volumes). The fractions containing the product were collected and concentrated in vacuo to afford N-((S)-1-(3-(4-chloro-1-(2,2-difluoroethyl)-3-(methylsulfonamido)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, 520 mg (99%).

$^{1}$H NMR (METHANOL-d$_4$, 500 MHz) δ8.2-8.3 (m, 2H), 7.97 (d, 1H, J=7.7 Hz), 7.40 (d, 1H, J=8.0 Hz), 7.28 (d, 1H, J=8.0 Hz), 6.5-6.9 (m, 4H), 6.00 (tt, 1H, J=4.1, 55.2 Hz), 4.75 (dd, 1H, J=4.8, 9.2 Hz), 4.6-4.7 (m, 2H), 4.38 (dtd, 1H, J=4.2, 13.3, 15.2 Hz), 4.12 (q, 1H, J=7.2 Hz), 3.9-4.0 (m, 1H), 3.3-3.5 (m, 1H), 3.3-3.3 (m, 3H), 3.06 (dd, 1H, J=9.2, 14.0 Hz), 2.4-2.5 (m, 2H), 2.0-2.0 (m, 2H), 1.3-1.4 (m, 2H), 1.22 (s, 12H), 1.0-1.1 (m, 1H)

Preparation of tert-butyl(S)-(1-(7-bromo-3-(4-chloro-1-(2,2-difluoroethyl)-3-(N-(4-methoxybenzyl) cyclopropanesulfonamido)-1H-indazol-7-yl)-4-oxo-3,4-dihydroquinazolin-2-yl)-2-(3,5-difluorophenyl)ethyl)carbamate

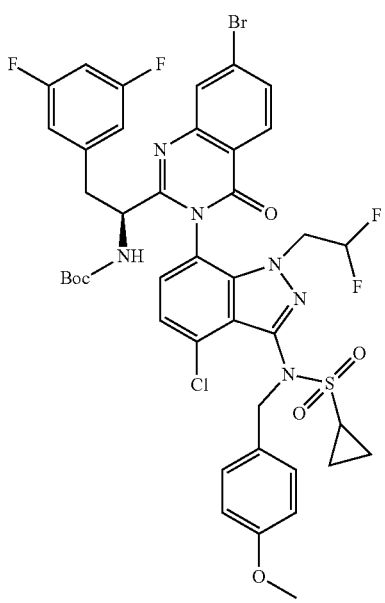 [SMILES: COc1ccc(CN(c2nn(CC(F)F)c3c(-n4c([C@H](Cc5cc(F)cc(F)c5)NC(=O)OC(C)(C)C)nc5cc(Br)ccc5c4=O)ccc(Cl)c23)S(=O)(=O)C2CC2)cc1]

To a stirred solution of (S)-2-((tert-butoxycarbonyl)amino)-3-(3,5-difluorophenyl)propanoic acid (15 g, 49.8 mmol) and 2-amino-4-bromobenzoic acid (12.91 g, 59.7 mmol) in pyridine (150 mL) in a sealed tube at 26° C. was added diphenyl phosphite (35.7 mL, 184 mmol). The reaction mixture was degassed with $N_2$ bubbling for each addition of reagents. The reaction mixture was heated to 80° C. and stirred for 2 hr. The reaction mixture was cooled to 26° C., then N-(7-amino-4-chloro-1-(2,2-difluoroethyl)-1H-indazol-3-yl)-N-(4-methoxybenzyl)cyclopropanesulfonamide (N66734-90-A2, 20.49 g, 34.9 mmol) was added. The mixture was heated at 80° C. for 16 h. The progress of the reaction was monitored by TLC ($SiO_2$, 30% EtOAc/Pet. Rf=0.3). The reaction mixture was cooled to 26° C. and then was concentrated under reduced pressure. The residue was diluted with water (150 mL) and extracted with ethyl acetate (2×500 mL). The combined organic layers were washed with aq. citric acid (5% w/v, 2×150 mL), then brine (250 mL); dried over anhydrous $Na_2SO_4$; filtered; and concentrated under reduced pressure to afford a brown gummy liquid (40 g). The above procedure was repeated, and the crude product of both iterations was combined. This material was then subjected to silica gel column chromatography (pet.:EtOAc, 60:40→55:45) to afforded tert-butyl (S)-(1-(7-bromo-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl) carbamate (mixture of diastereomers) as a yellow solid (42 g, 98%). LCMS: M+H=933.88 & 935.88; purity=76.91%.

Preparation of (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide

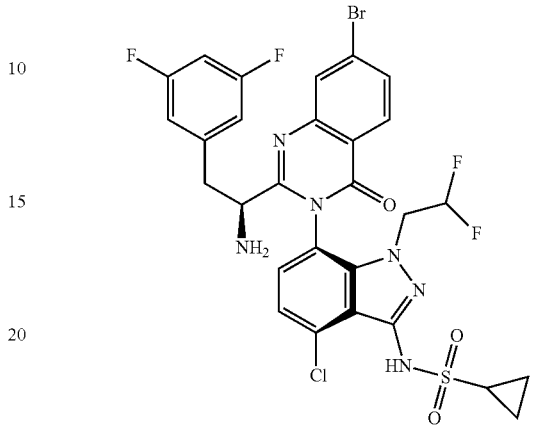

To a stirred solution of tert-butyl (S)-(1-(7-bromo-3-(4-chloro-1-(2,2-difluoroethyl)-3-(N-(4-methoxybenzyl)cyclopropanesulfonamido)-1H-indazol-7-yl)-4-oxo-3,4-dihydroquinazolin-2-yl)-2-(3,5-difluorophenyl)ethyl)carbamate (14 g, 11.53 mmol) in DCM (140 mL) at 27° C. under N2 atmosphere was added TFA (140 mL). The solution was stirred for 10 min. To the solution was added trifluoromethanesulfonic acid (7.16 mL, 81 mmol). The reaction mixture was stirred for 1 h at 27° C. The progress of the reaction was monitored by TLC ($SiO_2$, 50% EtOAc/pet, Rf=0.2). The solvent was removed under a gentle stream of nitrogen. The residue was dissolved in EtOAc (500 mL) and the organic layer was washed with aq. saturated $NaHCO_3$ (2×150 mL), brine (50 mL), dried over $Na_2SO_4$, filtered and concentrated to dryness to the crude compound as an off white solid (12 g). The above procedure was repeated twice more and the additional crude solids (2×14 g) were combined with the above. The combined material was dissolved in dichloromethane (500 mL) and concentrated to afford a homogeneous crude solid. This material was washed with pet. ether:EtOAc (80:20) and then dried under vacuum to afford a brown solid (30 g). This material was then subjected to C18 reverse phase chromatography under the following conditions: Column=RediSep Gold HP C18 275 g; Mobile Phase A=Water:MeCN:TFA (950:50:1); Mobile Phase B=Water:MeCN:TFA (50:950:1); flow rate=80 mL/min; gradient profile (time/% B)=5/5, 5/10, 5/15, 10/20, 15/30, 20/40, 15/45, 10/50; temperature=ambient. Fractions of the major peak were pooled and concentrated under reduced pressure to remove the non-aqueous solvent. The resulting aq. solution was neutralized via the addition of sat. aq. NaHCO3 (1000 mL), then was extracted with EtOAc (4×500 mL). The combined organics were washed with brine (500 mL), dried over anhydrous $Na_2SO_4$, filtered and concentrated to afford (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (single diastereomer) as an off white solid. The material was then subjected to SFC purification under the following conditions: Column/dimensions=Chiralpak OX-H (30×250 mm), 5μ; Solvent A=liquid $CO_2$; Solvent B=Methanol with 0.5% diethyl amine; Eluent=A:B (70:30);

Flow-rate=100.0 g/min; Back Pressure=100.0 bar; Detection=UV (214 nm); injection volume=1.3 mL (93 mg/injection); 160 injections. Two peaks were collected separately and the major peak was concentrated under reduced pressure to afford (S)-N-(7-(2-(1-amino-2-(3,5-difluorophenyl)ethyl)-7-bromo-4-oxoquinazolin-3 (4H)-yl)-4-chloro-1-(2,2-difluoroethyl)-1H-indazol-3-yl)cyclopropanesulfonamide (single stereoisomer) as a pale yellow solid, 7.5 g (20%). $^1$H NMR (400 MHz, DMSO-d$_6$) δ=8.11-8.04 (m, 2H), 7.82-7.78 (m, 1H), 7.47-7.39 (m, 2H), 7.02-6.95 (m, 1H), 6.76-6.69 (m, 2H), 6.38-6.19 (m, 1H), 4.48-4.37 (m, 1H), 4.32-4.24 (m, 1H), 3.54-3.48 (m, 1H), 3.3-3.20 (m, 1H), 2.97-2.90 (m, 1H), 2.83-2.76 (m, 1H), 1.05-0.99 (m, 4H). LCMS: M+H=712.94 and 714.94; purity=98.37%, chiral HPLC purity=96%.

Preparation of N-((S)-1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

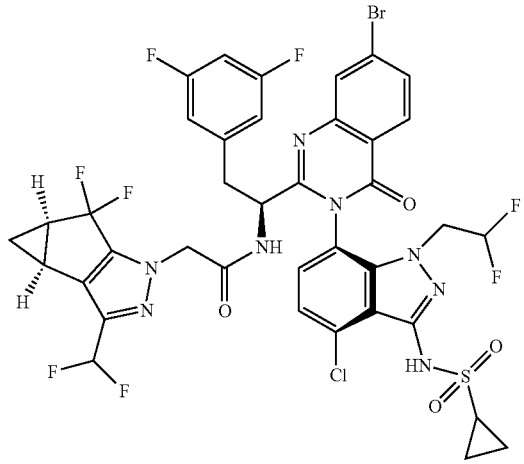

To a stirred solution of (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (500 mg, 0.700 mmol), 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (N68084-15-A1, 185 mg, 0.700 mmol), and HOBt (42.9 mg, 0.280 mmol) in DMF (5 mL) at 27° C. was added N-methylmorpholine (0.308 mL, 2.80 mmol) and N-(3-dimethylaminopropyl)-N'-ethylcarbodiimide hydrochloride (242 mg, 1.261 mmol). The reaction mixture was stirred at 27° C. for 16 h. The progress of the reaction was monitored by TLC (SiO$_2$, 50% EtOAc/Pet., Rf=0.3, UV-active). On completion, the reaction mixture was diluted with ice cold water (70 mL) and then stirred for 15 min at 27° C. The precipitated solids were collected by filtration and then dried under vacuum to obtain the crude compound as an off-white solid. The crude compound was subjected to silica gel chromatography (pet.:EtOAc (98:2→50:50) to afford N-((S)-1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide as an off-white solid, 550 mg (80%). $^1$H NMR (400 MHz, DMSO-d$_6$) δ=9.99 (s, 1H), 9.24 (d, J=8.1 Hz, 1H), 8.13 (d, J=8.8 Hz, 1H), 7.97 (d, J=1.8 Hz, 1H), 7.87-7.83 (m, 1H), 7.77 (d, J=7.9 Hz, 1H), 7.54 (d, J=7.9 Hz, 1H), 7.06-6.79 (m, 2H), 6.64-6.58 (m, 2H), 6.23-5.98 (m, 1H), 4.74-4.57 (m, 2H), 4.41-4.35 (m, 1H), 4.29-4.16 (m, 1H), 3.94-3.84 (m, 1H), 3.38-3.34 (m, 1H), 3.02-2.93 (m, 1H), 2.90-2.83 (m, 1H), 2.48-2.35 (m, 2H), 1.37-1.30 (m, 1H), 1.02-0.90 (m, 4H), 0.87-0.82 (m, 1H). LCMS analysis method F: RT=6.74 mins, (M+H)=959.0 and 961.0; LCMS Purity=98%; Chiral HPLC Purity=98%.

Preparation of N-((S)-1-(3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

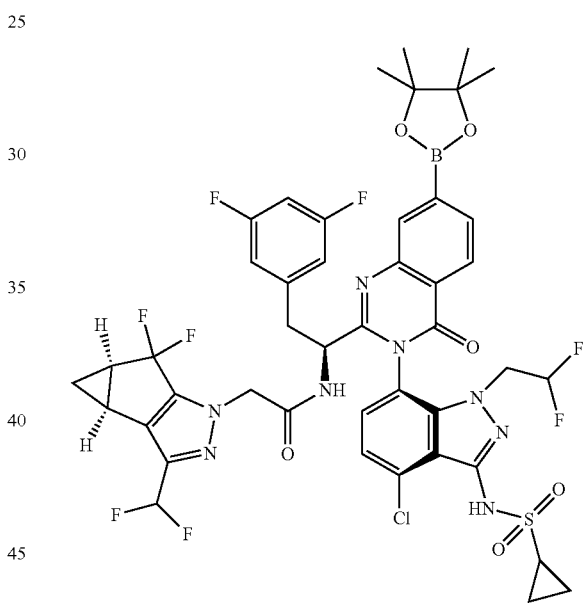

To a dry r.b. flask equipped with a stir bar was added N-((S)-1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (300 mg, 0.312 mmol), 4,4,4',4',5,5,5',5'-octamethyl-2,2'-bi(1,3,2-dioxaborolane) (119 mg, 0.469 mmol), potassium acetate (92 mg, 0.937 mmol) and PdCl$_2$(dppf) (22.86 mg, 0.031 mmol). The flask was sealed with a septum and then placed under argon atmosphere (vac/fill× 3). To the flask was added dioxane (6.3 mL). The flask was again placed under argon atmosphere (vac/fill×3). The resulting mixture was stirred at 60° C. for 16 h overnight. Upon cooling to ambient temperature the reaction was concentrated in vacuo and the resulting residue was adsorbed onto Celite. The resulting powder was subjected to silica gel column chromatography (hexanes:EtOAc 100:0→0:100 over 10 CV) to afford N-((S)-1-(3-(4-chloro-3-

(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide, 220 mg (70%). $^1$H NMR (METHANOL-$d_4$, 500 MHz) δ8.27 (d, 2H, J=6.2 Hz), 8.26 (s, 1H), 7.97 (dd, 1H, J=1.0, 7.9 Hz), 7.41 (d, 1H, J=7.7 Hz), 7.29 (d, 1H, J=7.7 Hz), 6.8-6.8 (m, 1H), 6.70 (br t, 1H, J=54.8 Hz), 6.55 (dd, 2H, J=2.1, 8.0 Hz), 6.01 (t, 1H, J=55.3 Hz), 4.74 (dd, 1H, J=4.8, 9.5 Hz), 4.68 (d, 1H, J=16.4 Hz), 4.59 (d, 1H, J=16.4 Hz), 4.38 (dd, 1H, J=4.2, 15.2 Hz), 4.12 (q, 1H, J=7.2 Hz), 3.91 (dd, 1H, J=3.9, 15.2 Hz), 3.68 (s, 1H), 3.06 (dd, 1H, J=9.4, 14.2 Hz), 2.9-2.9 (m, 1H), 2.4-2.5 (m, 2H), 2.03 (s, 2H), 1.45 (s, 12H), 1.1-1.1 (m, 2H), 1.0-1.0 (m, 3H).

Preparation of (S)-2-(3,5-b is (difluoromethyl)-1H-pyrazol-1-yl)-N-(1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)acetamide

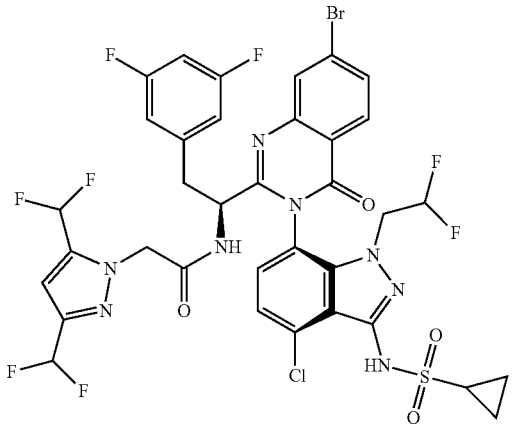

To a solution of (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (500 mg, 0.690 mmol), 2-(3,5-bis(difluoromethyl)-1H-pyrazol-1-yl)acetic acid (236 mg, 1.035 mmol) and HOBt (190 mg, 1.242 mmol) in DMF (10 mL) at 27° C. was added N-methylmorpholine (0.152 mL, 1.380 mmol) and N-(3-dimethylaminopropyl)-N'-ethylcarbodiimide hydrochloride (238 mg, 1.242 mmol). Then the reaction mixture was degassed for 10 min with nitrogen gas. The reaction mixture was stirred at 27° C. for 16 h; progress of the reaction was monitored by TLC (SiO$_2$, 50% EtOAc/Pet. Rf=0.2). After completion of reaction, the reaction mixture was diluted with ethyl acetate (50 mL) and washed with ice cold water (2×30 mL), and then brine (20 mL). The organic layer was separated, dried over anhydrous Na$_2$SO$_4$, filtered and concentrated to dryness to afford the crude compound as an off white solid (700 mg). This material was subjected to silica gel column chromatography using silica gel (pet:EtOAc, 100:0→50:50) to afford (S)-2-(3,5-bis(difluoromethyl)-1H-pyrazol-1-yl)-N-(1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)acetamide as an off white solid, 500 mg (76%). $^1$H NMR (400 MHz, DMSO-$d_6$) δ=9.99-9.94 (m, 1H), 9.31-9.25 (m, 1H), 8.14 (d, J=8.6 Hz, 1H), 7.99 (d, J=1.8 Hz, 1H), 7.88-7.83 (m, 1H), 7.75 (d, J=8.1 Hz, 1H), 7.52 (d, J=7.9 Hz, 1H), 7.07-6.82 (m, 4H), 6.65-6.57 (m, 2H), 6.19-5.99 (m, 1H), 4.94-4.81 (m, 2H), 4.45-4.38 (m, 1H), 4.31-4.19 (m, 1H), 3.97-3.87 (m, 1H), 3.39-3.34 (m, 1H), 3.01-2.94 (m, 1H), 2.89-2.82 (m, 1H), 1.00-0.92 (m, 4H). LCMS: M+H=921.24 and 923.12; purity=98.3%, chiral HPLC purity=99.46%.

Preparation of (S)-N-(1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-(5-cyclopropyl-3-(difluoromethyl)-1H-pyrazol-1-yl)acetamide

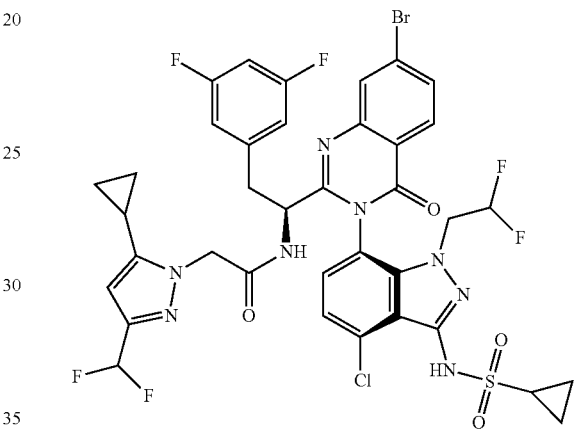

To a solution of (S)-N-(7-(2-(1-amino-2-(3,5-difluorophenyl)ethyl)-7-bromo-4-oxoquinazolin-3(4H)-yl)-4-chloro-1-(2,2-difluoroethyl)-1H-indazol-3-yl)cyclopropanesulfonamide (600 mg, 0.826 mmol), 2-(3-cyclopropyl-5-(difluoromethyl)-1H-pyrazol-1-yl)acetic acid (179 mg, 0.826 mmol) and HOBt (50.6 mg, 0.330 mmol) in DMF (5 mL) at 27° C. was added N-methylmorpholine (0.363 mL, 3.30 mmol) and N-(3-dimethylaminopropyl)-N'-ethylcarbodiimide hydrochloride (285 mg, 1.487 mmol). Then the reaction mixture was degassed for 10 min with nitrogen gas and then stirred at 27° C. for 16 h. The progress of the reaction was monitored by TLC (SiO$_2$, 50% EtOAc/Pet. Rf=0.3). The reaction mixture was diluted with ice cold water (70 mL) and then was stirred for 30 min at 27° C. The precipitated solid was isolated via filtration and then dried under vacuum to afford (S)-N-(1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl)-2-(5-cyclopropyl-3-(difluoromethyl)-1H-pyrazol-1-yl)acetamide as a pale yellow solid, 550 mg (68%). $^1$H NMR (400 MHz, DMSO-$d_6$) δ=10.02-9.85 (m, 1H), 9.17-9.10 (m, 1H), 8.14 (d, J=8.3 Hz, 1H), 7.99-7.95 (m, 1H), 7.87-7.84 (m, 1H), 7.77 (d, J=7.9 Hz, 1H), 7.52 (d, J=7.9 Hz, 1H), 7.07-7.00 (m, 1H), 6.86-6.59 (m, 3H), 6.20-5.98 (m, 2H), 4.77-4.67 (m, 2H), 4.50-4.43 (m, 1H), 4.33-4.22 (m, 1H), 4.00-3.87 (m, 1H), 3.39-3.32 (m, 1H), 3.06-2.94 (m, 2H), 2.60-2.55 (m, 1H), 1.46-1.38 (m, 1H), 1.00-0.91 (m, 4H), 0.75-0.64 (m, 2H), 0.57-0.46 (m, 2H). LCMS: M+H=910.89 and 912.91; purity=93.59%.

Preparation of Example 116

N-((S)-1-(3-(4-chloro-1-methyl-3-(methylsulfonamido)-1H-indazol-7-yl)-7-(2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

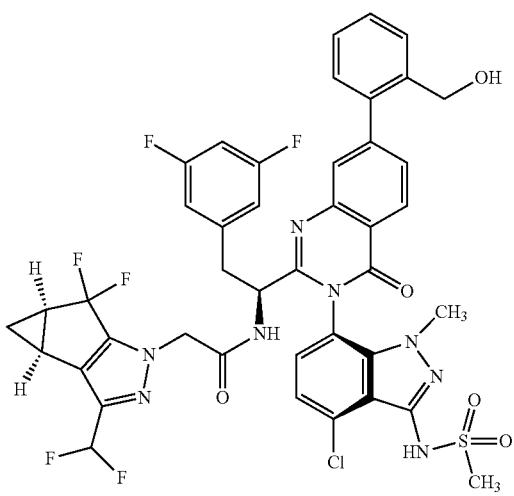

The title compound was prepared according to General Procedure A using (2-(hydroxymethyl)phenyl)boronic acid as the coupling partner. The experiment afforded the title compound, N-((S)-1-(3-(4-chloro-1-methyl-3-(methylsulfonamido)-1H-indazol-7-yl)-7-(2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.34 min.; observed ion=911.5 (M+H). 1H NMR (METHANOL-d4, 500 MHz) δ8.35 (d, 1H, J=8.2 Hz), 7.93 (d, 1H, J=1.3 Hz), 7.7-7.7 (m, 2H), 7.52 (dt, 1H, J=1.4, 7.5 Hz), 7.47 (dt, 1H, J=1.4, 7.5 Hz), 7.4-7.4 (m, 1H), 7.33 (d, 1H, J=7.9 Hz), 7.22 (d, 1H, J=7.9 Hz), 6.8-6.8 (m, 1H), 6.6-6.6 (m, 2H), 6.69 (t, 2H, J=54.7 Hz), 4.62 (s, 2H), 4.5-4.6 (m, 2H), 3.65 (s, 3H), 3.5-3.5 (m, 1H), 3.3-3.3 (m, 4H), 3.11 (dd, 1H, J=9.1, 14.2 Hz), 2.4-2.5 (m, 2H), 1.3-1.4 (m, 1H), 1.0-1.0 (m, 1H)

Preparation of Example 117

N-((S)-1-(3-(4-chloro-1-methyl-3-(methylsulfonamido)-1H-indazol-7-yl)-7-(4-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

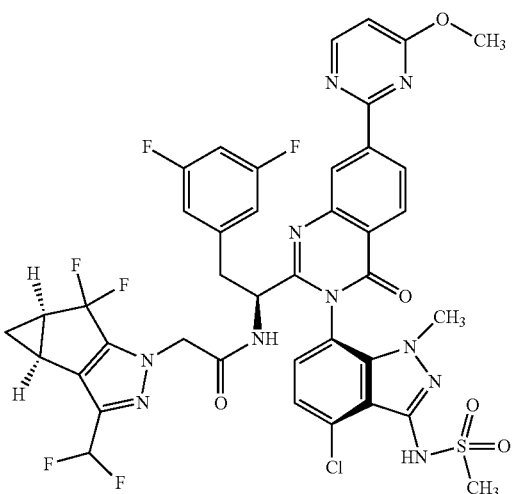

The title compound was prepared according to General Procedure D using 2-chloro-4-methoxypyrimidine as the coupling partner. The experiment afforded the title compound, N-((S)-1-(3-(4-chloro-1-methyl-3-(methylsulfonamido)-1H-indazol-7-yl)-7-(4-methoxypyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.42 min.; observed ion=913.7 (M+H). 1H NMR (METHANOL-d4, 500 MHz) δ8.94 (s, 1H), 8.69 (dd, 1H, J=1.8, 8.3 Hz), 8.67 (d, 1H, J=5.7 Hz), 8.40 (d, 1H, J=8.2 Hz), 7.32 (d, 1H, J=7.7 Hz), 7.23 (d, 1H, J=7.7 Hz), 6.92 (d, 1H, J=5.7 Hz), 6.6-6.8 (m, 4H), 4.5-4.6 (m, 2H), 4.20 (s, 3H), 3.64 (s, 3H), 3.5-3.5 (m, 1H), 3.2-3.3 (m, 4H), 3.1-3.2 (m, 1H), 2.4-2.5 (m, 2H), 1.3-1.4 (m, 1H), 1.0-1.0 (m, 1H)

Preparation of Example 118

N-((S)-1-(3-(4-chloro-1-methyl-3-(methylsulfonamido)-1H-indazol-7-yl)-4-oxo-7-(pyridin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

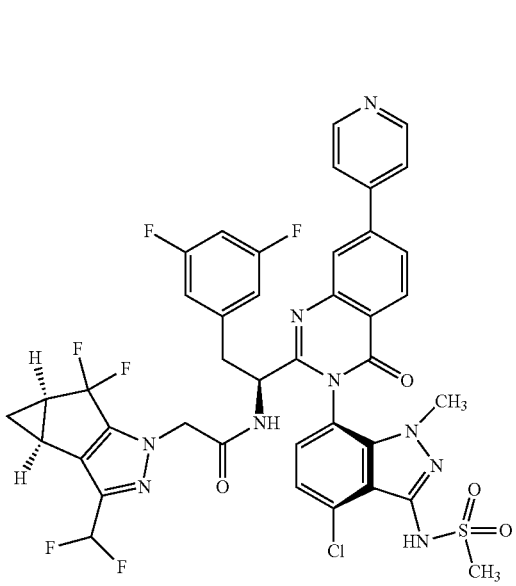

The title compound was prepared according to General Procedure D using 4-bromopyridine as the coupling partner. The experiment afforded the title compound, N-((S)-1-(3-(4-chloro-1-methyl-3-(methylsulfonamido)-1H-indazol-7-yl)-4-oxo-7-(pyridin-4-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.13 min.; observed ion=882.7 (M+H). 1H NMR (METHANOL-d4, 500 MHz) δ8.75 (d, 2H, J=6.3 Hz), 8.44 (d, 1H, J=8.3 Hz), 8.27 (d, 1H, J=1.8 Hz), 8.05 (dd, 1H, J=1.9, 8.2 Hz), 7.92 (d, 2H, J=5.2 Hz), 7.32 (d, 1H, J=8.0 Hz), 7.22 (d, 1H, J=7.7 Hz), 6.80 (tt, 1H, J=2.3, 9.2 Hz), 6.6-6.7 (m, 2H), 6.69 (br t, 1H, J=54.7 Hz), 4.9-4.9 (m, 1H), 4.54 (d, 2H, J=2.1 Hz), 3.64 (s, 3H), 3.5-3.5 (m, 1H), 3.26 (s, 3H), 3.13 (dd, 1H, J=8.9, 14.0 Hz), 2.43 (ddd, 2H, J=4.2, 7.7, 11.4 Hz), 1.3-1.4 (m, 1H), 1.0-1.0 (m, 1H)

Preparation of Example 119

N-((S)-1-(3-(4-chloro-1-methyl-3-(methylsulfonamido)-1H-indazol-7-yl)-7-(2-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

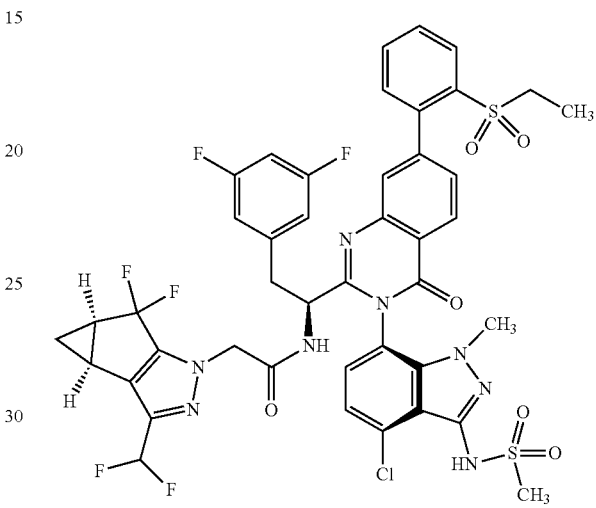

The title compound was prepared according to General Procedure D using 1-bromo-2-(ethylsulfonyl)benzene as the coupling partner. The experiment afforded the title compound, N-((S)-1-(3-(4-chloro-1-methyl-3-(methylsulfonamido)-1H-indazol-7-yl)-7-(2-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.37 min.; observed ion=973.7 (M+H). 1H NMR (METHANOL-d4, 500 MHz) δ8.35 (d, 1H, J=8.1 Hz), 8.23 (dd, 1H, J=1.2, 8.0 Hz), 7.94 (d, 1H, J=1.8 Hz), 7.87 (dt, 1H, J=1.3, 7.5 Hz), 7.78 (dt, 1H, J=1.5, 7.7 Hz), 7.69 (dd, 1H, J=1.8, 8.0 Hz), 7.55 (dd, 1H, J=1.3, 7.6 Hz), 7.32 (d, 1H, J=7.7 Hz), 7.22 (d, 1H, J=7.7 Hz), 6.78 (br t, 1H, J=2.2 Hz), 6.62 (dd, 2H, J=2.2, 8.2 Hz), 6.69 (t, 1H, J=54.8 Hz), 4.53 (d, 2H, J=2.7 Hz), 3.66 (s, 3H), 3.3-3.5 (m, 2H), 3.26 (s, 3H), 3.10 (dd, 1H, J=9.2, 14.0 Hz), 2.95 (q, 2H, J=7.5 Hz), 2.4-2.5 (m, 2H), 1.37 (br d, 1H, J=7.5 Hz), 1.14 (t, 3H, J=7.5 Hz), 1.0-1.0 (m, 1H)

199

Preparation of Example 120

N-((S)-1-(3-(4-chloro-1-methyl-3-(methylsulfonamido)-1H-indazol-7-yl)-7-(2-(isopropylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

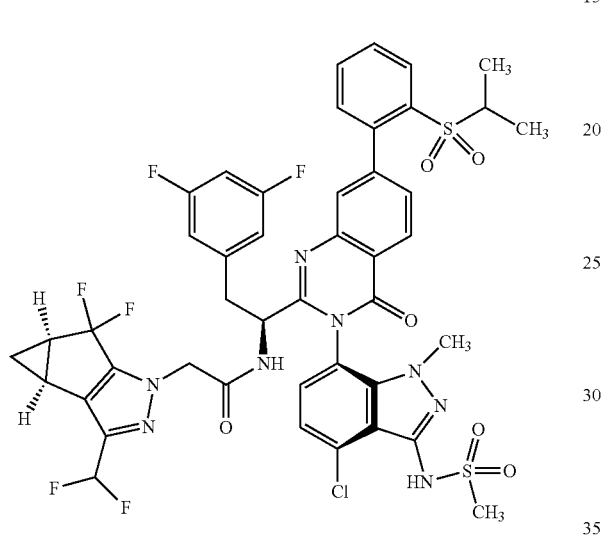

The title compound was prepared according to General Procedure D using 1-bromo-2-(isopropylsulfonyl)benzene as the coupling partner. The experiment afforded the title compound, N-((S)-1-(3-(4-chloro-1-methyl-3-(methylsulfonamido)-1H-indazol-7-yl)-7-(2-(isopropyl sulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=987.8 (M+H). 1H NMR (METHANOL-d4, 500 MHz) δ8.33 (d, 1H, J=8.1 Hz), 8.21 (dd, 1H, J=1.2, 8.0 Hz), 7.92 (d, 1H, J=1.8 Hz), 7.9-7.9 (m, 1H), 7.78 (dt, 1H, J=1.2, 7.7 Hz), 7.7-7.7 (m, 1H), 7.54 (dd, 1H, J=1.2, 7.5 Hz), 7.32 (d, 1H, J=7.7 Hz), 7.21 (d, 1H, J=7.7 Hz), 6.8-6.8 (m, 1H), 6.62 (dd, 2H, J=2.2, 8.2 Hz), 6.69 (br t, 1H, J=54.7 Hz), 4.9-4.9 (m, 2H), 4.53 (d, 2H, J=2.1 Hz), 3.66 (s, 3H), 3.26 (s, 3H), 3.10 (dd, 1H, J=8.9, 14.0 Hz), 2.9-3.0 (m, 1H), 2.4-2.5 (m, 2H), 1.3-1.4 (m, 1H), 1.16 (d, 3H, J=5.4 Hz), 1.15 (d, 3H, J=5.4 Hz), 1.01 (td, 1H, J=2.1, 3.6 Hz)

200

Preparation of Example 121

N-((S)-1-(3-(4-chloro-1-methyl-3-(methylsulfonamido)-1H-indazol-7-yl)-7-(3-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

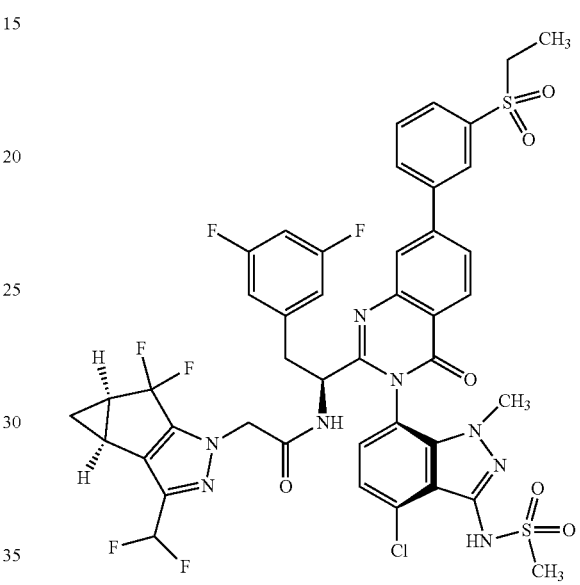

The title compound was prepared according to General Procedure D using 1-bromo-3-(ethylsulfonyl)benzene as the coupling partner. The experiment afforded the title compound, N-((S)-1-(3-(4-chloro-1-methyl-3-(methylsulfonamido)-1H-indazol-7-yl)-7-(3-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.35 min.; observed ion=973.7 (M+H). 1H NMR (METHANOL-d4, 500 MHz) δ8.43 (d, 1H, J=8.3 Hz), 8.35 (t, 1H, J=1.6 Hz), 8.22 (d, 1H, J=7.7 Hz), 8.20 (d, 1H, J=1.5 Hz), 8.07 (d, 1H, J=7.7 Hz), 8.02 (dd, 1H, J=1.8, 8.3 Hz), 7.88 (t, 1H, J=7.6 Hz), 7.32 (d, 1H, J=8.0 Hz), 7.23 (d, 1H, J=7.7 Hz), 6.8-6.8 (m, 1H), 6.63 (dd, 2H, J=2.2, 8.2 Hz), 6.70 (br t, 1H, J=54.7 Hz), 4.5-4.6 (m, 3H), 3.64 (s, 3H), 3.5-3.5 (m, 1H), 3.3-3.4 (m, 2H), 3.2-3.3 (m, 3H), 3.12 (dd, 1H, J=9.2, 14.0 Hz), 2.4-2.5 (m, 2H), 1.3-1.4 (m, 4H), 1.0-1.0 (m, 1H)

Preparation of Example 122

N-((S)-1-(3-(4-chloro-1-methyl-3-(methylsulfonamido)-1H-indazol-7-yl)-4-oxo-7-(3-(propylsulfonyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

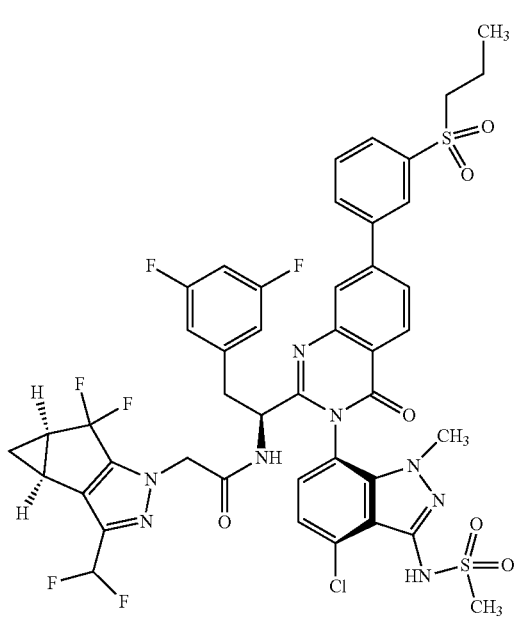

The title compound was prepared according to General Procedure D using 1-bromo-3-(propylsulfonyl)benzene as the coupling partner. The experiment afforded the title compound, N-((S)-1-(3-(4-chloro-1-methyl-3-(methylsulfonamido)-1H-indazol-7-yl)-4-oxo-7-(3-(propylsulfonyl)phenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.4 min.; observed ion=987.9 (M+H). 1H NMR (METHANOL-d4, 500 MHz) δ8.43 (br d, 1H, J=8.0 Hz), 8.35 (s, 1H), 8.2-8.2 (m, 2H), 8.07 (br d, 1H, J=8.0 Hz), 8.02 (br d, 1H, J=8.6 Hz), 7.87 (t, 1H, J=7.8 Hz), 7.32 (br d, 1H, J=7.2 Hz), 7.23 (br d, 1H, J=7.5 Hz), 6.6-6.8 (m, 4H), 4.56 (br d, 3H, J=5.7 Hz), 3.64 (s, 3H), 3.5-3.5 (m, 1H), 3.4-3.4 (m, 1H), 3.2-3.3 (m, 3H), 3.19 (s, 1H), 3.1-3.2 (m, 1H), 2.4-2.5 (m, 2H), 1.8-1.8 (m, 2H), 1.3-1.4 (m, 1H), 1.0-1.1 (m, 4H)

Preparation of Example 123

N-((S)-1-(3-(4-chloro-1-methyl-3-(methylsulfonamido)-1H-indazol-7-yl)-7-(3-(isopropylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

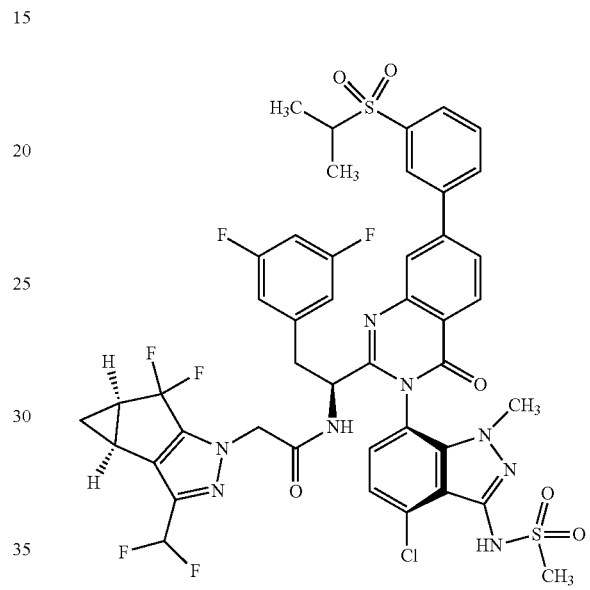

The title compound was prepared according to General Procedure D using 1-bromo-3-(isopropylsulfonyl)benzene as the coupling partner. The experiment afforded the title compound, N-((S)-1-(3-(4-chloro-1-methyl-3-(methylsulfonamido)-1H-indazol-7-yl)-7-(3-(isopropyl sulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.39 min.; observed ion=987.8 (M+H). 1H NMR (METHANOL-d4, 500 MHz) δ8.43 (d, 1H, J=8.3 Hz), 8.31 (t, 1H, J=1.6 Hz), 8.23 (d, 1H, J=7.6 Hz), 8.18 (d, 1H, J=1.2 Hz), 8.04 (d, 1H, J=7.8 Hz), 8.01 (dd, 1H, J=1.9, 8.2 Hz), 7.88 (t, 1H, J=7.5 Hz), 7.32 (d, 1H, J=7.7 Hz), 7.23 (d, 1H, J=7.7 Hz), 6.8-6.8 (m, 1H), 6.63 (dd, 2H, J=2.2, 8.2 Hz), 6.69 (br t, 1H, J=54.8 Hz), 4.56 (d, 2H, J=6.0 Hz), 3.63 (s, 3H), 3.5-3.5 (m, 2H), 3.2-3.3 (m, 3H), 3.19 (t, 1H, J=1.6 Hz), 3.12 (dd, 1H, J=9.2, 14.0 Hz), 2.4-2.5 (m, 2H), 1.35 (d, 7H, J=6.9 Hz), 1.0-1.0 (m, 1H)

Preparation of Example 124

N-((S)-1-(3-(4-chloro-1-(2,2-difluoroethyl)-3-(methylsulfonamido)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

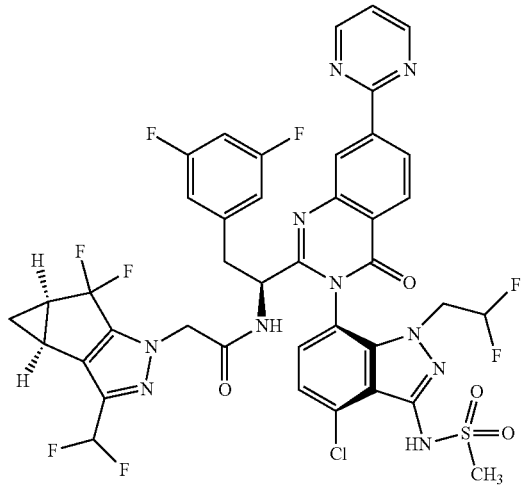

The title compound was prepared according to General Procedure I using 2-chloropyrimidine as the coupling partner. The experiment afforded the title compound, N-((S)-1-(3-(4-chloro-1-(2,2-difluoroethyl)-3-(methylsulfonamido)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.37 min.; observed ion=933.2 (M+H). 1H NMR (METHANOL-d4, 500 MHz) δ9.01 (d, 2H, J=5.1 Hz), 8.95 (d, 1H, J=1.5 Hz), 8.71 (dd, 1H, J=1.8, 8.3 Hz), 8.40 (d, 1H, J=8.2 Hz), 7.52 (t, 1H, J=4.9 Hz), 7.39 (d, 1H, J=8.3 Hz), 7.30 (d, 1H, J=8.0 Hz), 6.5-6.8 (m, 4H), 6.04 (br d, 1H, J=8.3 Hz), 6.04 (t, 1H, J=55.3 Hz), 4.78 (dd, 1H, J=4.8, 9.2 Hz), 4.38 (br s, 1H), 3.98 (br s, 1H), 3.4-3.5 (m, 2H), 3.2-3.3 (m, 3H), 3.10 (dd, 1H, J=9.4, 14.2 Hz), 2.4-2.5 (m, 2H), 1.3-1.4 (m, 1H), 1.0-1.0 (m, 1H)

Preparation of Example 125

N-((S)-1-(3-(4-chloro-1-(2,2-difluoroethyl)-3-(methylsulfonamido)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

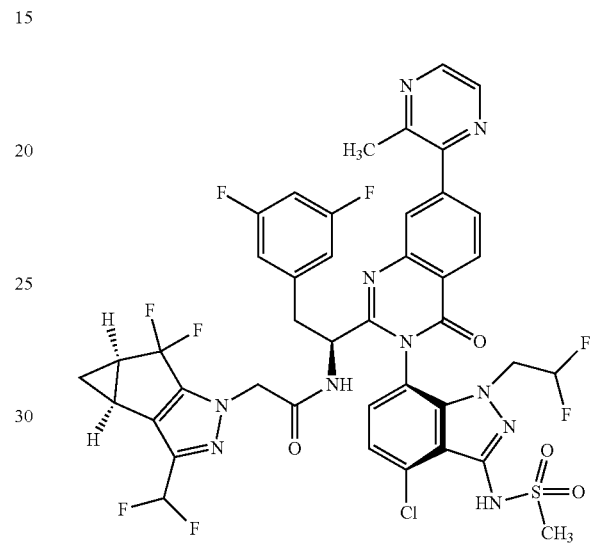

The title compound was prepared according to General Procedure I using 2-chloro-3-methylpyrazine as the coupling partner. The experiment afforded the title compound, N-((S)-1-(3-(4-chloro-1-(2,2-difluoroethyl)-3-(methylsulfonamido)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.32 min.; observed ion=947.2 (M+H). 1H NMR (METHANOL-d4, 500 MHz) δ8.65 (s, 1H), 8.63 (d, 1H, J=2.5 Hz), 8.43 (d, 1H, J=7.7 Hz), 8.12 (d, 1H, J=2.1 Hz), 7.91 (dd, 1H, J=1.8, 8.3 Hz), 7.40 (d, 1H, J=8.0 Hz), 7.31 (d, 1H, J=7.7 Hz), 6.6-6.8 (m, 4H), 5.9-6.2 (m, 1H), 4.77 (dd, 1H, J=4.8, 9.2 Hz), 4.62 (q, 2H, J=16.4 Hz), 4.40 (br dd, 1H, J=4.2, 15.2 Hz), 3.9-4.0 (m, 1H), 3.4-3.5 (m, 1H), 3.3-3.3 (m, 3H), 3.09 (dd, 1H, J=9.4, 14.2 Hz), 2.73 (s, 3H), 2.4-2.5 (m, 2H), 1.3-1.4 (m, 1H), 1.0-1.0 (m, 1H)

205

Preparation of Example 126

N-((S)-1-(3-(4-chloro-3-(cyclopropanesulfonamido)-1-(2,2-difluoroethyl)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

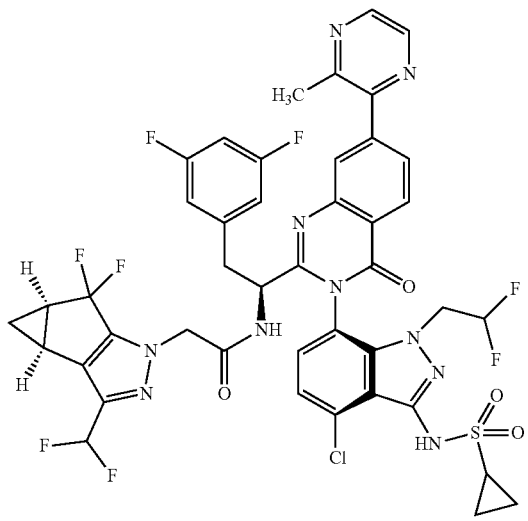

The title compound was prepared according to General Procedure K using 2-chloro-3-methylpyrazine as the coupling partner. The experiment afforded the title compound, N-((S)-1-(3-(4-chloro-3-(cyclopropanesulfonamido)-1-(2,2-difluoroethyl)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method E: retention time=1.75 min.; observed ion=973.4 (M+H). 1H NMR (METHANOL-d4, 500 MHz) δ8.65 (s, 1H), 8.63 (d, 1H, J=2.6 Hz), 8.43 (d, 1H, J=7.7 Hz), 8.12 (d, 1H, J=1.8 Hz), 7.91 (dd, 1H, J=1.8, 8.3 Hz), 7.41 (d, 1H, J=8.0 Hz), 7.32 (d, 1H, J=8.0 Hz), 6.8-6.8 (m, 1H), 6.69 (t, 1H, J=54.8 Hz), 6.5-6.6 (m, 2H), 6.06 (tt, 1H, J=4.2, 55.3 Hz), 4.76 (dd, 1H, J=4.8, 9.5 Hz), 4.67 (d, 1H, J=16.4 Hz), 4.60 (d, 1H, J=16.4 Hz), 4.4-4.5 (m, 1H), 3.9-4.0 (m, 1H), 3.43 (dd, 1H, J=4.8, 14.0 Hz), 3.08 (dd, 1H, J=9.5, 14.0 Hz), 2.92 (tt, 1H, J=4.8, 8.0 Hz), 2.73 (s, 3H), 2.4-2.5 (m, 2H), 1.3-1.4 (m, 1H), 1.1-1.2 (m, 2H), 1.0-1.0 (m, 3H)

206

Preparation of Example 127

N-((S)-1-(3-(4-chloro-3-(cyclopropanesulfonamido)-1-(2,2-difluoroethyl)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

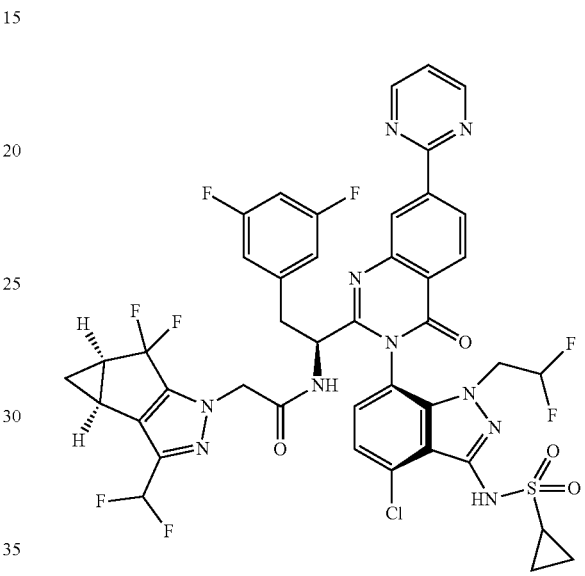

The title compound was prepared according to General Procedure J using 2-chloropyrimidine as the coupling partner. The experiment afforded the title compound, N-((S)-1-(3-(4-chloro-3-(cyclopropanesulfonamido)-1-(2,2-difluoroethyl)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method E: retention time=1.81 min.; observed ion=959.4 (M+H). 1H NMR (METHANOL-d4, 500 MHz) δ9.01 (d, 2H, J=5.1 Hz), 8.96 (d, 1H, J=1.2 Hz), 8.71 (dd, 1H, J=1.5, 8.3 Hz), 8.41 (d, 1H, J=8.3 Hz), 7.52 (t, 1H, J=4.9 Hz), 7.40 (d, 1H, J=7.5 Hz), 7.31 (d, 1H, J=8.0 Hz), 6.8-6.8 (m, 1H), 6.70 (br t, 1H, J=54.7 Hz), 6.5-6.6 (m, 2H), 6.04 (br d, 1H, J=8.3 Hz), 6.04 (t, 1H, J=55.4 Hz), 4.78 (dd, 1H, J=4.6, 9.4 Hz), 4.69 (d, 1H, J=16.4 Hz), 4.61 (d, 1H, J=16.4 Hz), 4.3-4.5 (m, 1H), 3.4-3.5 (m, 1H), 3.09 (dd, 1H, J=9.4, 14.2 Hz), 2.9-2.9 (m, 1H), 2.4-2.5 (m, 2H), 1.3-1.4 (m, 1H), 1.1-1.2 (m, 2H), 0.9-1.0 (m, 3H)

207

Preparation of Example 128

N-((S)-1-(3-(4-chloro-1-(2,2-difluoroethyl)-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

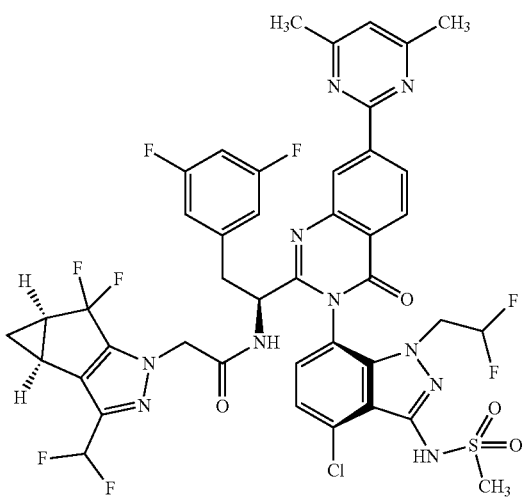

The title compound was prepared according to General Procedure I using 2-chloro-4,6-dimethylpyrimidine as the coupling partner. The experiment afforded the title compound, N-((S)-1-(3-(4-chloro-1-(2,2-difluoroethyl)-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method E: retention time=1.5 min.; observed ion=961.4 (M+H). 1H NMR (METHANOL-d4, 500 MHz) δ8.91 (d, 1H, J=1.5 Hz), 8.68 (dd, 1H, J=1.8, 8.3 Hz), 8.38 (d, 1H, J=8.3 Hz), 7.38 (d, 1H, J=7.7 Hz), 7.3-7.3 (m, 2H), 6.8-6.8 (m, 1H), 6.71 (t, 1H, J=54.8 Hz), 6.58 (br dd, 2H, J=2.1, 8.0 Hz), 6.16 (s, 1H), 6.04 (br d, 1H, J=8.3 Hz), 6.04 (t, 1H, J=55.3 Hz), 5.92 (s, 1H), 4.7-4.8 (m, 1H), 4.3-4.5 (m, 1H), 3.9-4.0 (m, 1H), 3.4-3.5 (m, 1H), 3.2-3.3 (m, 3H), 3.09 (dd, 1H, J=9.2, 14.0 Hz), 2.64 (s, 6H), 2.5-2.5 (m, 1H), 1.36 (dt, 1H, J=6.4, 7.2 Hz), 1.0-1.0 (m, 1H)

208

Preparation of Example 129

N-((S)-1-(3-(4-chloro-3-(cyclopropanesulfonamido)-1-(2,2-difluoroethyl)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

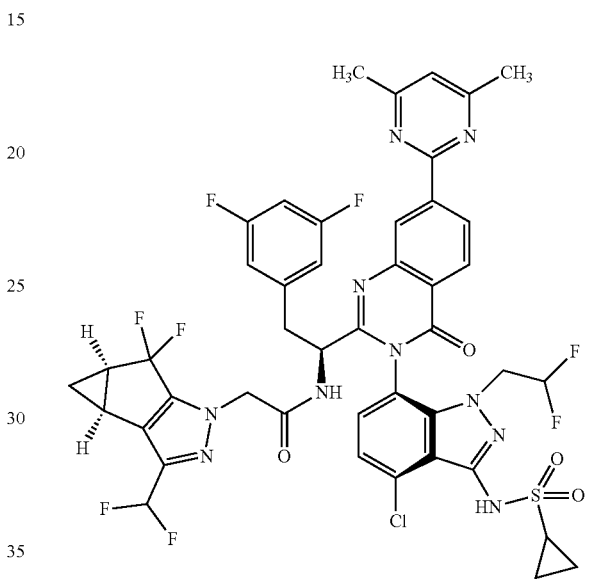

The title compound was prepared according to General Procedure J using 2-chloro-4,6-dimethylpyrimidine as the coupling partner. The experiment afforded the title compound, N-((S)-1-(3-(4-chloro-3-(cyclopropanesulfonamido)-1-(2,2-difluoroethyl)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method E: retention time=1.53 min.; observed ion=987.4 (M+H). 1H NMR (METHANOL-d4, 500 MHz) δ8.92 (d, 1H, J=1.2 Hz), 8.68 (dd, 1H, J=1.8, 8.3 Hz), 8.38 (d, 1H, J=8.3 Hz), 7.40 (br d, 1H, J=8.3 Hz), 7.30 (d, 2H, J=7.1 Hz), 7.29 (s, 1H), 6.5-6.8 (m, 4H), 5.9-6.2 (m, 1H), 4.9-4.9 (m, 1H), 4.78 (dd, 1H, J=4.8, 9.2 Hz), 4.3-4.4 (m, 1H), 3.9-4.0 (m, 1H), 3.4-3.5 (m, 1H), 3.08 (dd, 1H, J=9.4, 14.2 Hz), 2.92 (tt, 1H, J=4.8, 8.0 Hz), 2.64 (s, 6H), 2.4-2.5 (m, 2H), 1.36 (td, 1H, J=6.6, 7.9 Hz), 1.1-1.2 (m, 2H), 0.9-1.1 (m, 3H)

Preparation of Example 130

N-((S)-1-(3-(4-chloro-1-methyl-3-(methylsulfonamido)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

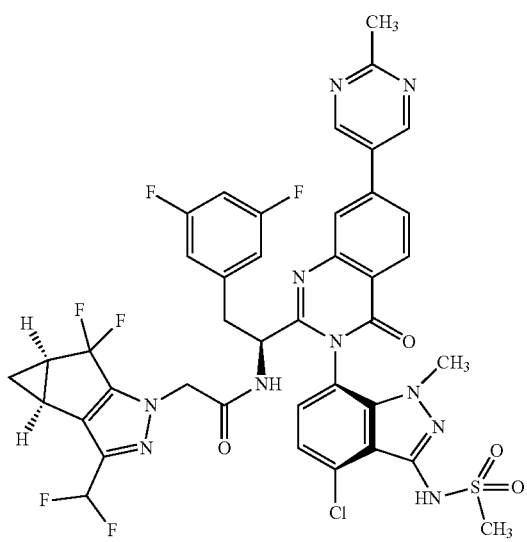

The title compound was prepared according to General Procedure D using 5-bromo-2-methylpyrimidine as the coupling partner. The experiment afforded the title compound, N-((S)-1-(3-(4-chloro-1-methyl-3-(methylsulfonamido)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method C: retention time=1.28 min.; observed ion=897.4 (M+H). 1H NMR (METHANOL-d4, 500 MHz) δ9.17 (s, 2H), 8.44 (d, 1H, J=8.3 Hz), 8.23 (d, 1H, J=1.5 Hz), 8.02 (dd, 1H, J=1.8, 8.3 Hz), 7.31 (d, 1H, J=7.7 Hz), 7.22 (d, 1H, J=7.7 Hz), 6.8-6.8 (m, 1H), 6.64 (dd, 2H, J=2.2, 8.2 Hz), 6.70 (br t, 1H, J=54.7 Hz), 4.8-4.9 (m, 1H), 4.53 (d, 2H, J=1.5 Hz), 3.63 (s, 3H), 3.5-3.5 (m, 1H), 3.2-3.3 (m, 3H), 3.1-3.2 (m, 1H), 2.83 (s, 3H), 2.43 (dt, 2H, J=4.0, 7.5 Hz), 1.3-1.4 (m, 1H), 1.0-1.0 (m, 1H)

Preparation of Example 131

N-((S)-1-(3-(4-chloro-1-methyl-3-(methylsulfonamido)-1H-indazol-7-yl)-7-(4-methoxy-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

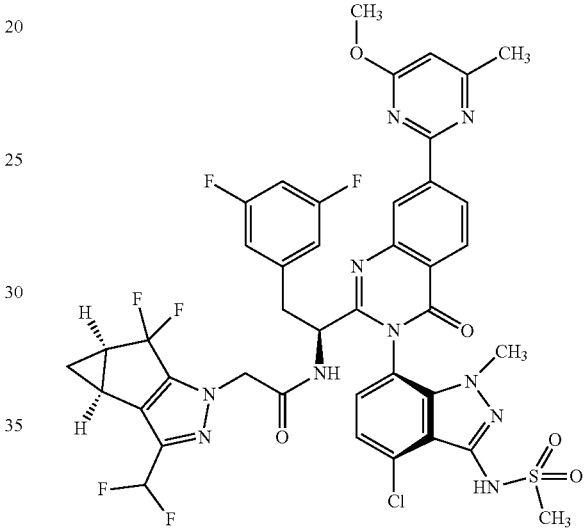

The title compound was prepared according to General Procedure D using 2-chloro-4-methoxy-6-methylpyrimidine as the coupling partner. The experiment afforded the title compound, N-((S)-1-(3-(4-chloro-1-methyl-3-(methylsulfonamido)-1H-indazol-7-yl)-7-(4-methoxy-6-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=927.5 (M+H). 1H NMR (METHANOL-d4, 500 MHz) Shift 8.94 (s, 1H), 8.69 (dd, 1H, J=1.5, 8.3 Hz), 8.39 (d, 1H, J=8.3 Hz), 7.31 (d, 1H, J=7.7 Hz), 7.23 (d, 1H, J=7.7 Hz), 6.63 (br d, 5H, J=2.1 Hz), 4.56 (d, 2H, J=5.4 Hz), 4.17 (s, 3H), 3.64 (s, 3H), 3.4-3.5 (m, 1H), 3.25 (s, 3H), 3.13 (dd, 1H, J=9.2, 14.0 Hz), 2.68 (s, 1H), 2.59 (s, 3H), 2.4-2.5 (m, 2H), 1.3-1.4 (m, 1H), 1.0-1.0 (m, 1H)

Preparation of Example 132

N-((S)-1-(3-(4-chloro-1-methyl-3-(methylsulfonamido)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

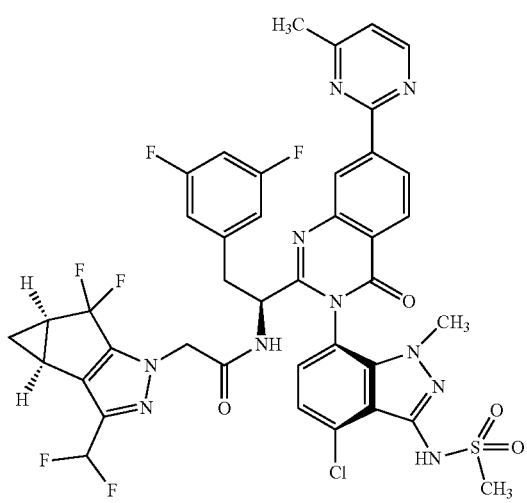

The title compound was prepared according to General Procedure D using 2-chloro-4-methylpyrimidine as the coupling partner. The experiment afforded the title compound, N-((S)-1-(3-(4-chloro-1-methyl-3-(methylsulfonamido)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=897.4 (M+H). 1H NMR (METHANOL-d4, 500 MHz) Shift 8.91 (d, 1H, J=1.2 Hz), 8.80 (d, 1H, J=5.1 Hz), 8.67 (dd, 1H, J=1.8, 8.3 Hz), 8.38 (d, 1H, J=8.3 Hz), 7.38 (d, 1H, J=5.7 Hz), 7.30 (d, 1H, J=7.7 Hz), 7.21 (d, 1H, J=8.0 Hz), 6.7-6.8 (m, 1H), 6.62 (dd, 2H, J=2.2, 8.2 Hz), 6.68 (br t, 1H, J=54.7 Hz), 4.9-4.9 (m, 1H), 4.53 (d, 2H, J=4.2 Hz), 3.6-3.7 (m, 3H), 3.49 (dd, 1H, J=5.1, 14.0 Hz), 3.24 (s, 3H), 3.11 (dd, 1H, J=9.2, 14.0 Hz), 2.67 (s, 3H), 2.4-2.5 (m, 2H), 1.34 (br dd, 1H, J=1.3, 7.0 Hz), 1.0-1.0 (m, 1H)

Preparation of Example 133

N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)propanamide

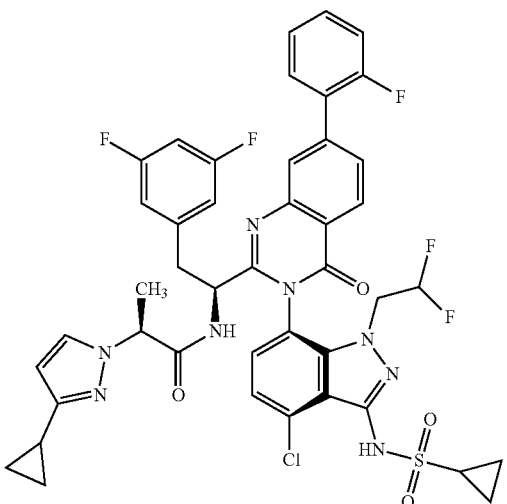

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (20 mg, 0.027 mmol), 2-(3-cyclopropyl-1H-pyrazol-1-yl)propanoic acid (4.94 mg, 0.027 mmol, single unknown enantiomer) and HOBt (1.678 mg, 10.95 μmol) in N,N-Dimethylformamide (DMF) (10 mL), were added N-methylmorpholine (3.01 μl, 0.027 mmol) and N-(3-Dimethylaminopropyl)-N'-ethylcarbodiimide hydrochloride (9.45 mg, 0.049 mmol) at 27° C. The reaction mixture was stirred at 27° C. for 16 h. The progress of the reaction was monitored by TLC (SiO₂, 30% EtOAc/Pet. Rf=0.2). The reaction mixture was diluted with EtOAc (30 mL) and washed with water (3×50 mL). The organic layer was dried over anhydrous sodium sulfate, filtered and concentrated under reduced pressure to get crude product as an off white solid. The above process was repeated and both batches were blended prior to HPLC purification. The crude sample was purified by HPLC under the following conditions: MOBILE PHASE A: 0.01M ammonium bicarbonate (aq); MOBILE PHASE B: Acetonitrile; Column: YMC C18 (150×25 mm), 10μ; Method (A:B)=30:70(isocratic); Flow: 25 ml/Min; Sample dissolved in MeCN+THF+Water; Temp: Ambient. Pure fractions pooled and then were lyophilized to afford N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)propanamide (19 mg, yield=48%, off white solid). ¹H NMR (400 MHz, METHANOL-d₄) δ=8.35-8.32 (m, 1H), 8.04 (t, J=1.4 Hz, 1H), 7.86-7.82 (m, 1H), 7.70-7.64 (m, 1H), 7.51 (ddt, J=1.8, 5.0, 7.8 Hz, 1H), 7.41-7.27 (m, 5H), 6.76-6.69 (m, 1H), 6.56-6.51 (m, 2H), 6.15-5.93 (m, 2H), 4.80-4.78 (m, 1H), 4.66-4.60 (m, 1H), 4.21-4.12 (m, 1H), 3.95-3.84 (m, 1H), 3.38-3.33 (m, 1H), 3.05-2.94 (m, 2H), 1.91-1.84 (m, 1H), 1.43-1.38 (m, 3H), 1.18-1.13 (m, 2H), 1.05-0.99 (m, 2H), 0.87-0.81 (m, 2H), 0.67-0.62 (m, 2H), LCMS: RT=2.99 mins, MH+=891.21, purity=99.08%, Chiral HPLC Purity=99.48%. Stereochemistry: Single unknown enantiomer. Specifically, the stereochemistry of the alpha-methyl has not been determined but is known to be the opposite of Example 138, and is drawn distinct from Example 138 to communicate this difference. All other stereochemistry is known and is as indicated above.

Preparation of Example 134

(S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)acetamide

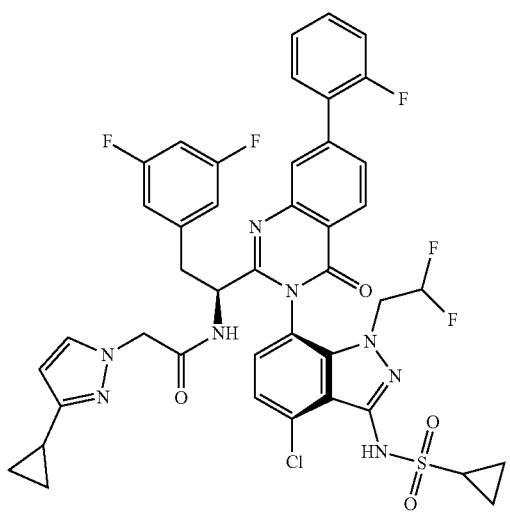

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (50 mg, 0.068 mmol), 2-(3-cyclopropyl-1H-pyrazol-1-yl)acetic acid (11.41 mg, 0.068 mmol), and HOBt (5.24 mg, 0.034 mmol) in N,N-Dimethylformamide (DMF) (3 mL) were added N-methylmorpholine (7.55 µL, 0.068 mmol) and N-(3-Dimethylaminopropyl)-N'-ethylcarbodiimide hydrochloride (23.62 mg, 0.123 mmol) at 27° C. The reaction mixture was stirred at 27° C. for 16 h. The progress of the reaction was monitored by TLC (SiO$_2$, 50% EtOAc/Pet. Rf=0.2). The reaction mixture was diluted with EtOAc (30 mL) and washed with water (3×50 mL). The organic layer was dried over anhydrous sodium sulfate, filtered and concentrated under reduced pressure to get crude product as an off white solid. The crude material was purified by silica gel chromatography (4 g silica gel column) eluted at 30-35% ethyl acetate and pet ether. The fractions containing product were collected and concentrated under reduced pressure to afford (S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)acetamide (25 mg, yield=41%, off white solid). $^1$H NMR (400 MHz, METHANOL-d$_4$) δ=8.37-8.33 (m, 1H), 8.10-8.05 (m, 1H), 7.88-7.82 (m, 1H), 7.72-7.67 (m, 1H), 7.54-7.49 (m, 1H), 7.40-7.25 (m, 5H), 6.79-6.72 (m, 1H), 6.59-6.52 (m, 2H), 6.14-5.94 (m, 2H), 4.83 (br s, 1H), 4.52-4.47 (m, 2H), 4.34-4.27 (m, 1H), 4.00-3.92 (m, 1H), 3.43-3.39 (m, 1H), 3.08-3.02 (m, 1H), 2.96-2.91 (m, 1H), 1.89-1.82 (m, 1H), 1.17-1.11 (m, 2H), 1.03-0.97 (m, 2H), 0.87-0.81 (m, 2H), 0.66-0.61 (m, 2H), LCMS: RT=2.88 mins, MH+=877.51, Purity=98.37%, Chiral HPLC Purity=99.10%.

Preparation of Example 135

(S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-isopropyl-1H-pyrazol-1-yl)acetamide

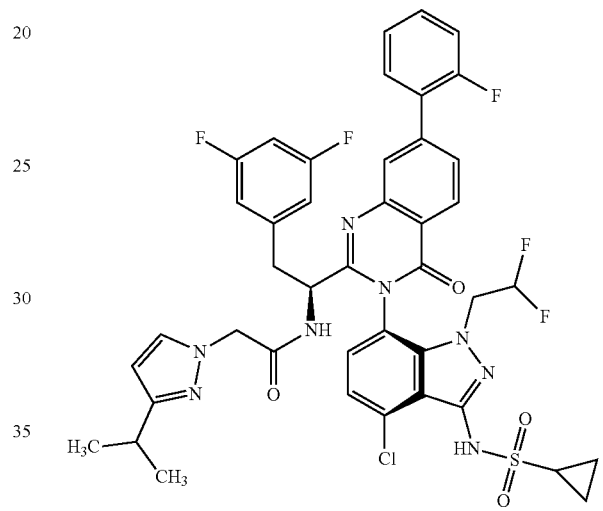

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (80 mg, 0.110 mmol), 2-(3-isopropyl-1H-pyrazol-1-yl)acetic acid (18.57 mg, 0.110 mmol), and HOBt (8.39 mg, 0.055 mmol) in N,N-Dimethylformamide (DMF) (10 mL) were added N-methylmorpholine (0.012 mL, 0.110 mmol) and N-(3-Dimethylaminopropyl)-N'-ethylcarbodiimide hydrochloride (37.8 mg, 0.197 mmol) at 27° C. The reaction mixture was stirred at 27° C. for 16 h. The progress of the reaction was monitored by TLC (SiO$_2$, 50% EtOAc/Pet. Rf=0.3). The reaction mixture was diluted with EtOAc (30 mL) and washed with water (3×50 mL). The organic layer was dried over anhydrous sodium sulfate, filtered and concentrated under reduced pressure to get crude product as an off white solid. The crude product was purified by silica gel chromatography (4 g silica gel column) eluted at 30-35% ethyl acetate and pet ether. The fractions containing product were collected and concentrated under reduced pressure to afford (S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-isopropyl-1H-pyrazol-1-yl)acetamide (48 mg, yield=49%, off white solid). $^1$H NMR (400 MHz, DMSO-d$_6$) δ=10.02-9.97 (m, 1H), 8.93-8.86 (m, 1H), 8.33-8.28 (m, 1H), 8.01-7.96 (m, 1H), 7.89-7.83 (m, 1H), 7.77-7.70 (m, 2H), 7.62-7.49 (m, 2H), 7.46-7.38 (m, 2H), 7.34-7.30 (m, 1H), 7.06-6.96 (m, 1H), 6.68-6.62 (m, 2H), 6.30-6.12 (m, 1H), 6.03-5.94 (m, 1H), 4.60-4.51 (m, 1H), 4.46-4.42 (m, 2H), 4.39-4.31 (m, 1H), 4.04-3.92 (m, 1H), 3.42-3.35 (m, 1H), 3.06-2.97 (m, 1H), 2.92-2.85 (m, 1H), 2.79-2.72 (m, 1H), 1.08 (d, J=6.8 Hz, 6H), 1.03-0.93 (m, 4H), LCMS: RT=2.98 mins, MH+=879.26, Purity=98.85%, Chiral HPLC Purity=97.41%.

Preparation of Example 136

(S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)acetamide

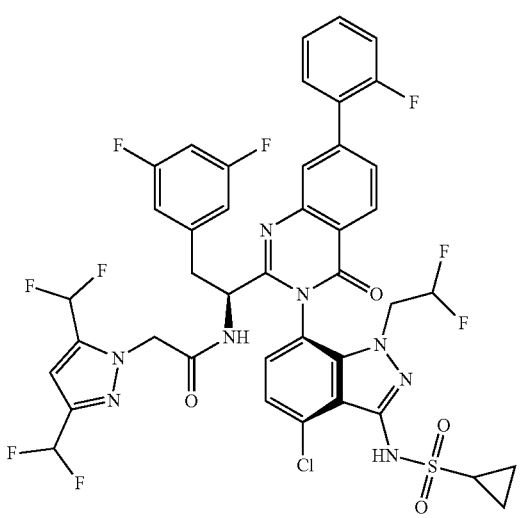

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropanesulfonamide (80 mg, 0.110 mmol), 2-(3,5-bis(difluoromethyl)-1H-pyrazol-1-yl)acetic acid (25.06 mg, 0.110 mmol), and HOBt (6.71 mg, 0.044 mmol) in N,N-Dimethylformamide (DMF) (10 mL) were added N-methylmorpholine (0.012 mL, 0.110 mmol) and N-(3-Dimethylaminopropyl)-N'-ethylcarbodiimide hydrochloride (37.8 mg, 0.197 mmol) at 27° C. The reaction mixture was stirred at 27° C. for 16 h. The progress of the reaction was monitored by TLC (SiO$_2$, 50% EtOAc/Pet. Rf=0.3). The reaction mixture was diluted with EtOAc (30 mL) and washed with water (3×50 mL). The organic layer was dried over anhydrous sodium sulfate, filtered and concentrated under reduced pressure to get crude product as an off white solid. The crude product was purified by silica gel chromatography (4 g silica gel column) eluted at 30-35% ethyl acetate and pet ether. The fractions containing product were collected and concentrated under reduced pressure to afford (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)acetamide (45 mg, yield=44%, off white solid). $^1$H NMR (400 MHz, DMSO-d$_6$) δ=9.98-9.94 (m, 1H), 9.31-9.26 (m, 1H), 8.31 (d, J=8.3 Hz, 1H), 8.02-7.99 (m, 1H), 7.89-7.83 (m, 1H), 7.78-7.71 (m, 2H), 7.59-7.51 (m, 2H), 7.47-7.40 (m, 2H), 7.11-6.97 (m, 2H), 6.91-6.74 (m, 2H), 6.66-6.57 (m, 2H), 6.26-6.06 (m, 1H), 4.97-4.81 (m, 2H), 4.49-4.41 (m, 1H), 4.34-4.22 (m, 1H), 4.06-3.95 (m, 1H), 3.43-3.35 (m, 1H), 3.07-2.99 (m, 1H), 2.90-2.82 (m, 1H), 1.00-0.88 (m, 4H), LCMS: RT=2.85 mins, MH+=937.21, Purity=99.21%, Chiral HPLC Purity=98.38%.

Preparation of Example 137

(S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-(difluoromethyl)-5-methyl-1H-pyrazol-1-yl)acetamide

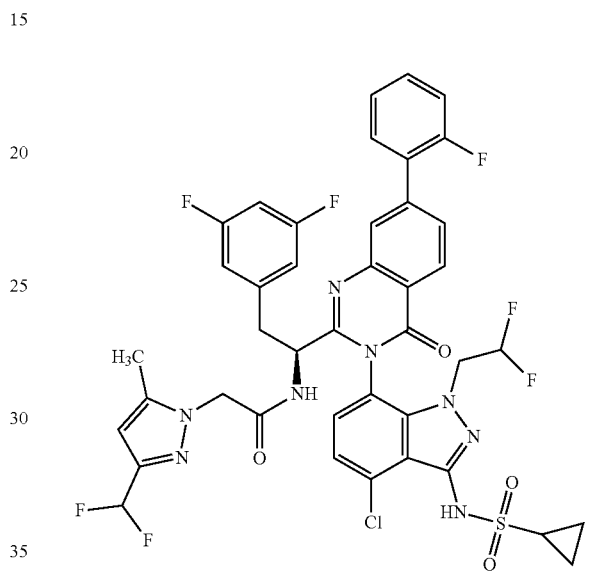

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropane sulfonamide (80 mg, 0.110 mmol), 2-(3-(difluoromethyl)-5-methyl-1H-pyrazol-1-yl)acetic acid (22.08 mg, 0.110 mmol), and HOBt (6.71 mg, 0.044 mmol) in N,N-Dimethylformamide (DMF) (10 mL) were added N-methylmorpholine (0.012 mL, 0.110 mmol) and N-(3-Dimethylaminopropyl)-N'-ethylcarbodiimide hydrochloride (37.8 mg, 0.197 mmol) at 27° C. The reaction mixture was stirred at 27° C. for 16 h. The progress of the reaction was monitored by TLC (SiO$_2$, 50% EtOAc/Pet. Rf=0.3). The reaction mixture was diluted with EtOAc (30 mL) and washed with water (3×50 mL). The organic layer was dried over anhydrous sodium sulfate, filtered and concentrated under reduced pressure to get crude product as an off white solid. The crude product was purified by HPLC under the following conditions: MOBILE PHASE A: 0.01M ammonium bicarbonate (aq); MOBILE PHASE B: Acetonitrile; Column: kromasilc18(150*25) mm, 10µ; Gradient method (minute/% of B): 0/30, 2/30, 10/80; Flow: 16 ml/min; Sample dissolved in ACN+THF; Temperature=Ambient; Pure fractions were collected and pooled, then were lyophilized to afford (S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-(difluoromethyl)-5-methyl-1H-pyrazol-1-yl)acetamide (39 mg, yield=39%, white solid). $^1$H NMR (400 MHz, DMSO-d$_6$) δ=9.99-9.95 (m, 1H), 9.13-9.10 (m, 1H), 8.33-8.29 (m, 1H), 8.01-7.99 (m, 1H), 7.88-

7.84 (m, 1H), 7.78-7.73 (m, 2H), 7.60-7.52 (m, 2H), 7.46-7.42 (m, 2H), 7.03-6.99 (m, 1H), 6.73-6.60 (m, 3H), 6.30-6.16 (m, 2H), 4.63-4.54 (m, 3H), 4.38-4.31 (m, 1H), 4.06-3.98 (m, 1H), 3.41-3.36 (m, 1H), 3.05-3.01 (m, 1H), 2.92-2.87 (m, 1H), 1.99-1.95 (m, 3H), 1.03-0.96 (m, 4H), LCMS: RT=2.83 mins, MH+=901.16, purity=99.14%, Chiral HPLC Purity=93.73%

Preparation of Example 138

N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)propanamide

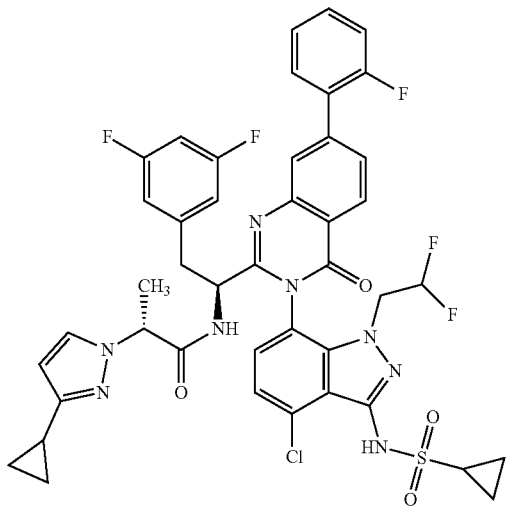 [SMILES: C[C@H](C(=O)N[C@@H](Cc1cc(F)cc(F)c1)c1nc2cc(-c3ccccc3F)ccc2c(=O)n1-c1ccc(Cl)c2c(NS(=O)(=O)C3CC3)nn(CC(F)F)c12)n1ccc(C2CC2)n1]

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropane sulfonamide (20 mg, 0.027 mmol), 2-(3-cyclopropyl-1H-pyrazol-1-yl)propanoic acid (5.41 mg, 0.027 mmol, single unknown enantiomer), and HOBt (1.678 mg, 10.95 μmol) in N,N-Dimethylformamide (DMF) (10 mL) were added N-methylmorpholine (3.01 μl, 0.027 mmol) and N-(3-Dimethylaminopropyl)-N'-ethylcarbodiimide hydrochloride (9.45 mg, 0.049 mmol) at 27° C. The reaction mixture was stirred at 27° C. for 16 h. The progress of the reaction was monitored by TLC (SiO₂, 30% EtOAc/Pet. Rf=0.2). The reaction mixture was diluted with ice-cold water (10 mL), then stirred for 15 min at 27° C. The precipitated solid was isolated by filtration and then dried under vacuum to afford crude product as an off white solid. The described procedure was repeated and both batches were combined prior to further purification. The crude material was subjected to HPLC purification under the following conditions: MOBILE PHASE A: 0.01M ammonium bicarbonate (aq); MOBILE PHASE B: Acetonitrile; Column: X-Bridge 150×19 mm, 5μ; Gradient method (minute/% B): 0/30, 2/30, 20/60, 20.50/90, 22/90; Flow: 18 mL/Min; Sample dissolved in ACN+THF+Water; Temperature: Ambient. Pure fractions were collected and pooled, and then were lyophilized to afford N-((S)-1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(3-cyclopropyl-1H-pyrazol-1-yl)propanamide (25 mg, yield=50%, off white solid). ¹H NMR (400 MHz, METHANOL-d₄) δ=8.36-8.32 (m, 1H), 8.06-8.03 (m, 1H), 7.86-7.81 (m, 1H), 7.71-7.65 (m, 1H), 7.55-7.48 (m, 1H), 7.45-7.28 (m, 5H), 6.81-6.73 (m, 1H), 6.50-6.45 (m, 2H), 6.09-5.90 (m, 2H), 4.79-4.78 (m, 1H), 4.74-4.70 (m, 1H), 4.17-4.06 (m, 1H), 3.91-3.80 (m, 1H), 3.35-3.32 (m, 1H), 3.04-2.89 (m, 2H), 1.87-1.80 (m, 1H), 1.42 (d, J=7.2 Hz, 3H), 1.15-1.11 (m, 2H), 1.03-0.98 (m, 2H), 0.82-0.77 (m, 2H), 0.65-0.60 (m, 2H), LCMS: RT=2.94 mins, MH+=891.27, Purity=98.13%, Chiral HPLC Purity=99.16%. Stereochemistry: single unknown enantiomer. Specifically, the stereochemistry of the alpha-methyl has not been determined but is known to be the opposite of Example 133, and is drawn distinct from Example 133 to communicate this difference. All other stereochemistry is known and is as indicated above.

Preparation of Example 139

(S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(1-cyclopropyl-1H-pyrazol-3-yl)acetamide

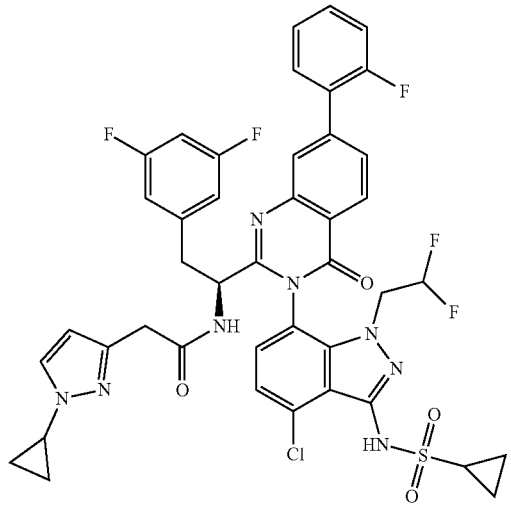 [SMILES: O=C(Cc1ccn(C2CC2)n1)N[C@@H](Cc1cc(F)cc(F)c1)c1nc2cc(-c3ccccc3F)ccc2c(=O)n1-c1ccc(Cl)c2c(NS(=O)(=O)C3CC3)nn(CC(F)F)c12]

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropane sulfonamide (20 mg, 0.027 mmol), 2-(1-cyclopropyl-1H-pyrazol-3-yl)acetic acid (6.53 mg, 0.027 mmol), and HOBt (1.678 mg, 10.95 μmol) in N,N-Dimethylformamide (DMF) (10 mL) were added N-methylmorpholine (3.01 μl, 0.027 mmol) and N-(3-Dimethylaminopropyl)-N'-ethylcarbodiimide hydrochloride (9.45 mg, 0.049 mmol) at 27° C. The reaction mixture was stirred at 27° C. for 16 h. The progress of the reaction was monitored by TLC (SiO₂, 30% EtOAc/Pet. Rf=0.2). The reaction mixture was diluted with EtOAc (30 mL) and washed with water (3×50 mL). The organic layer was dried over anhydrous sodium sulfate, filtered and concentrated under reduced pressure to afford crude product as an off white solid. The described procedure was repeated to afford a second batch of crude material. Both batches of crude material were combined before additional purification. The crude material was subjected to HPLC purification under the following conditions: MOBILE PHASE A: 0.01M ammonium bicarbonate (aq); MOBILE PHASE B: Acetonitrile; Column: kromasilc8 150×25 mm, 10μ; Gradient Method (minute/% B): 0/10, 2/10, 10/65; Flow: 25 mL/min.; Sample dissolved in ACN+THF; Temperature=Ambient. Pure fractions were collected and pooled, then were lyophilized to afford (S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(1-cyclopropyl-1H-pyrazol-3-yl)acetamide (22 mg, yield=66%, off white solid). $^1$H NMR (400 MHz, METHANOL-d$_4$) δ=8.36-8.32 (m, 1H), 8.06 (t, J=1.5 Hz, 1H), 7.84 (td, J=1.6, 8.3 Hz, 1H), 7.71-7.65 (m, 1H), 7.54-7.48 (m, 1H), 7.47-7.45 (m, 1H), 7.40-7.28 (m, 4H), 6.75-6.68 (m, 1H), 6.56-6.51 (m, 2H), 6.17-5.92 (m, 2H), 4.87-4.83 (m, 1H), 4.34-4.22 (m, 1H), 3.99-3.88 (m, 1H), 3.55-3.48 (m, 1H), 3.41-3.34 (m, 1H), 3.26-3.22 (m, 2H), 3.09-3.01 (m, 1H), 2.98-2.91 (m, 1H), 1.15-1.11 (m, 2H), 1.02-0.91 (m, 6H), LCMS: RT=2.78 mins, MH+=877.19 Purity:99.45%, Chiral HPLC Purity=99.03%.

Preparation of Example 140

(S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(1-isopropyl-1H-pyrazol-3-yl)acetamide

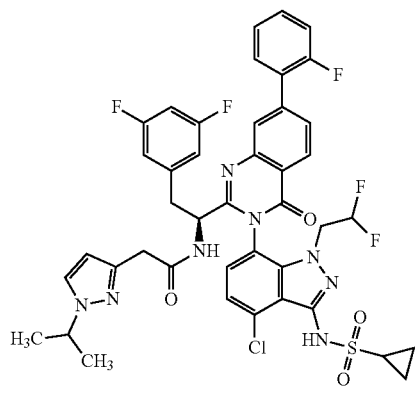 [SMILES: CC(C)n1ccc(CC(=O)N[C@@H](Cc2cc(F)cc(F)c2)c2nc3cc(-c4ccccc4F)ccc3c(=O)n2-c2ccc(Cl)c3c(NS(=O)(=O)C4CC4)nn(CC(F)F)c23)n1]

To a solution of (S)-N-(7-(2-(1-amino-2-(3,5-difluorophenyl)ethyl)-7-(2-fluorophenyl)-4-oxoquinazolin-3(4H)-yl)-4-chloro-1-(2,2-difluoroethyl)-1H-indazol-3-yl)cyclopropane sulfonamide (60 mg, 0.082 mmol), 2-(1-isopropyl-1H-pyrazol-3-yl)acetic acid (14.21 mg, 0.082 mmol), and HOBt (5.03 mg, 0.033 mmol) in N,N-Dimethylformamide (DMF) (10 mL) were added N-methylmorpholine (9.03 μl, 0.082 mmol) and N-(3-Dimethylaminopropyl)-N'-ethylcarbodiimide hydrochloride (28.3 mg, 0.148 mmol) at 27° C. The reaction mixture was degassed for 10 min with nitrogen gas. The reaction mixture was stirred at 27° C. for 16 h. The progress of the reaction was monitored by TLC (SiO$_2$, 50% EtOAc/Pet. Rf=0.3). The reaction mixture was diluted with EtOAc (30 mL) and washed with water (3×50 mL). The organic layer was dried over anhydrous sodium sulfate, filtered and concentrated under reduced pressure to afford a crude product as an off white solid. The crude product was subjected to HPLC purification under the following conditions: MOBILE PHASE A: 0.01M ammonium bicarbonate (aq); MOBILE PHASE B: Acetonitrile; Column: X-Bridge 150×19 mm, 5μ; Gradient method (minute/% B): 0/30, 20/60, 20.50/90, 22/90; Flow: 18 ml/Min; Sample dissolved in ACN+THF+water; Temperature=Ambient. Pure fractions were collected and pooled, then were lyophilized to afford (S)-N-(1-(3-(4-chloro-3-(cyclopropanesulfonamido)-1-(2,2-difluoroethyl)-1H-indazol-7-yl)-7-(2-fluorophenyl)-4-oxo-3,4-dihydroquinazolin-2-yl)-2-(3,5-difluorophenyl)ethyl)-2-(1-isopropyl-1H-pyrazol-3-yl)acetamide (38 mg, yield: 52%, off white solid). $^1$H NMR (400 MHz, DMSO-d6) δ=10.01-9.97 (m, 1H), 8.84-8.79 (m, 1H), 8.30 (d, J=8.3 Hz, 1H), 7.98-7.94 (m, 1H), 7.86-7.82 (m, 1H), 7.77-7.71 (m, 2H), 7.59-7.39 (m, 5H), 7.03-6.96 (m, 1H), 6.68-6.61 (m, 2H), 6.31-6.01 (m, 1H), 5.80-5.77 (m, 1H), 4.54-4.47 (m, 1H), 4.36-4.26 (m, 2H), 4.05-3.93 (m, 1H), 3.39-3.33 (m, 1H), 3.17 (s, 2H), 3.04-2.97 (m, 1H), 2.94-2.86 (m, 1H), 1.28 (dd, J=4.3, 6.7 Hz, 6H), 1.03-0.94 (m, 4H), LCMS: RT=2.84 mins, MH+=879.19, purity=99.08%, Chiral HPLC Purity=98.96%.

Preparation of (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)acetamide

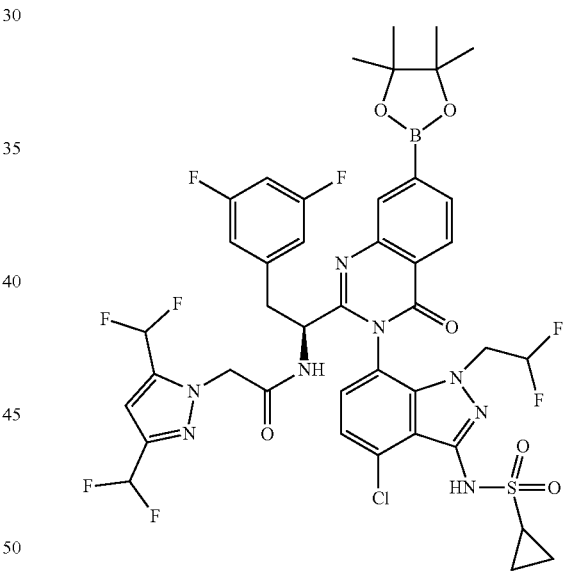

To a solution of (S)-2-(3,5-bis(difluoromethyl)-1H-pyrazol-1-yl)-N-(1-(7-bromo-3-(4-chloro-3-(cyclopropanesulfonamido)-1-(2,2-difluoroethyl)-1H-indazol-7-yl)-4-oxo-3,4-dihydroquinazolin-2-yl)-2-(3,5-difluorophenyl)ethyl) acetamide (140 mg, 0.152 mmol) in 1,4-Dioxane (10 mL) was added bis(pinacolato)diboron (96 mg, 0.380 mmol) and potassium acetate (74.5 mg, 0.759 mmol) at 26° C. and the reaction mixture was degassed under nitrogen for 10 minutes. Then PdCl$_2$(dppf) (11.11 mg, 0.015 mmol) was added to the reaction mixture and the mixture was stirred at 100° C. for 3 h. The progress of the reaction was monitored by TLC (SiO$_2$, 50% EtOAc/Pet., Rf=0.6, UV-active). On completion, the reaction mixture was filtered through a small pad of Celite and the filter pad was extracted with EtOAc (50 mL). The filtrate was concentrated under reduced pressure to afford the crude (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl) acetamide as a brown gummy solid (145 mg, 39%). LCMS Purity=39.5%. The material was used in subsequent chemistry without additional purification.

Preparation of N-((S)-1-(7-bromo-3-(4-chloro-3-(methylsulfonamido)-1-(2,2,2-trifluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

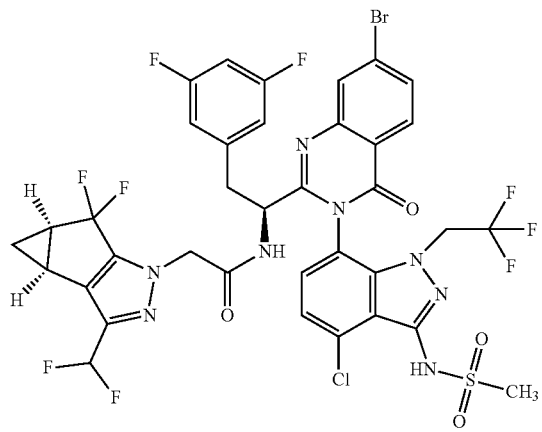 [SMILES: CS(=O)(=O)Nc1nn(CC(F)(F)F)c2c(-n3c([C@H](Cc4cc(F)cc(F)c4)NC(=O)Cn4nc(C(F)F)c5c4C(F)(F)[C@@H]4C[C@H]54)nc4cc(Br)ccc4c3=O)ccc(Cl)c12]

N-((S)-1-(7-bromo-3-(4-chloro-3-(methylsulfonamido)-1-(2,2,2-trifluoroethyl)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide was prepared according to the methods described for the preparation of N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide using N-(7-amino-4-chloro-1-(2,2,2-trifluoroethyl)-1H-indazol-3-yl)-N-(4-methoxybenzyl) methanesulfonamide instead of N-(7-amino-4-chloro-1-methyl-1H-indazol-3-yl)-N-(4-methoxybenzyl) methanesulfonamide.

Preparation of N-((S)-1-(7-bromo-3-(4-chloro-3-(methylsulfonamido)-1-(2,2,2-trifluoroethyl)-1H-indazol-7-yl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamide

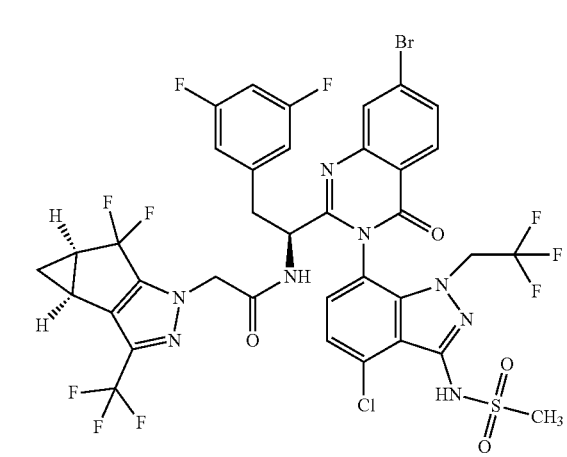 [SMILES: CS(=O)(=O)Nc1nn(CC(F)(F)F)c2c(-n3c([C@H](Cc4cc(F)cc(F)c4)NC(=O)Cn4nc(C(F)(F)F)c5c4C(F)(F)[C@@H]4C[C@H]54)nc4cc(Br)ccc4c3=O)ccc(Cl)c12]

N-((S)-1-(7-bromo-3-(4-chloro-3-(methylsulfonamido)-1-(2,2,2-trifluoroethyl)-1H-indazol-7-yl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide was prepared according to the methods described for the preparation of N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide using N-(7-amino-4-chloro-1-(2,2,2-trifluoroethyl)-1H-indazol-3-yl)-N-(4-methoxybenzyl) methane sulfonamide instead of N-(7-amino-4-chloro-1-methyl-1H-indazol-3-yl)-N-(4-methoxybenzyl) methanesulfonamide and 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid instead of 2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetic acid.

223

Preparation of (S)-N-(7-(2-(1-amino-2-(3,5-difluorophenyl)ethyl)-4-oxo-7-(4,4,5,5-tetramethyl-1,3,2-dioxaborolan-2-yl)quinazolin-3(4H)-yl)-4-chloro-1-methyl-1H-indazol-3-yl)methanesulfonamide

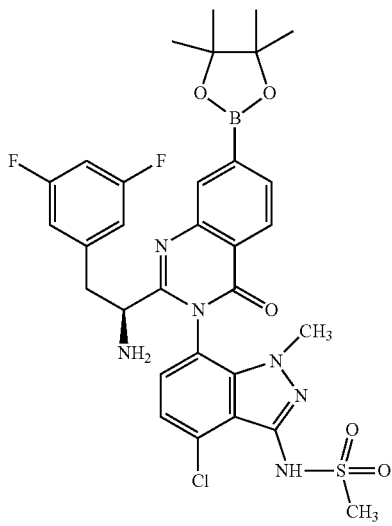 [SMILES: Cn1nc(NS(C)(=O)=O)c2c(Cl)ccc(-n3c([C@@H](N)Cc4cc(F)cc(F)c4)nc4cc(B5OC(C)(C)C(C)(C)O5)ccc4c3=O)c21]

In a dry round bottom flask was combined (S)-N-(7-(2-(1-amino-2-(3,5-difluorophenyl)ethyl)-7-bromo-4-oxoquinazolin-3(4H)-yl)-4-chloro-1-methyl-1H-indazol-3-yl)methanesulfonamide (500 mg, 0.784 mmol), 4,4,4',4',5,5,5',5'-octamethyl-2,2'-bi(1,3,2-dioxaborolane) (299 mg, 1.18 mmol), potassium acetate (231 mg, 2.35 mmol) and PdCl$_2$(dppf) (57 mg, 0.078 mmol). The flask was sealed with a rubber septum and then was placed under Ar atmosphere. To the flask was added dioxane (16 ml). The solution was degassed with Ar (vac/fill×3) and the resulting mixture was stirred at 60° C. for 16 h. The mixture was cooled to room temperature and then was concentrated in vacuo. The resulting residue was subjected to silica gel chromatography (hexanes:EtOAc 100:0→0:100 over 10 CVs) to afford (S)-N-(7-(2-(1-amino-2-(3,5-difluorophenyl)ethyl)-4-oxo-7-(4,4,5,5-tetramethyl-1,3,2-dioxaborolan-2-yl)quinazolin-3(4H)-yl)-4-chloro-1-methyl-1H-indazol-3-yl)methanesulfonamide (365 mg, 68%). LCMS analysis: Wavelength1: 220 nm, Wavelength2: 254 nm, Injection Vol.: 5.00 µl, Stop Time: 2.50 min, Grad. Time: 1.50 min, Start % B: 0, End % B: 100, Total Flow: 0.80 ml/min, Solvent A: 95:5 Water:MeCN 0.1% TFA, Solvent B: 5:95 Water:MeCN 0.1% TFA, Column: Acquity UPLC BEH C18 1.7 um, 2.1×50 mm; retention time: 1.018 min, mass detected: 603.10 (M+H). $^1$H NMR (METHANOL-d$_4$, 500 MHz) δ8.2-8.3 (m, 2H), 7.95 (d, 1H, J=7.8 Hz), 7.30 (d, 1H, J=8.0 Hz), 6.96 (d, 1H, J=7.5 Hz), 6.8-6.8 (m, 1H), 6.60 (d, 2H, J=7.4 Hz), 3.75 (s, 3H), 3.4-3.4 (m, 1H), 3.30 (s, 3H), 2.94 (d, 2H, J=7.5 Hz), 1.3-1.3 (m, 12H)

224

Preparation of (S)-N-(7-(2-(1-amino-2-(3,5-difluorophenyl)ethyl)-7-(4,6-dimethylpyrimidin-2-yl)-4-oxoquinazolin-3(4H)-yl)-4-chloro-1-methyl-1H-indazol-3-yl)methanesulfonamide

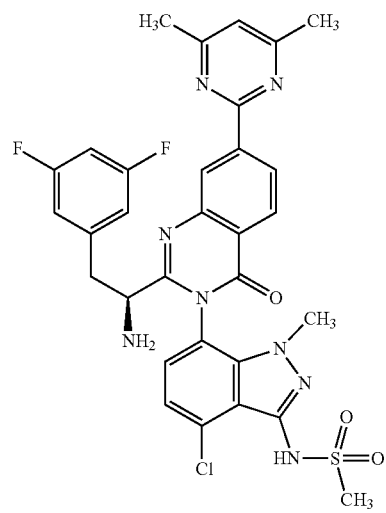 [SMILES: Cc1cc(C)nc(-c2ccc3c(=O)n(-c4ccc(Cl)c5c(NS(C)(=O)=O)nn(C)c45)c([C@@H](N)Cc4cc(F)cc(F)c4)nc3c2)n1]

To a 100 mL round bottom flask equipped with a stir bar was added dicyclohexyl(2',6'-dimethoxy-[1,1'-biphenyl]-2-yl)phosphane (54 mg, 0.13 mmol), Pd(OAc)$_2$ (15 mg, 0.066 mmol), tripotassium phosphate (418 mg, 1.97 mmol), (S)-N-(7-(2-(1-amino-2-(3,5-difluorophenyl)ethyl)-4-oxo-7-(4,4,5,5-tetramethyl-1,3,2-dioxaborolan-2-yl)quinazolin-3(4H)-yl)-4-chloro-1-methyl-1H-indazol-3-yl)methanesulfonamide (450 mg, 0.657 mmol), and 2-chloro-4,6-dimethylpyrimidine (281 mg, 1.97 mmol). The flask was sealed with a rubber septum and then placed under Ar atmosphere. To the flask was added THF (5.2 ml) and Water (1.3 ml). the mixture was degassed with Ar (vac/fill×3). The mixture was stirred at 60° C. for 12 hr. The mixture was cooled to room temperature and then was concentrated in vacuo. The resulting residue was subjected to silica gel chromatography (CH$_2$Cl$_2$:MeOH 100:0→0:100 over 10 CVs) to afford (S)-N-(7-(2-(1-amino-2-(3,5-difluorophenyl)ethyl)-7-(4,6-dimethylpyrimidin-2-yl)-4-oxoquinazolin-3(4H)-yl)-4-chloro-1-methyl-1H-indazol-3-yl)methanesulfonamide (403 mg, 69%). The material was carried forward into subsequent chemistry despite the presence of several impurities identified by LCMS. LCMS analysis: Wavelength1: 220 nm, Wavelength2: 254 nm, Injection Vol.: 5.00 Stop Time: 4.50 min, Grad. Time: 3.50 min, Start % B: 0, End % B: 100, Total Flow: 0.8 ml/min, Solvent A: 95:5 Water:MeCN 0.1% TFA, Solvent B: 5:95 Water:MeCN 0.1% TFA, Column: Acquity UPLC BEH C18 1.7 um, 2.1×100 mm, retention time: 2.365 min, mass detected=665.10 (M+H).

225

Preparation of tert-Butyl (R)-(1-(7-bromo-3-(4-(morpholinosulfonyl)phenyl)-4-oxo-3,4-dihydro-quinazolin-2-yl)-2-(3,5-difluorophenyl)ethyl)carbamate

226

Preparation of (R)-N-(1-(7-Bromo-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide (Target-21)

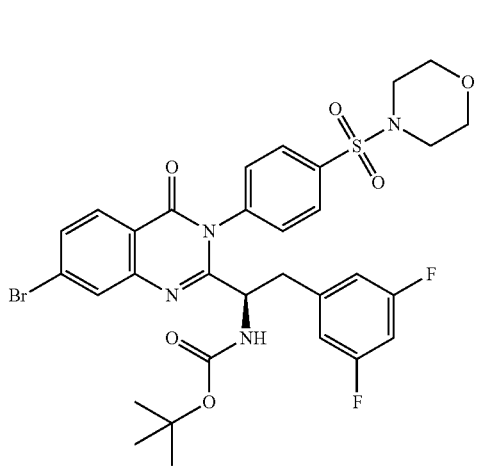 [SMILES: CC(C)(C)OC(=O)N[C@H](Cc1cc(F)cc(F)c1)c1nc2cc(Br)ccc2c(=O)n1-c1ccc(S(=O)(=O)N2CCOCC2)cc1]

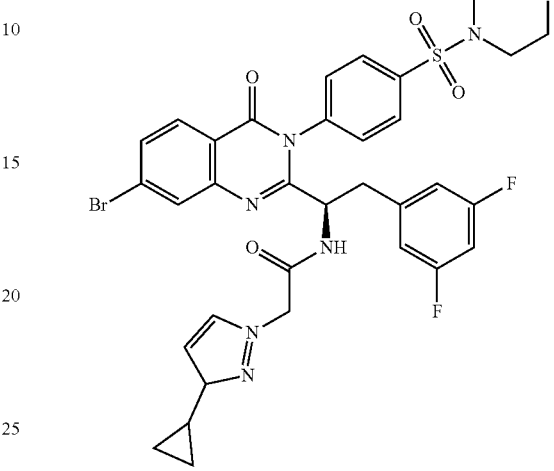

To a stirred solution of (S)-2-((tert-butoxycarbonyl)amino)-3-(3,5-difluorophenyl)propanoic acid (5.0 g, 16.61 mmol, 1.0 equiv.) in anhydrous pyridine (100 mL, 20 V) at 0° C. was added sequentially 2-amino-4-bromobenzoic acid (7.17 g, 33.22 mmol, 2.0 equiv.) and diphenyl phosphite (15.55 g, 66.44 mmol, 4.0 equiv.). The temperature was then slowly raised to room temperature and stirred for 24 h at the same temperature. To the solution was added 4-(morpholinosulfonyl)aniline (4.82 g, 19.93 mmol, 1.2 equiv.) and the solution was stirred for 3 days at room temperature. After completion of the reaction (monitored by TLC), the solution was diluted with water (500 mL) and MTBE (150 mL). The organic layer was reserved; the aqueous layer was extracted with MTBE (2×150 mL). The combined organic layers were washed with water (100 mL), brine (100 mL), dried over $Na_2SO_4$, filtered and concentrated in vacuo. The crude material was purified by silica column chromatography (20-40% EtOAc in Hexanes) to afford the desired product tert-butyl (R)-(1-(7-Bromo-3-(4-(morpholino sulfonyl) phenyl)-4-oxo-3,4-dihydroquinazolin-2-yl)-2-(3,5-difluorophenyl) ethyl) carbamate as an off-white solid (4.1 g, 35%). $^1$H NMR (400 MHz, $CDCl_3$): δ8.11 (d, J=8.4 Hz, 1H), 7.97 (s, 2H), 7.86 (s, 1H), 7.66 (d, J=7.7 Hz, 1H), 7.59 (s, 1H), 6.86 (s, 1H), 6.68 (s, 1H), 6.41 (s, 2H), 5.26 (s, 1H), 4.55 (d, J=8.1 Hz, 1H), 3.79 (s, 4H), 3.12-3.10 (m, 5H), 2.88-2.83 (m, 1H), 1.32 (s, 9H). LCMS: 705 [M+H]$^+$ Step 1: To a stirred solution of tert-butyl (R)-(1-(7-bromo-3-(4-(morpholinosulfonyl)phenyl)-4-oxo-3,4-dihydroquinazolin-2-yl)-2-(3,5-difluorophenyl)ethyl) carbamate (10.0 g, 14.2 mmol, 1.0 equiv.) in anhydrous DCM (100 mL) at 0° C. was slowly added trifluoroacetic acid (20 mL, 2V) via an addition funnel. Following the addition, the temperature was slowly raised to room temperature and the solution was then stirred for 4 h. After completion of the reaction (monitored by TLC), DCM was removed at below 40° C. in vacuo. The crude residue was dissolved in DCM (100 mL):water (100 mL), cooled to 0° C., and slowly quenched with saturated aq. $NaHCO_3$ solution. The organic layer was separated as reserved; the aqueous layer was extracted with DCM (100 mL). The combined organic layers were washed with brine (100 mL), dried over $Na_2SO_4$, filtered and concentrated in vacuo to afford crude (R)-2-(1-amino-2-(3,5-difluorophenyl)ethyl)-7-bromo-3-(4-(morpholinosulfonyl)phenyl)quinazolin-4(3H)-one. This crude material was used directly used in the next step without further purification.

Step 2: To a stirred solution of (R)-2-(1-amino-2-(3,5-difluorophenyl)ethyl)-7-bromo-3-(4-(morpholinosulfonyl) phenyl)quinazolin-4(3H)-one (the entirety of crude prepared above) in DMF (160 mL) at 0° C. was added DIPEA (4.61 mL, 26.49 mmol, 2.0 equiv.). The solution was stirred for 10 min. To the flask was added a solution of 2-(3-Cyclopropyl-1H-pyrazol-1-yl) acetic acid (2.2 g, 13.24 mmol, 1.0 equiv.) and HATU (5.29 g, 13.9 mmol, 1.05 equiv.) dissolved in DMF (80 mL) and cooled to 0° C. prior to addition. The reaction mass was allowed to warm to room temperature and then was stirred for 3 h. After completion of the reaction (monitored by TLC), the solution was diluted with water (750 mL) and MTBE (150 mL). The organic layer was separated as reserved; the aqueous layer was extracted with MTBE (2×150 mL). The combined organic layers were washed with brine (100 mL), dried over $Na_2SO_4$, filtered and concentrated in vacuo to afford the crude residue as a gummy liquid. To the residue was added MTBE (150 mL) and the mixture was aged for 12 h to afford a crystalline solid. The crystalline solid was collected via filtration and the solids were washed with hexanes (50 mL) and dried to afford the desired product (R)-N-(1-(7-Bromo-3-(4-(morpholinosulfonyl)phenyl)-4-oxo-3,4-dihydroquinazolin-2-yl)-2-(3,5-difluorophenyl) ethyl)-2-(3-cyclopropyl-1H-pyrazol-1-yl)acetamide as an off-white solid (8.4 g, 81% over the two steps). $^1$H NMR (400 MHz, CDCl$_3$): δ8.10 (d, J=8.4 Hz, 1H), 7.95 (s, 2H), 7.86 (d, J=6.5 Hz, 1H), 7.66 (d, J=7.0 Hz, 1H), 7.49 (dd, J=25.8, 7.3 Hz, 2H), 7.27 (s, 1H), 6.88 (d, J=6.9 Hz, 1H), 6.68 (s, 1H), 6.29 (d, J=5.0 Hz, 2H), 6.05 (s, 1H), 4.78 (d, J=7.2 Hz, 1H), 4.72-4.53 (m, 2H), 3.80 (s, 4H), 3.25-2.91 (m, 5H), 2.79 (dd, J=13.3, 6.7 Hz, 1H), 2.02 (s, 1H), 1.03 (d, J=6.2 Hz, 2H), 0.81 (s, 2H). LC-MS: 753 [M+H]$^+$ The general procedures and general purification methods used to prepare examples 141-195 are described above or detailed below. The experimental procedure supplied for each specific example identifies the general method used to prepare and purify that compound.

General Procedure Q:

Pd(OAc)$_2$ (0.1 equiv), dicyclohexyl(2',6'-dimethoxy-[1,1'-biphenyl]-2-yl)phosphane (0.2 equiv) tripotassium phosphate (3 equiv), and N-((S)-1-(3-(4-chloro-3-(methylsulfonamido)-1-(2,2,2-trifluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (1 equiv) were combined in a dry reaction vessel equipped with a stir bar under argon. To the vessel was added the appropriate aryl or heteroaryl halide (3 equiv). The vessel was degassed with argon and THF/water (4:1, 0.05M) was added. The mixture was degassed with argon and the mixture was then stirred at either ambient temperature, 45° C., or 60° C. for overnight (approximately 18 h). Upon cooling to ambient temperature, the mixture subjected to HPLC purification to afford the desired product.

General Procedure R:

To a stirred solution of (S)-N-(7-(2-(1-amino-2-(3,5-difluorophenyl)ethyl)-7-(2-fluorophenyl)-4-oxoquinazolin-3(4H)-yl)-4-chloro-1-methyl-1H-indazol-3-yl)methanesulfonamide (or structurally similar amine) (1 equiv), the appropriate carboxylic acid (2 equiv), and diisopropylethylamine (4 equiv) in either DMF or THF (0.1 M) was added HATU (2 equiv) at room temperature. The reaction was stirred until judged complete as determined by LCMS. The carboxylic acid may also couple with the sulfonamide portion of the molecule ("over-coupling"). To reverse this over-coupling the mixture was concentrated and the residue was then treated with 2M ammonia in methanol (2 mL); the mixture was stirred for 10 min. The mixture was then concentrated and the residue was subjected to HPLC purification to afford the desired product.

General Procedure S:

(R)-N-(1-(7-Bromo-3-(4-(morpholinosulfonyl)phenyl)-4-oxo-3,4-dihydroquinazolin-2-yl)-2-(3,5-difluorophenyl) ethyl)-2-(3-cyclopropyl-1H-pyrazol-1-yl)acetamide (typically 150 mg, 0.2 mmol, 1.0 equiv.) was dissolved in a pre-degassed mixture of dioxane (12 volumes, 0.83M) and water (3 volumes, 3M). To the mixture was added potassium acetate (3.3 equiv.) and the appropriate boronic acid (3.3 equiv.). The mixture was degassed with argon for 30 min. To the mixture was added dichlorobis(tricyclohexylphosphine) palladium (II) (0.30 equiv.). The mixture was degassed with argon for 10 min. The reaction mixture was stirred for 24 hrs at 90° C. After completion of the reaction (monitored by TLC), the reaction mixture was cooled to room temperature and was then diluted with ethyl acetate (10 mL); filtered through a celite bed extracting with ethyl acetate (5 mL). The filtrate was diluted with water (3.0 mL). The organic layer was separated and reserved; the aqueous layer was extracted with EtOAc (2×5.0 mL). The combined organic layers were washed with water (10 mL), brine (10 mL), dried over Na$_2$SO$_4$, filtered and concentrated in vacuo. The crude material was subjected to silica gel chromatography (typically 25-40% EtOAc in hexanes) to afford the indicated product.

General Procedure T:

To a solution of N-((S)-1-(7-bromo-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (typically 50 mg, 0.053 mmol, 1.0 equiv), in THF (80 volumes) and water (10 volumes) was added the appropriate boronic acid (1.5 equiv) and potassium phosphate tribasic (5 equiv) at 26° C. The reaction mixture was degassed for 10 min with nitrogen bubbling. To the mixture was added dichloro[9,9-dimethyl-4,5-bis(diphenylphosphino)xanthene]palladium(II) (0.06 equiv). The mixture was stirred at room temperature for 8-16 h. The reaction mixture was filtered through a pad of Celite, extracting with ethyl acetate (30 mL). The organic layer was dried over anhydrous Na$_2$SO$_4$, filtered and concentrated under reduced pressure to afford the crude product. The crude material was subjected to HPLC purification to afford the indicated product.

General Procedure U:

To a stirred solution of (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(4,4,5,5-tetramethyl-1,3,2-dioxaborolan-2-yl)-3,4-dihydroquinazolin-2-yl)-2-(3,5-difluorophenyl)ethyl) acetamide (typically 60 mg, 0.036 mmol, 1.0 equiv) and the halide (1.5 equiv) in THF (50 volumes) and Water (50 volumes) was added potassium phosphate dibasic (3 equiv). The mixture was degassed under nitrogen gas for 10 min. To the mixture was added dichloro[9,9-dimethyl-4,5-bis(diphenylphosphino)xanthene]palladium(II) (0.05 equiv). The mixture was stirred at 60° C. for 5 h under nitrogen atmosphere. The reaction mixture was allowed to cool to 26° C., filtered through small pad of Celite extracting with EtOAc. The filtrate was diluted with water (10 mL) and extracted with EtOAc (2×20 mL). The combined organic layers were dried over sodium sulfate, filtered and concentrated under reduced pressure to obtain the crude compound which was purified by HPLC to afford the indicated product.

LCMS Method G:

Wavelength1: 220 nm, Wavelength2: 254 nm, Injection Vol.: 5.00 μl, Start % B: 0, End % B: 100, Gradient Time: 3.5 min. then hold at 100% B for 1 min., Start Total Flow: 0.80 ml/min, Solvent A: 95:5 Water:MeCN 0.1% Formic acid, Solvent B: 5:95 Water:MeCN 0.1% Formic acid, Column: Acquity UPLC BEH C18, 2.1×100 mm, 1.7 μm particles.

LCMS Method H:

Wavelength1: 220 nm, Wavelength2: 254 nm, Injection Vol.: 5.00 Start % B: 0, End % B: 100, Gradient Time: 15 min. then hold at 100% B for 5 min., Start Total Flow: 0.50 ml/min, Solvent A: 95:5 Water:MeCN 0.05% TFA, Solvent B: 5:95 Water:MeCN 0.05% TFA, Column: Acquity UPLC BEH C18, 2.1×150 mm, 1.7 μm particles.

Preparation of Example 141

N-((S)-1-(3-(4-chloro-1-methyl-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide

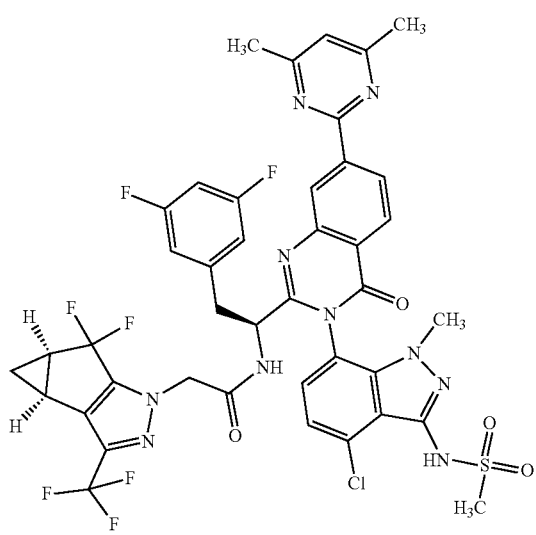 [SMILES: Cc1cc(C)nc(-c2ccc3c(=O)n(-c4ccc(Cl)c5c(NS(C)(=O)=O)nn(C)c45)c([C@H](Cc4cc(F)cc(F)c4)NC(=O)Cn4nc(C(F)(F)F)c5c4C(F)(F)[C@@H]4C[C@H]54)nc3c2)n1]

The title compound was prepared according to General Procedure R using 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid as the coupling partner. The experiment afforded the title compound, N-((S)-1-(3-(4-chloro-1-methyl-3-(methylsulfonamido)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide. The sample was analyzed using LCMS Method C: retention time=1.56 min.; observed ion=929.3 (M+H). 1H NMR (500 MHz, METHANOL-d4) δ ppm 8.93 (d, J=1.19 Hz, 1H), 8.68 (dd, J=8.35, 1.49 Hz, 1H), 8.39 (d, J=8.35 Hz, 1H), 7.33 (d, J=7.75 Hz, 1H), 7.29 (s, 1H), 7.22 (d, J=8.05 Hz, 1H), 6.79 (tt, J=9.20, 2.27 Hz, 1H), 6.61-6.67 (m, 2H), 4.86-4.88 (m, 1H), 4.63-4.67 (m, 1H), 4.56-4.61 (m, 1H), 3.64 (s, 3H), 3.52 (dd, J=14.01, 5.07 Hz, 1H), 3.27 (s, 3H), 3.13 (dd, J=13.86, 9.09 Hz, 1H), 2.63 (s, 6H), 2.45-2.51 (m, 2H), 1.37-1.42 (m, 1H), 1.05-1.09 (m, 1H)

Preparation of Example 142

(S)-2-(3-cyclopropyl-1H-pyrazol-1-yl)-N-(2-(3,5-difluorophenyl)-1-(7-(2-methoxyphenyl)-3-(4-(morpholinosulfonyl)phenyl)-4-oxo-3,4-dihydroquinazolin-2-yl)ethyl)acetamide

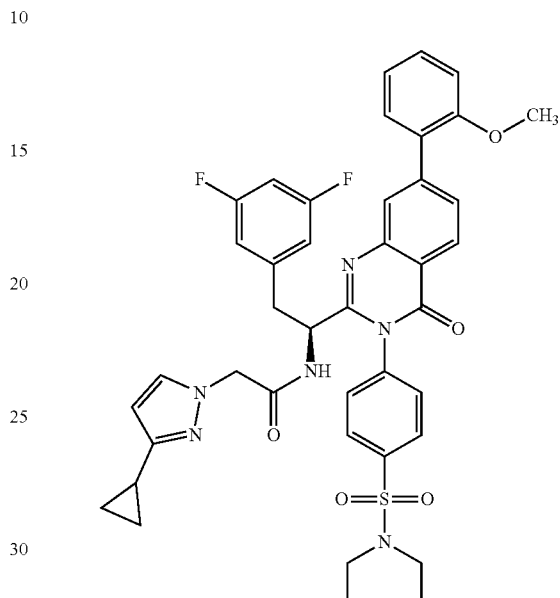

The title compound was prepared according to General Procedure S using 2-methoylphenylboronic acid as the coupling partner. The experiment afforded the title compound, (S)-2-(3-cyclopropyl-1H-pyrazol-1-yl)-N-(2-(3,5-difluorophenyl)-1-(7-(2-methoxyphenyl)-3-(4-(morpholinosulfonyl)phenyl)-4-oxo-3,4-dihydroquinazolin-2-yl)ethyl)acetamide. The sample was analyzed using LCMS Method H: retention time=11.825 min.; 1H NMR (METHANOL-d4, 500 MHz) Shift 8.13 (d, 1H, J=8.2 Hz), 7.8-7.9 (m, 3H), 7.66 (dd, 1H, J=1.5, 8.2 Hz), 7.58 (dd, 1H, J=2.0, 8.1 Hz), 7.3-7.4 (m, 4H), 7.08 (d, 1H, J=8.2 Hz), 7.02 (t, 1H, J=7.5 Hz), 6.68 (t, 1H, J=8.7 Hz), 6.52 (br d, 2H, J=6.1 Hz), 5.86 (d, 1H, J=2.4 Hz), 4.6-4.6 (m, 1H), 3.78 (s, 3H), 3.62 (t, 4H, J=4.6 Hz), 2.8-3.0 (m, 6H), 1.79 (s, 1H), 1.2-1.3 (m, 1H), 0.7-0.8 (m, 3H), 0.57 (dt, 2H, J=3.7, 5.0 Hz). 1H NMR (400 MHz, CDCl3): δ8.26 (d, J=8.3 Hz, 1H), 7.96 (dd, J=8.3, 1.8 Hz, 1H), 7.92-7.83 (m, 3H), 7.75 (d, J=8.2 Hz, 1H), 7.52 (dd, J=8.2, 1.9 Hz, 1H), 7.47-7.39 (m, 3H), 7.18-7.03 (m, 2H), 6.95 (dd, J=8.2, 1.9 Hz, 1H), 6.67 (t, J=8.9 Hz, 1H), 6.32 (d, J=5.8 Hz, 2H), 6.03 (d, J=2.1 Hz, 1H), 4.82 (dd, J=15.2, 7.1 Hz, 1H), 4.71-4.55 (m, 2H), 3.87 (s, 3H), 3.80 (t, J=4.4 Hz, 4H), 3.17-3.01 (m, 5H), 2.80 (dd, J=13.4, 6.8 Hz, 1H), 1.98-1.93 (m, 1H), 0.89 (d, J=8.2 Hz, 2H), 0.78 (d, J=4.9 Hz, 2H). LC-MS: 781 [M+H]+

Preparation of Example 143

(S)-2-(3-cyclopropyl-1H-pyrazol-1-yl)-N-(2-(3,5-difluorophenyl)-1-(3-(4-(morpholinosulfonyl)phenyl)-4-oxo-7-(o-tolyl)-3,4-dihydroquinazolin-2-yl)ethyl)acetamide

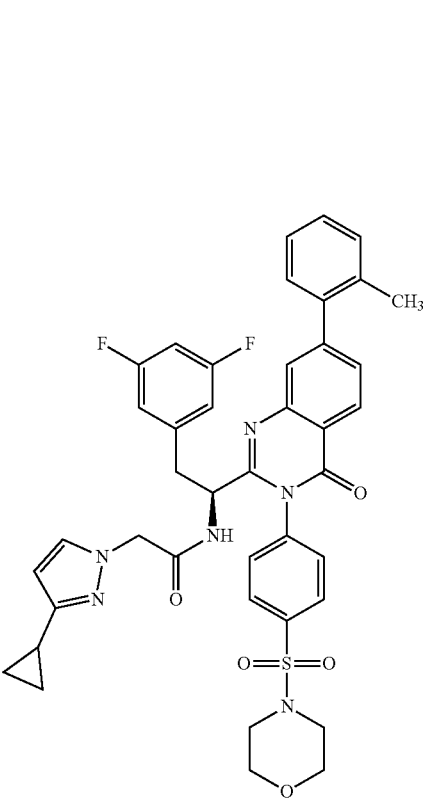 [SMILES: Cc1ccccc1-c1ccc2c(=O)n(-c3ccc(S(=O)(=O)N4CCOCC4)cc3)c([C@H](Cc3cc(F)cc(F)c3)NC(=O)Cn3ccc(C4CC4)n3)nc2c1]

The title compound was prepared according to General Procedure S using 2-methylphenylboronic acid as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-(o-tolyl)-3,4-dihydroquinazolin-2-yl)ethyl)acetamide. $^1$H NMR (400 MHz, CDCl$_3$): δ8.29 (d, J=8.2 Hz, 1H), 7.97 (d, J=8.2 Hz, 1H), 7.88 (d, J=8.1 Hz, 1H), 7.71 (s, 1H), 7.53 (d, J=7.7 Hz, 2H), 7.43 (d, J=8.2 Hz, 1H), 7.35-7.32 (m, 5H), 6.98 (d, J=8.2 Hz, 1H), 6.67 (t, J=8.9 Hz, 1H), 6.32 (d, J=5.8 Hz, 2H), 6.02 (d, J=2.0 Hz, 1H), 4.84 (dd, J=14.9, 7.0 Hz, 1H), 4.72-4.53 (m, 2H), 3.80 (t, J=4.4 Hz, 4H), 3.11-3.06 (m, 5H), 2.80 (dd, J=13.5, 7.0 Hz, 1H), 2.35 (s, 3H), 1.99-1.87 (m, 1H), 0.84 (dd, J=11.7, 6.3 Hz, 2H), 0.74 (d, J=4.9 Hz, 2H). ES-MS: 765 [M+H]$^+$

Preparation of Example 144

(S)-2-(3-cyclopropyl-1H-pyrazol-1-yl)-N-(2-(3,5-difluorophenyl)-1-(3-(4-(morpholinosulfonyl)phenyl)-4-oxo-7-phenyl-3,4-dihydroquinazolin-2-yl)ethyl)acetamide

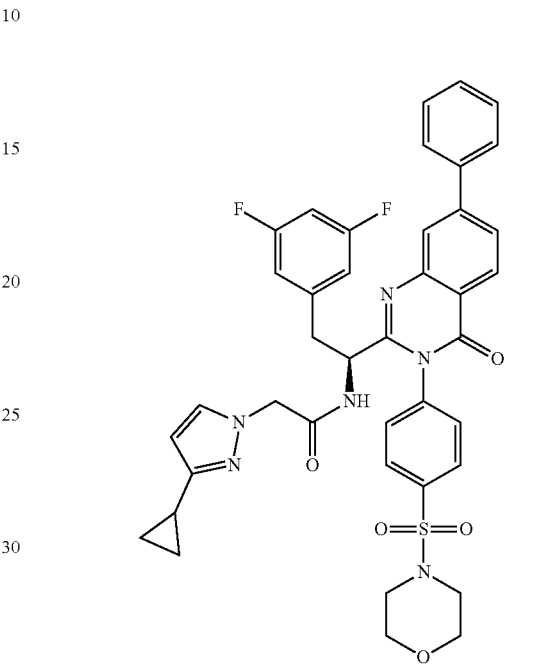

The title compound was prepared according to General Procedure S using phenylboronic acid as the coupling partner. The experiment afforded the title compound, (S)-2-(3-cyclopropyl-1H-pyrazol-1-yl)-N-(2-(3,5-difluorophenyl)-1-(3-(4-(morpholinosulfonyl)phenyl)-4-oxo-7-phenyl-3,4-dihydroquinazolin-2-yl)ethyl)acetamide. $^1$H NMR (400 MHz, CDCl$_3$): δ8.28 (dd, J=23.0, 7.6 Hz, 1H), 7.97 (d, J=12.6 Hz, 2H), 7.87 (d, J=8.2 Hz, 1H), 7.80 (d, J=8.3 Hz, 1H), 7.76 (d, J=7.3 Hz, 2H), 7.63-7.30 (m, 5H), 7.31-7.23 (m, 1H), 6.94 (d, J=7.0 Hz, 1H), 6.67 (t, J=8.8 Hz, 1H), 6.31 (d, J=5.9 Hz, 2H), 6.06 (d, J=1.8 Hz, 1H), 4.83 (dd, J=15.1, 7.3 Hz, 1H), 4.65 (q, J=16.8 Hz, 2H), 3.80 (t, J=4.3 Hz, 4H), 3.09-3.0 (m, 5H), 2.81 (dd, J=13.3, 6.7 Hz, 1H), 2.03-1.94 (m, 1H), 0.98-0.85 (m, 2H), 0.82 (d, J=4.7 Hz, 2H). $^1$H NMR (METHANOL-d4, 500 MHz) Shift 8.20 (dd, 1H, J=0.6, 8.2 Hz), 7.97 (d, 1H, J=1.9 Hz), 7.8-7.9 (m, 3H), 7.71 (d, 2H, J=7.4 Hz), 7.6-7.6 (m, 1H), 7.4-7.5 (m, 2H), 7.2-7.4 (m, 4H), 6.68 (t, 1H, J=8.9 Hz), 6.53 (d, 1H, J=2.2 Hz), 6.52 (d, 1H, J=2.2 Hz), 5.87 (d, 1H, J=2.2 Hz), 4.5-4.6 (m, 2H), 3.62 (t, 4H, J=4.6 Hz), 3.2-3.3 (m, 1H), 2.9-3.0 (m, 4H), 1.8-1.8 (m, 1H), 1.19 (s, 1H), 0.7-0.8 (m, 2H), 0.6-0.6 (m, 2H). LC-MS: 751 [M+H]$^+$

Preparation of Example 145

(S)-N-(1-(7-(2-chlorophenyl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

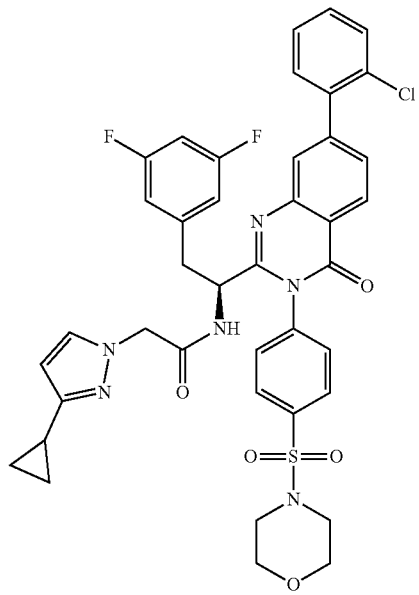 [SMILES: O=C(Cn1ccc(C2CC2)n1)N[C@@H](Cc1cc(F)cc(F)c1)c1nc2cc(-c3ccccc3Cl)ccc2c(=O)n1-c1ccc(S(=O)(=O)N2CCOCC2)cc1]

The title compound was prepared according to General Procedure S using 2-chlorophenylboronic acid as the coupling partner. The experiment afforded the title compound, (S)-N-(1-(7-(2-chlorophenyl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide. 1H NMR (400 MHz, CDCl3): δ8.31 (d, J=8.2 Hz, 1H), 7.97 (dd, J=8.2, 1.8 Hz, 1H), 7.88 (d, J=8.2 Hz, 1H), 7.83 (s, 1H), 7.64 (d, J=8.2 Hz, 1H), 7.59-7.51 (m, 2H), 7.48-7.37 (m, 5H), 7.00-6.94 (m, 1H), 6.67 (t, J=8.9 Hz, 1H), 6.31 (d, J=5.6 Hz, 2H), 6.02 (d, J=2.1 Hz, 1H), 4.83 (dd, J=15.3, 7.2 Hz, 1H), 4.72-4.55 (m, 2H), 3.80 (t, J=4.5 Hz, 4H), 3.09 (dd, J=18.4, 5.7 Hz, 5H), 2.80 (dd, J=13.4, 7.0 Hz, 1H), 1.95 (td, J=8.4, 4.3 Hz, 1H), 0.86 (dd, J=13.7, 5.6 Hz, 2H), 0.76 (d, J=4.7 Hz, 2H). LC-MS: 785 [M+H]+

Preparation of Example 146

(S)-N-(1-(7-([1,1'-biphenyl]-2-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

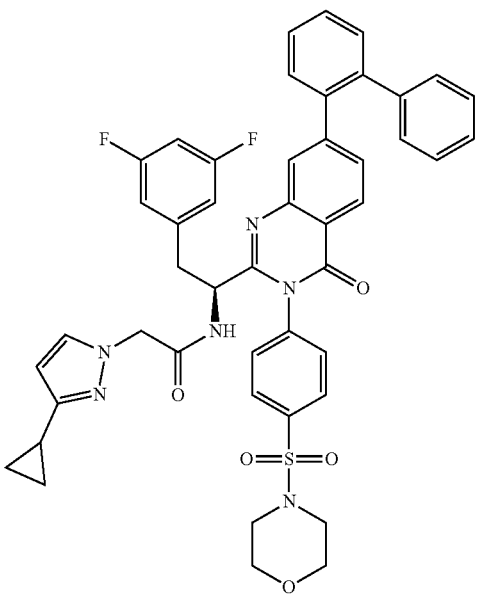 [SMILES: O=C(Cn1ccc(C2CC2)n1)N[C@@H](Cc1cc(F)cc(F)c1)c1nc2cc(-c3ccccc3-c3ccccc3)ccc2c(=O)n1-c1ccc(S(=O)(=O)N2CCOCC2)cc1]

The title compound was prepared according to General Procedure S using 2-phenylphenylboronic acid as the coupling partner. The experiment afforded the title compound, (S)-N-(1-(7-([1,1'-biphenyl]-2-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide. 1H NMR (400 MHz, CDCl3): δ7.97 (dd, J=13.2, 8.3 Hz, 2H), 7.86 (d, J=8.2 Hz, 1H), 7.69 (s, 1H), 7.55-7.51 (m, 5H), 7.38 (d, J=8.3 Hz, 1H), 7.27-7.25 (m, 4H), 7.17 (dd, J=10.6, 5.3 Hz, 3H), 6.92 (d, J=8.2 Hz, 1H), 6.67 (t, J=8.8 Hz, 1H), 6.28 (d, J=6.0 Hz, 2H), 6.04 (d, J=2.0 Hz, 1H), 4.79 (dd, J=14.9, 7.1 Hz, 1H), 4.71-4.51 (m, 2H), 3.80-3.78 (m, 4H), 3.18-2.96 (m, 5H), 2.77 (dd, J=13.3, 6.8 Hz, 1H), 1.97-1.93 (m, 1H), 0.97-0.82 (m, 2H), 0.78-0.75 (m, 2H). LC-MS: 827 [M+H]+

235
Preparation of Example 147

(S)-N-(1-(7-([1,1'-biphenyl]-3-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

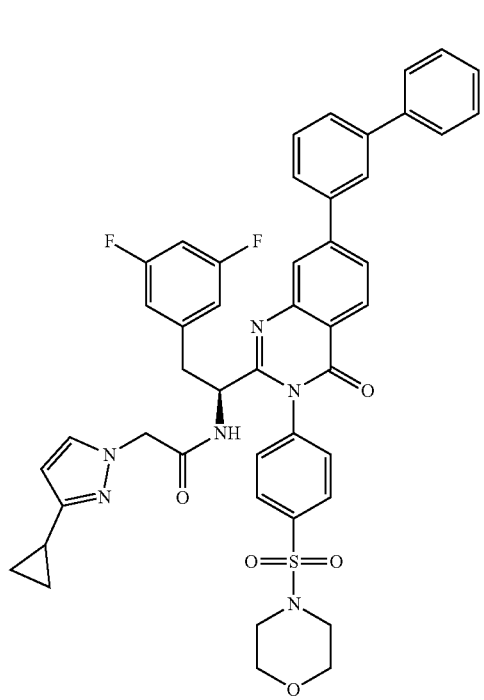 [SMILES: O=C(Cn1ccc(C2CC2)n1)N[C@@H](Cc1cc(F)cc(F)c1)c1nc2cc(-c3cccc(-c4ccccc4)c3)ccc2c(=O)n1-c1ccc(S(=O)(=O)N2CCOCC2)cc1]

The title compound was prepared according to General Procedure S using 3-phenyl-phenylboronic acid as the coupling partner. The experiment afforded the title compound, (S)-N-(1-(7-([1,1'-biphenyl]-3-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide. 1H NMR (400 MHz, CDCl3): δ8.33 (d, J=8.2 Hz, 1H), 8.04 (s, 1H), 7.97 (d, J=6.8 Hz, 2H), 7.86 (t, J=7.5 Hz, 2H), 7.77-7.59 (m, 4H), 7.48-7.40 (m, 6H), 7.27 (d, J=2.0 Hz, 1H), 6.94 (d, J=8.2 Hz, 1H), 6.67 (t, J=8.8 Hz, 1H), 6.31 (d, J=5.9 Hz, 2H), 6.05 (s, 1H), 4.83 (dd, J=15.1, 7.2 Hz, 1H), 4.65 (q, J=16.8 Hz, 2H), 3.80 (d, J=4.2 Hz, 4H), 3.11-3.07 (m, 5H), 2.81 (dd, J=13.4, 6.8 Hz, 1H), 2.06-1.88 (m, 1H), 0.88 (d, J=8.3 Hz, 2H), 0.80 (d, J=3.6 Hz, 2H). LC-MS: 827 [M+H]+

236
Preparation of Example 148

(S)-N-(1-(7-([1,1'-biphenyl]-4-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide

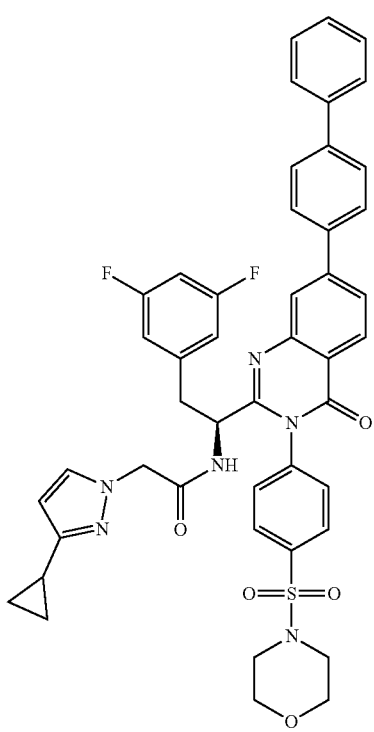 [SMILES: O=C(Cn1ccc(C2CC2)n1)N[C@@H](Cc1cc(F)cc(F)c1)c1nc2cc(-c3ccc(-c4ccccc4)cc3)ccc2c(=O)n1-c1ccc(S(=O)(=O)N2CCOCC2)cc1]

The title compound was prepared according to General Procedure S using 4-phenyl-phenylboronic acid as the coupling partner. The experiment afforded the title compound, (S)-N-(1-(7-([1,1'-biphenyl]-4-yl)-3-(4-(morpholinosulfonyl)phenyl)-4-oxo-3,4-dihydroquinazolin-2-yl)-2-(3,5-difluorophenyl)ethyl)-2-(3-cyclopropyl-1H-pyrazol-1-yl)acetamide. 1H NMR (400 MHz, CDCl3): δ8.33 (d, J=8.3 Hz, 1H), 8.04 (s, 1H), 7.97 (d, J=8.3 Hz, 1H), 7.91-7.81 (m, 4H), 7.78 (d, J=8.0 Hz, 2H), 7.70 (d, J=7.5 Hz, 2H), 7.55-7.50 (m, 4H), 7.41 (t, J=7.3 Hz, 1H), 7.29 (s, 1H), 6.95 (d, J=8.2 Hz, 1H), 6.68 (t, J=8.8 Hz, 1H), 6.32 (d, J=6.1 Hz, 2H), 6.07 (s, 1H), 4.84 (q, J=7.2 Hz, 1H), 4.65 (q, J=16.9 Hz, 2H), 3.80 (s, 4H), 3.11-3.07 (m, 5H), 2.82 (dd, J=13.4, 6.8 Hz, 1H), 2.02-1.98 (m, 1H), 0.95 (d, J=7.6 Hz, 2H), 0.85 (t, J=9.7 Hz, 2H). LC-MS: 827 [M+H]+

237

Preparation of Example 149

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,3-difluorophenyl)-3-(4-(morpholinosulfonyl)phenyl)-4-oxo-3,4-dihydroquinazolin-2-yl)ethyl)acetamide

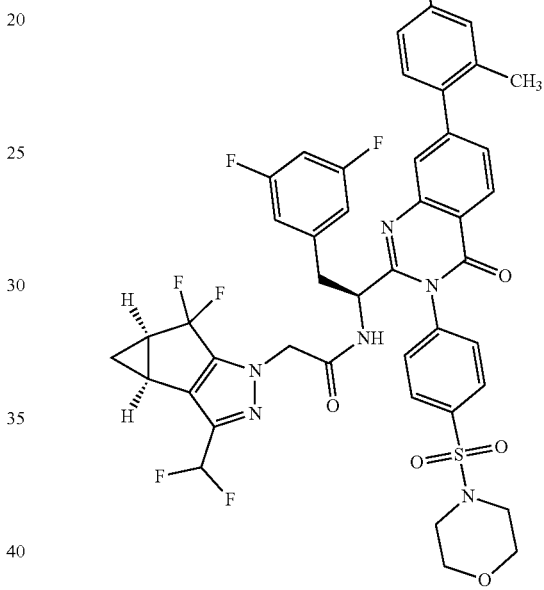

The title compound was prepared according to General Procedure A using (2,3-difluorophenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(2,3-difluorophenyl)-3-(4-(morpholinosulfonyl)phenyl)-4-oxo-3,4-dihydroquinazolin-2-yl)ethyl)acetamide. The sample was analyzed using LCMS Method C: retention time=1.54 min. 1H NMR (500 MHz, METHANOL-d4) δ ppm 8.32-8.39 (m, 1H) 8.03-8.10 (m, 1H) 7.91-7.99 (m, 2H) 7.81-7.86 (m, 1H) 7.66-7.71 (m, 1H) 7.31-7.50 (m, 4H) 6.58-6.87 (m, 4H) 4.69-4.84 (m, 3H) 3.72-3.77 (m, 4H) 3.39-3.45 (m, 1H) 3.00-3.11 (m, 5H) 2.43-2.51 (m, 2H) 1.36-1.42 (m, 1H) 1.01-1.06 (m, 1H).

238

Preparation of Example 150

2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(4-fluoro-2-methylphenyl)-3-(4-(morpholinosulfonyl)phenyl)-4-oxo-3,4-dihydroquinazolin-2-yl)ethyl)acetamide

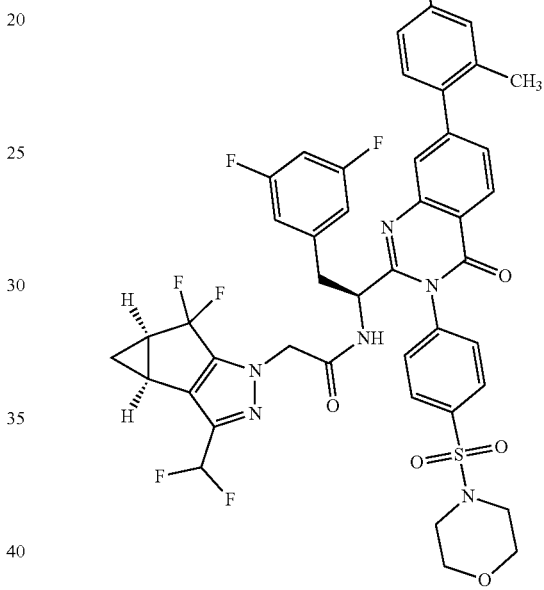

The title compound was prepared according to General Procedure A using (4-fluoro-2-methylphenyl)boronic acid as the coupling partner. The experiment afforded the title compound, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N-((S)-2-(3,5-difluorophenyl)-1-(7-(4-fluoro-2-methylphenyl)-3-(4-(morpholinosulfonyl)phenyl)-4-oxo-3,4-dihydroquinazolin-2-yl)ethyl)acetamide. The sample was analyzed using LCMS Method C: retention time=1.5 min. 1H NMR (500 MHz, METHANOL-d4) δ ppm 8.16-8.41 (m, 1H) 7.87-8.06 (m, 2H) 7.76-7.82 (m, 1H) 7.64-7.72 (m, 1H) 7.53-7.62 (m, 1H) 7.33-7.42 (m, 2H) 7.05-7.19 (m, 2H) 6.59-6.86 (m, 4H) 4.69-4.84 (m, 3H) 3.71-3.78 (m, 4H) 3.38-3.45 (m, 1H) 3.00-3.12 (m, 5H) 2.41-2.52 (m, 2H) 2.34-2.38 (m, 3H) 1.35-1.43 (m, 1H) 1.00-1.07 (m, 1H)

Preparation of Example 154

(S)-2-(3,5-bis(difluoromethyl)-1H-pyrazol-1-yl)-N-(1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)acetamide

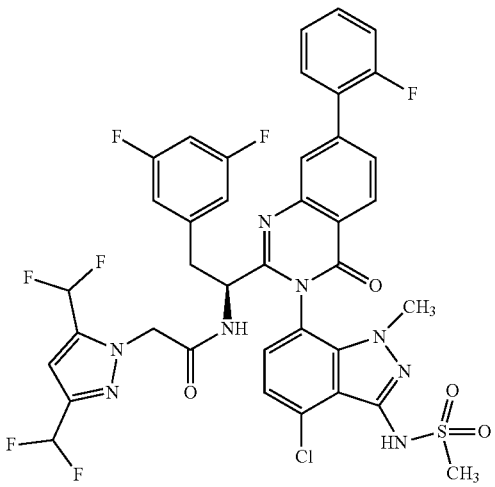 [SMILES: Cn1nc(NS(C)(=O)=O)c2c(Cl)ccc(-n3c([C@H](Cc4cc(F)cc(F)c4)NC(=O)Cn4nc(C(F)F)cc4C(F)F)nc4cc(-c5ccccc5F)ccc4c3=O)c21]

The title compound was prepared according to General Procedure R using 2-(3,5-bis(difluoromethyl)-1H-pyrazol-1-yl)acetic acid as the coupling partner. The experiment afforded the title compound, (S)-2-(3,5-bis(difluoromethyl)-1H-pyrazol-1-yl)-N-(1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)acetamide. The sample was analyzed using LCMS Method A: retention time=2.59 min.; observed ion=861.2 (M+H). 1H NMR (METHANOL-d4, 500 MHz) δ8.77 (br d, 1H, J=8.9 Hz), 8.26 (d, 1H, J=8.2 Hz), 7.98 (s, 1H), 7.74 (d, 1H, J=8.2 Hz), 7.57 (t, 1H, J=7.2 Hz), 7.41 (d, 1H, J=7.8 Hz), 7.2-7.3 (m, 2H), 7.07 (d, 1H, J=7.9 Hz), 6.6-6.8 (m, 4H), 6.65 (br t, 1H, J=54.0 Hz), 6.5-6.6 (m, 2H), 6.60 (br t, 1H, J=54.8 Hz), 5.32 (s, 2H), 4.8-4.8 (m, 1H), 4.6-4.7 (m, 2H), 3.51 (s, 2H), 3.3-3.4 (m, 1H), 3.14 (s, 2H), 3.0-3.1 (m, 1H)

Preparation of Example 155

(S)-N-(1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-(1-isopropyl-1H-pyrazol-3-yl)acetamide

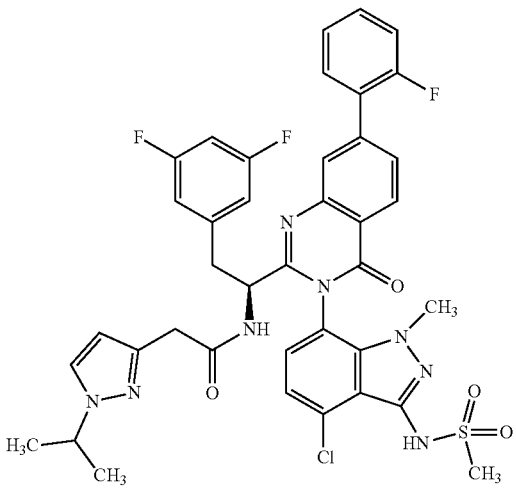 [SMILES: CC(C)n1ccc(CC(=O)N[C@@H](Cc2cc(F)cc(F)c2)c2nc3cc(-c4ccccc4F)ccc3c(=O)n2-c2ccc(Cl)c3c(NS(C)(=O)=O)nn(C)c23)n1]

The title compound was prepared according to General Procedure R using 2-(1-isopropyl-1H-pyrazol-3-yl)acetic acid as the coupling partner. The experiment afforded the title compound, (S)-N-(1-(3-(4-chloro-1-methyl-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-(1-isopropyl-1H-pyrazol-3-yl)acetamide. The sample was analyzed using LCMS Method D: retention time=2.44 min.; observed ion=803.2 (M+H). 1H NMR (METHANOL-d4, 500 MHz) δ8.37 (d, 1H, J=8.5 Hz), 8.07 (s, 1H), 7.85 (br d, 1H, J=8.5 Hz), 7.69 (br t, 1H, J=7.6 Hz), 7.5-7.6 (m, 2H), 7.3-7.4 (m, 3H), 7.2-7.3 (m, 1H), 6.74 (t, 1H, J=8.4 Hz), 6.6-6.6 (m, 2H), 5.92 (s, 1H), 4.99 (dd, 1H, J=5.2, 9.2 Hz), 4.4-4.4 (m, 1H), 3.61 (s, 3H), 3.4-3.5 (m, 1H), 3.28 (s, 3H), 3.20 (br d, 2H, J=18.0 Hz), 3.1-3.2 (m, 1H), 1.4-1.4 (m, 6H)

Preparation of Example 156

N-((S)-1-(3-(4-chloro-1-methyl-3-(methylsulfonamido)-1H-indazol-7-yl)-7-(4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

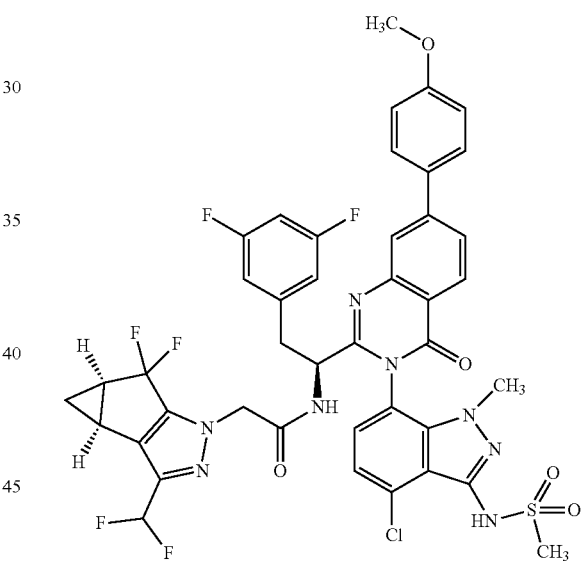

The title compound was prepared according to General Procedure K using (4-methoxyphenyl)boronic acid as the coupling partner. The experiment afforded the title compound, N-((S)-1-(3-(4-chloro-1-methyl-3-(methylsulfonamido)-1H-indazol-7-yl)-7-(4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.48 min.; observed ion=909.3 (M+H). 1H NMR (METHANOL-d4, 500 MHz) δ8.46 (s, 1H), 8.47 (d, 2H, J=4.4 Hz), 8.36 (d, 1H, J=8.3 Hz), 8.25 (dd, 1H, J=1.8, 8.3 Hz), 8.07 (d, 1H, J=8.3 Hz), 7.59 (dd, 1H, J=3.0, 8.6 Hz), 7.31 (d, 1H, J=7.7 Hz), 7.20 (d, 1H, J=7.7 Hz), 6.6-6.8 (m, 4H), 4.8-4.9 (m, 1H), 4.54 (s, 2H), 4.00 (s, 3H), 3.64 (s, 3H), 3.5-3.5 (m, 1H), 3.2-3.3 (m, 3H), 3.12 (dd, 1H, J=9.1, 14.2 Hz), 2.43 (br dd, 2H, J=4.8, 6.9 Hz), 1.36 (s, 1H), 1.0-1.0 (m, 1H)

241

Preparation of Example 157

N-((S)-1-(3-(4-chloro-3-(cyclopropanesulfonamido)-1-(2,2-difluoroethyl)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

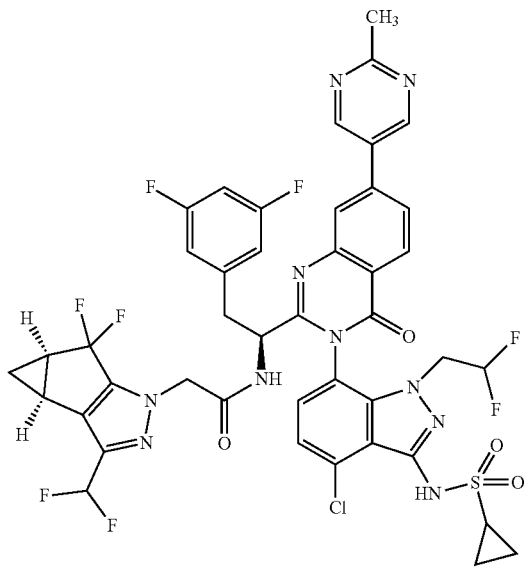 [SMILES: Cc1ncc(-c2ccc3c(=O)n(-c4ccc(Cl)c5c(NS(=O)(=O)C6CC6)nn(CC(F)F)c45)c([C@H](Cc4cc(F)cc(F)c4)NC(=O)Cn4nc(C(F)F)c5c4C(F)(F)[C@@H]4C[C@H]54)nc3c2)cn1]

The title compound was prepared according to General Procedure J using 5-bromo-2-methylpyrimidine as the coupling partner. The experiment afforded the title compound, N-((S)-1-(3-(4-chloro-3-(cyclopropanesulfonamido)-1-(2,2-difluoroethyl)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.52 min.; observed ion=964.2 (M+H). 1H NMR (METHANOL-d4, 500 MHz) Shift 9.18 (s, 2H), 8.43 (d, 1H, J=8.1 Hz), 8.23 (d, 1H, J=1.8 Hz), 8.03 (dd, 1H, J=1.8, 8.3 Hz), 7.40 (br d, 1H, J=8.0 Hz), 7.28 (d, 1H, J=7.7 Hz), 6.8-6.8 (m, 1H), 6.69 (br t, 1H, J=57.7 Hz), 6.5-6.6 (m, 2H), 6.04 (t, 1H, J=55.4 Hz), 4.76 (dd, 1H, J=4.8, 9.5 Hz), 4.6-4.7 (m, 2H), 4.3-4.4 (m, 1H), 3.9-4.0 (m, 1H), 3.4-3.5 (m, 1H), 3.0-3.1 (m, 1H), 2.92 (tt, 1H, J=4.9, 7.9 Hz), 2.83 (s, 3H), 2.44 (ddd, 2H, J=4.0, 7.5, 11.1 Hz), 1.3-1.4 (m, 1H), 1.1-1.2 (m, 2H), 0.9-1.1 (m, 3H)

242

Preparation of Example 158

N-((S)-1-(3-(4-chloro-3-(cyclopropanesulfonamido)-1-(2,2-difluoroethyl)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

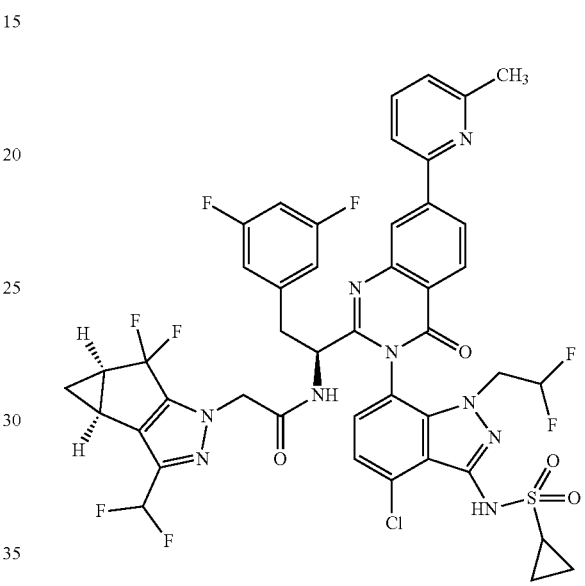

The title compound was prepared according to General Procedure J using 2-bromo-6-methylpyridine as the coupling partner. The experiment afforded the title compound, N-((S)-1-(3-(4-chloro-3-(cyclopropanesulfonamido)-1-(2,2-difluoroethyl)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.38 min.; observed ion=963.3 (M+H). 1H NMR (METHANOL-d4, 500 MHz) Shift 8.49 (d, 1H, J=1.2 Hz), 8.39 (d, 1H, J=8.3 Hz), 8.27 (dd, 1H, J=1.5, 8.3 Hz), 7.9-7.9 (m, 2H), 7.4-7.4 (m, 1H), 7.38 (d, 1H, J=1.2 Hz), 7.28 (d, 1H, J=7.7 Hz), 6.80 (tt, 1H, J=2.3, 9.2 Hz), 6.70 (br t, 1H, J=54.8 Hz), 6.5-6.6 (m, 2H), 6.04 (t, 1H, J=55.4 Hz), 4.77 (dd, 1H, J=4.9, 9.4 Hz), 4.6-4.7 (m, 2H), 4.3-4.4 (m, 1H), 3.9-4.0 (m, 1H), 3.4-3.5 (m, 1H), 3.09 (dd, 1H, J=9.4, 14.2 Hz), 2.92 (tt, 1H, J=4.8, 8.0 Hz), 2.69 (s, 3H), 2.4-2.5 (m, 2H), 1.3-1.4 (m, 1H), 1.1-1.1 (m, 2H), 0.9-1.0 (m, 3H)

Preparation of Example 159

N-((S)-1-(3-(4-chloro-3-(cyclopropanesulfonamido)-1-(2,2-difluoroethyl)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

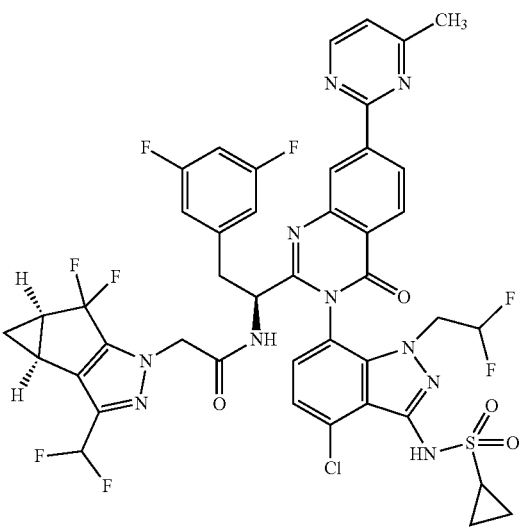 [SMILES: Cc1ccnc(-c2ccc3c(=O)n(-c4ccc(Cl)c5c(NS(=O)(=O)C6CC6)nn(CC(F)F)c45)c([C@H](Cc4cc(F)cc(F)c4)NC(=O)Cn4nc(C(F)F)c5c4C(F)(F)[C@@H]4C[C@H]54)nc3c2)n1]

The title compound was prepared according to General Procedure J using 2-chloro-4-methylpyrimidine as the coupling partner. The experiment afforded the title compound, N-((S)-1-(3-(4-chloro-3-(cyclopropanesulfonamido)-1-(2,2-difluoroethyl)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.3 min.; observed ion=933.2 (M+H). 1H NMR (METHANOL-d4, 500 MHz) Shift 8.94 (d, 1H, J=1.2 Hz), 8.82 (d, 1H, J=5.1 Hz), 8.69 (dd, 1H, J=1.8, 8.3 Hz), 8.39 (d, 1H, J=8.0 Hz), 7.4-7.4 (m, 2H), 7.31 (d, 1H, J=7.7 Hz), 6.8-6.8 (m, 1H), 6.71 (t, 1H, J=54.7 Hz), 6.5-6.6 (m, 2H), 6.04 (t, 1H, J=55.3 Hz), 4.78 (dd, 1H, J=4.9, 9.4 Hz), 4.6-4.7 (m, 2H), 4.3-4.4 (m, 1H), 3.9-4.0 (m, 1H), 3.4-3.5 (m, 1H), 3.09 (dd, 1H, J=9.2, 14.0 Hz), 2.92 (tt, 1H, J=4.9, 7.9 Hz), 2.70 (s, 3H), 2.4-2.5 (m, 2H), 1.36 (dt, 1H, J=6.4, 7.2 Hz), 1.1-1.1 (m, 2H), 0.9-1.1 (m, 3H)

Preparation of Example 160

N-((S)-1-(3-(4-chloro-3-(cyclopropanesulfonamido)-1-(2,2-difluoroethyl)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

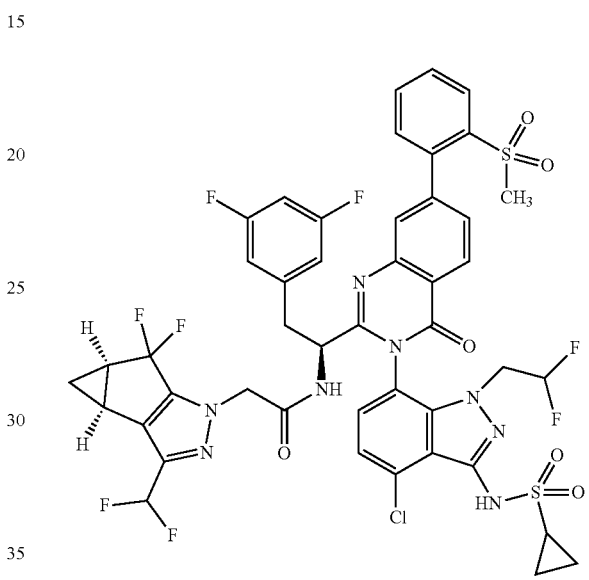

The title compound was prepared according to General Procedure J using 1-bromo-2-(methylsulfonyl)benzene as the coupling partner. The experiment afforded the title compound, N-((S)-1-(3-(4-chloro-3-(cyclopropanesulfonamido)-1-(2,2-difluoroethyl)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=1009.3 (M+H). 1H NMR (METHANOL-d4, 500 MHz) Shift 8.35 (d, 1H, J=7.8 Hz), 8.28 (dd, 1H, J=1.0, 7.9 Hz), 7.97 (d, 1H, J=2.1 Hz), 7.8-7.9 (m, 1H), 7.78 (dt, 1H, J=1.5, 7.7 Hz), 7.7-7.7 (m, 1H), 7.58 (dd, 1H, J=1.2, 7.5 Hz), 7.41 (br d, 1H, J=7.5 Hz), 7.32 (d, 1H, J=8.0 Hz), 6.8-6.8 (m, 1H), 6.69 (t, 1H, J=54.8 Hz), 6.5-6.6 (m, 2H), 6.06 (t, 1H, J=55.3 Hz), 4.77 (dd, 1H, J=4.6, 9.4 Hz), 4.6-4.6 (m, 2H), 4.4-4.5 (m, 1H), 3.9-4.0 (m, 1H), 3.42 (dd, 1H, J=4.6, 13.9 Hz), 3.07 (dd, 1H, J=9.5, 14.3 Hz), 2.9-2.9 (m, 4H), 2.4-2.5 (m, 2H), 1.3-1.4 (m, 1H), 1.1-1.1 (m, 2H), 0.9-1.1 (m, 3H)

245

Preparation of Example 161

N-((S)-1-(3-(4-chloro-3-(methylsulfonamido)-1-(2,2,2-trifluoroethyl)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

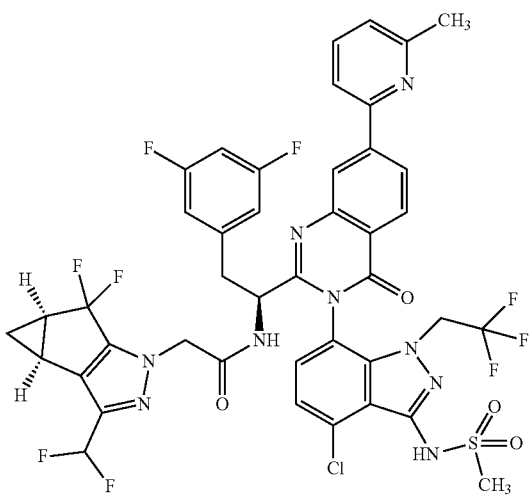 [SMILES: Cc1cccc(-c2ccc3c(=O)n(-c4ccc(Cl)c5c(NS(C)(=O)=O)nn(CC(F)(F)F)c45)c([C@H](Cc4cc(F)cc(F)c4)NC(=O)Cn4nc(C(F)F)c5c4C(F)(F)[C@@H]4C[C@H]54)nc3c2)n1]

The title compound was prepared according to General Procedure Q using 2-bromo-6-methylpyridine as the coupling partner. The experiment afforded the title compound, N-((S)-1-(3-(4-chloro-3-(methylsulfonamido)-1-(2,2,2-trifluoroethyl)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.5 min.; observed ion=964.2 (M+H). 1H NMR (METHANOL-d4, 500 MHz) Shift 8.46 (d, 1H, J=1.5 Hz), 8.34 (d, 1H, J=8.3 Hz), 8.24 (dd, 1H, J=1.8, 8.3 Hz), 7.8-7.9 (m, 2H), 7.3-7.4 (m, 3H), 6.7-6.8 (m, 1H), 6.68 (br t, 1H, J=54.7 Hz), 6.49 (d, 2H, J=6.9 Hz), 4.6-4.8 (m, 4H), 4.19 (dd, 1H, J=8.2, 16.2 Hz), 3.3-3.4 (m, 1H), 3.22 (s, 3H), 3.01 (dd, 1H, J=9.4, 14.2 Hz), 2.67 (s, 3H), 2.43 (br dd, 2H, J=4.0, 8.2 Hz), 1.3-1.4 (m, 1H), 1.0-1.0 (m, 1H)

246

Preparation of Example 162

N-((S)-1-(3-(4-chloro-3-(methylsulfonamido)-1-(2,2,2-trifluoroethyl)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

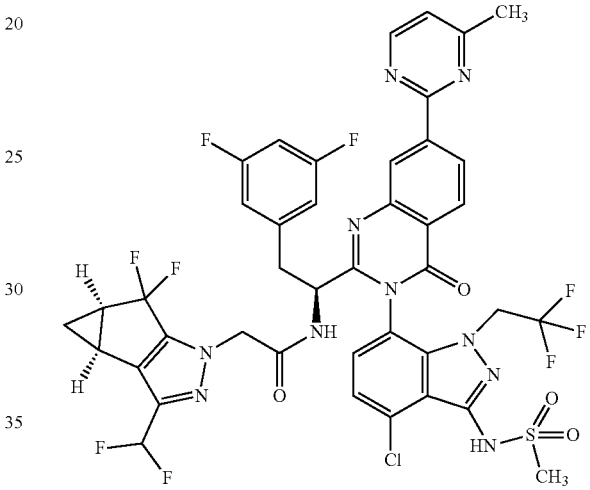

The title compound was prepared according to General Procedure Q using 2-chloro-4-methylpyrimidine as the coupling partner. The experiment afforded the title compound, N-((S)-1-(3-(4-chloro-3-(methylsulfonamido)-1-(2,2,2-trifluoroethyl)-1H-indazol-7-yl)-7-(4-methylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=965.2 (M+H). 1H NMR (METHANOL-d4, 500 MHz) Shift 8.92 (d, 1H, J=1.8 Hz), 8.82 (d, 1H, J=5.1 Hz), 8.69 (dd, 1H, J=1.5, 8.3 Hz), 8.37 (d, 1H, J=8.3 Hz), 7.4-7.5 (m, 3H), 6.8-6.8 (m, 1H), 6.71 (br t, 1H, J=54.7 Hz), 6.5-6.5 (m, 2H), 4.6-4.8 (m, 4H), 4.22 (dd, 1H, J=8.3, 16.1 Hz), 3.4-3.4 (m, 1H), 3.2-3.3 (m, 3H), 3.04 (dd, 1H, J=9.7, 13.9 Hz), 2.70 (s, 3H), 2.4-2.5 (m, 2H), 1.37 (td, 1H, J=6.6, 7.7 Hz), 1.0-1.0 (m, 1H)

247

Preparation of Example 163

N-((S)-1-(3-(4-chloro-3-(methylsulfonamido)-1-(2,2,2-trifluoroethyl)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

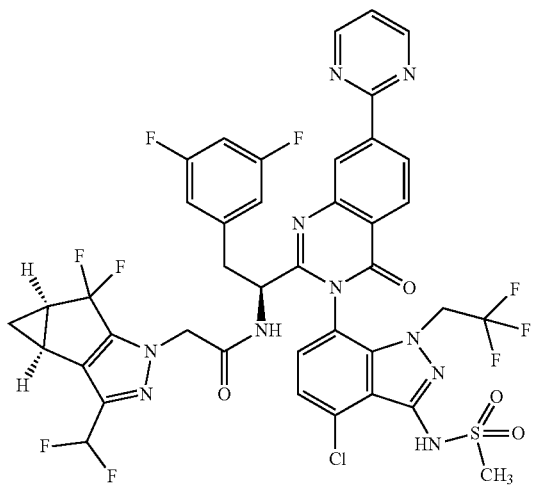 [SMILES: CS(=O)(=O)Nc1nn(CC(F)(F)F)c2c(-n3c([C@H](Cc4cc(F)cc(F)c4)NC(=O)Cn4nc(C(F)F)c5c4C(F)(F)[C@@H]4C[C@H]54)nc4cc(-c5ncccn5)ccc4c3=O)ccc(Cl)c12]

The title compound was prepared according to General Procedure Q using 2-chloropyrimidine as the coupling partner. The experiment afforded the title compound, N-((S)-1-(3-(4-chloro-3-(methylsulfonamido)-1-(2,2,2-trifluoroethyl)-1H-indazol-7-yl)-4-oxo-7-(pyrimidin-2-yl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.43 min.; observed ion=949 (M−H). 1H NMR (METHANOL-d4, 500 MHz) Shift 9.01 (d, 2H, J=4.8 Hz), 8.94 (d, 1H, J=1.2 Hz), 8.70 (dd, 1H, J=1.5, 8.3 Hz), 8.57 (s, 1H), 8.38 (d, 1H, J=8.3 Hz), 7.52 (t, 1H, J=4.9 Hz), 7.3-7.4 (m, 1H), 6.5-6.8 (m, 4H), 4.7-4.8 (m, 4H), 4.1-4.2 (m, 1H), 3.3-3.4 (m, 1H), 3.22 (br s, 3H), 3.0-3.1 (m, 1H), 2.4-2.5 (m, 2H), 1.3-1.4 (m, 1H), 1.0-1.0 (m, 1H)

248

Preparation of Example 164

N-((S)-1-(3-(4-chloro-3-(methylsulfonamido)-1-(2,2,2-trifluoroethyl)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

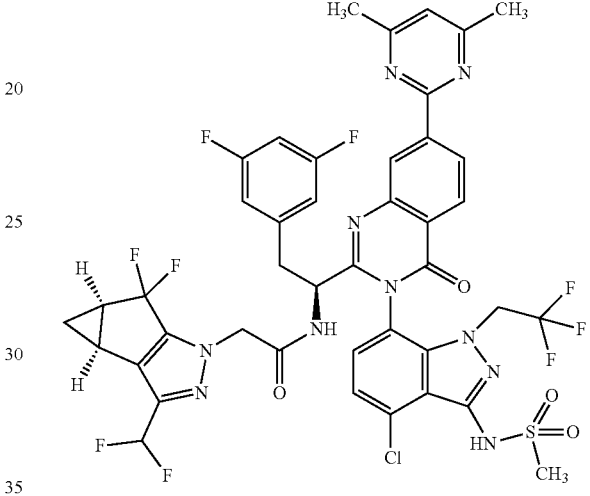

The title compound was prepared according to General Procedure Q using 2-chloro-4,6-dimethylpyrimidine as the coupling partner. The experiment afforded the title compound, N-((S)-1-(3-(4-chloro-3-(methylsulfonamido)-1-(2,2,2-trifluoroethyl)-1H-indazol-7-yl)-7-(4,6-dimethylpyrimidin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.55 min.; observed ion=979.4 (M+H). 1H NMR (METHANOL-d4, 500 MHz) Shift 8.90 (d, 1H, J=1.5 Hz), 8.67 (dd, 1H, J=1.5, 8.3 Hz), 8.36 (d, 1H, J=8.3 Hz), 7.44 (br d, 1H, J=8.0 Hz), 7.38 (d, 1H, J=8.0 Hz), 7.29 (s, 1H), 6.8-6.8 (m, 1H), 6.72 (t, 1H, J=54.7 Hz), 6.5-6.5 (m, 2H), 4.7-4.8 (m, 4H), 4.21 (dd, 1H, J=8.3, 16.1 Hz), 3.3-3.4 (m, 1H), 3.25 (s, 3H), 3.04 (dd, 1H, J=9.4, 14.2 Hz), 2.64 (s, 6H), 2.50 (br d, 1H, J=6.9 Hz), 2.42 (br d, 1H, J=4.8 Hz), 1.3-1.4 (m, 1H), 1.02 (br dd, 1H, J=1.9, 5.5 Hz)

249
Preparation of Example 165

N-((S)-1-(3-(4-chloro-3-(methylsulfonamido)-1-(2,2,2-trifluoroethyl)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

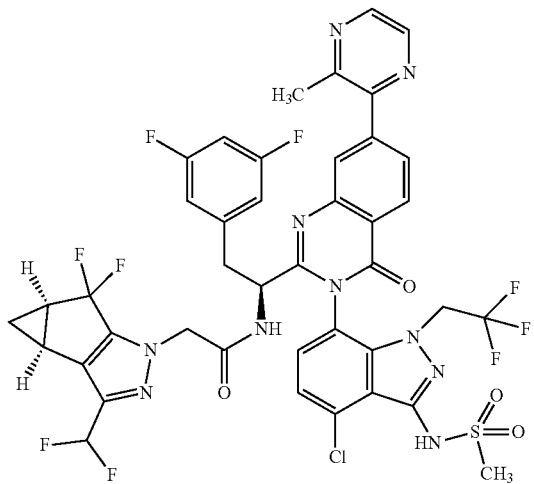 [SMILES: Cc1nccnc1-c1ccc2c(=O)n(-c3ccc(Cl)c4c(NS(C)(=O)=O)nn(CC(F)(F)F)c34)c([C@H](Cc3cc(F)cc(F)c3)NC(=O)Cn3nc(C(F)F)c4c3C(F)(F)[C@@H]3C[C@H]43)nc2c1]

The title compound was prepared according to General Procedure Q using 2-chloro-3-methylpyrazine as the coupling partner. The experiment afforded the title compound, N-((S)-1-(3-(4-chloro-3-(methylsulfonamido)-1-(2,2,2-trifluoroethyl)-1H-indazol-7-yl)-7-(3-methylpyrazin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.38 min.; observed ion=965.2 (M+H). 1H NMR (METHANOL-d4, 500 MHz) Shift 8.65 (s, 1H), 8.63 (d, 1H, J=2.6 Hz), 8.41 (d, 1H, J=8.3 Hz), 8.11 (d, 1H, J=1.5 Hz), 7.91 (dd, 1H, J=1.8, 8.0 Hz), 7.4-7.5 (m, 1H), 7.40 (d, 1H, J=7.5 Hz), 6.7-6.8 (m, 1H), 6.69 (t, 1H, J=54.8 Hz), 6.50 (dd, 2H, J=2.1, 8.0 Hz), 4.6-4.8 (m, 4H), 4.23 (dd, 1H, J=8.2, 16.2 Hz), 3.38 (dd, 1H, J=4.2, 14.3 Hz), 3.26 (s, 3H), 3.03 (dd, 1H, J=9.5, 14.3 Hz), 2.72 (s, 3H), 2.4-2.5 (m, 2H), 1.37 (br d, 1H, J=6.9 Hz), 1.0-1.0 (m, 1H)

250
Preparation of Example 166

N-((S)-1-(3-(4-chloro-3-(methylsulfonamido)-1-(2,2,2-trifluoroethyl)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

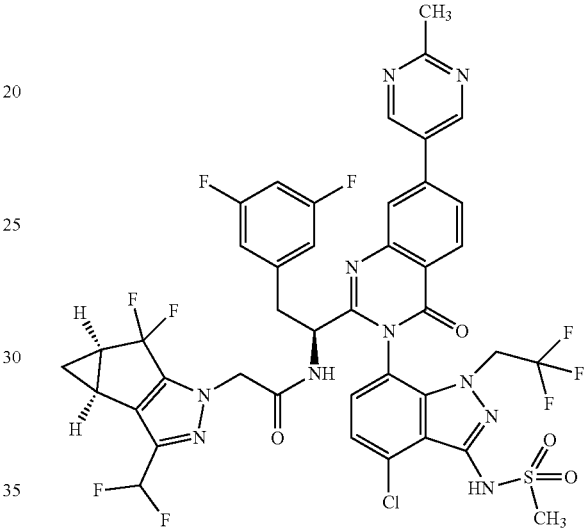

The title compound was prepared according to General Procedure Q using 5-bromo-2-methylpyrimidine as the coupling partner. The experiment afforded the title compound, N-((S)-1-(3-(4-chloro-3-(methylsulfonamido)-1-(2,2,2-trifluoroethyl)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.34 min.; observed ion=965.2 (M+H). 1H NMR (METHANOL-d4, 500 MHz) Shift 9.16 (s, 2H), 8.39 (d, 1H, J=7.7 Hz), 8.19 (d, 1H, J=1.8 Hz), 8.01 (dd, 1H, J=1.9, 8.2 Hz), 7.42 (d, 1H, J=7.7 Hz), 7.33 (d, 1H, J=7.7 Hz), 6.7-6.8 (m, 1H), 6.67 (t, 1H, J=54.8 Hz), 6.48 (d, 2H, J=6.6 Hz), 4.6-4.8 (m, 4H), 4.19 (dd, 1H, J=8.3, 16.1 Hz), 3.3-3.4 (m, 1H), 3.22 (s, 3H), 3.01 (dd, 1H, J=9.5, 14.0 Hz), 2.80 (s, 3H), 2.43 (ddd, 2H, J=3.9, 7.7, 11.1 Hz), 1.3-1.4 (m, 1H), 0.9-1.0 (m, 1H)

Preparation of Example 167

N-((S)-1-(3-(4-chloro-3-(methylsulfonamido)-1-(2,2,2-trifluoroethyl)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

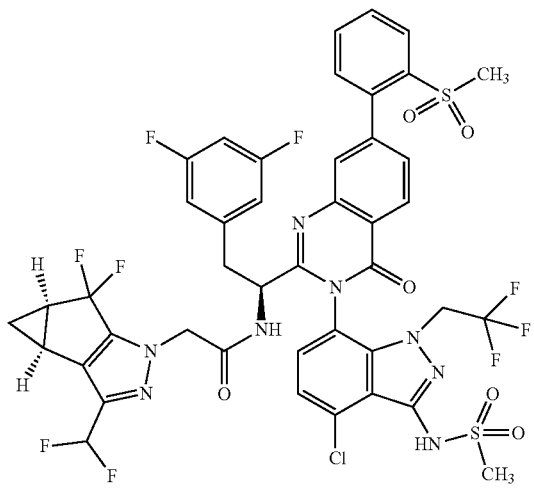 [SMILES: CS(=O)(=O)Nc1nn(CC(F)(F)F)c2c(-n3c([C@H](Cc4cc(F)cc(F)c4)NC(=O)Cn4nc(C(F)F)c5c4C(F)(F)[C@@H]4C[C@H]54)nc4cc(-c5ccccc5S(C)(=O)=O)ccc4c3=O)ccc(Cl)c12]

The title compound was prepared according to General Procedure Q using 1-bromo-2-(methylsulfonyl)benzene as the coupling partner. The experiment afforded the title compound, N-((S)-1-(3-(4-chloro-3-(methylsulfonamido)-1-(2,2,2-trifluoroethyl)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.42 min.; observed ion=1027.2 (M+H). 1H NMR (METHANOL-d4, 500 MHz) δ 8.33 (d, 1H, J=8.0 Hz), 8.28 (dd, 1H, J=1.2, 8.0 Hz), 7.96 (d, 1H, J=1.8 Hz), 7.8-7.9 (m, 1H), 7.78 (dt, 1H, J=1.2, 7.7 Hz), 7.72 (dd, 1H, J=1.6, 8.2 Hz), 7.58 (dd, 1H, J=1.0, 7.6 Hz), 7.46 (d, 1H, J=8.0 Hz), 7.39 (d, 1H, J=8.0 Hz), 6.5-6.8 (m, 4H), 4.8-4.8 (m, 1H), 4.6-4.8 (m, 3H), 4.24 (br d, 1H, J=8.0 Hz), 3.4-3.4 (m, 1H), 3.26 (s, 3H), 3.03 (dd, 1H, J=9.5, 14.3 Hz), 2.89 (s, 3H), 2.4-2.5 (m, 2H), 1.3-1.4 (m, 1H), 0.9-1.0 (m, 1H)

Preparation of Example 168

N-((S)-1-(3-(4-chloro-1-methyl-3-(methylsulfonamido)-1H-indazol-7-yl)-4-oxo-7-(2,3,4-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

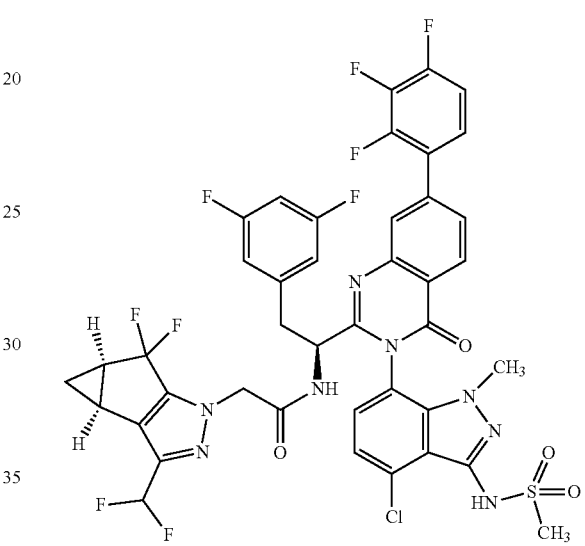

The title compound was prepared according to General Procedure D using 1-bromo-2,3,4-trifluorobenzene as the coupling partner. The experiment afforded the title compound, N-((S)-1-(3-(4-chloro-1-methyl-3-(methylsulfonamido)-1H-indazol-7-yl)-4-oxo-7-(2,3,4-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.59 min.; observed ion=933 (M−H). 1H NMR (METHANOL-d4, 500 MHz) Shift 8.40 (d, 1H, J=8.3 Hz), 8.08 (t, 1H, J=1.5 Hz), 7.84 (td, 1H, J=1.5, 8.3 Hz), 7.52 (br d, 1H, J=8.9 Hz), 7.3-7.4 (m, 2H), 7.23 (d, 1H, J=7.7 Hz), 6.6-6.8 (m, 4H), 4.62 (br s, 2H), 4.53 (d, 2H, J=3.6 Hz), 3.63 (s, 3H), 3.49 (dd, 1H, J=4.8, 14.0 Hz), 3.2-3.3 (m, 3H), 3.12 (dd, 1H, J=9.2, 14.0 Hz), 2.43 (ddd, 2H, J=4.2, 7.7, 11.4 Hz), 1.36 (br d, 1H, J=7.5 Hz), 1.0-1.0 (m, 1H)

253

Preparation of Example 169

N-((S)-1-(3-(4-chloro-1-methyl-3-(methylsulfonamido)-1H-indazol-7-yl)-7-(2,4-difluoro-3-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

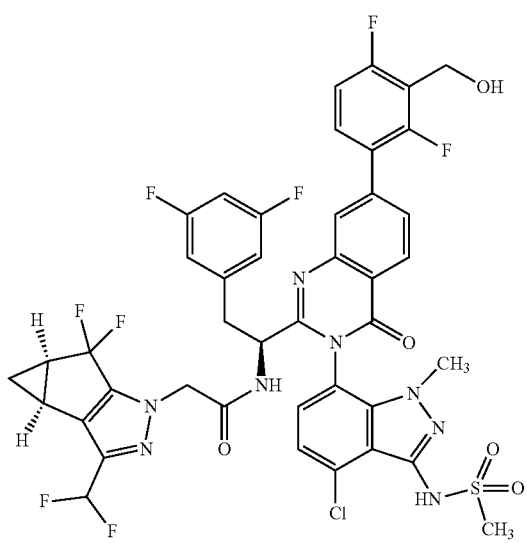 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5ccc(F)c(CO)c5F)ccc4c3=O)c21]

The title compound was prepared according to General Procedure D using (3-bromo-2,6-difluorophenyl)methanol as the coupling partner. The experiment afforded the title compound, N-((S)-1-(3-(4-chloro-1-methyl-3-(methylsulfonamido)-1H-indazol-7-yl)-7-(2,4-difluoro-3-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.4 min.; observed ion=947.2 (M+H). 1H NMR (METHANOL-d4, 500 MHz) Shift 8.38 (d, 1H, J=8.3 Hz), 8.07 (s, 1H), 7.84 (br d, 1H, J=8.3 Hz), 7.68 (br d, 1H, J=7.2 Hz), 7.32 (br d, 1H, J=7.7 Hz), 7.2-7.2 (m, 2H), 6.6-6.8 (m, 4H), 4.8-4.8 (m, 2H), 4.53 (br s, 2H), 3.71 (s, 2H), 3.64 (s, 3H), 3.5-3.5 (m, 1H), 3.2-3.3 (m, 3H), 3.12 (br s, 1H), 2.4-2.5 (m, 2H), 1.37 (br d, 1H, J=7.2 Hz), 1.01 (br s, 1H)

254

Preparation of Example 170

N-((S)-1-(3-(4-chloro-1-methyl-3-(methylsulfonamido)-1H-indazol-7-yl)-7-(3-cyano-2,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

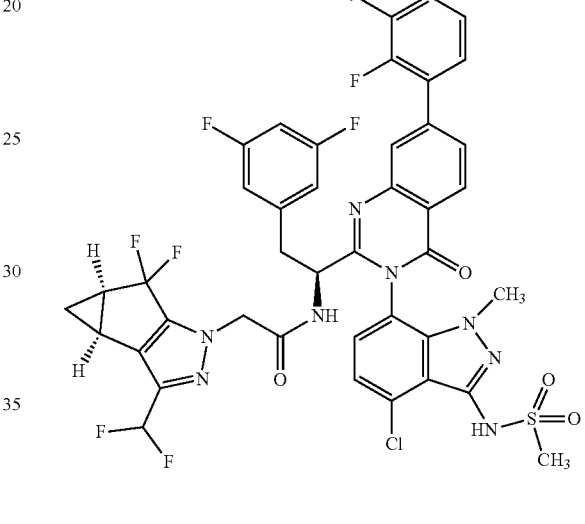

The title compound was prepared according to General Procedure D using 3-bromo-2,6-difluorobenzonitrile as the coupling partner. The experiment afforded the title compound, N-((S)-1-(3-(4-chloro-1-methyl-3-(methylsulfonamido)-1H-indazol-7-yl)-7-(3-cyano-2,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.51 min.; observed ion=940.2 (M−H). 1H NMR (METHANOL-d4, 500 MHz) Shift 8.42 (d, 1H, J=8.3 Hz), 8.1-8.1 (m, 2H), 7.85 (td, 1H, J=1.5, 8.3 Hz), 7.47 (t, 1H, J=8.3 Hz), 7.32 (d, 1H, J=7.7 Hz), 7.24 (d, 1H, J=7.7 Hz), 6.8-6.8 (m, 1H), 6.63 (dd, 2H, J=2.2, 8.2 Hz), 6.69 (br t, 2H, J=54.7 Hz), 4.53 (d, 2H, J=2.7 Hz), 3.64 (s, 3H), 3.5-3.5 (m, 1H), 3.26 (s, 3H), 3.12 (dd, 1H, J=9.4, 14.2 Hz), 2.4-2.5 (m, 2H), 1.37 (br d, 1H, J=7.5 Hz), 1.0-1.0 (m, 1H)

255
Preparation of Example 171

N-((S)-1-(3-(4-chloro-1-methyl-3-(methylsulfonamido)-1H-indazol-7-yl)-4-oxo-7-(2,4,5-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

256
Preparation of Example 172

N-((S)-1-(3-(4-chloro-1-methyl-3-(methylsulfonamido)-1H-indazol-7-yl)-4-oxo-7-(2,4,6-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

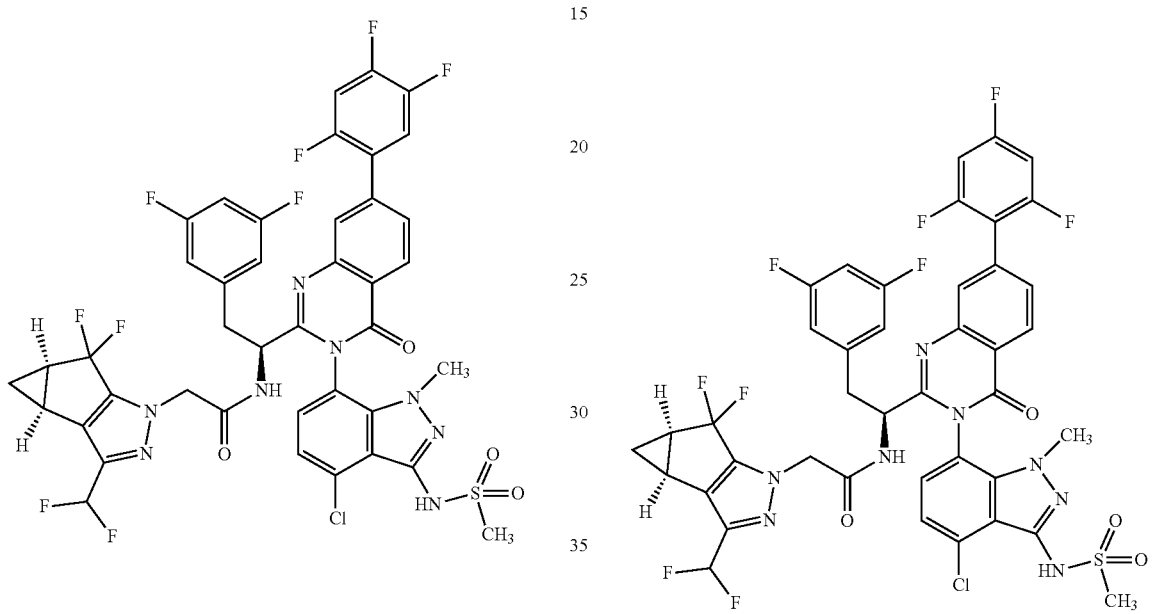

The title compound was prepared according to General Procedure D using 1-bromo-2,4,5-trifluorobenzene as the coupling partner. The experiment afforded the title compound, N-((S)-1-(3-(4-chloro-1-methyl-3-(methylsulfonamido)-1H-indazol-7-yl)-4-oxo-7-(2,4,5-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.58 min.; observed ion=933 (M−H). 1H NMR (METHANOL-d4, 500 MHz) Shift 8.39 (d, 1H, J=7.7 Hz), 8.08 (t, 1H, J=1.5 Hz), 7.84 (td, 1H, J=1.7, 8.2 Hz), 7.44 (br d, 1H, J=6.6 Hz), 7.32 (d, 1H, J=7.7 Hz), 7.23 (d, 1H, J=8.0 Hz), 6.8-6.8 (m, 1H), 6.63 (dd, 2H, J=2.4, 8.0 Hz), 6.69 (br t, 1H, J=54.8 Hz), 4.8-4.9 (m, 2H), 4.53 (d, 2H, J=3.6 Hz), 3.63 (s, 3H), 3.49 (dd, 1H, J=5.1, 14.3 Hz), 3.2-3.3 (m, 3H), 3.12 (dd, 1H, J=9.4, 14.2 Hz), 2.43 (dt, 2H, J=4.0, 7.5 Hz), 1.37 (br d, 1H, J=7.7 Hz), 1.01 (br dd, 1H, J=1.9, 3.4 Hz)

The title compound was prepared according to General Procedure D using 2-bromo-1,3,5-trifluorobenzene as the coupling partner. The experiment afforded the title compound, N-((S)-1-(3-(4-chloro-1-methyl-3-(methylsulfonamido)-1H-indazol-7-yl)-4-oxo-7-(2,4,6-trifluorophenyl)-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=935.1 (M+H). 1H NMR (METHANOL-d4, 500 MHz) Shift 8.39 (d, 1H, J=7.7 Hz), 7.99 (s, 1H), 7.74 (d, 1H, J=8.0 Hz), 7.33 (d, 1H, J=7.7 Hz), 7.25 (d, 1H, J=7.7 Hz), 7.13 (dd, 2H, J=8.0, 8.9 Hz), 6.8-6.8 (m, 1H), 6.6-6.7 (m, 2H), 6.69 (br t, 1H, J=54.7 Hz), 4.8-4.9 (m, 1H), 4.53 (d, 2H, J=4.5 Hz), 3.65 (s, 3H), 3.5-3.5 (m, 1H), 3.26 (s, 3H), 3.1-3.2 (m, 1H), 2.43 (ddd, 2H, J=4.0, 7.7, 11.3 Hz), 1.3-1.4 (m, 1H), 1.0-1.0 (m, 1H)

257

Preparation of Example 173

N-((S)-1-(3-(4-chloro-1-methyl-3-(methylsulfonamido)-1H-indazol-7-yl)-7-(3,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

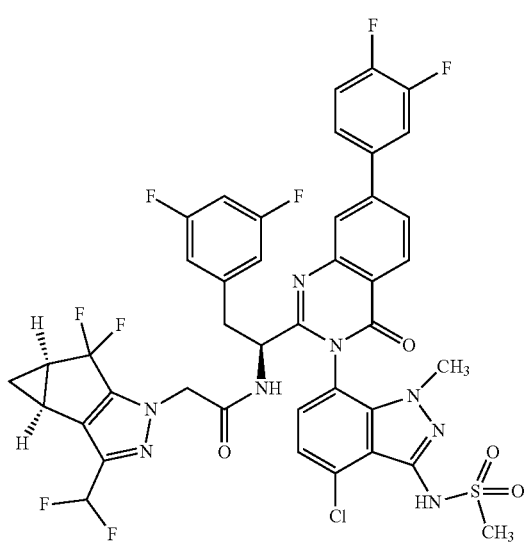 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5ccc(F)c(F)c5)ccc4c3=O)c21]

The title compound was prepared according to General Procedure D using 4-bromo-1,2-difluorobenzene as the coupling partner. The experiment afforded the title compound, N-((S)-1-(3-(4-chloro-1-methyl-3-(methylsulfonamido)-1H-indazol-7-yl)-7-(3,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.57 min.; observed ion=915.4 (M–H). 1H NMR (METHANOL-d4, 500 MHz) Shift 8.37 (d, 1H, J=8.6 Hz), 8.12 (d, 1H, J=1.5 Hz), 7.94 (dd, 1H, J=1.8, 8.3 Hz), 7.8-7.8 (m, 1H), 7.6-7.7 (m, 1H), 7.49 (td, 1H, J=8.6, 10.3 Hz), 7.31 (d, 1H, J=7.7 Hz), 7.21 (d, 1H, J=8.0 Hz), 6.8-6.8 (m, 1H), 6.64 (dd, 2H, J=2.2, 8.2 Hz), 6.70 (br t, 1H, J=54.8 Hz), 4.8-4.9 (m, 1H), 4.54 (d, 2H, J=2.4 Hz), 3.63 (s, 3H), 3.50 (dd, 1H, J=5.1, 14.0 Hz), 3.25 (s, 3H), 3.12 (dd, 1H, J=9.2, 14.0 Hz), 2.4-2.5 (m, 2H), 1.36 (br d, 1H, J=7.5 Hz), 1.01 (br dd, 1H, J=1.9, 3.4 Hz)

258

Preparation of Example 174

N-((S)-1-(3-(4-chloro-1-(2,2-difluoroethyl)-3-(methylsulfonamido)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

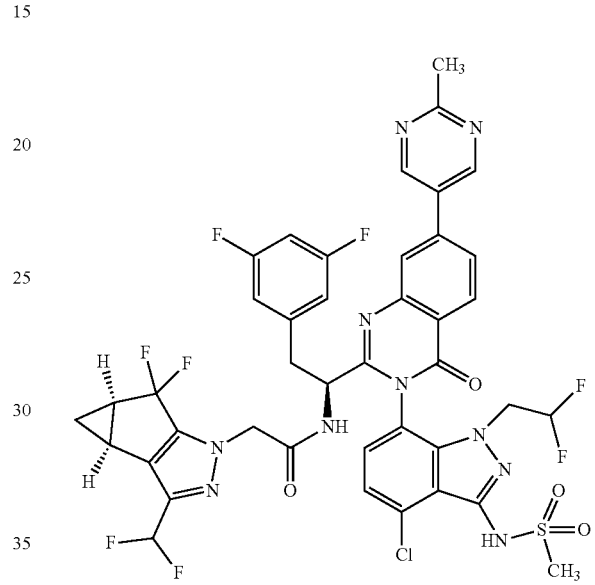

The title compound was prepared according to General Procedure I using 5-bromo-2-methylpyrimidine as the coupling partner. The experiment afforded the title compound, N-((S)-1-(3-(4-chloro-1-(2,2-difluoroethyl)-3-(methylsulfonamido)-1H-indazol-7-yl)-7-(2-methylpyrimidin-5-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.33 min.; observed ion=947.2 (M+H). 1H NMR (METHANOL-d4, 500 MHz) Shift 9.16 (s, 2H), 8.41 (d, 1H, J=8.2 Hz), 8.20 (d, 1H, J=1.5 Hz), 8.01 (dd, 1H, J=1.8, 8.3 Hz), 7.36 (d, 1H, J=8.0 Hz), 7.26 (d, 1H, J=8.0 Hz), 6.5-6.8 (m, 4H), 6.02 (br d, 1H, J=8.3 Hz), 6.02 (t, 1H, J=55.3 Hz), 4.74 (dd, 1H, J=4.9, 9.4 Hz), 4.6-4.7 (m, 2H), 4.3-4.4 (m, 1H), 3.92 (br dd, 1H, J=3.9, 14.9 Hz), 3.4-3.4 (m, 1H), 3.24 (s, 3H), 3.06 (dd, 1H, J=9.2, 14.0 Hz), 2.80 (s, 3H), 2.42 (ddd, 2H, J=4.2, 7.7, 11.4 Hz), 1.3-1.4 (m, 1H), 0.98 (td, 1H, J=2.1, 3.6 Hz)

Preparation of Example 175

N-((S)-1-(3-(4-chloro-1-(2,2-difluoroethyl)-3-(methylsulfonamido)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

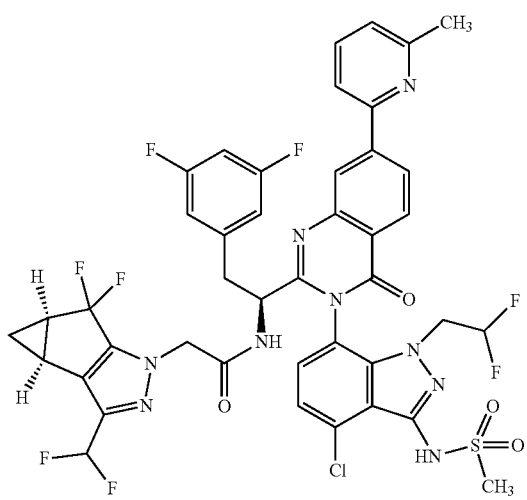 [SMILES: Cc1cccc(-c2ccc3c(=O)n(-c4ccc(Cl)c5c(NS(C)(=O)=O)nn(CC(F)F)c45)c([C@H](Cc4cc(F)cc(F)c4)NC(=O)Cn4nc(C(F)F)c5c4C(F)(F)[C@@H]4C[C@H]54)nc3c2)n1]

The title compound was prepared according to General Procedure I using 2-bromo-6-methylpyridine as the coupling partner. The experiment afforded the title compound, N-((S)-1-(3-(4-chloro-1-(2,2-difluoroethyl)-3-(methylsulfonamido)-1H-indazol-7-yl)-7-(6-methylpyridin-2-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.49 min.; observed ion=946.2 (M+H). 1H NMR (METHANOL-d4, 500 MHz) Shift 8.47 (d, 1H, J=1.2 Hz), 8.36 (d, 1H, J=8.1 Hz), 8.24 (dd, 1H, J=1.8, 8.3 Hz), 7.8-7.9 (m, 2H), 7.3-7.4 (m, 2H), 7.25 (d, 1H, J=8.0 Hz), 6.5-6.8 (m, 4H), 6.02 (br t, 1H, J=55.4 Hz), 4.75 (dd, 1H, J=4.9, 9.1 Hz), 4.6-4.6 (m, 2H), 4.3-4.4 (m, 1H), 3.9-4.0 (m, 1H), 3.4-3.4 (m, 1H), 3.23 (s, 3H), 3.07 (dd, 1H, J=9.1, 13.9 Hz), 2.67 (s, 3H), 2.4-2.5 (m, 2H), 1.33 (dt, 1H, J=5.5, 7.7 Hz), 0.99 (tdd, 1H, J=1.9, 3.7, 5.6 Hz)

Preparation of Example 176

N-((S)-1-(3-(4-chloro-1-(2,2-difluoroethyl)-3-(methylsulfonamido)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

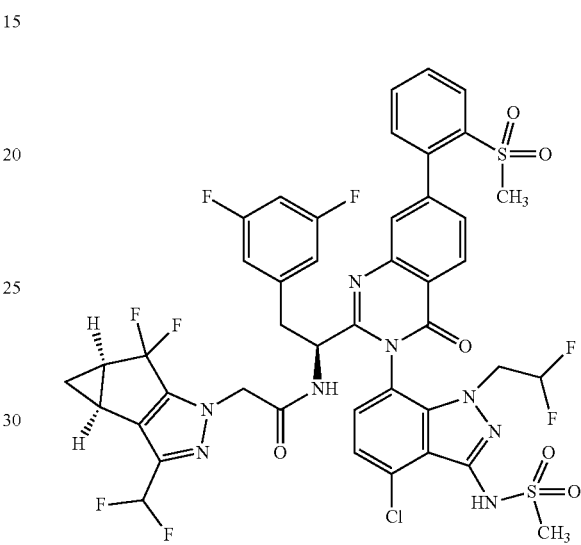

The title compound was prepared according to General Procedure I using 1-bromo-2-(methylsulfonyl)benzene as the coupling partner. The experiment afforded the title compound, N-((S)-1-(3-(4-chloro-1-(2,2-difluoroethyl)-3-(methylsulfonamido)-1H-indazol-7-yl)-7-(2-(methylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.41 min.; observed ion=1009.3 (M+H). 1H NMR (METHANOL-d4, 500 MHz) δ8.33 (d, 1H, J=8.0 Hz), 8.25 (dd, 1H, J=1.2, 8.0 Hz), 7.95 (d, 1H, J=1.8 Hz), 7.8-7.9 (m, 1H), 7.75 (dt, 1H, J=1.5, 7.7 Hz), 7.70 (dd, 1H, J=1.6, 8.2 Hz), 7.55 (dd, 1H, J=1.2, 7.5 Hz), 7.37 (d, 1H, J=7.7 Hz), 7.29 (d, 1H, J=7.7 Hz), 6.5-6.8 (m, 4H), 6.04 (br d, 1H, J=8.3 Hz), 6.04 (t, 1H, J=55.3 Hz), 5.92 (s, 1H), 4.75 (dd, 1H, J=4.8, 9.2 Hz), 4.5-4.6 (m, 2H), 4.3-4.4 (m, 1H), 3.9-4.0 (m, 1H), 3.24 (s, 3H), 3.05 (dd, 1H, J=9.2, 14.0 Hz), 2.87 (s, 3H), 2.4-2.4 (m, 2H), 1.3-1.4 (m, 1H), 1.0-1.0 (m, 1H)

Preparation of Example 177

N-((S)-1-(3-(4-chloro-1-(2,2-difluoroethyl)-3-(methylsulfonamido)-1H-indazol-7-yl)-7-(2-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

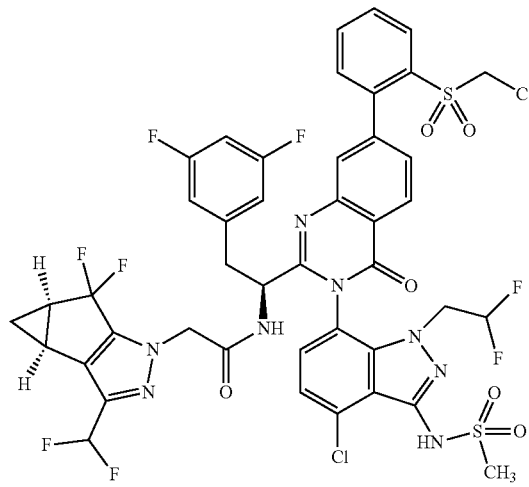 [SMILES: CS(=O)(=O)Nc1nn(CC(F)F)c2c(-n3c([C@H](Cc4cc(F)cc(F)c4)NC(=O)Cn4nc(C(F)F)c5c4C(F)(F)[C@@H]4C[C@H]54)nc4cc(-c5ccccc5S(C)(=O)=O)ccc4c3=O)ccc(Cl)c12]

The title compound was prepared according to General Procedure I using 1-bromo-2-(ethylsulfonyl)benzene as the coupling partner. The experiment afforded the title compound, N-((S)-1-(3-(4-chloro-1-(2,2-difluoroethyl)-3-(methylsulfonamido)-1H-indazol-7-yl)-7-(2-(ethylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.44 min.; observed ion=1023.1 (M+H). 1H NMR (METHANOL-d4, 500 MHz) Shift 8.32 (d, 1H, J=8.1 Hz), 8.22 (dd, 1H, J=0.9, 8.0 Hz), 7.93 (s, 1H), 7.8-7.9 (m, 1H), 7.7-7.8 (m, 1H), 7.6-7.7 (m, 1H), 7.5-7.6 (m, 1H), 7.38 (d, 1H, J=7.7 Hz), 7.29 (d, 1H, J=8.0 Hz), 6.5-6.8 (m, 4H), 6.04 (t, 1H, J=55.4 Hz), 4.7-4.8 (m, 1H), 4.5-4.6 (m, 2H), 4.3-4.4 (m, 1H), 3.95 (br dd, 1H, J=3.7, 15.1 Hz), 3.4-3.4 (m, 1H), 3.24 (s, 3H), 3.05 (dd, 1H, J=9.4, 14.2 Hz), 2.87 (q, 2H, J=7.5 Hz), 2.4-2.4 (m, 2H), 1.2-1.4 (m, 1H), 1.10 (t, 3H, J=7.5 Hz), 0.9-1.0 (m, 1H)

Preparation of Example 178

N-((S)-1-(3-(4-chloro-1-(2,2-difluoroethyl)-3-(methylsulfonamido)-1H-indazol-7-yl)-7-(2-(isopropylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

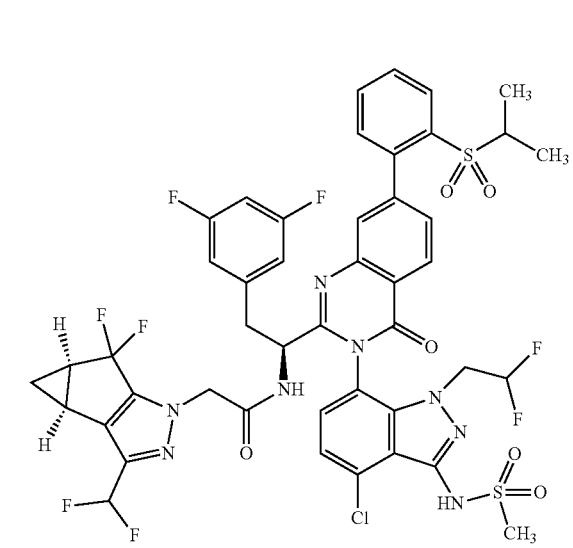 [SMILES: CC(C)S(=O)(=O)c1ccccc1-c1ccc2c(=O)n(-c3ccc(Cl)c4c(NS(C)(=O)=O)nn(CC(F)F)c34)c([C@H](Cc3cc(F)cc(F)c3)NC(=O)Cn3nc(C(F)F)c4c3C(F)(F)[C@@H]3C[C@H]43)nc2c1]

The title compound was prepared according to General Procedure I using 1-bromo-2-(isopropylsulfonyl)benzene as the coupling partner. The experiment afforded the title compound, N-((S)-1-(3-(4-chloro-1-(2,2-difluoroethyl)-3-(methylsulfonamido)-1H-indazol-7-yl)-7-(2-(isopropylsulfonyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.47 min.; observed ion=1037.2 (M+H). 1H NMR (METHANOL-d4, 500 MHz) Shift 8.31 (d, 1H, J=8.0 Hz), 8.20 (dd, 1H, J=1.3, 7.9 Hz), 7.92 (d, 1H, J=1.5 Hz), 7.85 (t, 1H, J=7.4 Hz), 7.76 (dt, 1H, J=1.5, 7.7 Hz), 7.68 (dd, 1H, J=1.6, 8.2 Hz), 7.56 (dd, 1H, J=1.3, 7.6 Hz), 7.37 (d, 1H, J=8.0 Hz), 7.28 (d, 1H, J=8.0 Hz), 6.5-6.8 (m, 4H), 6.04 (t, 1H, J=55.3 Hz), 4.76 (dd, 1H, J=4.8, 9.2 Hz), 4.6-4.6 (m, 2H), 4.3-4.4 (m, 1H), 3.9-4.0 (m, 1H), 3.41 (dd, 1H, J=4.8, 14.0 Hz), 3.24 (s, 3H), 3.05 (dd, 1H, J=9.4, 14.2 Hz), 2.8-2.8 (m, 1H), 2.4-2.4 (m, 2H), 1.3-1.4 (m, 1H), 1.11 (d, 3H, J=5.7 Hz), 1.10 (d, 3H, J=5.4 Hz), 1.0-1.0 (m, 1H)

263

Preparation of Example 179

N-((S)-1-(3-(4-chloro-1-methyl-3-(methylsulfonamido)-1H-indazol-7-yl)-7-(2-(hydroxymethyl)-4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

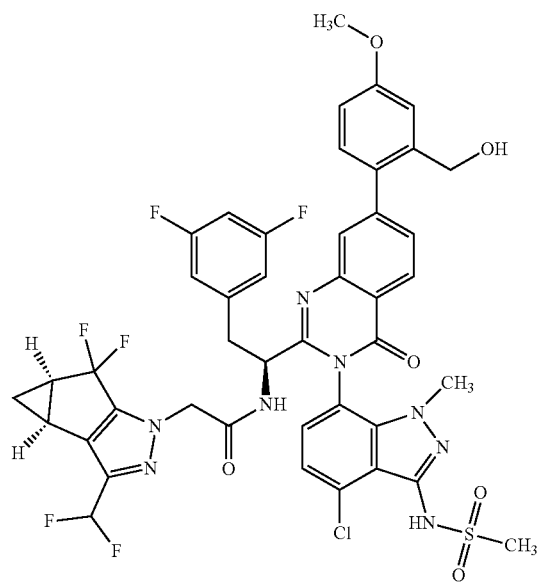 [SMILES: COc1ccc(-c2ccc3c(=O)n(-c4ccc(Cl)c5c(NS(C)(=O)=O)nn(C)c45)c([C@H](Cc4cc(F)cc(F)c4)NC(=O)Cn4nc(C(F)F)c5c4C(F)(F)[C@@H]4C[C@H]54)nc3c2)c(CO)c1]

The title compound was prepared according to General Procedure A using (2-(hydroxymethyl)-4-methoxyphenyl) boronic acid as the coupling partner. The experiment afforded the title compound, N-((S)-1-(3-(4-chloro-1-methyl-3-(methylsulfonamido)-1H-indazol-7-yl)-7-(2-(hydroxymethyl)-4-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.34 min.; observed ion=941.8 (M+H). 1H NMR (500 MHz, METHANOL-d4) δ ppm 8.32 (d, J=8.05 Hz, 1H), 7.89 (d, J=1.49 Hz, 1H), 7.68 (dd, J=8.20, 1.64 Hz, 1H), 7.35 (d, J=8.64 Hz, 1H), 7.29-7.33 (m, 1H), 7.26 (d, J=2.68 Hz, 1H), 7.21 (d, J=7.75 Hz, 1H), 7.03 (dd, J=8.34, 2.68 Hz, 1H), 6.54-6.82 (m, 4H), 4.87-4.90 (m, 1H), 4.62 (s, 2H), 4.54 (d, J=5.07 Hz, 2H), 3.92 (s, 3H), 3.64 (s, 3H), 3.45-3.51 (m, 1H), 3.25 (s, 3H), 3.11 (dd, J=14.01, 9.24 Hz, 1H), 2.38-2.47 (m, 2H), 1.33-1.41 (m, 1H), 0.98-1.06 (m, 1H).

264

Preparation of Example 180

N-((S)-1-(3-(4-chloro-1-methyl-3-(methylsulfonamido)-1H-indazol-7-yl)-7-(5-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl) acetamide

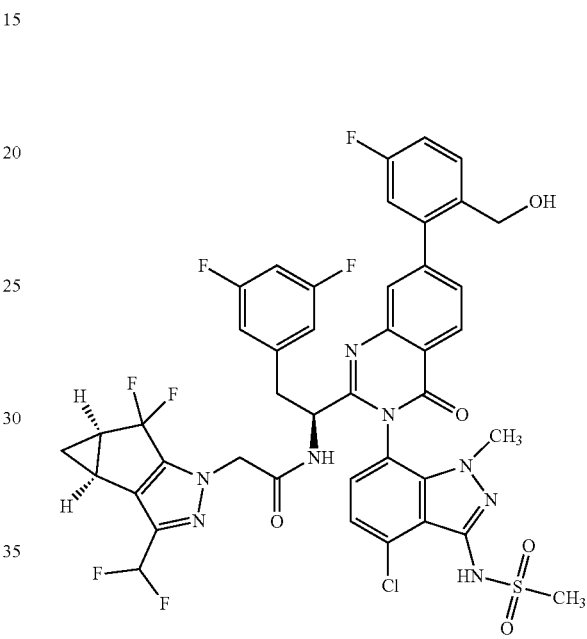

The title compound was prepared according to General Procedure A using (5-fluoro-2-(hydroxymethyl)phenyl)boronic acid as the coupling partner. The experiment afforded the title compound, N-((S)-1-(3-(4-chloro-1-methyl-3-(methylsulfonamido)-1H-indazol-7-yl)-7-(5-fluoro-2-(hydroxymethyl)phenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide.
The sample was analyzed using LCMS Method F: retention time=1.36 min.; observed ion=929.1 (M+H). 1H NMR (500 MHz, METHANOL-d4) δ ppm 8.37 (d, J=8.05 Hz, 1H), 7.94 (d, J=1.79 Hz, 1H), 7.64-7.74 (m, 2H), 7.32 (d, J=8.05 Hz, 1H), 7.15-7.28 (m, 3H), 6.52-6.84 (m, 4H), 4.87-4.90 (m, 1H), 4.58 (s, 2H), 4.54 (d, J=5.36 Hz, 2H), 3.65 (s, 3H), 3.46-3.51 (m, 1H), 3.26 (s, 3H), 3.08-3.15 (m, 1H), 2.37-2.49 (m, 2H), 1.33-1.41 (m, 1H), 0.97-1.04 (m, 1H)

Preparation of Example 181

N-((S)-1-(3-(4-chloro-1-methyl-3-(methylsulfonamido)-1H-indazol-7-yl)-7-(2-isopropoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

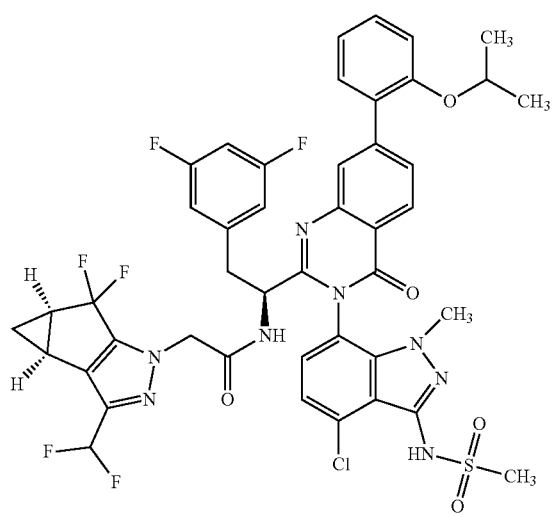 [SMILES: CC(C)Oc1ccccc1-c1ccc2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1]

The title compound was prepared according to General Procedure A using (2-isopropoxyphenyl)boronic acid as the coupling partner. The experiment afforded the title compound, N-((S)-1-(3-(4-chloro-1-methyl-3-(methylsulfonamido)-1H-indazol-7-yl)-7-(2-isopropoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.56 min.; observed ion=939.1 (M+H). 1H NMR (500 MHz, METHANOL-d4) δ ppm 8.29 (d, J=8.34 Hz, 1H), 8.03 (d, J=1.49 Hz, 1H), 7.84 (dd, J=8.34, 1.49 Hz, 1H), 7.41-7.50 (m, 2H), 7.31 (d, J=7.75 Hz, 1H), 7.19 (d, J=8.05 Hz, 2H), 7.12 (td, J=7.53, 1.04 Hz, 1H), 6.56-6.82 (m, 4H), 4.88-4.92 (m, 1H), 4.63-4.71 (m, 1H), 4.54 (s, 2H), 3.65 (s, 3H), 3.45-3.53 (m, 1H), 3.26 (s, 3H), 3.10 (dd, J=14.16, 9.09 Hz, 1H), 2.42 (ddd, J=11.25, 7.67, 4.02 Hz, 2H), 1.34-1.39 (m, 1H), 1.31 (dd, J=8.64, 5.96 Hz, 6H), 0.99-1.04 (m, 1H)

Preparation of Example 182

N-((S)-1-(3-(4-chloro-3-(methylsulfonamido)-1-(2,2,2-trifluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide

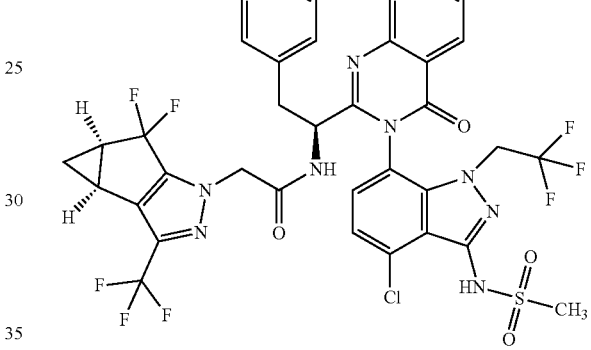

The title compound was prepared according to General Procedure A using (2-fluorophenyl)boronic acid as the coupling partner. The experiment afforded the title compound, N-((S)-1-(3-(4-chloro-3-(methylsulfonamido)-1-(2,2,2-trifluoroethyl)-1H-indazol-7-yl)-7-(2-fluorophenyl)-4-oxo-3,4-dihydroquinazolin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide. The sample was analyzed using LCMS Method G: retention time=3.46 min.; observed ion=985.1 (M+H). 1H NMR (500 MHz, METHANOL-d4) δ ppm 8.32 (d, J=8.34 Hz, 1H), 8.07 (t, J=1.34 Hz, 1H), 7.85 (dt, J=8.27, 1.53 Hz, 1H), 7.68 (td, J=7.75, 1.79 Hz, 1H), 7.49-7.55 (m, 1H), 7.44 (d, J=7.75 Hz, 1H), 7.38 (td, J=7.60, 1.19 Hz, 1H), 7.28-7.34 (m, 2H), 6.77 (tt, J=9.20, 2.27 Hz, 1H), 6.43-6.52 (m, 2H), 4.73-4.83 (m, 2H), 4.64-4.71 (m, 2H), 4.13-4.26 (m, 1H), 3.34-3.38 (m, 1H), 3.24 (s, 3H), 3.02 (dd, J=14.01, 9.54 Hz, 1H), 2.39-2.52 (m, 2H), 1.33-1.41 (m, 1H), 0.99-1.07 (m, 1H).

267

Preparation of Example 183

N-((S)-1-(3-(4-chloro-1-(2,2-difluoroethyl)-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

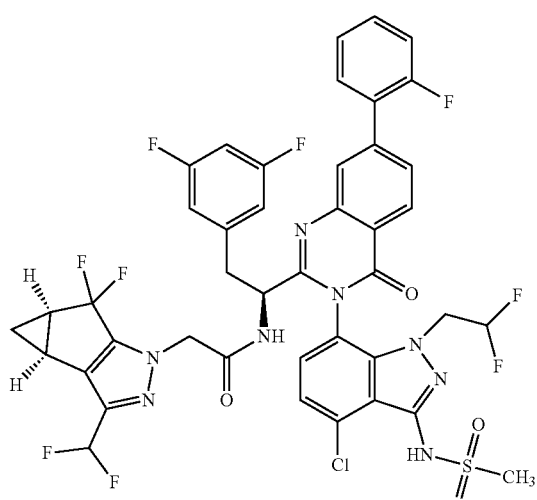

The title compound was prepared according to General Procedure A using (2-fluorophenyl)boronic acid as the coupling partner. The experiment afforded the title compound, N-((S)-1-(3-(4-chloro-1-(2,2-difluoroethyl)-3-(methylsulfonamido)-1H-indazol-7-yl)-7-(2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method G: retention time=3.36 min.; observed ion=949.1 (M+H). 1H NMR (500 MHz, METHANOL-d4) δ ppm 8.34 (d, J=8.35 Hz, 1H), 8.07 (t, J=1.34 Hz, 1H), 7.85 (dt, J=8.27, 1.53 Hz, 1H), 7.68 (td, J=7.82, 1.64 Hz, 1H), 7.47-7.55 (m, 1H), 7.35-7.40 (m, 2H), 7.26-7.34 (m, 2H), 6.50-6.81 (m, 4H), 5.88-6.16 (m, 1H), 4.74 (dd, J=9.24, 4.77 Hz, 1H), 4.54-4.68 (m, 2H), 4.39 (dtd, J=15.20, 13.26, 13.26, 4.17 Hz, 1H), 3.96 (dtd, J=15.05, 13.64, 13.64, 3.87 Hz, 1H), 3.41 (dd, J=14.01, 4.77 Hz, 1H), 3.25 (s, 3H), 3.07 (dd, J=14.16, 9.39 Hz, 1H), 2.34-2.45 (m, 2H), 1.31-1.37 (m, 1H), 0.93-1.02 (m, 1H).

268

Preparation of Example 184

N-((S)-1-(3-(4-chloro-1-methyl-3-(methylsulfonamido)-1H-indazol-7-yl)-7-(4-chloro-2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

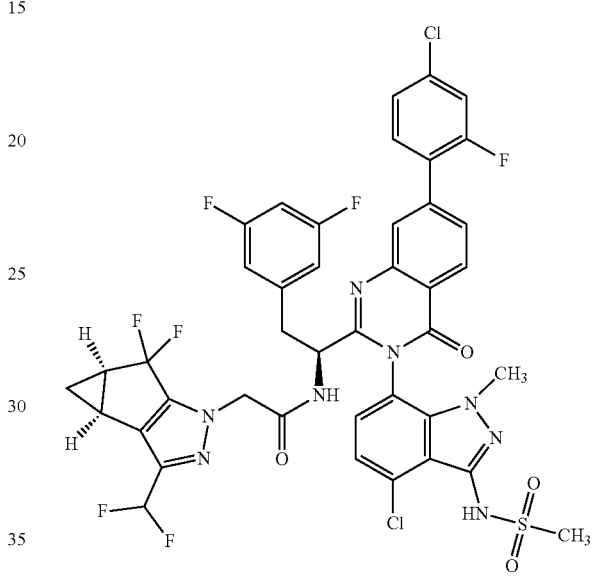

The title compound was prepared according to General Procedure A using (4-chloro-2-fluorophenyl)boronic acid as the coupling partner. The experiment afforded the title compound, N-((S)-1-(3-(4-chloro-1-methyl-3-(methylsulfonamido)-1H-indazol-7-yl)-7-(4-chloro-2-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. The sample was analyzed using LCMS Method F: retention time=1.59 min.; observed ion=933.2 (M+H). 1H NMR (500 MHz, METHANOL-d4) δ ppm 8.36 (d, J=8.34 Hz, 1H), 8.06 (t, J=1.49 Hz, 1H), 7.82 (dt, J=8.27, 1.53 Hz, 1H), 7.68 (t, J=8.49 Hz, 1H), 7.38-7.48 (m, 2H), 7.30 (d, J=7.75 Hz, 1H), 7.21 (d, J=7.75 Hz, 1H), 6.55-6.80 (m, 4H), 4.81-4.85 (m, 1H), 4.44-4.55 (m, 2H), 3.61 (s, 3H), 3.47 (dd, J=14.31, 5.07 Hz, 1H), 3.23 (s, 3H), 3.10 (dd, J=14.01, 9.24 Hz, 1H), 2.41 (ddd, J=11.33, 7.60, 4.02 Hz, 2H), 1.31-1.38 (m, 1H), 0.94-1.01 (m, 1H).

Preparation of Example 185

N-((S)-1-(3-(4-chloro-1-methyl-3-(methylsulfonamido)-1H-indazol-7-yl)-7-(2,6-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

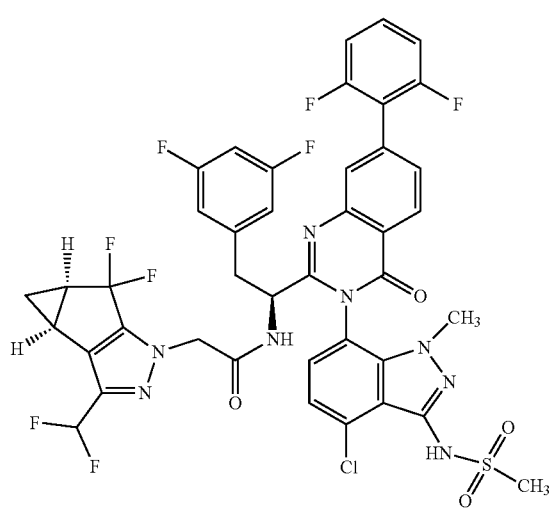 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5c(F)cccc5F)ccc4c3=O)c21]

The title compound was prepared according to General Procedure T using (2,6-difluorophenyl)boronic acid as the coupling partner. The experiment afforded the title compound, N-((S)-1-(3-(4-chloro-1-methyl-3-(methylsulfonamido)-1H-indazol-7-yl)-7-(2-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. $^1$H NMR (400 MHz, DMSO-$d_6$) δ=9.97-9.75 (m, 1H), 9.20-9.12 (m, 1H), 8.32 (d, J=8.1 Hz, 1H), 7.94-7.88 (m, 1H), 7.77-7.69 (m, 2H), 7.65-7.56 (m, 1H), 7.44 (d, J=7.8 Hz, 1H), 7.38-7.29 (m, 2H), 7.06-6.77 (m, 2H), 6.69-6.60 (m, 2H), 4.69-4.59 (m, 1H), 4.56-4.48 (m, 2H), 3.62-3.51 (m, 3H), 3.46-3.38 (m, 1H), 3.23-3.15 (m, 3H), 3.05-2.97 (m, 1H), 2.48-2.40 (m, 2H), 1.39-1.30 (m, 1H), 0.88-0.81 (m, 1H). LCMS: RT=6.49 min, (M+H)=917.0, LCMS Purity=99.73%, Chiral HPLC Purity=99.51%.

Preparation of Example 186

N-((S)-1-(3-(4-chloro-1-methyl-3-(methylsulfonamido)-1H-indazol-7-yl)-7-(2-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide The title compound was prepared according to General Procedure T using (2-methoxyphenyl)boronic acid as the coupling partner. The experiment afforded the title compound, N-((S)-1-(3-(4-chloro-1-methyl-3-(methylsulfonamido)-1H-indazol-7-yl)-7-(2-methoxyphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, DMSO-d6) δ=10.61-10.45 (m, 1H), 9.14-9.10 (m, 1H), 8.23 (d, J=8.1 Hz, 1H), 7.94-7.91 (m, 1H), 7.74 (dd, J=1.6, 8.2 Hz, 1H), 7.63-7.58 (m, 1H), 7.51-7.45 (m, 2H), 7.32-7.26 (m, 1H), 7.24-7.21 (m, 1H), 7.16-7.12 (m, 1H), 7.05-6.91 (m, 2H), 6.67-6.61 (m, 2H), 4.70-4.63 (m, 1H), 4.57-4.52 (m, 2H), 3.87-3.81 (m, 3H), 3.48-3.37 (m, 4H), 3.10-2.97 (m, 4H), 2.47-2.41 (m, 2H), 1.37-1.32 (m, 1H), 0.87-0.84 (m, 1H). LCMS: RT=6.55 min, (M+H)=911.10, LCMS Purity=99.34%, Chiral HPLC Purity=99.54%.

271

Preparation of Example 187

N-((S)-1-(3-(4-chloro-1-methyl-3-(methylsulfonamido)-1H-indazol-7-yl)-7-(2,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

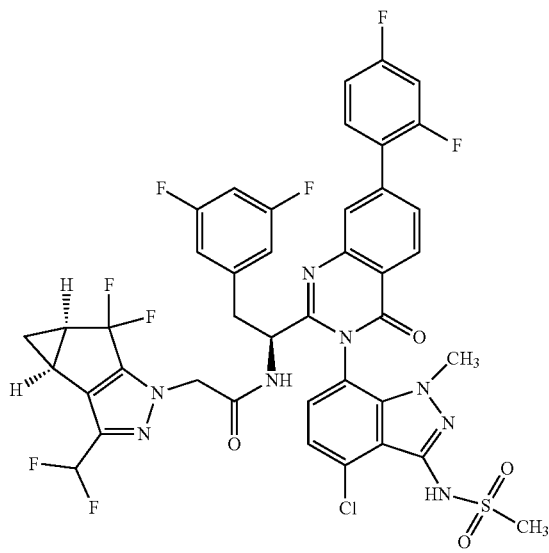 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5ccc(F)cc5F)ccc4c3=O)c21]

The title compound was prepared according to General Procedure T using (2,4-difluorophenyl)boronic acid as the coupling partner. The experiment afforded the title compound, N-((S)-1-(3-(4-chloro-1-methyl-3-(methylsulfonamido)-1H-indazol-7-yl)-7-(2,4-difluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, DMSO-d6) δ=10.06-9.86 (m, 1H), 9.13-9.07 (m, 1H), 8.30 (d, J=8.3 Hz, 1H), 7.96-7.93 (m, 1H), 7.85-7.77 (m, 2H), 7.66-7.61 (m, 1H), 7.54-7.45 (m, 1H), 7.36-7.27 (m, 2H), 7.07-6.84 (m, 2H), 6.76-6.60 (m, 2H), 4.69-4.50 (m, 3H), 3.51-3.37 (m, 4H), 3.13-2.97 (m, 4H), 2.47-2.38 (m, 2H), 1.38-1.30 (m, 1H), 0.88-0.82 (m, 1H). LCMS: RT=6.61 min, (M+H)=917.0, LCMS Purity=99%, Chiral HPLC Purity=98.52%.

272

Preparation of Example 188

N-((S)-1-(3-(4-chloro-1-methyl-3-(methylsulfonamido)-1H-indazol-7-yl)-7-(4-fluoro-2-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

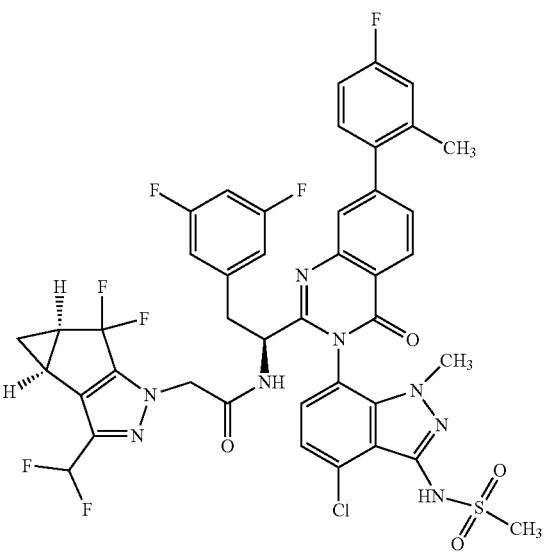 [SMILES: Cc1cc(F)ccc1-c1ccc2c(=O)n(-c3ccc(Cl)c4c(NS(C)(=O)=O)nn(C)c34)c([C@H](Cc3cc(F)cc(F)c3)NC(=O)Cn3nc(C(F)F)c4c3C(F)(F)[C@@H]3C[C@H]43)nc2c1]

The title compound was prepared according to General Procedure T using (4-fluoro-2-methylphenyl)boronic acid as the coupling partner. The experiment afforded the title compound, N-((S)-1-(3-(4-chloro-1-methyl-3-(methylsulfonamido)-1H-indazol-7-yl)-7-(4-fluoro-2-methylphenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, DMSO-d6) δ=9.87-9.78 (m, 1H), 9.16-9.12 (m, 1H), 8.29-8.25 (m, 1H), 7.73-7.69 (m, 2H), 7.64-7.61 (m, 1H), 7.44-7.36 (m, 2H), 7.30-7.25 (m, 1H), 7.22-7.17 (m, 1H), 7.05-6.90 (m, 2H), 6.69-6.63 (m, 2H), 4.68-4.62 (m, 1H), 4.56-4.49 (m, 2H), 3.54 (s, 3H), 3.45-3.40 (m, 1H), 3.21-3.15 (m, 3H), 3.06-2.99 (m, 1H), 2.47-2.42 (m, 2H), 2.33 (s, 3H), 1.37-1.32 (m, 1H), 0.87-0.82 (m, 1H). LCMS: RT=6.73 min, (M+H)=913.1, LCMS Purity=99.46%, Chiral HPLC Purity=99.55%.

Preparation of Example 189

(S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(pyrimidin-2-yl)-3,4-dihydroquinazolin-2-yl)-2-(3,5-difluorophenyl)ethyl)acetamide

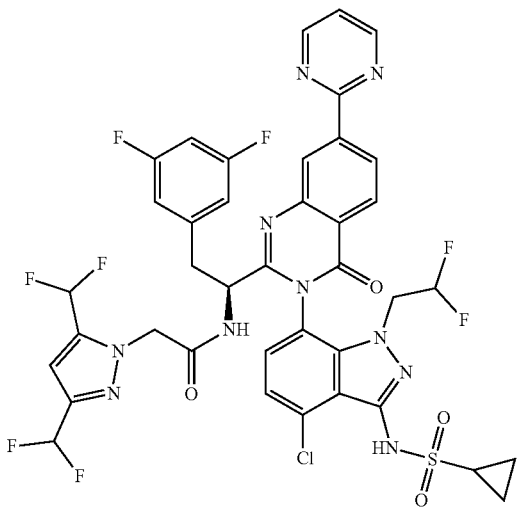 [SMILES: O=C(Cn1nc(C(F)F)cc1C(F)F)N[C@@H](Cc1cc(F)cc(F)c1)c1nc2cc(-c3ncccn3)ccc2c(=O)n1-c1ccc(Cl)c2c(NS(=O)(=O)C3CC3)nn(CC(F)F)c12]

The title compound was prepared according to General Procedure U using 2-bromopyrimidine as the coupling partner. The experiment afforded the title compound, (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(pyrimidin-2-yl)-3,4-dihydroquinazolin-2-yl)-2-(3,5-difluorophenyl)ethyl)acetamide. 1H NMR (400 MHz, MeOH-d4) δ=8.98 (d, J=4.8 Hz, 2H), 8.94 (d, J=1.5 Hz, 1H), 8.69 (dd, J=1.6, 8.4 Hz, 1H), 8.39 (d, J=8.8 Hz, 1H), 7.50 (t, J=4.9 Hz, 1H), 7.38 (d, J=7.9 Hz, 1H), 7.27 (d, J=7.9 Hz, 1H), 6.91-6.62 (m, 4H), 6.59-6.52 (m, 2H), 6.16-5.85 (m, 1H), 4.83 (m, 1H), 4.80-4.75 (m, 2H), 4.39-4.28 (m, 1H), 4.02-3.88 (m, 1H), 3.48-3.40 (m, 1H), 3.15-3.07 (m, 1H), 2.92-2.86 (m, 1H), 1.13-1.05 (m, 2H), 1.02-0.94 (m, 2H). LCMS: RT=2.64 mins, M+H=921.24, LCMS purity: 97.75%. HPLC Purity=99%, Chiral HPLC Purity=97.6%.

Preparation of Example 190

(S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(pyridin-2-yl)-3,4-dihydroquinazolin-2-yl)-2-(3,5-difluorophenyl)ethyl)acetamide

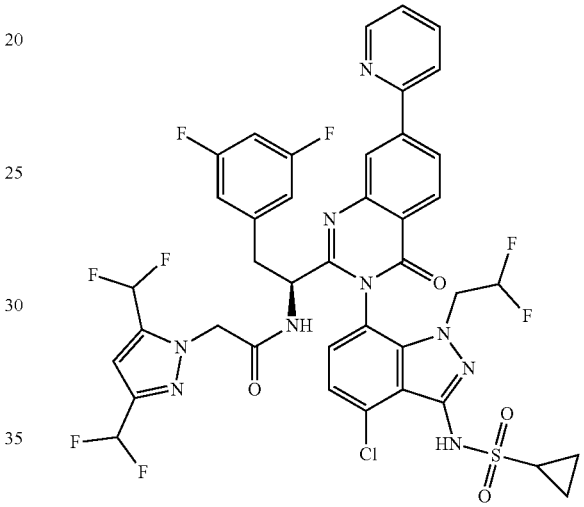

The title compound was prepared according to General Procedure U using 2-bromopyridine as the coupling partner. The experiment afforded the title compound, (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-4-oxo-7-(pyridin-2-yl)-3,4-dihydroquinazolin-2-yl)-2-(3,5-difluorophenyl)ethyl)acetamide. 1HNMR (400 MHz, MeOH-d4) δ=8.78-8.75 (m, 1H), 8.51-8.48 (m, 1H), 8.40-8.36 (m, 1H), 8.28-8.25 (m, 1H), 8.11-8.09 (m, 1H), 8.05-7.99 (m, 1H), 7.53-7.47 (m, 1H), 7.40-7.35 (m, 1H), 7.25-7.22 (m, 1H), 6.92-6.70 (m, 4H), 6.59-6.53 (m, 2H), 6.10-5.95 (m, 1H), 4.80-4.76 (m, 3H), 4.36-4.26 (m, 1H), 4.00-3.90 (m, 1H), 3.46-3.40 (m, 1H), 3.12-3.06 (m, 1H), 2.92-2.85 (m, 1H), 1.11-1.07 (m, 2H), 0.99-0.94 (m, 2H). LCMS: RT=2.67 min, M+H=920.24, LCMS Purity=97.5%. HPLC: Purity=98.1%, Chiral HPLC Purity=99.9%.

Preparation of Example 191

(S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-7-(3-methylpyrazin-2-yl)-4-oxo-3,4-dihydroquinazolin-2-yl)-2-(3,5-difluorophenyl)ethyl)acetamide

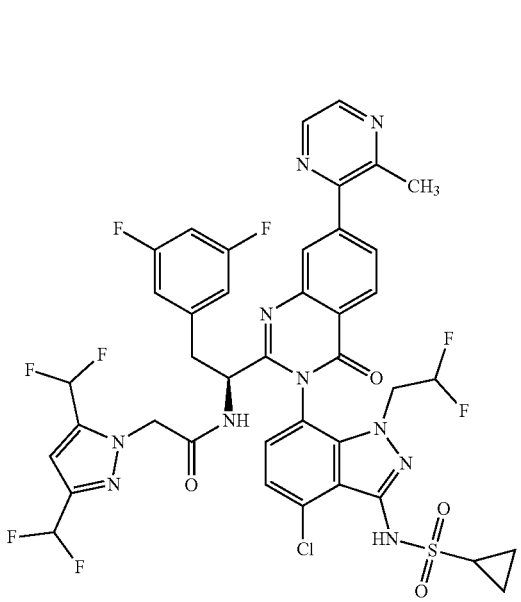 [SMILES: Cc1nccnc1-c1ccc2c(=O)n(-c3ccc(Cl)c4c(NS(=O)(=O)C5CC5)nn(CC(F)F)c34)c([C@H](Cc3cc(F)cc(F)c3)NC(=O)Cn3nc(C(F)F)cc3C(F)F)nc2c1]

The title compound was prepared according to General Procedure U using 2-chloro-3-methylpyrazine as the coupling partner. The experiment afforded the title compound, (S)-2-(3,5-bis(difluoromethyl)-1H-pyrazol-1-yl)-N-(1-(3-(4-chloro-3-(cyclopropanesulfonamido)-1-(2,2-difluoroethyl)-1H-indazol-7-yl)-7-(3-methylpyrazin-2-yl)-4-oxo-3,4-dihydroquinazolin-2-yl)-2-(3,5-difluorophenyl)ethyl)acetamide. 1HNMR (400 MHz, MeOH-d4) δ=8.63-8.60 (m, 2H), 8.42-8.39 (m, 1H), 8.12-8.10 (m, 1H), 7.90-7.88 (m, 1H), 7.41-7.37 (m, 1H), 7.29-7.26 (m, 1H), 6.84-6.70 (m, 4H), 6.57-6.53 (m, 2H), 6.06-5.97 (m, 1H), 4.80-4.79 (m, 1H), 4.78-4.74 (m, 2H), 4.37-4.31 (m, 1H), 4.00-3.94 (m, 1H), 3.44-3.40 (m, 1H), 3.11-3.06 (m, 1H), 2.92-2.87 (m, 1H), 2.70 (s, 3H), 1.12-1.07 (m, 2H), 1.00-0.96 (m, 2H). LCMS: RT=2.53 mins, M+H=935.21, LCMS Purity=98.4%. HPLC Purity=97.7%, Chiral HPLC Purity=99.6%.

Preparation of Example 192

N-((S)-1-(7-(4-(tert-butyl)phenyl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

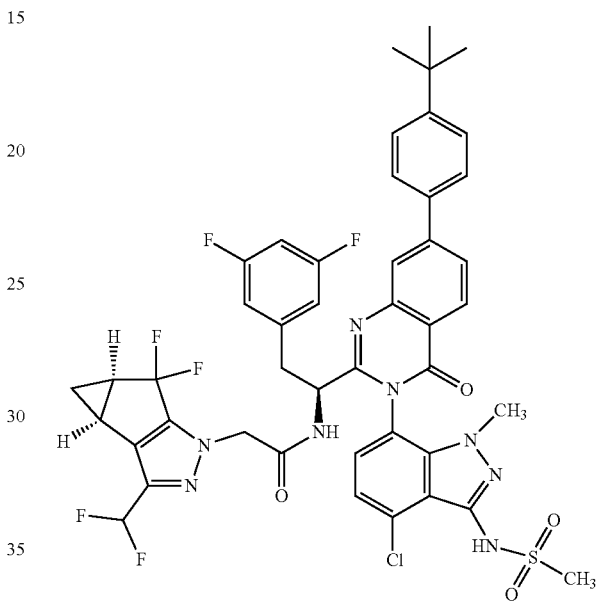

The title compound was prepared according to General Procedure T using (4-(tert-butyl)phenyl)boronic acid as the coupling partner. The experiment afforded the title compound, N-((S)-1-(7-(4-(tert-butyl)phenyl)-3-(4-chloro-1-methyl-3-(methylsulfonamido)-1H-indazol-7-yl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, DMSO-d6) δ=9.85-9.81 (m, 1H), 9.17-9.12 (m, 1H), 8.27 (d, J=8.3 Hz, 1H), 8.02 (d, J=1.5 Hz, 1H), 7.99-7.95 (m, 1H), 7.83-7.79 (m, 2H), 7.70 (d, J=7.9 Hz, 1H), 7.63-7.59 (m, 2H), 7.43 (d, J=7.9 Hz, 1H), 7.07-6.91 (m, 2H), 6.72-6.64 (m, 2H), 4.69-4.63 (m, 1H), 4.57-4.50 (m, 2H), 3.54 (s, 3H), 3.47-3.40 (m, 1H), 3.19 (s, 3H), 3.08-3.01 (m, 1H), 2.48-2.41 (m, 2H), 1.36 (s, 9H), 1.25-1.20 (m, 1H), 0.88-0.83 (m, 1H). LCMS: RT=7.26 min, (M+H)=937.1, LCMS Purity=99.26%, Chiral HPLC Purity=98.88%.

Preparation of Example 193

N-((S)-1-(3-(4-chloro-1-methyl-3-(methylsulfonamido)-1H-indazol-7-yl)-7-(4-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

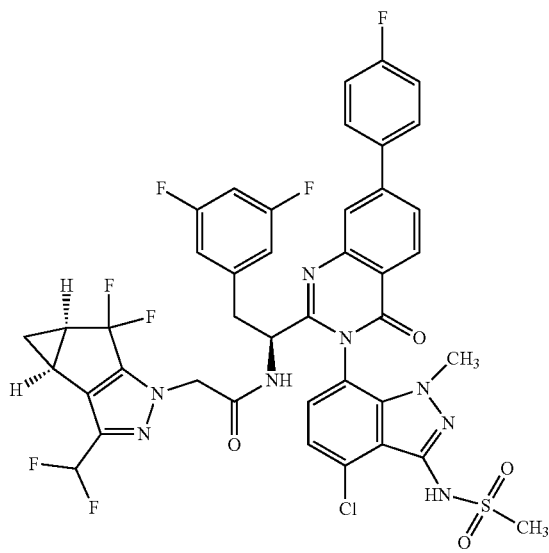 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5ccc(F)cc5)ccc4c3=O)c21]

The title compound was prepared according to General Procedure T using (4-fluorophenyl)boronic acid as the coupling partner. The experiment afforded the title compound, N-((S)-1-(3-(4-chloro-1-methyl-3-(methylsulfonamido)-1H-indazol-7-yl)-7-(4-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, METHANOL-d4) δ=8.36-8.32 (m, 1H), 8.08 (d, J=1.5 Hz, 1H), 7.94-7.89 (m, 1H), 7.88-7.81 (m, 2H), 7.33-7.26 (m, 3H), 7.18 (d, J=7.9 Hz, 1H), 6.82-6.54 (m, 4H), 4.88-4.83 (m, 1H), 4.54-4.49 (m, 2H), 3.65-3.59 (m, 3H), 3.51-3.43 (m, 1H), 3.26-3.21 (m, 3H), 3.13-3.05 (m, 1H), 2.45-2.36 (m, 2H), 1.39-1.32 (m, 1H), 1.01-0.96 (m, 1H). LCMS: RT=6.56 min, (M+H)=899.0, LCMS Purity=98.05%, Chiral HPLC Purity=99.56%.

Preparation of Example 194

N-((S)-1-(3-(4-chloro-1-methyl-3-(methylsulfonamido)-1H-indazol-7-yl)-7-(4-chloro-3-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

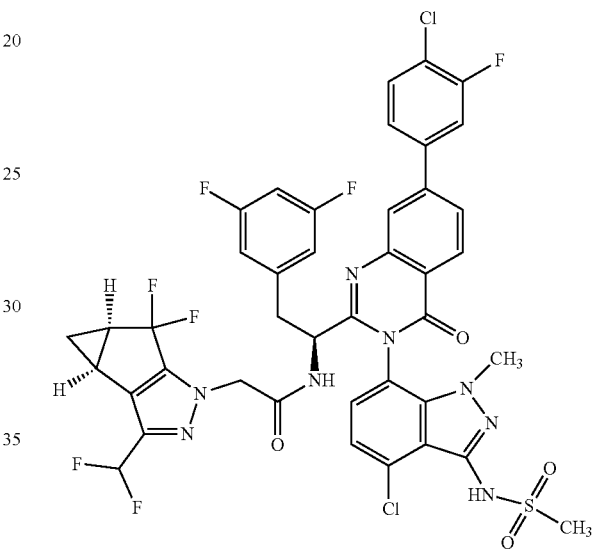

The title compound was prepared according to General Procedure T using (4-chloro-3-fluorophenyl)boronic acid as the coupling partner. The experiment afforded the title compound, N-((S)-1-(3-(4-chloro-1-methyl-3-(methylsulfonamido)-1H-indazol-7-yl)-7-(4-chloro-3-fluorophenyl)-4-oxo-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, DMSO-d6) δ=9.89-9.79 (m, 1H), 9.08-9.05 (m, 1H), 8.31-8.28 (m, 1H), 8.06 (d, J=1.5 Hz, 1H), 8.01-7.95 (m, 2H), 7.82-7.75 (m, 2H), 7.65-7.60 (m, 1H), 7.37-7.31 (m, 1H), 7.07-6.99 (m, 2H), 6.71-6.65 (m, 2H), 4.65-4.54 (m, 3H), 3.52-3.45 (m, 4H), 3.16-3.04 (m, 4H), 2.46-2.39 (m, 2H), 1.38-1.33 (m, 1H), 0.87-0.84 (m, 1H). LCMS: RT=6.86 min, (M+H)=933.0, LCMS Purity=99.37%, Chiral HPLC Purity=96.95%.

Preparation of Example 195

N-((S)-1-(3-(4-chloro-1-methyl-3-(methylsulfonamido)-1H-indazol-7-yl)-4-oxo-7-phenyl-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide

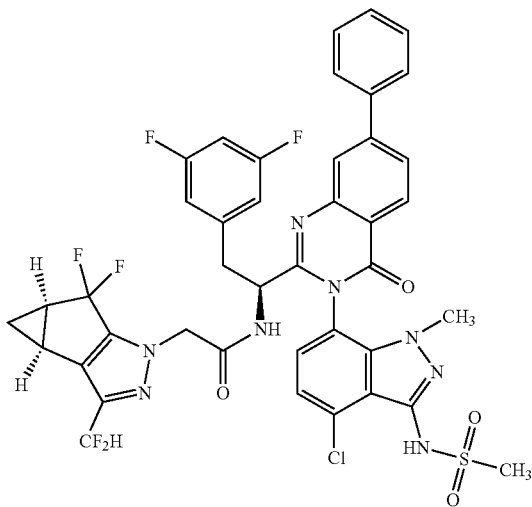 [SMILES: Cn1nc(NS(C)(=O)=O)c2c(Cl)ccc(-n3c([C@H](Cc4cc(F)cc(F)c4)NC(=O)Cn4nc(C(F)F)c5c4C(F)(F)[C@@H]4C[C@H]54)nc4cc(-c5ccccc5)ccc4c3=O)c21]

The title compound was prepared according to General Procedure T using phenylboronic acid as the coupling partner. The experiment afforded the title compound, N-((S)-1-(3-(4-chloro-1-methyl-3-(methylsulfonamido)-1H-indazol-7-yl)-4-oxo-7-phenyl-3,4-dihydroquinazolin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide. 1H NMR (400 MHz, METHANOL-d4) δ=8.36-8.33 (m, 1H), 8.12-8.09 (m, 1H), 7.96-7.92 (m, 1H), 7.83-7.79 (m, 2H), 7.59-7.54 (m, 2H), 7.52-7.46 (m, 1H), 7.31-7.29 (m, 1H), 7.21-7.17 (m, 1H), 6.80-6.59 (m, 4H), 4.88-4.84 (m, 1H), 4.57-4.51 (m, 2H), 3.64-3.59 (m, 3H), 3.50-3.45 (m, 1H), 3.26-3.23 (m, 3H), 3.14-3.07 (m, 1H), 2.44-2.37 (m, 2H), 1.36-1.31 (m, 1H), 1.01-0.96 (m, 1H). LCMS: RT=6.53 min, (M+H)=881.1, LCMS Purity=99.50%, Chiral HPLC Purity=96.56%.

Biological Methods

HIV cell culture assay—MT-2 cells, 293T cells and the proviral DNA clone of $NL_{4-3}$ virus were obtained from the NIH AIDS Research and Reference Reagent Program. MT-2 cells were propagated in RPMI 1640 media supplemented with 10% heat inactivated fetal bovine serum (FBS), 100 μg/ml penicillin G and up to 100 units/mL streptomycin. The 293T cells were propagated in DMEM media supplemented with 10% heat inactivated FBS, 100 μg/mL penicillin G and 100 μg/mL streptomycin. A recombinant $NL_{4-3}$ proviral clone, in which a section of the nef gene was replaced with the Renilla luciferase gene, was used to make the reference virus used in these studies. The recombinant virus was prepared through transfection of the recombinant $NL_{4-3}$ proviral clone into 293T cells using Transit-293 Transfection Reagent from Mirus Bio LLC (Madison, Wis.). Supernatent was harvested after 2-3 days and the amount of virus present was titered in MT-2 cells using luciferase enzyme activity as a marker by measuring luciferase enzyme activity. Luciferase was quantitated using the EnduRen Live Cell Substrate from Promega (Madison, Wis.). Antiviral activities of compounds toward the recombinant virus were quantified by measuring luciferase activity in MT-2 cells infected for 4-5 days with the recombinant virus in the presence of serial dilutions of the compound.

The 50% effective concentration ($EC_{50}$) was calculated by using the exponential form of the median effect equation where $(Fa)=1/[1+(ED_{50}/drug\ conc.)^m]$ (Johnson VA, Byington RT. Infectivity Assay. In Techniques in HIV Research. ed. Aldovini A, Walker BD. 71-76. New York: Stockton Press. 1990). Curve fitting and analysis were performed with ActivityBase XE Runner software version 9.1.0.4 using model 203 (ID Business Solutions, LTD, Guildford, UK).

Compound cytotoxicity and the corresponding $CC_{50}$ values were determined using the same protocol as described in the antiviral assay except that uninfected cells were used. Cytotoxicity was assessed on day 4 in uninfected MT2 cells by using a XTT (2,3-bis[2-Methoxy-4-nitro-5-sulfophenyl]-2H-tetrazolium-5-carboxyanilide inner salt)-based colorimetric assay (Sigma-Aldrich, St Louis, Mo.).

| Example | $EC_{50}$ nM | $CC_{50}$ μM |
|---|---|---|
| Example 1 | 209.1 | >1 |
| Example 2 | 0.53 | >1 |
| Example 3 | 63.1 | >1 |
| Example 4 | 1.1 | >1 |
| Example 5 | 62.7 | >1 |
| Example 6 | 0.30 | >1 |
| Example 7 | 4125.7 | >1 |
| Example 8 | 0.613 | >1 |
| Example 9 | 4.6 | >1 |
| Example 12 | 8.3 | >1 |
| Example 14 | 9.8 | >1 |
| Example 15 | 43 | >1 |
| Example 17 | 9.7 | >1 |
| Example 18 | 0.34 | >1 |
| Example 19 | 8.9 | >1 |
| Example 20 | 3.7 | >1 |
| Example 22 | 7.9 | >1 |
| Example 24 | 4.3 | >1 |
| Example 25 | 0.25 | >1 |
| Example 26 | 0.72 | >1 |
| Example 27 | 5.8 | >1 |
| Example 28 | 3.2 | >1 |
| Example 29 | 2.9 | >1 |
| Example 30 | 0.88 | >1 |
| Example 31 | 4.7 | >1 |
| Example 32 | 5.8 | >1 |
| Example 34 | 0.46 | >1 |
| Example 37 | 8.8 | >1 |
| Example 38 | 10 | >1 |
| Example 39 | 0.052 | >1 |
| Example 40 | 0.025 | >1 |
| Example 41 | 4.5 | >1 |
| Example 42 | 54 | >1 |
| Example 43 | 0.69 | >1 |
| Example 44 | 0.12 | >1 |
| Example 45 | 4.5 | >1 |
| Example 46 | 0.56 | >1 |
| Example 49 | 30 | >1 |
| Example 50 | 70 | >1 |
| Example 51 | 3.3 | >1 |
| Example 53 | 2.1 | >1 |
| Example 54 | 0.21 | >1 |
| Example 55 | 8.7 | >1 |
| Example 57 | 17 | >1 |
| Example 58 | 0.34 | >1 |
| Example 59 | 5.3 | >1 |
| Example 60 | 0.32 | >1 |
| Example 62 | 0.48 | >1 |

-continued

| Example | EC$_{50}$ nM | CC$_{50}$ μM |
|---|---|---|
| Example 63 | 7.0 | >1 |
| Example 68 | 0.63 | >1 |
| Example 69 | 1.0 | >1 |
| Example 70 | 0.92 | >1 |
| Example 71 | 0.18 | >1 |
| Example 74 | 16 | >1 |
| Example 75 | 29 | >1 |
| Example 77 | 4.2 | >1 |
| Example 78 | 0.12 | >1 |
| Example 80 | 8.0 | >1 |
| Example 81 | 56 | >1 |
| Example 82 | 7.0 | >1 |
| Example 83 | 5.0 | >1 |
| Example 84 | 0.068 | >1 |
| Example 86 | 0.50 | >1 |
| Example 87 | 0.090 | >1 |
| Example 88 | 0.73 | >1 |
| Example 89 | 3.4 | >1 |
| Example 90 | 5.7 | >1 |
| Example 91 | 0.39 | >1 |
| Example 94 | 0.44 | >1 |
| Example 96 | 0.076 | >1 |
| Example 97 | 0.40 | >1 |
| Example 98 | 0.39 | >1 |
| Example 99 | 0.68 | >1 |
| Example 100 | 6.5 | >1 |
| Example 101 | 62 | >1 |
| Example 102 | 48 | >1 |
| Example 103 | 0.88 | >1 |
| Example 104 | 0.68 | >1 |
| Example 105 | 0.34 | >1 |
| Example 107 | 10 | >1 |
| Example 108 | 0.78 | >1 |
| Example 109 | 0.11 | >1 |
| Example 112 | 4.0 | >1 |
| Example 114 | 15 | >1 |
| Example 115 | 0.469 | >10 |
| Example 116 | 0.14 | >0.5 |
| Example 117 | 0.058 | >0.5 |
| Example 118 | 0.16 | >0.5 |
| Example 119 | 0.100 | >0.5 |
| Example 120 | 0.13 | >0.5 |
| Example 121 | 0.11 | >0.5 |
| Example 122 | 0.17 | >0.5 |
| Example 123 | 0.15 | >0.5 |
| Example 124 | 0.058 | >0.5 |
| Example 125 | 0.054 | >0.5 |
| Example 126 | 0.052 | >0.5 |
| Example 127 | 0.059 | >0.5 |
| Example 128 | 0.069 | >0.5 |
| Example 129 | 0.095 | >0.5 |
| Example 130 | 0.030 | >0.5 |
| Example 131 | 0.11 | >0.5 |
| Example 133 | 1.6 | >0.5 |
| Example 134 | 10 | >1 |
| Example 135 | 13 | >1 |
| Example 136 | 9.5 | >1 |
| Example 137 | 8.4 | >1 |
| Example 138 | 9.0 | >0.5 |
| Example 139 | 0.57 | >0.5 |
| Example 140 | 0.35 | >0.5 |
| Example 141 | 0.11 | >0.5 |
| Example 142 | 66 | >1 |
| Example 143 | 42 | >1 |
| Example 144 | 16 | >0.5 |
| Example 145 | 16 | >0.5 |
| Example 146 | 69 | >0.5 |
| Example 147 | 121 | >1 |
| Example 148 | 71 | >0.5 |
| Example 149 | 8.1 | >1 |
| Example 150 | 11 | >0.5 |
| Example 154 | 4.8 | >1 |
| Example 155 | 0.76 | >1 |
| Example 156 | 0.79 | >0.5 |
| Example 157 | 0.060 | >0.5 |
| Example 158 | 0.14 | >0.5 |
| Example 159 | 0.10 | >0.5 |

-continued

| Example | EC$_{50}$ nM | CC$_{50}$ μM |
|---|---|---|
| Example 160 | 0.082 | >0.5 |
| Example 161 | 0.12 | >0.5 |
| Example 162 | 0.059 | >0.5 |
| Example 163 | 0.046 | >0.5 |
| Example 164 | 0.096 | >0.5 |
| Example 165 | 0.050 | >0.5 |
| Example 166 | 0.037 | >0.5 |
| Example 167 | 0.080 | >0.5 |
| Example 168 | 0.70 | >0.5 |
| Example 170 | 0.58 | >0.5 |
| Example 171 | 0.48 | |
| Example 172 | 0.25 | >0.5 |
| Example 173 | 0.68 | >0.5 |
| Example 174 | 0.033 | >0.5 |
| Example 175 | 0.080 | >0.5 |
| Example 176 | 0.066 | >0.5 |
| Example 177 | 0.053 | >0.5 |
| Example 178 | 0.065 | >0.5 |
| Example 179 | 0.235 | >0.5 |
| Example 180 | 0.20 | >0.5 |
| Example 181 | 0.71 | >0.5 |
| Example 182 | 0.87 | >0.5 |
| Example 183 | 0.39 | >0.5 |
| Example 184 | 1.8 | >0.5 |
| Example 185 | 0.62 | >1 |
| Example 186 | 2.4 | >1 |
| Example 187 | 0.28 | >1 |
| Example 188 | 1.7 | >1 |
| Example 189 | 1.3 | >0.5 |
| Example 190 | 2.1 | >0.5 |
| Example 191 | 1.5 | >0.5 |
| Example 192 | 5.1 | >1 |
| Example 193 | 0.95 | >1 |
| Example 194 | 7.7 | >1 |
| Example 195 | 0.36 | >1 |

The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

What is claimed is:

1. A compound of Formula III, or a pharmaceutically acceptable salt thereof:

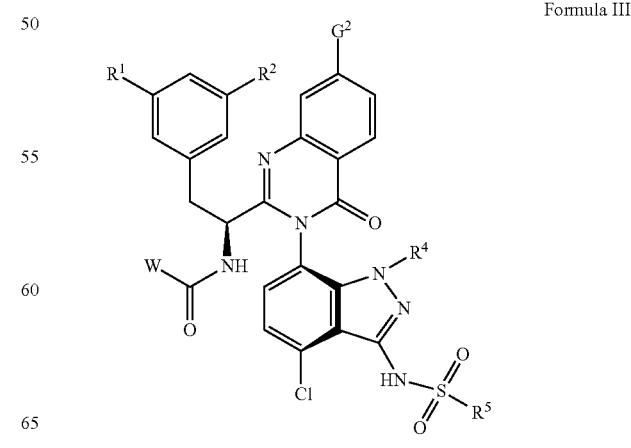

Formula III wherein:
each $R^1$ and $R^2$ is independently H, F, or Cl;
$G^2$ is selected from:

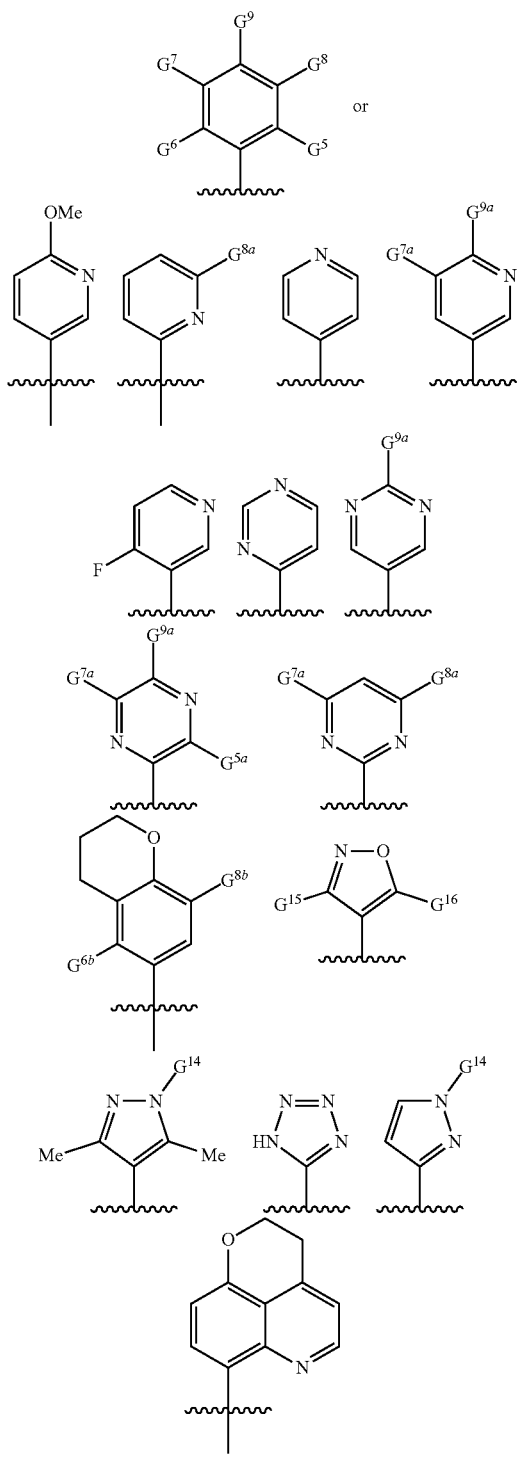

$G^5$ is hydrogen, methyl, fluoro, chloro, phenyl, $OC_1$-$C_3$alkyl, cyano, —$CH_2OH$, OPh, or —$SO_2(C_1$-$C_3$alkyl);
$G^{5a}$ is hydrogen or methyl;
$G^6$ is hydrogen, methyl, fluoro, chloro, phenyl, $OC_1$-$C_3$alkyl, or OPh;
$G^{6b}$ is hydrogen or methyl;
$G^7$ is hydrogen, methyl, fluoro, chloro, phenyl, $OC_1$-$C_3$alkyl, OPh, COOH, or CON($G^{10}$)($G^{11}$);
$G^{7a}$ is hydrogen, methyl, or fluoro;
$G^8$ is hydrogen, $C_1$-$C_4$ alkyl, fluoro, chloro, phenyl, O $C_1$-$C_3$alkyl, OPh, COOH, cyano, —$CH_2OH$, —$SO_2$($C_1$-$C_3$alkyl) or CON($G^{10}$)($G^{11}$);
$G^{8a}$ is hydrogen, methyl or $OC_1$-$C_3$alkyl;
$G^{8b}$ is hydrogen or fluoro;
$G^9$ is hydrogen, $C_1$-$C_4$ alkyl, fluoro, chloro, phenyl, $OC_1$-$C_3$alkyl, OPh, COOH, CON($G^{10}$)($G^{11}$), C($CH_3$)$_2$ $CH_2OH$, or —$SO_2$-morpholine wherein methyl is optionally substituted with 1-3 fluorines;
$G^{9a}$ is hydrogen, $C_1$-$C_4$alkyl, or fluoro;
$G^{10}$ is hydrogen or methyl;
$G^{11}$ is hydrogen or methyl;
or $G^{10}$ and $G^{11}$ are joined together form a piperidine
$G^{12}$ is hydrogen or $C_1$-$C_3$alkyl;
$G^{13}$ is hydrogen or $C_1$-$C_3$alkyl;
$G^{14}$ is hydrogen or $C_1$-$C_3$alkyl;
$G^{15}$ is hydrogen or $C_1$-$C_3$alkyl;
$G^{16}$ is hydrogen or $C_1$-$C_3$alkyl;
$R^4$ is methyl, 2,2-difluoroethyl, or 2,2,2-trifluoroethyl; $R^5$ is methyl or cyclopropyl;
and W is one of the following:

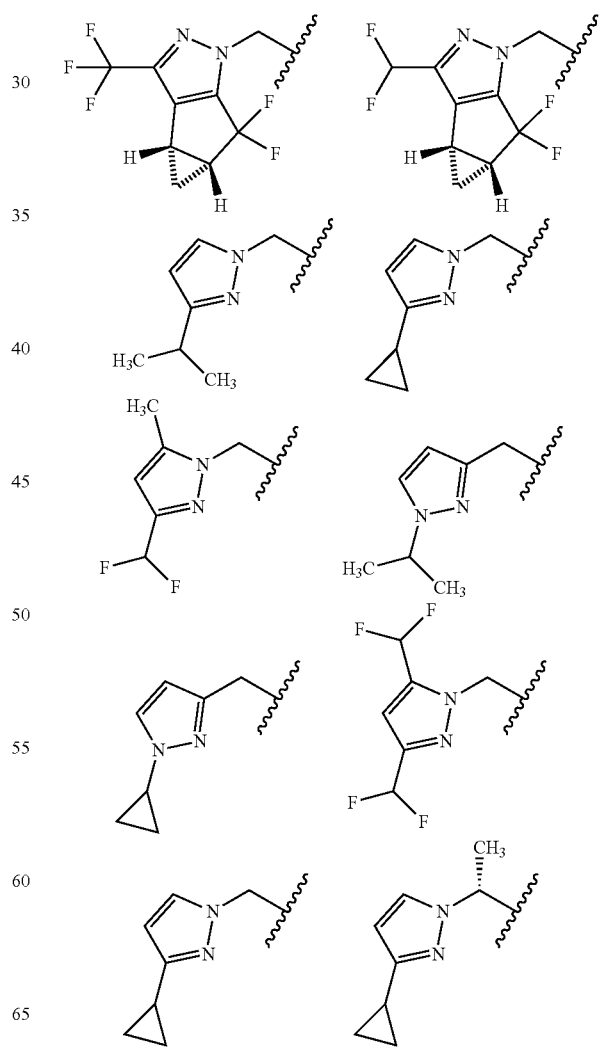

-continued

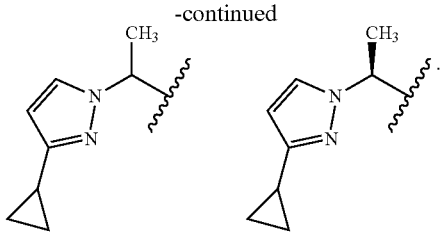

2. The compound or a pharmaceutically acceptable salt thereof, according to claim 1 wherein $R^1$ and $R^2$ are F.

3. The pharmaceutical composition comprising a compound or a pharmaceutically acceptable salt thereof, according to claim 1, further comprising a pharmaceutically acceptable excipient.

4. A method of treating HIV infection in a human comprising administration of a therapeutically effective amount of a compound or a pharmaceutically acceptable salt thereof, according to claim 1.

* * * * *